US 8,778,847 B2

(12) United States Patent
Golding et al.

(10) Patent No.: US 8,778,847 B2
(45) Date of Patent: Jul. 15, 2014

(54) IMMUNOGENIC PEPTIDES OF INFLUENZA VIRUS

(75) Inventors: Hana Golding, Rockville, MD (US);
Surender Khurana, Clarksburg, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 1045 days.

(21) Appl. No.: 12/664,052

(22) PCT Filed: Jun. 13, 2008

(86) PCT No.: PCT/US2008/067001
§ 371 (c)(1),
(2), (4) Date: Jul. 12, 2010

(87) PCT Pub. No.: WO2008/157419
PCT Pub. Date: Dec. 24, 2008

(65) Prior Publication Data
US 2010/0285982 A1 Nov. 11, 2010

Related U.S. Application Data

(60) Provisional application No. 60/929,119, filed on Jun. 13, 2007, provisional application No. 61/014,587, filed on Dec. 18, 2007, provisional application No. 61/057,514, filed on May 30, 2008.

(51) Int. Cl.
C40B 40/10 (2006.01)

(52) U.S. Cl.
USPC .......................................................... 506/18

(58) Field of Classification Search
None
See application file for complete search history.

(56) References Cited

U.S. PATENT DOCUMENTS

2007/0042001 A1   2/2007   Weeks-Levy et al.

FOREIGN PATENT DOCUMENTS

| WO | WO 2005/116258 A | 12/2005 | |
| WO | WO 2006/069262 A | 6/2006 | |
| WO | WO 2006/069262 A2 * | 6/2006 | ............ C07K 19/00 |
| WO | WO 2006/082398 A | 8/2006 | |
| WO | WO 2007/011904 A | 1/2007 | |
| WO | WO 2007/051036 A | 5/2007 | |

* cited by examiner

Primary Examiner — Christian Boesen
(74) Attorney, Agent, or Firm — Kilpatrick Townsend & Stockton LLP

(57) ABSTRACT

Peptides and polypeptides that elicit immunogenic responses in a mammal; especially neutralizing antibodies, against human and avian influenza strains H1N1, H3N2, H5N1 and H7N7 are disclosed Immunogenic compositions including these peptides, and polypeptides are also provided. Compositions including these peptides and polypeptides with or without adjuvants are disclosed. Nucleic acids and expression cassettes encoding these peptides and polypeptides are also disclosed. Methods of inhibiting infection by influenza, with or without cell entry, are also disclosed using these peptides and polypeptides.

6 Claims, 23 Drawing Sheets

Library of phages, each displaying a unique peptide sequence fused to gIIIp on the surface

Figure 3

**SEQUENCE DIVERSITY OF INSERTS IN COMPLETE
H5N1
GENE FRAGMENT PHAGE DISPLAY LIBRARY**

Figure 5

**B-CELL EPITOPE PROFILE FOLLOWING H3N2
INFECTION USING H3N2-PHAGE LIBRARY**

Figure 6A

EPITOPE SEQUENCES REQUIRED FOR BINDING OF FLA 5.10 IDENTIFIED USING PHAGE DISPLAY

```
A/Vietnam/1203/2004    1    VKMNKIVKTATVNLVESDQICIGYHANNSTEQVDTIMEKNVTVTHAQDILEKEHNGKLC
A/Indonesia/5/05-HA.   1    ........L.................................T.....

A/Vietnam/1203/2004   61    DLDGVKPLILRDCSVAGWLLGNPMCDEFINVPEWSYIVEKANPVNDLCYPGDFNDYEELK
A/Indonesia/5/05-HA.   2    ....................FLA.5.10......T.....S......

A/Vietnam/1203/2004  121    HLLSRINHFEKIQIIPKSSWSSHEASLGVSSACPYQGKSSFFRNVVWLIKKNSTYPTIK
A/Indonesia/5/05-HA.   4    .................D....S.........L.S?...............K A/Vietnam/1203/2004  181    SYNNTNQEDLLVLWGIHHPNDAAEQTKLYQNPTTYISVGTSTLNQRLVPRIATRSKVNGQ
A/Indonesia/5/05-HA.  10    ....................R.........L.......R........
                            RECEPTOR BINDING (RB)
A/Vietnam/1203/2004  241    SGRMEFFWTILKPNDAINFESNGNFIAPEYAYKIVKKGDSTIMKSELEYGNCNTKCQT
A/Indonesia/5/05-HA.  13    ...........................A..................
                                                                                 HA1 | HA2
A/Vietnam/1203/2004  301    GAINSSMPFHNIHPLTIGECPKYVKSNRLVLATGLRNSPQRERRRKRGLFGAIAGFIEG
A/Indonesia/5/05-HA.  14    .....................................S..|.........

A/Vietnam/1203/2004  361    GWQGMVDGWYGYHHSNEQGSGYAADKESTQKAIDGVTNKVNSIIDKMNTQFEAVGREFNN
A/Indonesia/5/05-HA.  15    ....................................................

A/Vietnam/1203/2004  421    LERRIENLNKKMEDGFLDVWTYNAELLVLMENERTLDFHDSNVKNLYDKVRLQLRDNAKE
A/Indonesia/5/05-HA.  15    ....................................................

A/Vietnam/1203/2004  481    LGNGCFEFYHKCDNECMESVRNGTYDYPQYSEEARLKREEISGVKLESIGIYQILSIYST
A/Indonesia/5/05-HA.  15    ...........I.....N..................T.......

A/Vietnam/1203/2004  541    VASSLALAIMVAGLSLWMCSNGSLQCRICI*
A/Indonesia/5/05-HA.  18    ..........M.................-*
```

Figure 6B

EPITOPE SEQUENCES REQUIRED FOR BINDING OF FLD21.140 IDENTIFIED USING PHAGE DISPLAY

```
A/Vietnam/1203/2004    1   YKNXXIYLLFAIVSLVKSDQICIGYHANNSTEQVDTIMEKNVTVTHAQD ILEKKHNGKLC
A/Indonesia/5/05-HA.   1   ........S...........................................T.....

A/Vietnam/1203/2004   61   DLDGVKPLILRDCSVAGWLLGNPMCDEFINVPEWSYIVEKANPVNDLCYPGDFNDYEELK
A/Indonesia/5/05-HA.   2   ..........................................S...............

A/Vietnam/1203/2004  121   HLLSRINHFEKIQIIPKSSWSNHEASLGVSSACPYQGKSSFFRNVVWLIKKNSTYPTIKR
A/Indonesia/5/05-HA.   4   ...........T..........S....P.....................K.........
                            FLD21.140       RECEPTOR BINDING (RBS)

A/Vietnam/1203/2004  181   SYNNTNQEDLLVLWGIHHPNDAAEQTKLYQNPTTYISVGTSTLNQRLVPKIATRSKVNGQ
A/Indonesia/5/05-HA.  10   ........................................R...........K.....

A/Vietnam/1203/2004  241   SGRMEFFWTILKPNDAINFESNGNFIAPEYAYKIVKKGDSTIMKSELEYGNCNTKCQTPM
A/Indonesia/5/05-HA.  13   ................................A..........................

A/Vietnam/1203/2004  301   GAINSSMPFHNIHPLTIGECPKYVKSNRLVLATGLRNS QRESRRKK RGLFGAIAGFIEG
A/Indonesia/5/05-HA.  14   .............................S.............................
                                                                HA1   HA2

A/Vietnam/1203/2004  361   GWQGMVDGWYGYHHSNEQGSGYAADKESTQKAIDGVTNKVNSIIDKMNTQFEAVGREFNN
A/Indonesia/5/05-HA.  15   ............................................................

A/Vietnam/1203/2004  421   LERRIENLNKKMEDGFLDVWTYNAELLVLMENERTLDFHDSNVKNLYDKVRLQLRDNAKE
A/Indonesia/5/05-HA.  15   ............................................................

A/Vietnam/1203/2004  481   LGNGCFEFYHKCDNECMESVRNGTYDYPQYSEEARLKREEISGVKLESIGIYQILSIYST
A/Indonesia/5/05-HA.  15   ................I......N.........................T.........

A/Vietnam/1203/2004  541   VASSLALAIMVA GLSLWMCSNGSLQCRICI*
A/Indonesia/5/05-HA.  18   ..........M.................--
```

Figure 6C

EPITOPE SEQUENCES REQUIRED FOR BINDING OF FLA3.14 IDENTIFIED USING PHAGE DISPLAY

```
A/Vietnam/1203/2004    1    VEMEKIVLLFAIVSLVKSDQICIGYHANNSTEQVDTIMEKNVTVTHAQDILEKTHNGKLC
A/Indonesia/5/05-HA.   1    ..........E.................................T......

A/Vietnam/1203/2004   61    DLDGVKPLILRDCSVAGWLLGNPMCDEFINVPEWSYIVEKAN PVDLCYPGNFNDYEELK
A/Indonesia/5/05-HA.   2    ...........................................T.....S......

A/Vietnam/1203/2004  121    HLLSRINHFEKIQIIPKSSWSSHEASLGVSSACPYQGKSSFFRNVVWLIKKNSTYPTIKR
A/Indonesia/5/05-HA.   4    ................D.....S..........L.S...................K
                                                    RECEPTOR BINDING (RB)
A/Vietnam/1203/2004  181    SYNNTNQEDLLVLWGIHHPNDAAEQTKLYQNPTTYISVGTSTLNQRLVPKIATRSKVNGQ
A/Indonesia/5/05-HA.  10    .......................R.......I...........K...........

A/Vietnam/1203/2004  241    SGRMEFFWTILKPNDAINFESNGNFIAPEYAYKIVKKGDSTIMKSELEYGNCNTKCQT M
A/Indonesia/5/05-HA.  13    ...........................A...........................
                                                                              HA1 HA2
A/Vietnam/1203/2004  301    GSIRSSM PFHNIHPLTIGEC PKYVKSNRLVLATGLRNS PQRERRRKKRGLFGAIAGFIEG
A/Indonesia/5/05-HA.  14    ..............................S...........|........

A/Vietnam/1203/2004  361    GWQGMVDGWYGYHHSNEQGSGYAADKESTQKAIDGVTNKVNSIIDKMNTQFEAVGREFNN
A/Indonesia/5/05-HA.  15    ............................................................

A/Vietnam/1203/2004  421    LERRIENLNKKMEDGFLDVWTYNAELLVLMENERTLDFHDSNVKNLYDKVRLQLRDNAKE
A/Indonesia/5/05-HA.  15    ............................................................

A/Vietnam/1203/2004  481    LGNGCFEFY

Figure 7

(a) BINDING SPECIFICITY OF 5.10-101 IDENTIFIED USING RPL ON FLA 5.10 WTH OF HUMAN H5 HA MAbs

REACTIVITIY OF H5 MAbs WITH 5.10 PEPTIDE IN ELISA

- FLD20.19
- FLD21.140
- FLA3.14
- FLA5.10

PEPTIDE CONCENTRATION (b) LEUCINE IS THE CRITICAL RESIDUE REQUIRED FOR BINDING TO FLA 5.10

- 5.10-101
- 5.10-101-L1A

PEPTIDE CONCENTRATION

FIG. 9A  STRUCTURAL MAP OF FLA5.10 EPITOPE
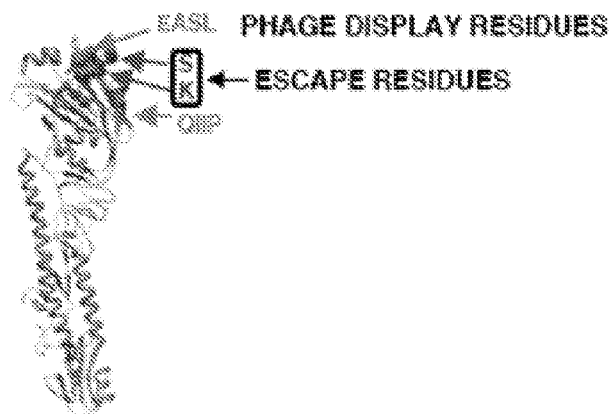
FIG. 9B  STRUCTURAL MAP OF FLD21.140 EPITOPE
FIG. 9C  STRUCTURAL MAP OF FLA3.14 EPITOPE
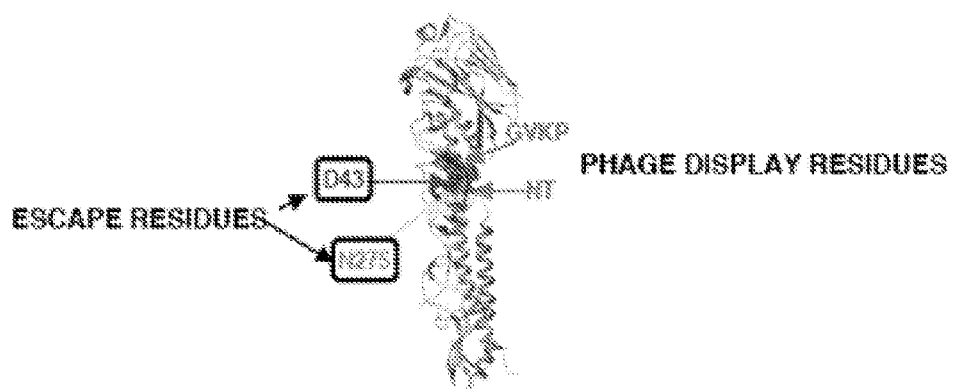

Fig.12

**B-CELL EPITOPE PROFILE FOLLOWING H5N1 INFECTION
(EXCLUDING HA & NA)**

B-CELL EPITOPE PROFILE FOLLOWING H5N1 VACCINATION
USING H5N1-PHAGE LIBRARY

FIG. 14A

- COMPLETE PROTEOME SEQUENCE OF H5N1- A/VIETNAM/1203/2004

Sequence Range: 1 to 6552

```
         10        20        30        40        50        60        70        80        90       100
MERIKELRDLMSQSRTREILTKTTVDHMAIIKKYTSGRQEKNPALRMKWMMAMKYPITADKRIMEMIPERNEQGTLMSKTKDAGSDPVMUSFLAVIWWN
                                          POLYMERASE PROTEIN-PB2

110       120       130       140       150       160       170       180       190       200
RNGPATSAVHYPKVYKTYFEKVERLKHGTFGPVHFRNQVKIRRRVDINPGHADLSAKEAQDVIMEVVFPNEVGARILTSESQLTITKEKKEELQDCKIAP
                                          POLYMERASE PROTEIN-PB2

210       220       230       240       250       260       270       280       290       300
LMVAYMLERELVRKTRFLPVAGGTSSVYIEVLHLTQGTCWEQMYTPGGEVRNDDVDQSLIIAARNIVRRATVSADPLASLLEMCHSTQIGGIRMVDILRQ
                                          POLYMERASE PROTEIN-PB2

310       320       330       340       350       360       370       380       390       400
NPTEEQAVDICKAAMGLRISSSFSFGGFTFKRTSGSSVKREEEVLTGNLQTLKIRVHEGYEEFTMVGRRATAILRKATRRLIQLIVSGRDQQSIAEAIIV
                                          POLYMERASE PROTEIN-PB2

410       420       430       440       450       460       470       480       490       500
AMVFSQEDCMIKAVRGDLNFVNRANQRLNPMHQLLRHFQKDAKVLFQNWGIEPIDNVMGMIGILPDMTPSTEMSLRGVRVSKMGVDEYSSTERVVVSIDR
                                          POLYMERASE PROTEIN-PB2

510       520       530       540       550       560       570       580       590       600
FLRVRDQRGNVLLSPEEVSETQGTEKLTITYSSSMMNKINGPESVLVNTYQWIIRNWETVKIQWSQDPTMLYNKMEFEPFQSLVPKAARGQYSGFVRTLF
                                          POLYMERASE PROTEIN-PB2

610       620       630       640       650       660       670       680       690       700
QQMRDVLGTFDTVQIIKLLPFAAAPPKQSRMQFSSLTVNVRGSGMRILVRGNSPVFNYNKATKRLTVLGKDAGALTEDPDEGTAGVESAVLPQFLISKE
                                          POLYMERASE PROTEIN-PB2

710       720       730       740       750       760       770       780       790       800
DKRYGPALSINELSNLAKGEKANVLIGQGDVVLVMKRKRDSSILTDSQTATKRIRMAIN---MDVNPTLLFLKVPVQNAISTTFPYTSDPPYSHGTGTGY
                            POLYMERASE PROTEIN-PB2 >                    POLYMERASE PROTEIN-PB1 >

810       820       830       840       850       860       870       880       890       900
TMDTVNRTHQYSEKCKWTTNTETGAPQLNPIDGPLPEDNEPSGYAQTDCVLEAMAFLEESHPGIFENSCLETMEIVQQTRVDKLTQGRQTYDWTLNRNQP
                                          POLYMERASE PROTEIN-PB1

910       920       930       940       950       960       970       980       990      1000
AATALANTIEIFRSNGLTANESGRLIDFLKDVMESHDKEEMEITTBFQRKRRVRDNMTKKMVTQRTIGRKEKQPIAKKSVLIRALTINIMTMTGDREERGKLKR
                                          POLYMERASE PROTEIN-PB1

1010      1020      1030      1040      1050      1060      1070      1080      1090      1100
RAIATPGMQIRGFVYFVETLARSICEKLEQSGLPVGGNEKKAKLANVVRKMMTNSQDTELSFTITGDNTKWNENQNPRMFLAMITYITRNQPEWFRNVLS
                                          POLYMERASE PROTEIN-PB1

1110      1120      1130      1140      1150      1160      1170      1180      1190      1200
IAPIMFSNKMARLGKGYMFESKSMKLRTQIPAEMLANIDLKYFNELTKKKIEKIRPLLIDGTASLSPGMMMGMFNMLSTVLGVSILNLGQKRYTKTTYWW
                                          POLYMERASE PROTEIN-PB1

1210      1220      1230      1240      1250      1260      1270      1280      1290      1300
DGLQSSDDFALIVNAPNHEGIQAGVDRFYRTCKLVGINMSKKKSYINRTGTFEFTSFFYRYGFVANFSMELPSFGVSGINESADMSIGVTVIKNNMIND
                                          POLYMERASE PROTEIN-PB1

1310      1320      1330      1340      1350      1360      1370      1380      1390      1400
LGPATAQMALQLFIKDYRYTYRCHRGDTQIQTRRSFELKKLWEQTRSKAGLLVSDGGPNLYNIRNLHIPEVCLKWELMDEDYQGRLCNFLNPFVSKKEIE
                                          POLYMERASE PROTEIN-PB1

1410      1420      1430      1440      1450      1460      1470      1480      1490      1500
SVNNAVMPAHGPAKSMEYDAVATTHSWIPKRNRSILNTSQRGILEDEQMYQKCCNLFEKFFPSSSYRRPVGISSMVEAMVSRARIDARIDFESGRIKKE
                                          POLYMERASE PROTEIN-PB1

1510      1520      1530      1540      1550      1560      1570      1580      1590      1600
EFAEIMKICSTIEELRRQK----MEQGQQDTIWIQSTEHTNIQKRGSGQQTQRLEHEMSTRLMDEXLRIMSFVGTBKQIVYWKQWLSLKNFTQGSLKTRVLK
                                          POLYMERASE PROTEIN-PB1
                                                                    PB1-F2
```

Figure-15A- COMPLETE PROTEOME SEQUENCE OF H3N2- A/CALIFORNIA/7/2004

Sequence Range: 1 to 4629

10 20 30 40 50 60 70 80 90 100
MERIKELRNLMSQSRTREILTKTTVDHMAIIKKYTSGRQEKNPSLRMKWMMAMKYPITADKRITEMVPERNEQGQTLWSKMSDAGSDRVMVSPLAVTWWN
POLYMERASE- PB2

110 120 130 140 150 160 170 180 190 200
RNGPVTSTVHYPKVYKTYFDKVERLKHGTFGPVHFRNQVKIRRRVDINPGHADLSAKEAQDVIMEVVFPNEVGARILTSESQLTITKEKKEELRDCKISP
POLYMERASE- PB2

210 220 230 240 250 260 270 280 290 300
LMVAYMLERELVRKTRFLPVAGGTSSIYIEVLHLTQGTCWEQMYTPVRSEDDDVDPSLNYCGPGNIVRRAAVSAIPLASLLEMCHSTQIGGTRMVDILRQ
POLYMERASE- PB2

310 320 330 340 350 360 370 380 390 400
NPTEEQAVDICKAAMGLRISSSFSFGGFTFKRTSGSSVKKEEEVLTGNLQTLKIRVHEGYEEFTMVGKRATAILRKATRRLVQLIVSGRDEQSIAEAIIV
POLYMERASE- PB2

410 420 430 440 450 460 470 480 490 500
AMVFSQEDCMIKAVRGDLNFVNRANQRLNPMHQLLRHFQKDAKVLFQNWGIEHIDSVMGMVGVLPDMTPSTEMSMRGIRVSKMGVDEYSSTERVVVSIDR
POLYMERASE- PB2

510 520 530 540 550 560 570 580 590 600
FLRVRDQRGNVLLSPEEVSETQGTESLTITYSSSMMWEINGPESDLVNTYQWIIRNWEAVKIQWSQNPAMLYNKMEFEPFQSLVPKAIRSQYSGFVRTLF
POLYMERASE- PB2

610 620 630 640 650 660 670 680 690 700
QQMRDVLGTFDTTQIIKLLPFAAAPPKQSRMQFSSLTVNVRGSGMRILVRGNSPVFNYNKTTKRLTILGKDAGTLIEDPDESTSGVESAVLRGFLIIGKE
POLYMERASE- PB2

710 720 730 740 750 760 770 780 790 800
DRRYGPALSINELSNLAKGEKANVLIGQGDVVLVMKRKRDSSILTDSQTATKRIRMAINYC----MDVNPTLLFLKVPAQNAISTTFPYTGDPPYSHGTG
POLYMERASE- PB2
POLYMERASE- PB1

810 820 830 840 850 860 870 880 890 900
TGYTMDTVNRTHQYSEKGKWTTNTETGAPQLNPIDGPLPEDNEPSGYAQTDCVLEAMAFLEESHPGIFENSCLETMEVVQQTRVDKLTQGRQTYDWTLNR
POLYMERASE- PB1

910 920 930 940 950 960 970 980 990 1000
NQPAATALANTIEVFRSNGLTAMESGRLIDFLKDVMESMDKEEMEITTHFQRKRRVRDNMTKKMVTQRTIGKKKQRVNKRGYLIRALTLNTMTKDAERGK
POLYMERASE- PB1

Figure 15B

```
         1010      1020      1030      1040      1050      1060      1070      1080      1090      1100
LKRRAIATPGMQIRGFVYFVETLARSICEKLEQSGLPVGGNEKKAKLANVVRKMMTNSQDTELSFTITGDNTKWNENQNPRMFLAMITYITKNQPEWFRN
                                                    POLYMERASE- PB1                                     >

1110      1120      1130      1140      1150      1160      1170      1180      1190      1200
ILSIAPIMFSNKMARLGKCYMFESKRMKLRTQIPAEMLASIDLKYFNESTRKKIEKIRPLLIDGTASLSPGMMMGMFNMLSTVLGVSILNLGQKKYTKTT
                                                    POLYMERASE- PB1                                     >

1210      1220      1230      1240      1250      1260      1270      1280      1290      1300
YEWDGLQSSDDFALIVNAPNHEGIQAGVDRFYRTCKLVGINMSKKKSYINKTGTFEFTSFFYRYGFVANFSMELPSFGVSGINESADMSIGVTVIKNNMI
                                                    POLYMERASE- PB1                                     >

1310      1320      1330      1340      1350      1360      1370      1380      1390      1400
NNDLGPATAQMALQLFIKDYRYTYRCHRGDTQIQTRRSFELKKLWDQTQSRAGLLVSDGGPNLYNIRNLHIPEVCLKWELMDENYRGRLCNPLNPFVSHK
                                                    POLYMERASE- PB1                                     >

1410      1420      1430      1440      1450      1460      1470      1480      1490      1500
EIESVNNAVVMPAHGPAKSMEYDAVATTHSWIPKRNRSILNTSQRGILEDEQMYQKCCNLFEKFFPPSSSYRRPIGISSMVEAMVSRARIDARIDFESGRI
                                                    POLYMERASE- PB1                                     >

1510      1520      1530      1540      1550      1560      1570      1580      1590      1600
KKEEFSEIMKICSTIEELRRQK-----MEQEQGTPWTQSTEHTNIQRPGSGRQIQKLGHPNSTQLMDHYLRIMSRVDMHKQTVSWRLMPSLKNPTQVSLR
     POLYMERASE- PB1     >
                                                                  PB1-F2                                >

1610      1620      1630      1640      1650      1660      1670      1680      1690      1700
THALKQWKSFNKQGWTN---KEDPVRQCFNPMIVELAEKAMKEYGEDLKIETNKFAAICTHLEVCFMYSDFHFINEQGESIMVELDDPNALLKHRFEIIE
     PB1-F2     >
                                                     POLYMERASE- PA                                     >

1710      1720      1730      1740      1750      1760      1770      1780      1790      1800
GRDRTMAWTVVNSICNTTGAEKPKFLPDLYDYKENRFIEIGVTRREVHIYYLEKANKIKSENTHIHIFSFTGEEMATKADYTLDEESRARIKTRLFTIRQ
                                                    POLYMERASE- PA                                      >

1810      1820      1830      1840      1850      1860      1870      1880      1890      1900
EMANRGLWDSFRQSERGEETIEEKFENLRTMRSFADQSLPPNFSCLEXLEPMWMDSNPTGCIEGKLSQMSKEVNAKIEPFLKKTPRFIKLENGPPCYQRS
                                                    POLYMERASE- PA                                      >

1910      1920      1930      1940      1950      1960      1970      1980      1990      2000
KFLMDALKLSIEDPSHEGEGIPLYDAIKCMKTPFGWKEPYIVKPHEKGINSNYLLSWKQVLSELQDIENEEKIPRTKNMKKTSQLKWALGENMAPEKVD
                                                    POLYMERASE- PA                                      >

2010      2020      2030      2040      2050      2060      2070      2080      2090      2100
PDNCRDISDLKQYDSDEPELRSLSSWIQNEFNKACELTDSIWIELDEIGEDVAPIEYIASMRRNYFTAEVSHCRATEYIMKGVYINTALLNASCAAMDDF
                                                    POLYMERASE- PA                                      >
```

Figure 15C

```
        2110      2120      2130      2140      2150      2160      2170      2180      2190      2200
QLIPMISKCRTKEGTRKTNLYGFIIKGRSHLRNDTDVVNFVSMEFSLTDPRLEPHKWEKYCVLEIGDMLLRSAIGQISRPMFLYVRTNGTSKVKMKWGME
__________________________________________POLYMERASE- PA______________________________________________>

2210      2220      2230      2240      2250      2260      2270      2280      2290      2300
MRRCLLQSLQQIESMIEAESSIKEKDMTKEFFENKSEAWPIGESPKGVEEGSIGKVCRTILAKSVFNSLYASPQLEGFSAESRKLLLVVQALRDNLEPGT
__________________________________________POLYMERASE- PA______________________________________________>

2310      2320      2330      2340      2350      2360      2370      2380      2390      2400
FDLGGLYEAIEECLINDPWVLLNASWFNSFLTHALK----MVQLVRPQRKQGIILLTMKTIIALSYILCLVFAQKLPGNDNSTATLCLGHHAVPNGTIVK
_________POLYMERASE- PA__________>
                                        ____________________HAEMAGGLUTININ- HA_____________________>

2410      2420      2430      2440      2450      2460      2470      2480      2490      2500
TITNDQIEVTNATELVQSSSTGGICDSPHQILDGENCTLIDALLGDPQCDGFQNKKWDLFVERSKAYSNCYPYDVPDYASLRSLVASSGTLEFNNESFNW
________________________________________HAEMAGGLUTININ- HA__________________________________________>

2510      2520      2530      2540      2550      2560      2570      2580      2590      2600
TGVTQNGTSSSCKRRSNNSFFSRLNWLTHLKFKYPALNVTMPNNEKFDKLYIWGVHHPGTNHDQISLYTQASGRITVSTKRSQQTVIPNIGSRPRVRDIP
________________________________________HAEMAGGLUTININ- HA__________________________________________>

2610      2620      2630      2640      2650      2660      2670      2680      2690      2700
SRISIYWTIVKPGDILLINSTGNLIAPRGYFKIRSGKSSIMRSDAPIGKCNSECITPNGSIPNDKPFQNVNRITYGACPRYVKQNTLKLATGMRNVPEKQ
________________________________________HAEMAGGLUTININ- HA__________________________________________>

2710      2720      2730      2740      2750      2760      2770      2780      2790      2800
TRGIFGAIAGFIENGWEGMVDGWYGFRHQNSEGIGQAADLKSTQAAINQINGKLNRLIGKTNEKFHQIEKEFSEVEGRIQDLEKYVEDTKIDLWSYNAEL
________________________________________HAEMAGGLUTININ- HA__________________________________________>

2810      2820      2830      2840      2850      2860      2870      2880      2890      2900
LVALENQHTIDLTDSEMNKLFEKTKKQLRENAEDMGNGCFKIYHKCDNACIGSIRNGTYDHDVYRDEALNNRFQIKGVELKSGYKDWILWISFAISCFLL
________________________________________HAEMAGGLUTININ- HA__________________________________________>

2910      2920      2930      2940      2950      2960      2970      2980      2990      3000
CVALLGFIMWACQKGNIRCNICI-----MASQGTKRSYEQMETDGDRQNATEIRASVGKMIDGIGRFYIQMCTELKLSDHEGRLIQNSLTIEKMVLSAFD
___HAEMAGGLUTININ- _____>
                            __________________________NUCLEOPROTEIN- NP__________________________>

3010      3020      3030      3040      3050      3060      3070      3080      3090      3100
ERRNKYLEEHPSAGKDPKKTGGPIYRRVDGKWMRELVLYDKEEIRRIWRQANNGEDATAGLTHIMIWHSNLNDATYQRTRALVRTGMDPRMCSLMQGSTL
________________________________________NUCLEOPROTEIN- NP___________________________________________>
```

Figure 15D

```
         3110      3120      3130      3140      3150      3160      3170      3180      3190      3200
PRRSGAAGAAVKGVGTMVMELIRMVKRGINDRNFWRGENGRRKTRSAYERMCNILKGKFQTAAQRAMVDQVRESRNPGNAEIEDLIFLARSALILRGSVAH
                                             NUCLEOPROTEIN- NP 3210      3220      3230      3240      3250      3260      3270      3280      3290      3300
KSCLPACAYGPAVSSGYDFEKEGYSLVGIDPFKLLQNSQIYSLIRPNENPAHKSQLVWMACHSAAFEDLRLLSFIRGKKVSFRGKLSTRGVQIASNENMD
                                             NUCLEOPROTEIN- NP 3310      3320      3330      3340      3350      3360      3370      3380      3390      3400
NMGSSTLELRSGYWAIRTRSGGNTNQQRASAGQTSVQPTFSVQRNLPFEKSTIMAAFTGNTEGRTSDMRAEIIRMMEGAKPEEVSFRGRGVFELSDEKAA
                                             NUCLEOPROTEIN- NP 3410      3420      3430      3440      3450      3460      3470      3480      3490      3500
NPIVPSFDMS-----MNPNQKIITIGSVSLTISTICFFMQIAILITTVTLHFKQYEFNSPPNNQVMLCEPTIIERNITEIVYLTNTTIEKEICPKLAEYRN
                                             NEURAMINADASE- NA 3510      3520      3530      3540      3550      3560      3570      3580      3590      3600
WSKPQCDITGFAPFSKDNSIRLSAGGDIWVTREPYVSCDPDKCYQFALGQGTTLNNVHSNDTVHDRTPYRTLLMNELGVPFHLGTKQVCIAWSSSSCHDG
                                             NEURAMINADASE- NA 3610      3620      3630      3640      3650      3660      3670      3680      3690      3700
KAWLHVCVTGDDKNATASFIYNGRLVDSIVSWSKEILRTQESECVCINGTCTVVMTDGSASGKADTKILFIEEGKIVHTSTLSGSAQHVEECSCYPRYPG
                                             NEURAMINADASE- NA 3710      3720      3730      3740      3750      3760      3770      3780      3790      3800
VRCVCRDNWKGSNRPIVDINIKDYSIVSSYVCSGLVGDTPRKNDSSSSHCLDPNNEEGGHGVKGWAFDDGNDVWMGRTISEKLRSGYETFKVIEGWSNP
                                             NEURAMINADASE- NA 3810      3820      3830      3840      3850      3860      3870      3880      3890      3900
NSKLQINRQVIVDRGNRSGYSGIFSVEGKSCINRCFYVELIRGRKEETEVLWTSNSIVVFCGTSGTYGTGSWPDGADINLMPI
                                             NEURAMINADASE- NA 3910      3920      3930      3940      3950      3960      3970      3980      3990      4000
---MSLLTEVETYVLSIVPSGPLKAEIAQRLEDVFAGKNTDLEALMEWLKTRPILSPLTKGILGFVFTLTVPSERGLQRRFVQNALNGNGDPNNMDKAV
                                             MATRIX PROTEIN- M1

4010      4020      4030      4040      4050      4060      4070      4080      4090      4100
KLYRKLKREITFHGAKEIALSYSAGALASCMGLIYNRMGAVTTEVAFGLVCATCEQIADSQHRSHRQMVATTNPLIRHENRMVLASTTAKAMEQMAGSSE
                                             MATRIX PROTEIN- M1

4110      4120      4130      4140      4150      4160      4170      4180      4190      4200
QAAEAMEIASQARQMVHAMRAVGTHPSSSTGLRDDLLENLQTYQKRMGVQMQRFK----MIFLKICRPIRNEWGCRCNDSSDPLVVAASIIGILHLILWIL
                                MATRIX PROTEIN- M1
                                                                MATRIX PROTEIN- M2
```

Figure 15E

```
        4210      4220      4230      4240      4250      4260      4270      4280      4290      4300
DRLFFKCVYRLFKRGLKRGPSTEGVPESMREEYRKEQQNAVDADDSHFVSFIGVKNYLISTLINTAEQ----MDSNTVSSFQVDCFLWHIRKQVVDQELS
                        .............MATRIX PROTEIN- M2.............>
                                                                      ........NON-STRUCTURAL PROTEIN NS1>

4310      4320      4330      4340      4350      4360      4370      4380      4390      4400
DAPFLDRLRPDQRSLRGRGNTLGLDIKAATHVGKQIVEKILKEESDEALKMTMVSTPASRYITDMTIEELSRNWFMLMPKQKVEGPLCIRMDQAIMEKNI
             ........................NON-STRUCTURAL PROTEIN- NS1.......................................>

4410      4420      4430      4440      4450      4460      4470      4480      4490      4500
MLKANFSVIFDRLETIVLLRAFTEEGAIVGEISPLPSFPGHTIEDVKNAIGVLIGGLEWNDNTVRVSKNLQPFAWRSSNENGGPPLTPKQKRKVARTARS
                  ........................NON-STRUCTURAL PROTEIN- NS1.......................................>

4510      4520      4530      4540      4550      4560      4570      4580      4590      4600
KV----MDSNTVSSPQDILLRPMSKMQLGSSSEDLNGMITQFESLKIYRDSLGEAVMRMGDLHLLQNRNGKWREQLGQKFEEIRWLIEEVRHRLKTTENSF
                 ....................NON-STRUCTURAL PROTEIN- NS2.......................................>

4610      4620
EQITFMQALQLPEVEQEIRTFSFHLI--
.......NON-STRUCTURAL PROTEIN NS2.......>
```

US 8,778,847 B2

IMMUNOGENIC PEPTIDES OF INFLUENZA VIRUS

CROSS-REFERENCE TO RELATED PATENT APPLICATIONS

The present patent application is a US national phase application of PCT/US2008/067001, filed Jun. 13, 2008, which is incorporated herein by reference.

This application is being filed on 13 Jun. 2008, as a PCT International Patent application in the name of The Government of the United States of America as represented by the Secretary, Department of Health and Human Services, a U.S. national corporation, applicant for the designation of all countries except the US, and Hana Golding, a citizen of the U.S., and Surender Khurana, a citizen of India, applicants for the designation of the US only, and claims priority to U.S. Provisional Patent Application Ser. Nos. 60/929,119, filed Jun. 13, 2007, 61/014,587, filed Dec. 18, 2007, and 61/057,514, filed May 30, 2008.

GOVERNMENT FUNDING

The invention described herein was developed with the support of the Department of Health and Human Services. The United States Government has certain rights in the invention.

FIELD OF THE INVENTION

This invention pertains to the general field of immunology and further to the field of viral immunology and specifically in the field of vaccines, therapeutics and diagnostics for influenza.

BACKGROUND OF THE INVENTION

Influenza is a contagious acute respiratory disease caused by infection of the upper respiratory and gastrointestinal tract by influenza virus. The viral genome is made up of several negative sense single stranded RNA molecules. Several proteins are encoded by the viral genome. NA is a viral surface glycoprotein that cleaves terminal sialic acid residues from carbohydrate moieties on the surfaces of infected cells, promoting the release of progeny viruses. HA is one of the major viral surface glycoproteins and involved in the binding of the virus to sialic acids on the surface of susceptible cells (Uiprasertkul M, et al. Emerg. Infect. Dis. 11, 1036-1041 (2005)). The M2 protein is an ion channel protein. The HA, NA, and M2 protein are present in the viral envelope which is derived from the host cell plasma membrane. A ribonucleoprotein complex comprises an RNA segment associated with nucleoprotein (NP) and three polymerases, PA, PB1, and PB2. The M1 protein is associated with both ribonucleoprotien and the envelope.

Annual epidemics of influenza occur when the antigenic properties of the viral surface protein hemagglutinin (HA) and neuraminidase (NA) are altered. The mechanism of altered antigenicity is twofold: antigenic shift, caused by genetic rearrangement between human and animal viruses after double infection of host cells, which can cause a pandemic; and antigenic drift, caused by small changes in the HA and NA proteins on the virus surface, which can cause influenza epidemics. The emergence of variant virus strains by these two mechanisms is the cause of influenza epidemics.

It is therefore desirable to develop new vaccine candidates likely to generate heterotypic cross-protection and for differential diagnostics for the exposure to avian and seasonal influenza in the face of seasonal vaccinated generated immunity.

SUMMARY OF THE INVENTION

The disclosure provides one or more polypeptides, polynucleotides, and assays useful to generate an immune response to influenza virus, prepare antibodies to influenza virus, and to conduct serodiagnosis or differential diagnosis of influenza virus. The disclosure also provides genome flu phage display libraries useful for epitope mapping and in sero or differential diagnosis. The phage display libraries are utilized to identify portions of influenza polypeptides that bind to antibodies from an infected and/or vaccinated individual. The disclosure provides kits and diagnostic assays In some embodiments, the disclosure provides one or more isolated and purified influenza polypeptides from an influenza virus that specifically bind to an antibody from a subject infected and/or vaccinated with the influenza virus selected from the group consisting of: a) hemagglutinin (HA), b) neuraminidase (NA), c) basic polymerase 2 (PB2), d) basic polymerase 1(PB1), e) basic polymerase 1 frame 2(PB 1-F2), f) acidic polymerase PA, g) nucleoprotein (NP), h) matrix protein 1 (M1), i) matrix protein 2 (M2), j) Non structural protein NS1, k) Non structural protein NS2, and fragments thereof, wherein the polypeptides exclude the corresponding full length native polypeptides. In some embodiment, the polypeptides are from an influenza virus is selected from the group consisting of H5N1, H3N2, H1N1, and H7N7. In specific embodiments, the polypeptides include one or more of the polypeptides having a sequence of SEQ ID NO:1-123. These polypeptides may form a part of a fusion protein and may be coupled to a solid substrate for use in diagnostic assays. These polypeptides are useful in immunogenic compositions to generate antibodies useful therapeutically, or to provide a protective immune response.

The disclosure also includes polynucleotides encoding the polypeptides and vectors comprising the polynucleotides. In some embodiments, the vector is a phage display vector and a library comprising a plurality of fusion proteins including one or more sequences from an influenza gene segment is formed. In other embodiments, one or more of the polynucleotides are utilized in an immunogenic compositions in order to generate antibodies and/or a protective immune response.

The disclosure also includes methods of using the polypeptides and/or polynucleotides to treat influenza virus infection and to immunize animals. Methods also include assays useful for surveillance of out breaks of infection.

BRIEF DESCRIPTION OF THE DRAWINGS

FIG. 3 illustrates the sequence diversity of inserts in complete H5N1 gene fragment phage display library.

FIG. 5 illustrates an exemplary B-cell epitope map of hemagglutinin (HA) from H3N2 expressed from a gene fragment phage display library and screened against polyclonal sera collected before vaccination and after the influenza season from convalescent patients in the placebo arm of the study done in 2003-2004 season.

FIG. 6 (a) illustrates epitope sequences recognized by H5N1 neutralizing monoclonal antibody FLA5.10 identified using influenza complete genome-fragment phage display library (GFPDL). Epitope sequences are boxed on the aligned sequence of A/Vietnam/1203/2004 (SEQ ID NO:178) & A/Indonesia/5/05 (SEQ ID NO:179) of the haemagglutinin (HA). Amino acid number 1 corresponds to H3 (A/California/7/2004) amino acid −10. HA sequences recognized by FLA5.10 include amino acids 9-241; (b) illustrates epitope sequences recognized by H5N1 neutralizing monoclonal antibody FLD 21.140 identified using influenza complete genome-fragment phage display library (GFPDL). Epitope sequences are boxed on the aligned sequence of A/Vietnam/1203/2004 (SEQ ID NO:178) & A/Indonesia/5/05 (SEQ ID NO:179) of the haemagglutinin (HA). Amino acid number 1 corresponds to H3 (A/California/7/2004) amino acid −10. HA sequences recognized by FLD 21.140 include amino acids 50-338; and (c) illustrates epitope sequences recognized by H5N1 neutralizing monoclonal antibody FLA 3.14 identified using influenza complete genome-fragment phage display library (GFPDL). Epitope sequences are boxed on the aligned sequence of A/Vietnam/1203/2004 (SEQ ID NO:178) & A/Indonesia/5/05 (SEQ ID NO:179) of the haemagglutinin (HA). Amino acid number 1 corresponds to H3 (A/California/7/2004) amino acid −10. HA sequences recognized by FLA 3.14 include amino acids 47-338. The sequence shown in this figure has accession no. AAW80717. The contact residues shown in each of the figures as encircled or boxed residues were identified using random peptide phage display library (RPL) aligned to HA1 sequence.

FIG. 7 (a) illustrates the binding specificity of 5.10-101 (SEQ ID NO:41) with FLA5.10 compared to other Human H5 monoclonal antibodies; and (b) illustrates loss of binding of 5.10-101 peptide to FLA5.10 upon mutation of leucine to Alanine.

FIG. 9 (a) illustrates the location of the epitope sequences (SEQ ID NOS:180 and 181) recognized by FLA 5.10 on a crystal structure model of hemagglutinin; (b) illustrates the location of the epitope sequences recognized by FLD 21.140 on a crystal structure model of hemagglutinin; (c) illustrates the location of the epitope sequences (SEQ ID NO:182) recognized by FLA 3.14 on a crystal structure model of hemagglutinin; The residues identified using RPL are shown on the structure of HA (PDB Id-1JSM) for FLA5.10, FLD21.140 and FLA3.14 respectively. In-vivo challenge studies with suboptimal amounts of FLA5.10 identified two mutated residues that are encircled (in a), and for FLA3.14 (in c) and are represented on the HA structure (in a & c).

FIG. 12: Antibody epitopes in H5N1 internal proteins (HA and NA excluded) recognized by pooled sera from H5N1 (Vietnam) infected individuals (a) Schematic alignment of the unique peptide sequences in various Influenza proteins identified using GFPDL off all internal genes. The predicted influenza encoded proteins are numbered according to the intact complete proteome (FIG. 14). Arrows indicate that inserts are in the right orientation. Each bar represents a unique peptide sequence. The filled rectangles represent the peptide sequences were chemically synthesized and tested with individual H5N1 survivor sera.

FIG. 13 illustrates B cell epitope profile following pre- & post-vaccination with H5N1 subunit vaccine with no adjuvant, alum adjuvant or MF59 adjuvant. Samples were obtained from the clinical trial study described in Bernstein et al, JID; 2008:197; 1-9.

FIG. 14A-C provides the complete proteome of H5N1-A/VIETNAM/1203/2004 (SEQ ID NOS:125-135). Amino acid numbering of H5N1 polypeptides in this patent application is based on the numbering shown in this figure.

FIG. 15A-E provides the complete proteome of H3N2-A/CALIFORNIA/7/2004 (SEQ ID NOS:137-147). Amino acid numbering of H3N2 polypeptides in this patent application is based on the numbering shown in this figure.

DETAILED DESCRIPTION

Figure 1:
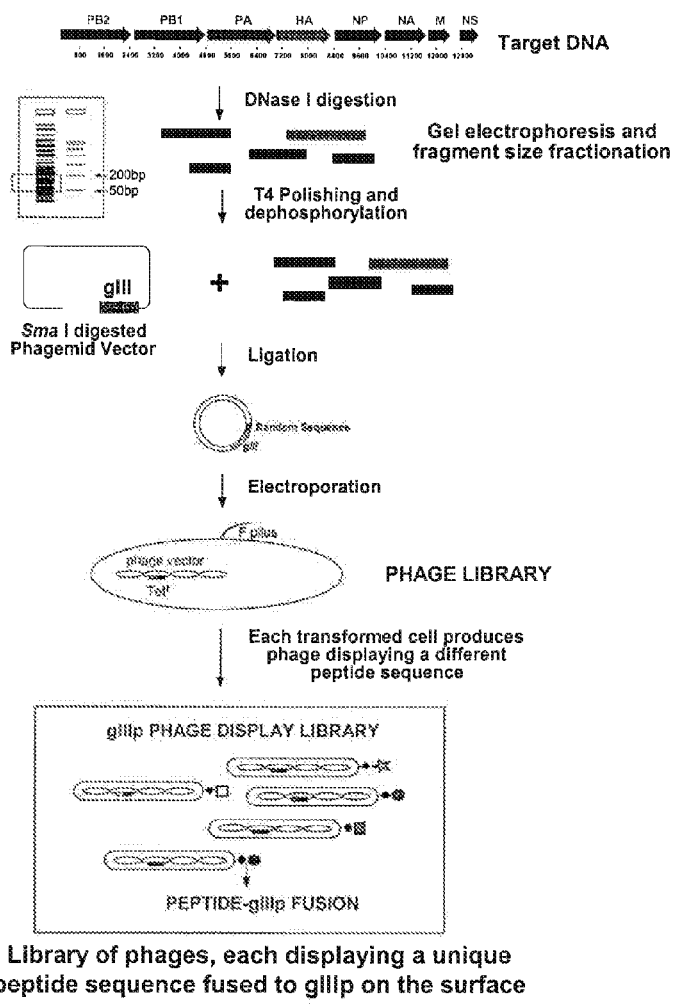
FIG. 1 illustrates a flow diagram of a process for constructing a gene fragment phage display library from influenza virus genes.

Among the eight genes encoded by influenza virus (HA, NA, M1, M2, NP, NS, PA, PB1 and PB2), immunity against hemagglutinin (HA) and neuraminidase (NA) play a central role in protection against influenza. Thus, in developing an effective influenza vaccine for use during a pandemic, HA and NA would be the target antigens along with other antigens, for example, NP.

Highly pathogenic avian H5N1 influenza A virus has caused influenza outbreaks in poultry and migratory birds in Asia, Europe and Africa. A cluster of cases of deadly H5N1 influenza in humans occurred in 2006, in which the WHO deemed that human-to-human transmission was the most probable cause of viral spread. The ability to be transmitted from human to human represents the final barrier to a new pandemic of this deadly avian strain of H5N1 influenza virus, and thus, there remains a need for effective treatments and surveillance assays should such a pandemic arise. Currently licensed human vaccines are strain specific and do not protect against heterotypic influenza viruses. This is problematic, as influenza A (H5N1) continues to evolve into antigenically distinct clades.

The disclosure provides a method of epitope mapping of Influenza virus A proteome using sera from subjects that have been infected and/or vaccinated. The epitope mapping identifies epitopes on influenza virus A proteins that are associated with a protective immune response. The identification of these epitopes is useful in the preparation of immunogenic compositions and antagonists of influenza virus infection. The identification of unique epitopes in infected versus vaccinated, and infected with H5N1 versus H3N2 can be used in assays for surveillance of influenza outbreaks, to distinguish between human and avian influenza strains, to diagnose new infection in previously vaccinated individuals, and rapid analysis of immune response to candidate vaccines in order to predict the likelihood of protection against H5N1 infection.

DEFINITIONS

Unless defined otherwise, technical and scientific terms used herein have the same meaning as commonly understood by one of ordinary skill in the art to which this invention belongs. See, e.g., Singleton P and Sainsbury D., Dictionary of Microbiology and Molecular Biology 3rd ed., J. Wiley & Sons, Chichester, N.Y. 2001, and Fields Virology 4th ed., Knipe D. M. and Howley P. M. eds, Lippincott Williams & Wilkins, Philadelphia 2001.

The terms "a", "an" and "the" as used herein are defined to mean "one or more" and include the plural unless the context is inappropriate.

By "isolated" is meant peptide or protein free from at least some of the components with which it naturally occurs.

"Peptides", "polypeptides", and "proteins" are used interchangeably and are defined herein as chains of amino acids (typically L-amino acids) in which the carbonyl group of one amino acid is linked to the amino group of a second amino acid by an amide linkage. The terminal amino acid at one end of the chain (i.e., the amino terminal) has a free amino group, while the terminal amino acid at the other end of the chain (i.e., the carboxy terminal) has a free carboxyl group.

Typically, the amino acids making up a peptide are numbered in order, starting at the amino terminal and increasing in the direction of the carboxy terminal of the peptide. Thus, when one amino acid is said to "follow" another, that amino acid is positioned closer to the carboxy terminal of the peptide than the "preceding" amino acid.

The term "residue" is used herein to refer to an amino acid (D or L) or an amino acid mimetic that is incorporated into a peptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e. amino acid mimetics). Moreover, an amide bond mimetic includes peptide backbone modifications well known to those skilled in the art.

Peptide and protein sequences defined herein are represented by one-letter symbols for amino acid residues as follows:

| | |
|---|---|
| A | alanine |
| R | arginine |
| N | asparagine |
| D | aspartic acid |
| C | cysteine |
| Q | glutamine |
| E | glutamic acid |
| G | glycine |
| H | histidine |
| I | isoleucine |
| L | leucine |
| K | lysine |
| M | methionine |
| F | phenylalanine |
| P | proline |
| S | serine |
| T | threonine |
| W | tryptophan |
| Y | tyrosine |
| V | valine |

The term "proteome" as used herein refers to all of the proteins expressed by a genome. An exemplary proteome of H5N1 (strain A/VIETNAM/1203/2004) is shown in FIG. 14. An exemplary proteome of H3N2 (strain A/CALIFORNIA/7/2004) is shown in FIG. 15.

"Antigen" refers to a molecule which can induce an immune response in an animal, preferably a mammal and most preferably a human. It induces the formation of an antibody. The term includes immunogens.

"Epitope" or "determinant" refers to the antibody binding site on an antigen.

"Antibody" refers to a molecule produced by animals in response to antigen which has the particular property of combining specifically with the antigen which induced its formation.

"Neutralizing antibody" refers to an antibody that blocks viral infection of a cell.

"Neutralizing antigenic epitope" or "neutralizing epitope" refers to an epitope that elicits a neutralizing antibody.

The phrases "specifically binds to a peptide" or "specifically immunoreactive with", when referring to an antibody, refers to a binding reaction which is determinative of the presence of the peptide, or an antibody to the peptide, in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein or a particular epitope. In some embodiments, antibodies bind to a protein of one subtype or clade of influenza and not another, for example, antibodies bind to hemagglutinin from H5N1 subtype of influenza and not to H3N2. A variety of immunoassay formats may be used to select antibodies specifically immunoreactive with a particular protein.

For example, solution or solid phase immunoassays are routinely used to select monoclonal antibodies specifically immunoreactive with a protein. See, Harlow and Lane (1988) Antibodies, A Laboratory Manual, Cold Spring Harbor Publications, New York, for a description of immunoassay formats and conditions that can be used to determine specific immunoreactivity.

The term as "clade" as used herein refers to a taxonomic group (such as one of organisms) comprising a single common ancestor and all the descendants of that ancestor.

"Conservative variations" or "conservative modified variations" of a particular sequence refers to amino acids encoded by nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given peptide. Such nucleic acid variations are silent variations, which are one species of conservatively modified variations. One of skill will recognize that each codon in a nucleic acid (except AUG, which is ordinarily the only codon for methionine) can be modified to yield a functionally identical molecule by standard techniques. Accordingly, each silent variation of a nucleic acid which encodes a peptide is implicit in any described amino acid sequence. Furthermore, one of skill will recognize that individual substitutions, deletions or additions which alter, add or delete a single amino acid or a small percentage of amino acids in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Two polypeptides are said to be "identical" if the sequence of amino acid residues in the two sequences is the same when aligned for maximum correspondence. Optimal alignment of sequences for comparison may be conducted by the local homology algorithm of Smith and Waterman 1981 Adv Appl Math 2:482-489, by the homology alignment algorithm of Needleman and Wunsch 1970 J Mol Biol 48:443-453, by the search for similarity method of Pearson and Lipman 1988 Proc Natl Acad Sci USA 85:2444-2448, by computerized implementations of these algorithms (GAP, BESTFIT, FASTA, and TFASTA in the Wisconsin Genetics Software Package, Genetics Computer Group, 575 Science Dr., Madison, Wis.), or by inspection. When using BESTFIT or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The term "substantial identity" means that a polypeptide comprises a sequence that has at least 55%, 60%, 65%, 70%, 75%, 80%, or 85% sequence identity, preferably 90%, more preferably 95% or more, compared to a reference sequence. Another indication that polypeptide sequences are substantially identical is if one peptide is immunologically reactive with antibodies raised against the disclosed peptide. Thus, the peptides of the invention include peptides immunologically reactive with antibodies raised against the disclosed immunogenic peptides.

The term "phage coat protein" means a protein, at least a portion of which is present on the surface of a phage virus particle. From a functional perspective, a phage coat protein is any protein which associates with a virus particle during the viral assembly process in a host cell, and remains associated with the assembled virus until it infects another host cell. The phage coat protein may be the major coat protein or may be a minor coat protein. A "major" phage coat protein is generally a coat protein which is present in the viral coat at preferably at least about 5, more preferably at least about 7, even more preferably at least about 10 copies of the protein or more. A major phage coat protein may be present in tens, hundreds or even thousands of copies per virion. An example of a major coat protein is the pVIII protein of filamentous phage.

A "fusion protein" and a "fusion polypeptide" refers to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each W other. Preferably, the two portions of the polypeptide are obtained from heterologous or different polypeptides.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display 1-3 copies of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

The term "host cell" means a cell that contains a heterologous nucleic acid, such as a vector, and supports the replication and/or expression of the nucleic acid. Host cells can be prokaryotic cells such as *E. coli*, or eukaryotic cells such as yeast, insect, amphibian, avian or mammalian cells, including human cells. Exemplary host cells can include, but are not limited to Vero (African green monkey kidney) cells, BHK (baby hamster kidney) cells, primary chick kidney (PCK) cells, MDCK (Madin-Darby Canine Kidney), 293 cells, and COS cells.

An "immunogenic effective amount" of an influenza polypeptide or polynucleotide refers to an amount of a polypeptide or polynucleotide that is capable of inducing an immune response in an animal. The immune response may be determined by measuring a T or B cell response. Levels of induced immunity can be monitored, for example, by measuring amounts of neutralizing secretory and/or serum antibodies, by plaque neutralization, complement fixation, enzyme-linked immunosorbent, microneutralization assay, or assays for T cell function. Typically, the induction of an immune response is indicated by the detection of antibodies specific for an influenza polypeptide.

As used herein, the term "immunogenic fragment thereof" refers to a fragment of an influenza polypeptide that is of a sufficient size to elicit an immune response in an animal. Typically, immunogenic fragments are at least 8 amino acids long and may include up to the full-length polypeptide. In some embodiments, an immunogenic fragment is about 9 amino acids, an immunogenic fragment is about 10 amino acids, 15 amino acids, 30 amino acids, or 45 amino acids or longer fragments. The immunogenic fragment is capable of stimulating an antibody or T cell response specific for at least one influenza polypeptide as defined herein. The sequence of immunogenic fragments can be readily predicted using available programs such as Epiredict. The immune response includes both a T and B cell response. In some cases, the immune response is identified by the ability of the fragment to elicit antibodies or to stimulate a T cell response.

A "protective immune response" against influenza virus refers to an immune response exhibited by an animal that is protective against disease when the animal is subsequently exposed to and/or infected with such influenza virus. In some instances, the influenza virus can still cause infection, but the infection is less than serious in non-immune controls. A protective immune response can be characterized by % decrease in morbidity, % increase in survival, a decrease in viral load, an increase in hemagglutinin inhibition titer and/or an increase in neutralization titer. Typically, the protective immune response results in detectable levels of host-engendered serum and secretory antibodies or cytotoxic T-lymphocyte responses that are capable of reacting with antigens from virus of the same strain and/or subgroup and in some cases, also of a different, non-vaccine strain and/or subgroup in vitro and in vivo.

Whole Genome Phage Display Libraries
Vectors

One aspect of the invention includes a replicable expression vector comprising a nucleic acid sequence encoding a fusion protein, wherein the fusion protein comprises a portion of or a segment of influenza viral gene fused to all or a portion of a viral coat protein. Also included is a library of diverse replicable expression vectors comprising a plurality of gene fusions encoding a plurality of different fusion proteins including a plurality of different portions or segments of influenza genes. The vectors can include a variety of components and are preferably constructed to allow for movement of the gene segments between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein pIII, major coat protein pVIII, p3, Soc (T4), Hoc (T4), gpD (of bacteriophage lambda), minor bacteriophage coat protein 6 (pVI) (filamentous phage; J Immunol Methods. 1999 Dec. 10; 231(1-2):39-51), variants of the M13 bacteriophage major coat protein (P8) (Protein Sci 2000 April; 9(4):647-54). In some embodiments, influenza gene segments can include from about 30 base pairs up to about 2000 base pairs. When the influenza gene segments or portions thereof include about 300 to 2000 base pairs, the viral coat protein utilized is the pIII protein because this protein can accommodate larger nucleic acid fragments. For gene segments or portions thereof of 300 base pairs or less, pVIII or pVI may also be utilized.

The fusion protein can be displayed on the surface of a phage and suitable phage systems include M13KO7 helper phage, M13R408, M13-VCS, and Phi X 174, pJuFo phage system (J Virol. 2001 August; 75(15):7107-13.v), hyperphage (Nat Biotechnol. 2001 January; 19(1):75-8). The preferred helper phage is M13KO7, and the preferred coat protein is the M13 Phage gene III coat protein. The preferred host is *E. coli*, and protease deficient strains of *E. coli*. Vectors, such as the fth1 vector (Nucleic Acids Res. 2001 May 15; 29(10):E50-0) can be useful for the expression of the fusion protein.

Nucleic acid cassettes can be cloned into any suitable vector for expression of a portion of or the entire influenza gene segment. According to methods detailed in the invention, the nucleic acid cassette is cloned into a vector allowing production of a portion of or the entire influenza gene segment fused to all or a portion of a viral coat protein (ie., creating a fusion protein) and displayed on the surface of a particle or cell. While several types of vectors are available, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

The expression vector also can have a secretory signal sequence fused to the DNA encoding each influenza gene segment or portion thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, gIIIss, pelBss, LamB or OmpF (Wong et al., Gene, 68:1931 (1983), MalE, PhoA and other genes. A preferred prokaryotic signal sequence for practicing this invention is the *E. coli* heat-stable enterotoxin II (STII) signal sequence and malE.

The vector also typically includes a promoter to drive expression of the fusion protein. Promoters most commonly used in prokaryotic vectors include the gIII promoter, lac Z promoter system, the alkaline phosphatase pho A promoter (Ap), the bacteriophage $\square_{PL}$ promoter (a temperature sensitive promoter), the tac promoter (a hybrid trp-lac promoter that is regulated by the lac repressor), the tryptophan promoter, and the bacteriophage T7 promoter. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (eg., GFP), or beta-galactosidase protein or glutathione S transferase which can be useful for detection or purification of the fusion protein expressed on the surface of the phage or cell. Nucleic acid sequences encoding, for example, a gD tag, also provide for positive or negative selection of cells or virus expressing the fusion protein. Nucleic acid sequences encoding, for example, a polyhistidine tag, are useful for identifying fusion proteins using immunohistochemistry.

Another useful component of the vectors used to practice this invention is phenotypic selection genes. Typical phenotypic selection genes are those encoding proteins that confer antibiotic resistance upon the host cell. By way of illustration, the ampicillin resistance gene (ampr), and the tetracycline resistance gene (tetr) are readily employed for this purpose.

The vector can also include nucleic acid sequences containing unique restriction sites and suppressible stop codons. The unique restriction sites are useful for moving influenza gene segments between different vectors and expression systems. The suppressible stop codons are useful to control the level of expression of the fusion protein and to facilitate purification of soluble influenza gene fragments. For example, an amber stop codon can be read as Gln in a supE host to enable phage display, while in a non-supE host it is read as a stop codon to produce soluble influenza gene fragments without fusion to phage coat proteins.

It is preferable to use vector systems that allow the nucleic acid encoding an influenza gene segment to be easily removed from the vector system and placed into another vector system. For example, appropriate restriction sites can be engineered in a vector system to facilitate the removal of the nucleic acid sequence encoding the influenza gene segment. The restriction sequences are usually chosen to be unique in the vectors to facilitate efficient excision and ligation into new vectors. Influenza gene segments can then be expressed from vectors without extraneous fusion sequences, such as viral coat proteins or other sequence tags.

Introduction of Vectors into Host Cells

Vectors constructed are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Selection (Sorting) and Screening for Binders to Targets of Choice

One approach involves constructing a family of variant replicable vectors containing a transcription regulatory element operably linked to a polynucleotide encoding a fusion polypeptide, transforming suitable host cells, culturing the transformed cells to form phage particles which display the fusion polypeptide on the surface of the phage particle, followed by a process that entails selection or sorting by contacting the recombinant phage particles with an antibody that specifically binds an influenza protein so that at least a portion of the population of particles bind to the antibody with the objective to increase and enrich the subsets of the particles which bind from particles relative to particles that do not bind in the process of selection. The selected pool can be amplified by infecting host cells, such as fresh TG1, K91 or XL1-Blue cells, for another round of sorting on the same antibody with different or same stringency.

In some embodiments, the resulting pool of variants are then screened against naïve or synthetic libraries of antibody fragment to identify novel high affinity antibodies. These novel high affinity antibodies can be useful as therapeutic agents as antagonists or agonists, and/or as diagonostic agents. For example, antibodies or antigen binding fragments can be screened for binding to an epitope on a H5N1 clade 1 HA protein and not to H5N1 clade 2 HA. For diagnostic purposes, such antibodies can be used to distinguish whether a subject is infected with clade 1 or clade 2. For therapeutic purposes, an antibody that binds to an epitope on several H5N1 influenza strains or that neutralizes the activity of HA or NA from several different clades would be selected.

Fusion polypeptides can be expressed on the surface of a phage, phagemid particle or a cell and then selected and/or screened for the ability of members of the group of fusion polypeptides to bind a target antibody. The processes of selection for binders to target can also be include sorting on a generic protein such as a tag specific antibody which binds to a tag that is fused to the influenza gene segment.

In some embodiments, a solid support method is employed, the target antibody or polypeptide may be attached to a suitable solid or semi solid matrix which are known in the art such as agarose beads, magnetic beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described in Methods in Enzymology, 44 (1976), or by other means known in the art.

After attachment of the target antibody or polypeptide to the matrix, the immobilized target is contacted with the library expressing the fusion polypeptides under conditions suitable for binding of at least a subset of the phage particle population with the immobilized target antibody or influenza polypeptide frgaments. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the excess target molecule, altering pH and/or ionic strength, and methods known in the art. Selection of binders typically involves elution from an affinity matrix with a suitable elution material such as acid like 0.1M HCl or excess target molecule. Elution with increasing concentrations of target molecule could elute displayed binding molecules of increasing affinity.

The binders can be isolated and then re-amplified in suitable host cells by infecting the cells with the viral particles that are binders (and helper phage if necessary, e.g. when viral particle is a phagemid particle) and the host cells are cultured under conditions suitable for amplification of the particles that display the desired fusion polypeptide. The phage particles are then collected and the selection process is repeated one or more times until binders of the target antibody or polypeptide are enriched. Any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine.

After binders are identified by binding to the target antibody or polypeptide, the insert sequence is identified using, PCR with suitable primers, and sequenced by typical sequencing method. DNA of the binders can be restriction enzyme digested and then inserted into a vector for protein expression.

Figure 4:
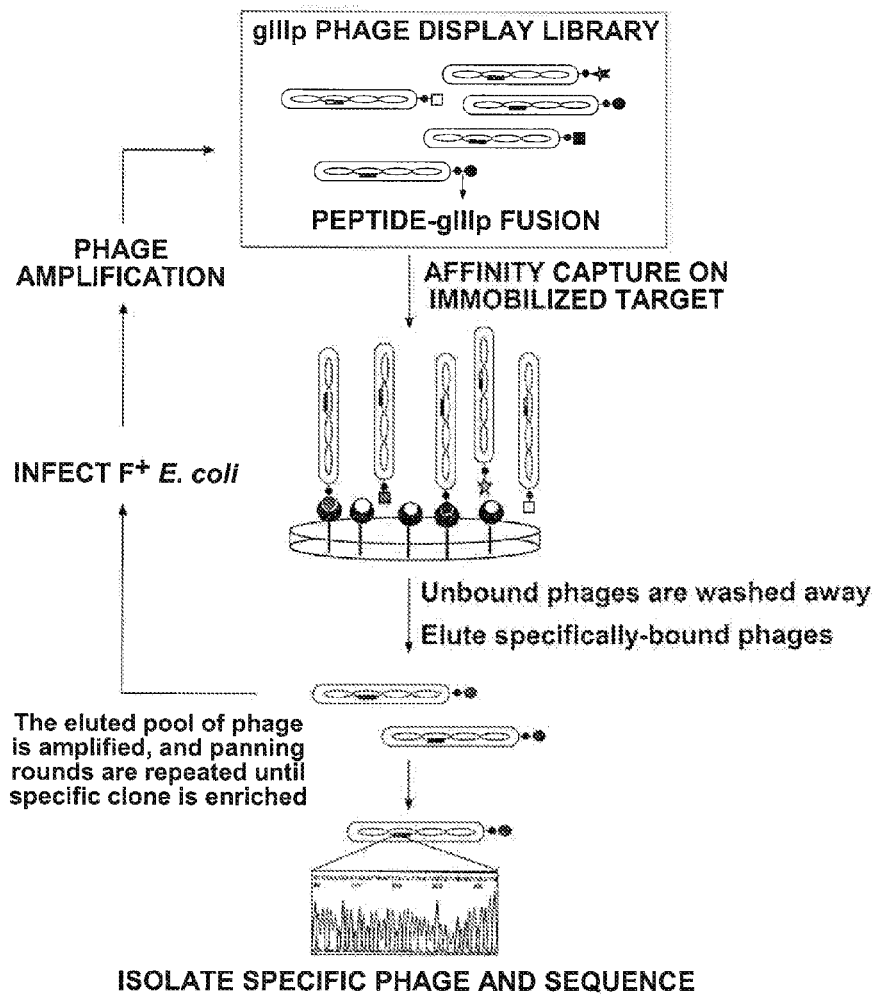
FIG. 4 illustrates a flow diagram for affinity panning the phage display library (specifically-bound phage sequence=SEQ ID NO:177).

Genome of influenza phage display libraries are constructed by isolating cDNAs from each influenza gene segment and partially digesting the cDNAs with DNase. Fragments of 50 to 200 base pairs or 200 to 1000 base pairs are isolated and cloned into a vector containing a nucleic acid encoding a phage coat protein. An exemplary scheme is shown in FIG. 1. Vectors containing all or portions of influenza gene segments are selected by affinity selection using desired ligand including, without limitation, monoclonal antibodies whether neutralizing or not, vaccinated animal or human sera, post-infection sera. After multiple rounds of affinity selection, clones containing influenza gene fragment inserts are sequenced and may be further selected using post infection and/or post vaccination sera. In some embodiments, the library comprises at least the polynucleotides encoding the sequence of SEQ ID NO:1-31, SEQ ID NO:32-123, or SEQ ID NO:148-176. An exemplary process is shown in FIG. 4. In embodiments, the libraries contain at least two different sequences from an influenza gene segment and more preferably, at least 3, 4, 5, or any integer up to 100 different sequences from each gene segment.

Epitope Mapping Using Whole Genome Phage Display Libraries

Preparation for pandemic influenza threats requires improved cross-reactivity and long-term protection of interpandemic influenza vaccines, the immunogenic peptides provided here can elicit antibody responses based on binding to monoclonal antibodies, sera from vaccinated, infected individuals or convalescent individuals, demonstrating broad cross-protection against interpandemic (seasonal) and pandemic influenza strains. In case of mass vaccination, it would be preferable to rapidly distinguish between exposures to human influenza versus avian influenza, especially in the seasonal influenza vaccinated populations.

A high throughput approach based on the construction of whole viral genome phage display libraries as described herein can identify peptides and polypeptides that specifically bind to antibodies from a subject post infection and/or post vaccination. Separate libraries were created for each influenza strain to express complete sets of protein fragments encoded by human and avian influenza strains H1N1, H3N2, H5N1 and H7N7 or other strains and the peptides are identified by binding of phage clones to the antibodies followed by elution, amplification, and sequencing. The polypeptides encoded by the portions of the influenza gene segments that are selected by binding to the antibodies are identified by sequencing.

Using these libraries, peptides are identified that bind to antibodies that provide broad heterotypic neutralizing activity as well as a set of epitopes that are important for serodiagnosis as well as differential diagnosis. The genome flu phage display libraries are incubated with serum samples from a subject vaccinated or infected with an influenza virus of a certain subtype, for example, H3N2 or H5N1 or different clades of H5N1. Using serum samples that are obtained from individuals infected with different strains of influenza with libraries obtained with different subtypes of influenza provides identification of unique as well as shared or overlapping epitopes between different subtypes or clades.

In some embodiments, the epitope mapping includes further mapping using a random dodecamer phage display library and binding to the same antibody or antibodies.

In some embodiments, the peptides listed in the Table 4 and Table 5 below identify highly conserved protective epitopes that are useful in broadly-reactive influenza vaccines. The peptides can be used to generate neutralizing antibodies both in vitro or in vivo that can be used for passive therapy. These peptides would be also useful in studies of viral protein-protein, viral RNA-protein and viral-host protein interactions. The peptides are further applicable to new serological assays for surveillance of pandemic influenza outbreaks. The peptides are further applicable to new serological assays to distinguish between exposure to human and bird influenza strains.

The peptides further provide the means to diagnose true influenza infections in previously vaccinated individuals, rapid analyses of immune sera from pre-clinical and clinical trials of novel influenza vaccines and the ability to map monoclonal and polyclonal antibodies against different influenza gene products.

Polypeptides and Compositions

One aspect of the disclosure provides compositions and methods for priming or enhancing the immune response of an animal to influenza A antigens. The present disclosure provides at least one polypeptide that binds to an antibody from a subject infected with and/or vaccinated with an influenza A virus or subunit thereof and compositions comprising an effective amount of the polypeptide. In some embodiments, an effective amount of the polypeptide is an amount that is effective for treatment of influenza infection. In some embodiments, effectiveness for treatment is determined by a decrease in viral load or a decrease in symptoms. In other embodiments, the effective amount of the polypeptide is effective for inhibition of influenza virus fusion with, or entry into, mammalian cells. In that case, effectiveness of inhibition can be measured by the ability of the peptide to elicit, bind, or stimulate neutralizing antibodies or to elicit or bind hemagglutinin inhibiting antibodies. In yet other embodiments, the effective amount of the polypeptide is effective for eliciting an immune response in a subject.

In embodiments, the disclosure includes one or more isolated and purified influenza polypeptides that specifically bind to an antibody from a subject infected and/or vaccinated with influenza virus selected from the group consisting of: a) hemagglutinin (HA), b) neuraminidase (NA), c) basic polymerase B2 (PB2), d) basic polymerase B1 (PB1), e) basic polymerase frame 2 PB1-F2 (PB1-F2), f) acidic polymerase PA, g) nucleoprotein (NP), h) matrix protein 1 (M1), i) matrix protein 2 (M2), j) non-structural protein 1 (NS1), k) non-structural protein 2 (NS2), and fragments thereof. In some embodiments the polypeptides exclude the corresponding full length native polypeptides. In some embodiments, the influenza virus is selected from the group consisting of H5N1, H3N2, H1N1, and H7N7.

In embodiments, a polypeptide corresponds to the corresponding H5N1 polypeptide having a sequence as represented by the sequence in the proteome as shown in FIG. 14. For example, the sequence of the proteome provides a reference sequence for each one of the expressed H5N1 polypeptides. This reference sequence provides for amino acid numbering of H5N1 sequences and to determine amino acid numbering of a corresponding H5N1 sequence. Many examples of H5N1 sequences are known and alignments of these sequences for a polypeptide can readily be obtained as shown in Table 6 (alignments of H5N1 HA sequences) and Table 7 (alignments of H5N1 NA sequences). The sequences as are obtained from publicly available data bases such as the influenza virus database at the NCBI and can be aligned with the reference sequence in order to identify a polypeptide corresponding to that of the reference sequence.

In embodiments, a polypeptide corresponds to the corresponding H3N2 polypeptide having a sequence as represented by the sequence in the proteome as shown in FIG. 15. For example, the sequence of the proteome provides a reference sequence for each one of the expressed H3N2 polypeptides. This reference sequence provides for amino acid numbering of H3N2 sequences and to determine amino acid numbering of a corresponding H3N2 sequence. Many examples of H3N2 sequences are known and alignments of these sequences for a polypeptide can readily be obtained from publicly available data bases such as the influenza virus database at the NCBI and can be aligned with the reference sequence in order to identify a polypeptide corresponding to that of the reference sequence.

Any of the polypeptides from a strain isolated from nature can be utilized in the compositions described herein, and these polypeptides are referred to as naturally occurring, The amino acid sequences that correspond to the polypeptides that are identified by binding to an antibody from a subject infected or vaccinated with influenza can be determined by aligning the sequence to the reference sequence.

In other embodiments, the corresponding polypeptides may be variants of a reference influenza polypeptide. A variant may have substantial identity to the reference sequence. The term "substantial identity" means that a polypeptide comprises a sequence that has at least 55% to 100% identity or any integer included within the range. In embodiments, the polypeptide has at least, 60%, 65%, 70%, 75%, 80%, or 85% sequence identity, preferably 90%, more preferably 95% or more, compared to the reference sequence of the polypeptides as shown in FIG. 14 or FIG. 15. Another indication that polypeptide sequences are substantially identical is if one peptide is immunologically reactive with antibodies raised against the disclosed peptide. Thus, the peptides of the disclosure include peptides immunologically reactive with antibodies raised against the disclosed immunogenic peptides. In some embodiments, it may be desirable to align the variant with the reference sequence and retain the amino acid sequence that binds to an antibody from a subject infected and/or vaccinated with an influenza virus. In some embodiments, conservative substitutions may be made without affecting the ability of the polypeptide to bind to such antibodies. In a specific embodiment, a variant polypeptide preferably has 90% sequence identity to the reference polypeptide.

Guidance in determining which amino acid residue may be inserted, substituted or deleted without adversely affecting the desired activity may be found by comparing the sequence of the polypeptide with that of homologous known protein molecules and minimizing the number of amino acid sequence changes made in regions of high homology. In addition, the crystal structure of many of the influenza virus proteins are known and can be accessed at the Protein Data Bank. Modeling of the effect of any amino acids changes on the structure can be determined by using available computer programs.

Functional domains can also be identified in those polypeptides that have homology to known polypeptides. For example, certain positions in the polypeptide show more variability than others. These positions can be identified using sequence alignments and changes made to those amino acid positions showing high variability (e.g. 3 or more different amino acids in that position when a number of sequences are aligned). For example, when full length HA proteins are aligned from several different isolates or strains, amino acid positions corresponding to positions 55, 102, 103, 105, 113, 144, 150 and 162 have variant amino acids as shown in the alignment in Table 6.

The sequences of these functional domains can be compared and aligned to other known sequences that may be provided at the Los Alamos website or GenBank, and locations of amino acid positions for substitutions can be identified as those positions that show a high degree of variability in amino acids, i.e., at least 3 different amino acids are found at that position when different sequences are aligned and compared or have a lower percentage of sequence identity i.e., less than 90% sequence identity. When sequences are aligned, the positions that show variability can either have conservative amino acid substitutions or non-conservative amino acid substitutions. If the position has conservative amino acid substitutions, that would indicate that the amino acid substituted at that position should be of the same type as those observed to be at that position in naturally occurring proteins. In some embodiments, amino acid sequences identified to be associated with virulence can be modified or deleted, such as the HA basic residues PQGERRRKKR/GL (SEQ ID NO:183).

In some embodiments, it may be desirable to exclude variants of the full length sequence. For example, variants of full length sequences can be made using reverse genetic engineering as described in Wood et al, Nat Rev. Microbiology 2:842 (2004). In this case, a naturally occurring sequence can be altered to change the virulence of the encoded protein, such as a modified H5N1 HA lacking or mutated PQGERRRKKR/GL (SEQ ID NO:183) residues. In embodiments, it is preferred that the variants of full length sequences are changed not more than 10%, that is the variants excluded have at least 90% sequence identity to the corresponding polypeptide.

In some embodiments, the H5N1 HA polypeptide corresponds to a H5N1 HA polypeptide having a sequence of amino acids 2335-2902 of FIG. 14 (SEQ ID NO:129) and comprises the amino acid sequence corresponding to the polypeptide starting at any one of amino acids 2339 to 2365 and ending at any one of amino acids 2581 to 2685 of FIG. 14 or a fragment thereof, wherein the polypeptide does not include the corresponding full length H5N1 HA. In a specific embodiment, the isolated and purified HA polypeptide is selected from the group consisting of a polypeptide comprising amino acids 2440 to 2484 of FIG. 14 excluding the corresponding full length sequence of amino acids 2335-2902 of FIG. 14 (SEQ ID NO:129), a polypeptide comprising amino acid 2390 to amino acid 2624 of FIG. 14 excluding the full length sequence of amino acids 2335-2902 of FIG. 14 (SEQ ID NO:129), SEQ ID NO:32, SEQ ID NO:54; SEQ ID NO:55, SEQ ID NO:56, SEQ ID NO:57, SEQ ID NO:58, SEQ ID NO:59, SEQ ID NO:60, SEQ ID NO:61, SEQ ID NO:62, amino acids 2627 to 2669 of FIG. 14, amino acids 2642 to 2685 of FIG. 14, and combinations thereof.

In a specific embodiment, the isolated and purified HA polypeptide is selected from the group consisting of a polypeptide comprising amino acids 2672 to 2902 of FIG. 14 excluding the sequence of amino acids 2335-2902 of FIG. 14 (SEQ ID NO:129), SEQ ID NO:63, SEQ ID NO:64; SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, and combinations thereof.

In some embodiments, the isolated and purified polypeptide corresponds to a H5N1 NA polypeptide having the sequence of amino acids 3410 to 3855 of FIG. 14 (SEQ ID NO:131) and comprises the amino acid sequence corresponding to the polypeptide having the sequence of amino acids 3431 to 3855 of FIG. 14 or a fragment thereof, wherein the polypeptide does not include the corresponding full length H5N1 NA. In specific embodiments, the isolated, and purified polypeptide is selected from the group consisting of a polypeptide comprising amino acids 3477 to 3803 of FIG. 14 excluding the polypeptide having a sequence of 3410 to 3855 of FIG. 14 (SEQ ID NO:131), a polypeptide comprising amino acid 3807 to amino acid 3832 of FIG. 14 excluding the polypeptide having the sequence of 3410 to 3855 of FIG. 14 (SEQ ID NO:131), SEQ ID NO:84, SEQ ID NO:85, SEQ ID NO:86, SEQ ID NO:87, SEQ ID NO:88, SEQ ID NO:89, SEQ ID NO:90, amino acids 3638 to 3662 of FIG. 14, SEQ ID NO:91, SEQ ID NO:92, SEQ ID NO:93, SEQ ID NO:94, SEQ ID NO:95, SEQ ID NO:96 and combinations thereof.

In some embodiments, the isolated and purified polypeptide corresponds to a H5N1 PB2 polypeptide having the sequence of amino acids 1 to 760 of FIG. 14 (SEQ ID NO:125) and comprises the amino acid sequence corresponding to the polypeptide having the sequence of amino acids 344 to 516 of FIG. 14 or a fragment thereof, wherein the polypeptide does not include the corresponding full length H5N1 PB2. In specific embodiments, the isolated and purified polypeptide is selected from the group consisting of a polypeptide comprising the amino acid sequence of SEQ ID NO:42 or SEQ ID NO:43 and combinations thereof.

In some embodiments, the isolated and purified polypeptide corresponds to a H5N1 PB1 polypeptide having the sequence of amino acids 764 to 1612 of FIG. 14 (SEQ ID NO:126) and comprises the amino acid sequence corresponding to the polypeptide having the sequence of amino acids 1290 to 1437 of FIG. 14 or a fragment thereof, wherein the polypeptide does not include the corresponding full length H5N1 PB1. In specific embodiments, the isolated and purified polypeptide is selected from the group consisting of a polypeptide comprising the amino acid sequence of SEQ ID NO:44, SEQ ID NO:45, SEQ ID NO:46 and combinations thereof.

In some embodiments, the isolated and purified polypeptide corresponds to a H5N1 PB1-F2 polypeptide having the sequence of amino acids 1524 to 1612 of FIG. 14 (SEQ ID NO:127) and comprises the amino acid sequence corresponding to the polypeptide having the sequence of amino acids 1524 to 1608 of FIG. 14 or a fragment thereof, wherein the polypeptide does not include the corresponding full length H5N1 PB1-F2. In specific embodiments, the isolated and purified polypeptide is selected from the group consisting of a polypeptide comprising the amino acid sequence of SEQ ID NO:47, SEQ ID NO:48, SEQ ID NO:49, SEQ ID NO:50, SEQ ID NO:51 and combinations thereof.

In some embodiments, the isolated and purified polypeptide corresponds to a H5N1 PA polypeptide having the sequence of amino acids 1616 to 2331 of FIG. 14 (SEQ ID NO:128) and comprises the amino acid sequence corresponding to the polypeptide having the sequence of amino acids 1852 to 2251 of FIG. 14 or a fragment thereof, wherein the polypeptide does not include the corresponding full length H5N1 PA. In a specific embodiment, the isolated and purified polypeptide is selected from the group consisting of a polypeptide comprising the amino acid sequence of SEQ ID NO:52, SEQ ID NO:53 and combinations thereof.

In some embodiments, the isolated and purified polypeptide corresponds to a H5N1 NP polypeptide having the sequence of amino acids 2906 to 3403 of FIG. 14 (SEQ ID NO:130) and comprises the amino acid sequence corresponding to the polypeptide having the sequence of amino acids 2906 to 3068 or amino acids 3197 to 3399 of FIG. 14 or a fragment thereof, wherein the polypeptide does not include the corresponding full length H5N1 NP. In specific embodiments, the isolated and purified polypeptide is selected from the group consisting of a polypeptide comprising the amino acid sequence of SEQ ID NO:75, SEQ ID NO:76, SEQ ID NO:77, SEQ ID NO:78, SEQ ID NO:79, SEQ ID.NO:80, SEQ ID NO:81, SEQ ID NO:82, SEQ ID NO:83, amino acids 3347 to 3385 of FIG. 14 and combinations thereof.

In some embodiments, the isolated and purified polypeptide corresponds to a H5N1 M1 polypeptide having the sequence of amino acids 3859 to 4110 of FIG. 14 (SEQ ID NO:132) and comprises the amino acid sequence corresponding to the polypeptide having the sequence of amino acids 3859 to 4109 of FIG. 14 or a fragment thereof, wherein the polypeptide does not include the corresponding full length H5N1 M1. In specific embodiments, the isolated and purified polypeptide is selected from the group consisting of a polypeptide comprising the amino acid sequence of SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105 and combinations thereof.

In some embodiments, the isolated and purified polypeptide corresponds to a H5N1 M2 polypeptide having the sequence of amino acids 4114 to 4210 of FIG. 14 (SEQ ID NO:133) and comprises the amino acid sequence corresponding to the polypeptide having the sequence of amino acids 4115 to 4209 of FIG. 14 or a fragment thereof, wherein the polypeptide does not include the corresponding full length H5N1 M2. In a specific embodiment, the isolated and purified M2 polypeptide has the amino acid sequence of SEQ ID NO:107.

In some embodiments, the isolated and purified polypeptide corresponds to a H5N1 NS1 polypeptide having the sequence of amino acids 4214 to 4428 of FIG. 14 (SEQ ID NO:134) and comprises the amino acid sequence corresponding to the polypeptide having the sequence of amino acids 4220 to 4294 or amino acids 4378 to 4428 of FIG. 14 or a fragment thereof, wherein the polypeptide does not include the corresponding full length H5N1 NS1. In specific embodiments, the isolated and purified polypeptide is selected from the group consisting of a polypeptide comprising the amino acid sequence of SEQ ID NO:108, SEQ ID NO:109, SEQ ID NO:110, SEQ ID NO:111, SEQ ID NO:112 and combinations thereof.

In some embodiments, the isolated and purified polypeptide corresponds to a H5N1 NS2 polypeptide having the sequence of amino acids 4432 to 4552 of FIG. 14 (SEQ ID NO:135) and comprises the amino acid sequence corresponding to the polypeptide having the sequence of amino acids 4468 to 4509 of FIG. 14 (SEQ ID NO:113) or a fragment thereof, wherein the polypeptide does not include the corresponding full length H5N1 NS2.

Other embodiments include any of the H3N2 polypeptides as shown in Table 5, excluding the corresponding full length H3N2 polypeptide. The polypeptides include polypeptides comprising any one of sequences having SEQ ID NO: 1 to 31.

Polypeptides can be Obtained by Recombinant Methods or by Amino Acid Synthesis.

Fusion Polypeptides

As described previously any of these polypeptides can form a fusion polypeptide. A fusion polypeptide can include all or a portion of a viral coat protein. Examples of viral coat proteins include infectivity protein pIII, major coat protein pVIII, p3, Soc (T4), Hoc (T4), gpD (of bacteriophage lambda), minor bacteriophage coat protein 6 (pVI) (filamentous phage; J Immunol Methods. 1999 Dec. 10; 231(1-2):39-51), variants of the M13 bacteriophage major coat protein (P8) (Protein Sci 2000 April; 9(4):647-54). Heterologous sequences encoding gD tags, c-Myc epitopes, poly-histidine tags, fluorescence proteins (eg., GFP), or beta-galactosidase protein or glutathione S transferase which can be useful for detection or purification of the fusion protein expressed on the surface of the phage or cell can be present. In other embodiments, any of the polypeptide identified herein can be combined with a carrier protein such as selected from the group consisting of bovine serum albumin, keyhole limpet hemacyanin, ovalbumin, mouse serum albumin, rabbit serum albumin.

In addition, the polypeptides as described herein can be inserted into the corresponding influenza virus but of a different subtype. For example, a polypeptide comprising the amino acid sequence of amino acids 9-241 of H5N1 HA can be inserted in the place of corresponding residues in H3N2 HA. The insertion can be done by cassette mutagenesis or by mutating one or more of the residues of H3N2 HA to the sequence of the H5N1 HA fragment.

Compositions

One or more of the polypeptides identified by epitope mapping as described herein can be combined in a composition and used to immunize a mammal. Examples of other influenza components include hemagglutinin (HA), neuraminidase (NA), and immunogenic fragments thereof. Examples of conserved influenza components include matrix protein 1 (M1), nucleoprotein (NP), acidic polymerase (PA), basic polymerase 1 (PB1), basic polymerase 2 (PB2), nonstructural protein 1 (NS1), nonstructural protein 2 (NS2), and immunogenic fragments thereof. In some embodiments, the same polynucleotide encoding one or more HA polypeptides does not encode a nucleoprotein or M1 protein either as individual proteins or as fusions to HA. In other embodiments, the same polynucleotide does not encode matrix protein 1 (M1), nucleoprotein (NP) acidic polymerase (PA), basic polymerase 1 (PB1), basic polymerase 2 (PB2), nonstructural protein 1 (NS 1), or nonstructural protein 2 (NS2). Influenza amino acid and nucleic acid sequences for these variable and conserved influenza components are known in the art and can be found, for example, using GenBank (www-ncbi-nlm-gov) or the Influenza Sequence Database at the Los Alamos website (http://www-flu-lanl-gov).

In some embodiments, the immunogenic compositions of the disclosure can be combined with other influenza vaccines, such as heat killed or subunit vaccines or can be combined with other components of different subtypes using reverse engineering and reassortment.

Compositions can include one or more or a combination of any of the polypeptide described herein, including any of the polypeptides in Tables 4 and Table 5. In some embodiments, the polypeptides are selected that are identified at a frequency in the phage display library of at least 5 clones following affinity selection. In other embodiments, polypeptides are selected that bind to neutralizing antibodies or hemagglutinin inhibiting antibodies. In yet other embodiments, peptides are selected that bind to an antibody in a biological sample with a titer of at least 500 or at least 5 fold increased over control biological sample.

In some embodiments, compositions of the disclosure may consist essentially of one or more of the polypeptides. The compositions that consist essentially include ingredients that do not affect the binding and/or immunogenic properties of the polypeptides such as carriers, excipients, adjuvants, and may exclude the full length corresponding polypeptide.

In some embodiments, the immunogenic compositions of the invention comprise an immunogenic effective amount of the polypeptides as described herein. The immunogenic compositions are useful to provide a protective immune response as well as to provide for monoclonal and/or humanized antibodies for therapeutic purposes.

Compositions may include a carrier, excipient or adjuvant. Adjuvants include, for example, aluminum hydroxide, lipid A, killed bacteria, polysaccharide, mineral oil, Freund's incomplete adjuvant, Freund's complete adjuvant, aluminum phosphate, iron, zinc, a calcium salt, acylated tyrosine, an acylated sugar, a CpG oligonucleotide, a cationically derivatized polysaccharide, an anionically derivatized polysaccharide, a polyphosphazine, a biodegradable microsphere, a monophosphoryl lipid A, MF59, oil in water emulsions AS03 and AS04, ISCOM, and quil A.

Polynucleotides and Vectors

The disclosure also include polynucleotides including one or more of the polypeptides identified herein by epitope mapping. The polynucleotides may be present in a phage vector as a part of a library useful for epitope mapping of immune responses or in a vector useful for immunizing an animal. Phage display vectors have been described previously herein. Polynucleotide sequences encoding any of the polypeptides as described herein can be readily obtained using publicly available databases. Polynucleotide sequence can be prepared using recombinant or synthetic methods.

In some embodiments, one or more polynucleotides is present in a composition in an immunogenic effective amount. In specific embodiments, the polynucleotides encode one or more of the polypeptides as described herein, for example, any one of the polypeptides having a sequence of SEQ ID NO:1-123 or SEQ ID NO:148 to 176. An immunogenic effective amount is an amount of polynucleotide that induces an immune response to the encoded polypeptide when administered to a host, for example an animal. In an embodiment, the polynucleotides are incorporated into host cells in vivo and an immunogenic effective amount of the encoded influenza A polypeptide or fragment thereof is produced in vivo. The actual amount of the immunogenic composition may vary depending on the animal to be immunized, the route of administration and adjuvants. Immunogenic dosages can be determined by those of skill in the art. The immune response can be humoral, cellular, or both. Generally, the immune response inhibits the influenza viral levels in the immunized host compared to influenza viral levels in non-immunized hosts.

An embodiment provides an immunogenic composition according to the present disclosure also including both polypeptides and/or polynucleotides encoding polypeptides as described herein.

The immunogenic composition optionally includes a pharmaceutically acceptable excipient or carrier. The immunogenic composition may further comprise immunomodulators such as cytokines or chemokines. In some embodiments, a nucleic acid encodes the immunomodulator or adjuvant. Immunomodulators refers to substances that potentiate an immune response including, but not limited to cytokines and chemokines. Examples of cytokines include but are not limited to IL-2, IL-15, IL-12, or GM-CSF.

An embodiment provides an immunogenic composition further comprising an adjuvant. Such adjuvants may include ganglioside receptor-binding toxins (cholera toxin, LT enterotoxin, their B subunits and mutants); surface immunoglobulin binding complex CTA1-DD; TLR4 binding lipopolysaccharide; TLR2-binding muramyl dipeptide; mannose receptor-binding mannan; dectin-1-binding ss 1,3/1,6 glucans; TLR9-binding CpG-oligodeoxynucleotides; cytokines and chemokines; antigen-presenting cell targeting ISCOMATRIX and ISCOM. Adjuvants such as lipids (fatty acids, phospholipids, Freund's incomplete adjuvant in particular), Vaxfectin, M59, polaxomer, anionic copolymers, CpG units, etc. may be added to the composition. In addition, adjuvants able to prime the mucosal immune system following a systemic immunization, include 25(OH)2D3, cholera toxin, CTA1-DD alone or in combination with ISCOM, AS03, and AS04. In some embodiments, the adjuvant may be encoded or expressed by the expression vector used herein.

An embodiment provides an immunogenic composition comprising at least one naked DNA or a naked RNA encoding at least one polypeptide according to the disclosure. Naked DNA or RNA is DNA or RNA that does not have proteins or lipids associated with it.

In certain embodiments, the immunogenic composition comprises at least one recombinant vector or DNA comprising a nucleic acid sequence encoding any of the polypeptides described herein such as those shown in Tables 4 and 5. Examples of vectors include, but are not limited to, recombinant viral vectors, such as poxvirus, vaccinia virus, lenti virus, or adenovirus, and plasmids. Typically a plasmid contains an origin of replication that is functional in bacterial host cells, e.g., *Escherichia coli*, and selectable markers for detecting bacterial host cells containing the plasmid. Plasmids of the present invention may include genetic elements as described herein arranged such that an inserted coding sequence can be transcribed and translated in eukaryotic cells. In certain embodiments described herein, a plasmid is a closed circular DNA molecule.

Examples of plasmids that can be used in the present invention include expression vector VR1012 or VR10551 (Vical, San Diego, Calif.). These vectors are built on a modified pUC18 background (see Yanisch et al., 1985, Gene, 33:103-119), and contain a kanamycin resistance gene, the human cytomegalovirus immediate early promoter/enhancer and intron A, and the bovine growth hormone transcription termination signal, and a polylinker for inserting foreign genes (see Hartikka et al., 1996, Hum. Gene Ther., 7:1205-1217). Other commercially available eukaryotic expression vectors can be used in the present invention, including, but not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, pVAX200, and pZeoSV2 (Invitrogen, San Diego, Calif.), plasmid pCI (Promega, Madison, Wis.) and plasmid pDNA-VACC (Nature Tech. Corp., Lincoln, Neb.).

In an embodiment, the immunogenic composition includes a plasmid that comprises a nucleic acid sequence encoding at least one polypeptide or immunogenic fragment thereof from an influenza A virus under the transcriptional control of a promoter region active in a variety of cells. In an embodiment, the promoter region is a human cytomegalovirus (CMV) promoter. In an embodiment, the plasmid is pVR1012. The polypeptides can be naturally occurring, variant, or an immunogenic fragment thereof. To permit selection of plasmid-containing bacteria during the production process, the plasmid may also contain an antibiotic resistance gene with a bacterial origin of replication. DNA is generally less costly to produce than peptide or protein, and is chemically stable under a variety of conditions. DNA is generally administered intramuscularly, using either a needle and syringe or a needle-free injector, or intranasally.

The polypeptide, or fragment thereof, may be expressed in a modified form, such as a fusion protein, and may include secretion signals and/or additional heterologous functional regions. For example, a region of additional amino acids may be added to the N-terminus or C-terminus of the polypeptide to facilitate detection or purification, improve immunogenicity, improve half-life, or improve persistence in the host cell during, for example, purification or subsequent handling and storage. Examples of additional amino acids include peptide tags that may be added to the polypeptide to facilitate detection and/or purification. Such peptide tags include, but are not limited to, His, HA, Avi, biotin, c-Myc, VSV-G, HSV, V5, or FLAG™. Examples of a polypeptide that can enhance immunogenicity include bovine serum albumin, and/or keyhole lymphocyte hemocyanin (KLH). Examples of molecules that improve half-life include polyethylene glycol.

The immunogenic compositions comprising polypeptides and/or polynucleotides of the disclosure can also include a carrier. Carriers include pharmaceutically acceptable carriers, excipients, or stabilizers which are nontoxic to the cell or animal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONIC™.

The immunogenic compositions comprising polypeptides and/or polynucleotides of the disclosure can be in the form of sterile injectable preparations, such as sterile injectable aqueous or oleagenous suspensions. For administration as injectable solutions or suspensions, the immunogenic compositions can be formulated according to techniques well-known in the art, using suitable dispersing or wetting and suspending agents, such as sterile oils, including synthetic mono- or diglycerides, and fatty acids, including oleic acid.

Method of Making Polypeptides and/or Polynucleotides

Polynucleotides encoding influenza polypeptides, recombinant vectors, and host cells containing the recombinant vectors, as well as methods of making such vectors and host cells by recombinant methods are useful to produce the polypeptides as described herein for use in assays or immunogenic compositions.

The polynucleotides of the disclosure may be synthesized or prepared by techniques well known in the art. See, for example, Creighton, Proteins: Structures and Molecular Principles, W. H. Freeman & Co., New York, N.Y. (1983). Nucleotide sequences encoding the influenza polypeptides of the disclosure may be synthesized, and/or cloned, and expressed according to techniques well known to those of ordinary skill in the art. See, for example, Sambrook, et al., Molecular Cloning, A Laboratory Manual, Vols. 1-3, Cold Spring Harbor Press, Cold Spring Harbor, N.Y. (1989). In some embodiments, the polynucleotide sequences will be codon optimized for a particular recipient using standard methodologies. For example, the DNA construct encoding a H5N1 HA polypeptide can be codon optimized for expression in humans.

The polynucleotides may be produced by standard recombinant methods known in the art, such as polymerase chain reaction (PCR) or reverse transcriptase PCR (Sambrook, et al., 1989, Molecular Cloning, A Laboratory Manual, Vols. 1-3, Cold Spring Harbor Press, Cold Spring Harbor, N.Y.), reverse engineering, or the DNA can be synthesized and optimized for expression in bacteria or eukaryotic cells. Primers can be prepared using the polynucleotide sequences that are available in publicly available databases. The polynucleotide constructs may be assembled from polymerase chain reaction cassettes sequentially cloned into a vector containing a selectable marker for propagation in a host. Such markers include but are not limited to dihydrofolate reductase or neomycin resistance for eukaryotic cell culture and tetracycline, ampicillin, or kanamycin resistance genes for culturing in *E. coli* and other bacteria.

Representative examples of appropriate hosts include, but are not limited to, bacterial cells such as *E. coli, Streptomyces* and *Salmonella typherium*, fungal cells such as yeast; insect cells such as *Drosophilia* S2 and *Spodoptera* Sf9, animal cells such as CHO, COS, and Bowes melanoma cells, and plant cells. Appropriate culture medium and conditions for the above-described host cells are known in the art.

Introduction of the recombinant vector into the host cell can be effected by injection, by mucosal administration such as by the intranasal route, or by calcium phosphate transfection, DEAE-dextran mediated transfection, cationic lipid-mediated transfection, electroporation, transduction, infection, or other methods. Such methods are described in standard laboratory manuals such as Sambrook, et al., 1989, Molecular Cloning, A Laboratory Manual, Vols. 1-3, Cold Spring Harbor Press, Cold Spring Harbor, N.Y. or Davis et al., 1986, Basic Methods in Molecular Biology. Commercial transfection reagents, such as Lipofectamine (Invitrogen, Carlsbad, Calif.), Effectene (Qiagen, Valencia, Calif.) and FuGENE 6™ (Roche Diagnostics, Indianapolis, Ind.), are also available.

The influenza polypeptide can be recovered and purified from recombinant cell cultures by methods known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography.

Naturally occurring polynucleotides encoding influenza virus polypeptides can be isolated from cloning out viral isolates from infected individuals at various times post infection. Such polynucleotides can be obtained using primers for amplifying polynucleotide encoding a polyeptdie such a showin in Table 5 Such polynucleotides or polypeptides may be utilized in the immunogenic compositions described herein.

The disclosure also includes variants of nucleic acid molecules encoding the polypeptides as described herein. In some embodiments, the disclosure includes polynucleotides having at least about 70% sequence identity, more preferably about 75% sequence identity, more preferably about 80% sequence identity, more preferably about 85% sequence identity, more preferably about 90% sequence identity, more preferably about 95% sequence identity, and even up to 100% sequence identity to a polynucleotide sequence encoding a polypeptide having an amino acid sequence as shown in the reference sequence of FIG. 14 or FIG. 15. Preferably, the variants generate antibodies that cross react with the corresponding polypeptide from different strains of the same subtype and/or provide protective immunity.

Animal Models

A variety of animal models are available for testing of any of the immunogenic compositions described herein. For example, well-established models include mice, poultry, ferrets, pigs, guinea pigs, or non-human primates. An animal model that provides for an immune response and has a response to challenge with infectious virus is suitable for testing of the immunogenic compositions.

Mouse models systems are available and in some embodiments, include challenge with mouse adapted influenza strains. The mouse model system includes immunizing the mice with an polypeptide or fragment thereof and/or a polynucleotide encoding an polypeptide or fragment thereof. After the mice are immunized, the mice are challenged with an influenza virus strain and evidence of infection can be determined by viral titers in tissues including the respiratory tract or in the case of systemic infection, other tissues as well, and/or by weight loss and/or death. Suitable mice include BALB/c mice, as well as any of the commercially available mice such as knockout mice and mice that have a human immune system.

Another model system for influenza infection is ferrets. Ferrets are naturally susceptible to infection with human influenza viruses, as well as avian, equine, and swine influenza viruses. Influenza virus infection in ferrets can be detected by detecting viral titers, and/or weight loss, fever, and respiratory symptoms such as nasal discharge. Other symptoms may be detected in ferrets having a systemic infection including neurological symptoms, diarrhea, and lethargy.

Uses and Methods

The present disclosure is also directed to uses and methods for immunizing an animal, including a human, other mammal, or bird, with the immunogenic compositions of the invention to inhibit, control, or prevent influenza infection.

In an embodiment, the method comprises administering to an animal an immunogenic effective amount of an immunogenic composition. An immunogenic effective amount is an amount of polynucleotide and/or polypeptide that induces an immune response to the encoded polypeptide when administered to a host, for example an animal. In an embodiment, the animal is a human, pig, horse, birds including domestic birds, or other animals, especially those used in animal models such as mouse, rat, ferret, or non-human primate. In an embodiment, the polynucleotides are incorporated into host cells in vivo and an immunogenic effective amount of the encoded polypeptide or fragment thereof is produced in vivo. The actual amount of the immunogenic composition may vary depending on the animal to be immunized, the route of administration and adjuvants.

Immunogenic dosages can be determined by those of skill in the art. The immune response may be indicated by T and/or B cell responses. Typically, the immune response is detected by the presence of antibodies that specifically bind to a particular polypeptide. The immune response can also be determined by detecting the presence of neutralizing antibodies or hemagglutinin inhibiting activity. Methods of detecting antibodies to polypeptides are known to those of skill in the art and include such assays as ELISA assays, western blot assays, functional and competition assays. Methods of detecting T cell responses include ELISPOT assays, ICS assays, and in-vitro and in-vivo cytotoxicity assays. The particular region of the polypeptide that is stimulating a T cell or antibody response can be mapped using whole genome phage display libraries as described herein.

In some embodiments, the immunogenic composition administered to an animal includes a polynucleotide and/or polypeptides or immunogenic fragments thereof and one or more of variable influenza components, one or more conserved influenza component, or a combination thereof. In an embodiment, the conserved influenza component is M1, NP, PA, PB1, PB2, NS1, NS2, an immunogenic fragment thereof or combination thereof. In some embodiments, the same polynucleotide does not encode an influenza component such as M1 and/or NP. In other embodiments, the polynucleotide does not encode an influenza component selected from the group consisting of M1, NP, PA, PB1, PB2, NS1, NS2, an immunogenic fragment thereof and combinations thereof.

In an embodiment, an animal is immunized with an immunogenic composition of the invention and then boosted one or more times with the immunogenic composition. In an embodiment, the animal is boosted about 2 to about 4 weeks after the initial administration of the immunogenic composition. If the animal is to be boosted more than once, there is about a 2 to 12 week interval between boosts. In an embodiment, the animal is boosted at about 12 weeks and about 36 weeks after the initial administration of the immunogenic composition. In another embodiment, the animal is a mouse and the mouse is boosted 3 times at 2 week intervals. In yet another embodiment, the animal is a primate and the primate is boosted 1 month and 6 months after the initial administration of the immunogenic composition. The dose used to boost the immune response can include one more cytokines, chemokines, or immunomodulators not present in the priming dose of the immunogenic composition.

The methods of the invention also include prime-boost immunization methods utilizing the immunogenic compositions of the invention. Providing influenza polypeptides in different forms in the prime and boost maximizes the immune response to the polypeptide. In some embodiment, an animal is primed with a polynucleotide encoding a polypeptide, such as shown in Tables 4 or 5, in one vector. The animal may be primed 1 to 8 times. Typically there is a 1, 2, or 3 week interval between administrations. In an embodiment, the animal is primed 3 times at 2 week intervals. The primed animal is then boosted with the same polypeptide or polynucleotide encoding the same polypeptide in a second vector that is different from the first vector. In an embodiment, the animal is boosted with the second vector at least 2 weeks after the last dose of the first viral vector. In an embodiment, the animal is boosted with the second vector at 4 weeks after the last dose of the first viral vector. The dose used to boost the immune response can include one more cytokines, chemokines, immunomodulators, or influenza antigens not present in the priming dose.

Viral delivery vectors are known and commercially available. Examples of viral vectors include, but are not limited to, recombinant poxvirus including vaccinia virus, lentivirus, or adenovirus. In an embodiment, the viral vector is adenovirus type 5. Examples of commercially available viral delivery vectors include, but are not limited to, VIRAPOWER™ lentivirus expression system, VIRAPOWER™ adenovirus expression system (Invitrogen, Carlsbad, Calif.), and ADENO-X adenovirus expression system (Clontech, Mountain View, Calif.).

The methods of the invention also include methods for protecting an animal against a lethal influenza challenge. In some embodiments, the method of the disclosure provides for protective immunity against an infection with virus of the same subtype, and against heterosubtypic virus. In an embodiment, the influenza is a highly pathogenic H5N1.

The methods of the invention can be used to immunize birds to prevent the spread of avian influenza. In an embodiment, the avian influenza is H5N1. In an embodiment, the birds are domesticated poultry.

Any mode of administration can be used in the methods of the inventions so long as the mode results in the expression of the desired peptide or protein, in the desired tissue, in an amount sufficient to generate an immune response to influenza A and/or to generate a prophylactically or therapeutically effective immune response to influenza A in an animal. The immunogenic compositions of the invention can be administered by intramuscular (i.m.), intra-nasally (i.n.), subcutaneous (s.c.), or intrapulmonary route in dosage unit formulations containing conventional non-toxic pharmaceutically acceptable carriers, adjuvants, or vehicles. Other suitable routes of administration include, but are not limited to intratracheal, transdermal, intraocular, intranasal, inhalation, intracavity, and intravenous (i.v.) administration. Transdermal delivery includes, but is not limited to intradermal, transdermal, and transmucosal administration. Intracavity administration includes, but is not limited to administration into oral or nasal cavities. The immunogenic compositions can be coated onto particles or nanofibers for delivery or formulated in liposomes.

Administration modes of the present invention include needle injection; catheter infusion; biolistic injectors; particle accelerators such as, for example, "gene guns" or pneumatic "needleless" injectors such as Med-E-Jet (Vahlsing et al., 1994, J. Immunol. Methods, 171:11-22), Pigjet (Schrijver et al., 1997, Vaccine, 15:1908-1916), Biojector (Davis et al., 1994, Vaccine, 12:1503-1509; Gramzinski et al., 1998, Mol. Med., 4: 109-118), AdvantaJet (Linmayer et al., 1986, Diabetes Care, 9:294-297), or Medi-jector (Martins and Roedl, 1979, Occup. Med., 21:821-824); gelfoam sponge depots; other commercially available depot materials such as, for example, hydrogels, osmotic pumps, oral or suppositorial solid (tablet or pill) pharmaceutical formulations, topical skin creams, and decanting, polynucleotide coated suture (Qin, Y., et al., 1999, Life Sci., 65: 2193-2203), or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir et al., 1999, Proc. Natl. Acad. Sci USA, 96:4262-7; Hartikka et al., 2001, Mol. Ther., 4:407-15; Mathiesen, 1999, Gene Ther., 6:508-14; Rizzuto et al., 2000, Hum. Gen. Ther. 11:1891-900.

The present disclosure is also directed to kits for practicing the methods of the invention. In some embodiments, the kit includes a plasmid expression vector of the invention, a viral vector of the invention, and instructions for priming an animal (including human) with the plasmid expression vector and boosting the animal with the viral vector. In some embodiments, the kit comprises a plasmid expression vector and a viral vector each comprising a polynucleotide encoding a polypeptide from A/H3N2 or A/H5N1. In some embodiments, the kit may further comprise a polypeptide composition. In some cases, the polypeptide of the polypeptide composition and the polypeptide encoded by the plasmid and viral expression vector have the same sequence. In some embodiments, the kit may further comprise at least one adjuvant or immunomodulator. The adjuvant or immunomodulator can be encoded by a polynucleotide. In a specific embodiment, the adjuvant is MF59, CTA1-DD alone or in combination with ISCOM.

Diagnostic Assays

Serodiagnostic or surveillance assays are also provided. Using the epitopes identified by the whole genome libraries, assays and kits can be provided that distinguish between different subtypes of influenza virus infection, for example, H5N1 infection from H3N2 infection; between vaccinated and infected subjects; and between different clades of influenza virus subtypes. These assays can be very important in surveillance of emerging pandemics and especially in countries that do not have the ability to run PCR type assays.

The diagnostic methods of the invention include a method for determining the presence of a H5N1 infection in a subject comprising analyzing a biological sample to detect the presence of an antibody that specifically binds to one or more polypeptides as described herein, wherein the presence of the antibody is indicative of H5N1 infection. Such polypeptides include anyone of the polypeptides of SEQ ID NO:32 to SEQ ID NO:120 or SEQ ID NO:148 to 176. Preferably a polypeptide is selected that is conserved in H5N1 strains as can be determined using publicly available sequence information such as shown in Tables 6 and 7. All of the peptides in Table 2, 3 and Table 5 from the H5N1 sequence are peptides for differential serodiagnosis development, as evident from absence of ELISA reactivity with the uninfected Vietnam serum samples. These peptides can help differential diagnosis of H5N1 vaccine v/s infected individuals as well as H5N1 infected from other seasonal influenza infected individuals.

In other embodiments, the method further comprises, analyzing the biological sample to detect the presence of an antibody that specifically binds to any one of the polypeptides of SEQ ID NO:1-31, wherein a lack of binding to any one of the polypeptides is indicative of a lack of infection with H3N2 influenza virus and binding to one or more of the polypeptides is indicative of infection with H3N2 strain of influenza.

In yet other embodiments, the method further comprises analyzing the biological sample to detect presence of an antibody that binds to a polypeptide comprising SEQ ID NO:41, wherein binding of the polypeptide is indicative of infection with a strain of H5N1 of clade 1.

Biological samples include serum, tissue, urine samples, and biopsy samples. One or more of the polypeptides may be attached to a solid substrate such as a bead, ELISA plate, dipstick, or microarray.

The presence or absence of the antibody in the biological sample can be determined using methods known to those of skill in the art to detect the antigen antibody complex. Such methods include contacting the antibody antigen complex with a detectably labeled moiety that will bind to the antigen antibody complex and not to antibody or antigen alone.

Antibodies

Polyclonal Antibodies

Polyclonal antibodies to a polypeptide of the disclosure are preferably raised in animals by multiple subcutaneous (sc), intramuscularly (i.m.), intranasally (i.n.) or intraperitoneal (ip) injections of the polynucleotide encoding one or more polypeptides or fragments thereof and/or the polypeptide, and optionally an adjuvant. Polyclonal antibodies may be useful to treat influenza virus infection via passive immunity or to produce chimeric or humanized antibodies.

It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ½ to ⅟₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

The polyclonal antibodies generated by the immunizations may undergo a screen for antagonist activity or neutralizing activity. Preferably, antibodies to the polypeptide decrease the infectivity of virus produced or inhibit viral levels. In an embodiment, antibodies that specifically bind a HA or NA polypeptide as show in Table 4 or Table 5 reduce or inhibit influenza viral levels. An antagonist antibody would be screened to determine if there was a decrease or inhibition of viral levels in infected cells.

The polyclonal antibodies are also screened by enzymelinked immunoabsorbent assay (ELISA) to characterize binding. The antigen panel includes all experimental immunogens. Animals with sera samples that test positive for binding to one or more experimental immunogens are candidates for use in monoclonal antibody production. The criteria for selection for monoclonal antibody production is based on a number of factors including, but not limited to, binding patterns against a panel of structured influenza immunogens.

Cross-competition experiments using other mapped Mabs, human sera and peptides can also be performed. Screening methods for identifying antibodies that bind to epitopes shared by all or a number of the influenza viruses of the same subtype, or even of the same clade and not another clade can be selected.

Monoclonal Antibodies

Monoclonal antibodies to a polypeptide of the disclosure may be made using the hybridoma method first described by Kohler et al., *Nature,* 256:495 (1975), or may be made by recombinant DNA methods (U.S. Pat. No. 4,816,567). Monoclonal antibodies may be useful to treat influenza virus infection via passive immunity or to produce chimeric or humanized antibodies.

In the hybridoma method, a mouse or other appropriate host animal, is immunized as hereinabove described to elicit lymphocytes that produce or are capable of producing antibodies that will specifically bind to the polypeptide used for immunization. Alternatively, cells producing monoclonal antibodies can be obtained from infected or vaccinated individuals. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells are than seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The monoclonal antibodies are characterized for specificity of binding using assays as described previously. Antibodies can also be screened for antagonist activity as described previously. Cross-competition experiments using other mapped Mabs, human sera and peptides can also be performed. Screening methods for identifying antibodies that bind to epitopes shared by all or a number of the influenza viruses of the same subtype, or even of the same clade and not another clade can be selected.

Human or Humanized Antibodies

Humanized forms of non-human (e.g., murine) antibodies are chimeric antibodies that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, rabbit or nonhuman primate having the desired specificity, affinity, and capacity. Useful non-human antibodies are monoclonal antibodies that bind specifically to Useful non-human antibodies also include antibodies that inhibit or reduce viral levels. Furthermore, humanized antibodies may comprise residues that are not found in the recipient antibody or the donor antibody. These modifications may be made to improve antibody affinity or functional activity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech* 5:428-433 (1994).

Human antibodies that specifically bind and/or antagonize influenza hemagglutinin or neuraminidase activity and/or inhibit viral infectivity can also be made using the transgenic mice available for this purpose or through use of phage display techniques.

For example, in some embodiments, the polypeptides as described herein are then screened against naïve or synthetic libraries of antibody fragments to identify novel high affinity antibodies. These novel high affinity antibodies can be useful as therapeutic agents as antagonists or agonists, and/or as diagonostic agents. For example, antibodies or antigen binding fragments can be screened for binding to an epitope on a H5N1 clade 1 HA protein and not to H5N1 clade 2 epitope. For diagnostic purposes, such antibodies can be used to distinguish whether a subject is infected with clade 1 or clade 2. For therapeutic purposes, an antibody that binds to an epitope on several H5N1 influenza strains or that neutralizes the activity of HA or NA from several different clades would be selected.

Antibody Conjugates

The antibodies specific for a polypeptide or fragment thereof can be combined with heterologous moieties to provide a detectable label or for targeted delivery of an inhibitory agent or for serodiagnosis.

Detectable labels include radionuclides, biotin, dyes, enzymes, and fluorescent molecules. Inhibitory agents include cytotoxic agents such as toxins.

Compositions

Compositions comprising one or more antibodies may be useful to treat influenza virus infection or to use prophylactically in the event an outbreak of infection arises. Antibodies may be present in the compositions as polyclonal antibodies, chimeric antibodies, human, human antibodies or antigen binding fragments. Compositions may include physiological excipients, or carriers as described previously.

Dosing may be determined by the physician. Guidance for dosing can be found in antibody compositions used to treat rabies, or for any of the antibody compositions currently used to treat cancer.

The following examples are provided for illustrative purposes only, and are in no way intended to limit the scope of the present disclosure.

Example 1

Influenza Whole Genome Flu Phage Display Library (GFPDL) Construction

In order to prepare for the pandemic influenza threat and to improve the cross-reactivity and long-term protection of interpandemic influenza vaccines, it is important to identify all the dominant antibody responses of vaccinated and/or infected individuals. The ability to rapidly distinguish between exposure to human influenza vs. bird influenza will be useful in the surveillance of disease. There is only limited knowledge about the viral proteins/epitopes which are recognized by the immune system of infected individuals. Careful analyses of the immune responses against the new candidate vaccines is required in order to identify the best correlate of protection against seasonal human influenza strains and potential pandemic strains (transmitted from wild birds).

To address these challenges we developed an unbiased high throughput approach based on the construction of Whole Viral Genome Phage Display Libraries, expressing complete sets of protein fragments encoded by several Human and Avian Influenza strains including H1N1, H3N2, H5N1 and H7N7. These libraries are being used for in depth analyses of plasma samples from: a) individuals exposed to human influenza; b) individuals exposed to avian (bird) influenza; c) individuals vaccinated with traditional influenza vaccines; d) individuals vaccinated with new generation vaccines against human and bird influenza viruses.

By using these libraries we have identified a large set of peptides that are shown to provide broad heterotypic neutralizing activity as well a set of epitopes that will be important for serodiagnosis as well as differential diagnosis.

Eight gene segments were cloned from each of the following influenza strains: H1N1-A/New Caledonia/20/99; H3N2-A/California/7/2004; H5N1-A/Vietnam/1203/2004; H5N1 A/Indonesia/5/05; and H7N7-A/Netherlands/2003 were reverse transcribed to form cDNAs of each gene segment and then were digested with DNase in order to form influenza gene segment fragments. These gene fragments were cloned into a phage display vector and phage clones bearing influenza gene segments were selected for binding to antibodies specific for each of the influenza virus proteins. These libraries were utilized to map the antibody response to H3N2 post infection or post vaccination and to map antibody response to H5N1 post infection in human survivors and post vaccination with a H5N1 subunit vaccine.

Cloning of Influenza Gene Segments

Figure 2:
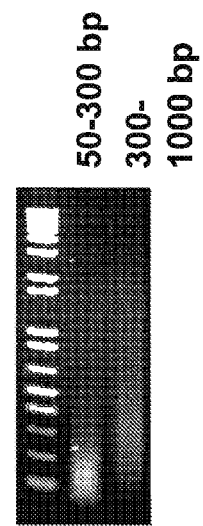
FIG. 2 illustrates a representative gel electrophoresis of genome fragments generated by DNAase digestion of influenza virus genes

A representative scheme for preparing whole genome influenza gene libraries is shown in FIG. 1. From each strain identified above, cDNAs corresponding to all eight gene segments of the A/H5N1Nietnam/1203/2004 were generated from RNA isolated from egg-grown virus strain and were used for cloning Phage display libraries were constructed individually for HA & NA genes and the rest of the six gene segments (PB2, PB1, PA, NP, M & NS). Purified DNA containing equimolar ratio of HA & NA (HA-NA) or the rest of the six genes (PB2-NS) were digested with DNase I using DNase shotgun cleavage kit (Novagen) as per manufacturer's instructions to obtain majority of the DNA fragments in the size range of 50-200 and 200-1000 bp for each of the two gene segment pools. The digested DNA was isolated from agarose gels, purified, and the overhangs were filled/removed using T4 DNA polymerase. A representative gel electropherogram is shown in FIG. 2. The end repaired DNA was then dephosphorylated using calf intestinal alkaline phosphatase (OP), and 500 ng of random dephosphorylated blunt ended DNA fragments were ligated with 100 ng of Sma I digested fSKSrf9-3 vector in a 50 µl reaction (25° C.; 1 h) in the presence of 20 U of T4 DNA ligase and 25 U of SrfI. fSKSrfl-9-3 is a gIIIp display based phage vector where the desired polypeptide can be expressed as gIIIp fusion protein constructed in inventor's lab.

Ligated products were used for electroporating *E. coli* TG1 cells. For producing phages, $10^9$ cells from each library were added to 200 ml 2×YT with 20 ug per ml tetracycline and grown for 16 h at 32° C. and 200 rpm. The cell-free phage supernatant was isolated by centrifugation and phage titre determined as Tet$^r$ transduction units.

Four libraries were constructed; fSK9-3 HA-NA (50-200 bp), fSK9-3 H5HA-NA (200-1000 bp), fSK9-3 H5t-PB2-NS (50-200 bp) & fSK9-3 H5PB2-NS (200-1000 bp) for each influenza stain.

Affinity Selection of H5N1 MAb or Sera Specific Phages

The influenza genome libraries were then used to characterize the human antibody response to infection and/or vaccination. A representative scheme for affinity panning is shown in FIG. 4. The phage display library was incubated with antibodies from serum from infected individuals or vaccinated individual bound to a solid substrate or in-solution, unbound phages were washed away, and bound phages were eluted.

For removal of serum components, which could non-specifically interact with phage proteins, sera were incubated with UV-killed M13K07 coated petri dishes. Affinity selection was carried out on antibody coated wells as well as in-solution (with Protein A/G).

Eight wells of Nunc Maxisorp microtitre strips (NUNC Inc, Naperville, Ill., USA) were coated with a mixture of 500 ng each of goat anti-human IgG-Fc specific antibodies and blocked with 350 µl PBST (PBS containing 0.1% Tween-20) containing 2% BSA at RT for 1 h to block the unoccupied reactive sites. After three washes with PBST, 1 µg of MAb or 100-fold dilution (final dilution) of VCSM13-preadsorbed human serum (100 µl in 1% BSA-PBST) was added to wells and incubated for 1 h at RT. The wells were washed thrice with PBST and $10^{10}$ phages (from gene-fragment library) in 100 µl PBST containing 1% BSA were added to all the eight wells and incubated at RT for 1 h. The unbound phages were removed in ten washes with PBST followed by three washes with PBS. The bound phages were eluted by addition of 100 µl of 0.1N HCl (adjusted to pH 2.2 with glycine and BSA added at 1 mg/ml) to each well and incubated for 10 min at 37° C. The eluted phages were collected and neutralized by adding 64 µl of 2 M Tris solution (pH not adjusted).

For in-solution panning, $10^{10}$ phages (from gene-fragment library) in 500 µl PBST containing 1% BSA were added to 200 µl of 50% Ultralink Protein A/G slurry (Pierce) and incubated for 1 h at RT on end-to-end shaker. Following brief centrifugation, 500 µl of supernatant was added to 5 µg of human anti-H5N1 MAb or 100 µl of 10-fold VCSM13-preadsorbed human serum (100 µl in 1% BSA-PBST) and incubated for 1 h at RT on end-to-end shaker, followed by 200 µl of 50% Ultralink Protein A/G slurry (Pierce, Rockford, Ill.) on end-to-end shaker at RT for 1 h. The unbound phages were removed in ten washes with PBST followed by three washes with PBS. The bound phages were eluted by addition of 800 µl of 0.1N HCl (adjusted to pH 2.2 with glycine and BSA), and incubated for 10 min at RT on end-to-end shaker. The eluates was collected and neutralized by adding 64 µl of 2 M Tris solution.

After each round of affinity selection, bound phages were eluted and sequenced. Ninety-six clones were randomly isolated and sequenced to ensure that the library reflected segments of the entire genome. The results for a representative library are shown in FIG. 3. The results show that several sequences for each gene segment were obtained representing random distribution of size and sequence in the gene-fragment phage display libraries (GFPDL).

Example 2

Epitope Mapping Polyclonal Sera and Monoclonal Antibody Sera Using H3N2 Phage Display Library Epitope mapping using the H3N2 whole genome library with the pool of larger fragments was conducted with polyclonal antisera from individuals pre- & post-vaccinated, or post-infection with H3N2. An exemplary B-cell epitope map of hemagglutinin (HA) from H3N2 expressed from a gene fragment phage display library and screened against polyclonal sera collected before vaccination and after the influenza season from convalescent patients in the placebo arm of the study done in 2003-2004 season is shown in FIG. 5. The results show that sera taken from individuals pre-vaccination and post infection at end of the seasonal flu season contained antibodies that predominantly reacted with HA, NA, M1 and M2 proteins as compared to sera from individuals before the start of the season.

Some of the clones were isolated and sequenced and are represented as sequences of SEQ ID NO:1-31 of Table 4.

Example 3

Epitope Mapping Using H5N1 Library Using Monoclonal Antibodies Derived from H5N1 Infected Humans Who Survived Infection Two H5N1 libraries were constructed as described in Example 1: one library was made from strain H5N1 from Vietnam and another from H5N1 from Indonesia. Examination of strains isolated from different outbreaks has revealed that there are several clades of H5N1 influenza viruses. Clade 1 includes H5N1 strains from Vietnam and Clade 2 includes H5N1 strains from Indonesia.

We characterized the epitopes recognized by the monoclonal antibodies from the infected individuals using the whole genome libraries. These antibodies have been described in Simmons et al, Plos Medicine 4:e178(2007). Three monoclonal antibodies were tested: FLA 5.10, FLD 21.140, and FLA 3.14. Two of these monoclonal antibodies, FLD 21.140, and FLA 3.14, have been shown to protect mice against lethal infection with both the Vietnam and Indonesia strains and thus, are characterized as broadly neutralizing. Monoclonal antibody FLA 5.10 was protective only for the Vietnam strain.

Phage clones were affinity selected as described in Example 1, and were sequenced.

Phage ELISA

Phage ELISA was performed to analyze the reactivity of affinity selected clones using H5N1 positive and normal healthy individual sera. Microtitre plates coated with 1000-fold dilution of anti-phage antibody (GE Healthcare, Piscataway, N.J.) were blocked with EMEM containing 2% BSA and 0.1% Tween-20 (blocking solution). The phages ($10^{10}$/100 µl/well) diluted in blocking solution were then added and incubated for 1 h at room temperature (RT). 100 µl of serially diluted sample was added to the wells in duplicate and incubated at RT for 1 h. All the antibody and phage dilutions were made in blocking solution. Plates were washed with PBST using a microplate washer. The bound serum antibodies were probed with 100 µl of 2000-fold dilution of HRP-conjugated goat anti-human IgG-Fc specific or goat anti-human IgA-α-chain specific antibody. After three washes with PBST followed by three washes with PBS, the reaction was revealed with 100 µl of OPD substrate solution. Cut-off was calculated as mean+3SD (standard deviation) of the phage reactivity in duplicate with three normal random serum samples for each of the phage clone selected for immunoanalysis.

Affinity Selection using Random Peptide Phage Display Library

To further map the epitope regions of the monoclonal antibodies, a phage display library with random dodecamers connected to the p3 protein via a linker was used. This library is referred to as random phage library (RPL). The dodecamers have a sequence of the following formula: X-X-X-X-X-X-X-X-X-X-X-X, where X is any naturally occurring amino acid. The library was purchased from New England Biolabs. Each of the monoclonal antibodies were incubated with the dodecamer library and the high affinity binders from the random dodecamer library were isolated and sequenced.

The results for each antibody are shown in FIG. 6. The HA sequence shown in this figure has accession no. AAW80717.

The results for the H5N1 neutralizing monoclonal antibody FLA5.10 identified using influenza complete genome-fragment phage display library (GFPDL) are shown in FIG. 6A. Epitope sequences are boxed on the aligned sequence of A/Vietnam/1203/2004 and A/Indonesia/5/05 of the haemagglutinin (HA). Amino acid number 1 corresponds to H3 (A/California/7/2004) amino acid −10. HA sequences recognized by FLA5.10 include amino acids 9-241.

The contact residues shown in each of the figures as encircled or boxed residues were identified using random peptide phage display library (RPL) aligned to HA1 sequence. In FIG. 6A, the results for monoclonal antibody FLA5.10 show binding to peptides including amino acids in the receptor binding site: QIIP (SEQ ID NO:181) and EASL (SEQ ID NO:180). Serine (S) and lysine (K) residues were identified by in vivo challenge studies with suboptimal amounts of FLA5.10 are shown in italics. When mapped to the crystal structure of HA (as shown in FIG. 9A), these residues form a contiguous patch on a B sheet in the globular receptor binding domain.

As shown in FIG. 7(a), monoclonal antibody FLA5.10 binds to a peptide having the amino acid sequence LTAET-QIQFFHH (SEQ ID NO:41). This sequence has a partial match to HA sequence as shown in FIG. 6. Other human antibodies did not bind to this sequence. When the leucine in this sequence is mutated to alanine, the antibody no longer can bind the peptide. See FIG. 7 (b). This may provide the explanation for why monoclonal antibody FLA5.10 does not neutralize or protect mice against infection with the Indonesia strain. The EASL (SEQ ID NO:180) sequence is found in the Vietnam strain but not the Indonesia strain. The sequence in the Indonesia strain is SASS (SEQ ID NO:184), where the L has been changed to an S.

Monoclonal antibody FLD21.140 was also incubated with the H5N1 Vietnam library and with the random dodecamer library. The results are shown in FIG. 6B. HA sequences from the GFPDL library recognized by FLD 21.140 include amino acids 50-338. The antibody bound to peptides from the RPL library including the amino acid sequence SWS and peptides including YNNT (SEQ ID NO:185) in the 50-338 fragment of the receptor binding domain. Monoclonal antibody FLD21.140 protects mice against infection with both the Vietnam and Indonesia strains and binds to epitopes containing sequences conserved between the Vietnam and Indonesia strains. These residues also were mapped to the crystal structure of H5N1 HA molecule and are located near the top of the globular receptor binding domain as shown in FIG. 9B.

Monoclonal antibody 3.14 was also incubated with the H5N1 Vietnam library and with the random dodecamer library. The results are shown in FIG. 6C. HA sequences from GFPDL recognized by FLA 3.14 include amino acids 47-338. The antibody bound to peptides from the RPL library including the amino acid sequence GVKP (SEQ ID NO:182) (amino acids 64-67) and peptides including NT (amino acids 231-232). Monoclonal antibody FLA3.14 protects mice against infection with both the Vietnam and Indonesia strains and binds to epitopes containing sequences conserved between the Vietnam and Indonesia strains. These residues also were mapped to the crystal structure of H5N1 HA molecule and even though they are at different ends of the molecule, they are brought together by a disulfide bond and appear to flank the globular receptor binding domain as shown in FIG. 9C.

In-vivo challenge studies with suboptimal amounts of FLA5.10 identified two mutated residues that are encircled (in a), and for FLA3.14 (in c) and are represented on the HA structure (in a & c). These mutated residues resulted in virus which is resistant to neutralizing monoclonal antibodies. Asp-61 and Asn-231 were found to be important residues in in-vivo escape studies with FLA3.14. Using two different approaches [epitope mapping using phage display libraries and in vivo escape mutant studies] similar residues were identified as important for the binding of these monoclonal antibodies.

Figure 8:
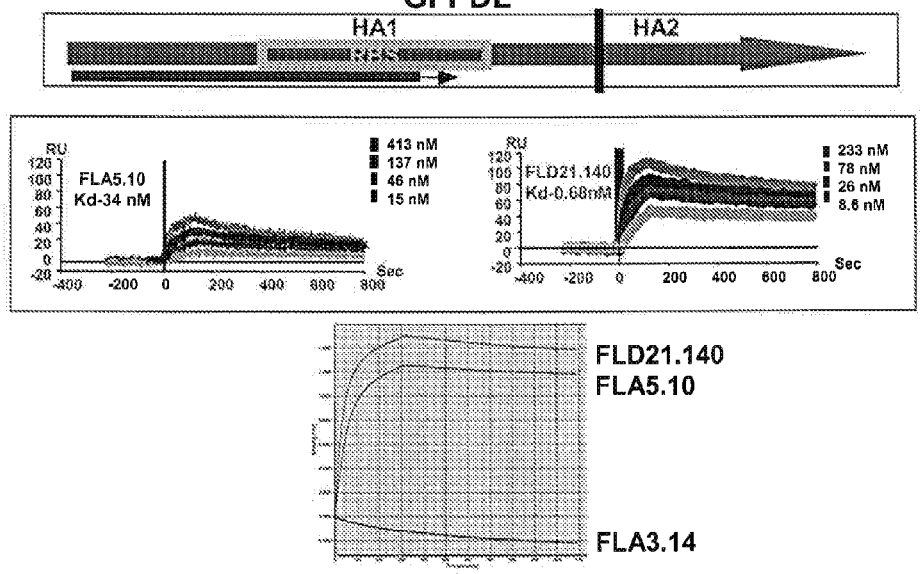
FIG. 8 Binding of human monoclonal antibodies to purified HA segment. Serial dilution of MAbs were run on a chip coated with E. coli expressed and purified HA 9-241 (FLA5.10 epitope) to determine the affinity constants using ProtOn system (BioRad) (a) illustrates the binding affinity of H5N1 neutralizing monoclonal antibody FLA 5.10 to recombinant purified protein; (b) illustrates the binding affinity of H5N1 neutralizing monoclonal antibodies FLD 21.140 to recombinant purified protein; and (c) illustrates the binding affinity of H5N1 neutralizing monoclonal antibodies FLD 21.140, FLA 5.10 and FLA 3.14 to recombinant purified protein.

Binding of human monoclonal antibodies to purified HA segments is shown in FIG. 8. Briefly, serial dilution of MAbs were run on a chip coated with *E. coli* expressed and purified HA 9-241 (FLA5.10 epitope) to determine the affinity constants using ProtOn system (BioRad). The results show that monoclonal antibody FLD 21.140 bound with the highest affinity to this purified polypeptide exhibiting a Kd of 0.68 nM. Monoclonal antibody FLA 5.10 exhibited a Kd of 34 nM, and antibody FLA3.14 did not bind to this polypeptide at all.

When the recombinant purified polypeptide HA polypeptide 9-241 was incubated with sheep anti-A/Vietnam vaccinated sera, the neutralizing activity was absorbed by the polypeptide. Other peptides including amino acids of HA such as 35-96, 99-121, 120-149, 185-206, and 491-534 did not adsorb neutralizing activity of post infection sera. GST-His has same molecular weight and was purified under similar conditions as HA9-241-His, and was used as negative control. Similar results were obtained with ferret anti-A/Vietnam infected sera. See Table 1.

TABLE 1

ADSORPTION OF NEUTRALIZATION ACTIVITY
USING HA PEPTIDE SEQUENCES

| Peptides added | TITER |
|---|---|
| Sheep anti-A/Vietnam/1203/04-HA-sera | |
| No peptide | 640 |
| HA 9-241 – FLOW-THROUGH | <40 |
| HA 9-241 – ELUATE | 640 |
| GST-His – FLOW-THROUGH | 640 |
| GST-His – ELUATE | <40 |
| HA 35-96 + HA 99-121 FLOW-THROUGH | 640 |
| HA 120-149 + HA 185-206 FLOW-THROUGH | 640 |
| HA 491-534 FLOW-THROUGH | 640 |
| Ferret anti-A/Vietnam/1203/04-infected sera (2004-53) | |
| No peptide | 640 |
| HA 9-241 FLOW-THROUGH | <40 |
| HA 35-96 + HA 99-121 FLOW-THROUGH | 640 |
| HA 120-149 + HA 185-206 FLOW-THROUGH | 640 |
| HA 491-534 FLOW-THROUGH | 640 |

This data suggests that most of the neutralizing antibodies in either the vaccinated sheep sera or the infected ferret sera can be adsorbed by a H5-HA 9-241 protein. Moreover most neutralizing antibodies are conformation dependent as most smaller peptides within HA9-241 cannot adsorb any neutralizing reactivity from either the vaccinated or infected sera.

Therefore, HA9-241 will be a good vaccine candidate to generate high-affinity neutralizing antibodies as well as to be used a bait for production of neutralizing monoclonal antibodies by various approaches.

Example 4

Elucidation of Epitope Profile of H5N1 Survivors

Individual serum samples were obtained from 5 survivors of H5N1/Vietnam infection was evaluated for epitope specificity. Epitope specificity was determined both by affinity selection using GFPDL followed by peptide ELISA using chemically synthesized peptides or recombinantly expressed peptides.

Peptide ELISA

Biotinylated peptides (1 μg/well) were captured onto wells coated with 500 ng of streptavidin. After blocking with PBST containing 2% Milk, serial dilutions of human serum in blocking solution were added to each well, incubated for 1 hr at RT, followed by addition of 2000-fold dilution of HRP-conjugated goat anti-human IgG-Fc specific or goat anti-human IgA-α-chain specific antibody and developed by 100 μl of OPD substrate solution. Absorbance was measured at 490 nm. Cut-off was calculated as mean+3SD of the peptide reactivity (in duplicate) with three normal random serum samples for each of the phage clone selected for immunoanalysis.

Figure 10:
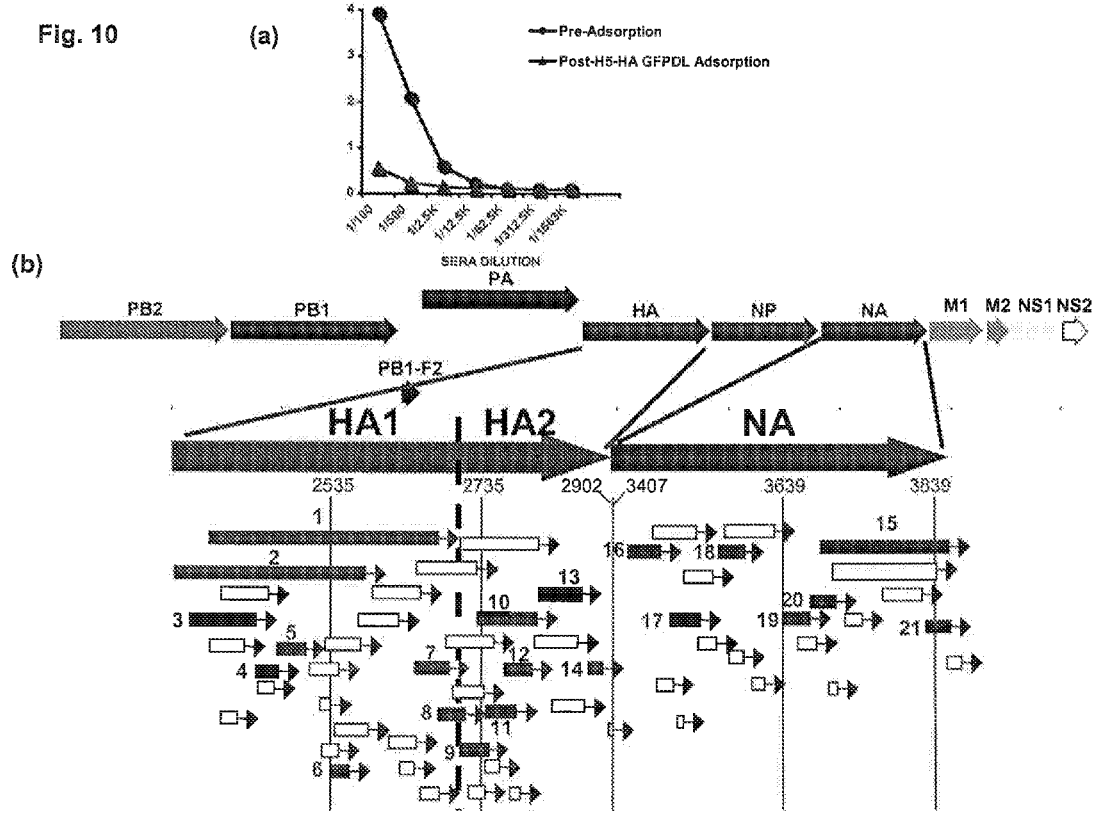
FIG. 10 Elucidation of epitope profile recognized by antibodies in individuals that survived H5N1 infections in Vietnam: (a) Reactivity of pooled sera from five H5N1 survivors with recombinant H5 HA (Vietnam 1203) before (closed circles) and after (triangles) adsorption on H5GFPDL. (b) Elucidation of epitope profile in HA and NA recognized by antibodies in individuals that survived H5N1 infections in Vietnam. Alignment of the unique peptide sequences recognized by the pooled sera from H5N1-infected individuals identified using HA and NA GFPDLs. The predicted Influenza encoded proteins are shown and numbered according to the intact complete proteome (FIG. 14). Arrows indicate that inserts are in right orientation with the coding sequence. Each bar represents a unique peptide sequence. The peptide sequences represented in filled bars were either expressed and purified from E. coli or chemically synthesized. These peptides were selected based on the frequency of the phage clones displaying these peptide sequences following affinity selection on H5N1 exposed sera. Their numbers correspond to the peptide IDs in the ELISA assays.

The results are shown in FIG. 10. The pooled serum was incubated with H5-HA-GFPDL and antibodies binding to H5-HA that remained after incubation were determined in ELISA. The H5-HA-GFPDL adsorbed all of the antibodies that specifically bind to HA. See FIG. 10A.

The B cell epitope profile of the phage that bound to the pooled sera was determined by isolating and sequencing clones that bound to the pooled sera. The results For HA and NA are shown in FIG. 10(*b*). The unique peptide sequences recognized by the pooled sera from H5N1-infected individuals identified using HA and NA GFPDLs were aligned to the reference sequence for HA and NA. Their numbers correspond to the peptide IDs in the ELISA assays. The predicted influenza encoded proteins are shown and numbered according to the intact complete proteome reference sequence (FIG. 14). Arrows indicate that inserts are in right orientation with the coding sequence. Each bar represents a unique peptide sequence.

The peptide sequences represented in filled bars were either expressed and purified from *E. coli* or chemically synthesized. These peptides were selected based on the frequency of the phage clones displaying these peptide sequences following affinity selection on H5N1 exposed sera. (See Table 5) The peptides were analyzed for binding to antibodies in the sera. ELISA reactivities of sera from individual H5N1-infected patients (Viet1-5) and pooled sera from 20 uninfected age-matched women from Vietnam with HA1 peptides 1-8, HA2 peptide 9-14, and NA peptides 15-21 (as indicated in FIG. 10 b) The end-point titers are shown. Days post admission represent the time of serum collection for each patient. See Table 2.

TABLE 2

| | | IgG RESPONSES | | | | | | |
|---|---|---|---|---|---|---|---|---|
| | | Viet-1 | Viet-2 | Viet-3 | Viet-4 | Viet-5 | ANTIGENIC | Uninfected Vietnam |
| | | Days Post-Admission | | | | | | |
| ALIGNED ID | PEPTIDE | 54 | 69 | 73 | 113 | 182 | CLUSTER | Sera |
| 1 | HA-2376-2659 | 12500 | >12500 | >12500 | >12500 | 2500 | | 500 |
| 2 | HA-2339-2581 | >12500 | 12500 | 12500 | 12500 | 500 | | 100 |
| 3 | HA-2365-2427 | 500 | 2500 | 2500 | 500 | 100 | I | <100 |
| 4 | HA-2431-2453 | 2500 | 12500 | 2500 | 500 | 100 | | 100 |
| 5 | HA-2452-2481 | 500 | 500 | 500 | 500 | 100 | II | <100 |
| 6 | HA-2517-2538 | 500 | 500 | 500 | 500 | 100 | | <100 |
| 7 | HA-2627-2668 | 12500 | 2500 | 500 | 500 | 100 | III | <100 |
| 8 | HA-2641-2684 | 2500 | 2500 | 2500 | 2500 | 500 | | <100 |
| 9 | HA-2682-2703 | 500 | 500 | 100 | 100 | 100 | IV | <100 |
| 10 | HA-2695-2756 | 500 | 2500 | 500 | 500 | 100 | | 100 |
| 11 | HA-2703-2731 | 500 | 500 | 500 | 500 | 500 | V | <100 |
| 12 | HA-2722-2762 | 500 | 500 | 500 | 500 | 500 | | 100 |
| 13 | HA-2759-2814 | 500 | 500 | 500 | 500 | 100 | | <100 |
| 14 | HA-2838-2866 | 2500 | 2500 | >12500 | >12500 | >12500 | VI | <100 |
| 15 | NA-3676-3854 | 2500 | 12500 | 12500 | 12500 | 2500 | | 100 |
| 16 | NA-3431-3481 | 500 | 2500 | 500 | 500 | 100 | | <100 |
| 17 | NA-3489-3530 | 500 | 500 | 500 | 500 | 100 | | <100 |
| 18 | NA-3541-3576 | 500 | 100 | 500 | 500 | 100 | | <100 |
| 19 | NA-3638-3662 | 500 | 100 | 100 | 100 | 100 | | <100 |
| 20 | NA-3659-3689 | 500 | 500 | 2500 | 500 | 100 | | <100 |
| 21 | NA-3834-3854 | 500 | 100 | 100 | 100 | 100 | | <100 |

The results show that for HA, 3 antigenic clusters are found on HA1 and three on HA2. The antigenic clusters on HA1 include amino acids 2365-2427 (SEQ ID NO:54) and 2431-2453, (SEQ ID NO:57) in antigenic cluster I, amino acids 2452-2481 (SEQ ID NO:59) and amino acids 2517 to 2538 (SEQ ID NO:60) in antigenic cluster II, and amino acids 2627-2668 of FIG. 14 and amino acids 2642-2685 of FIG. 14 in antigenic cluster III.

Figure 11:
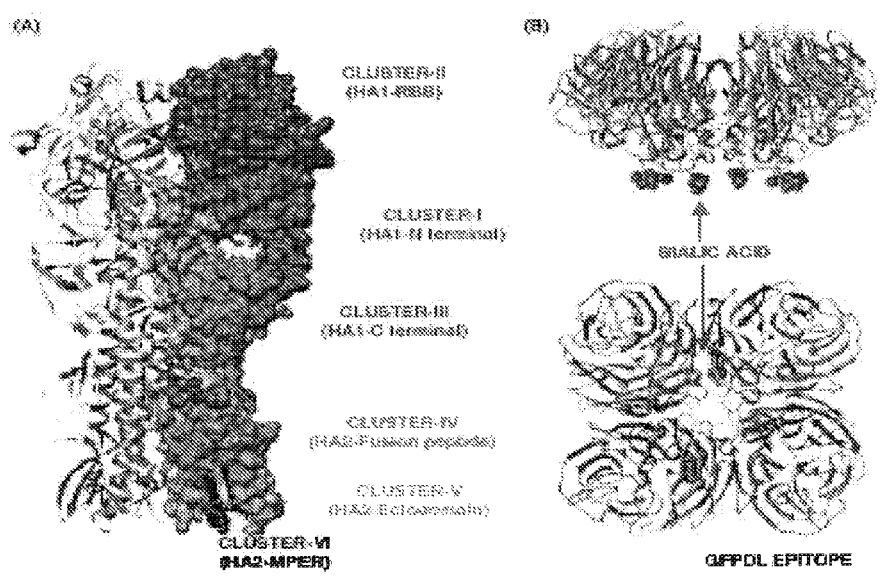
FIG. 11: Antigenic clusters in structure of HA and NA recognized by antibodies from H5N1/Vietnam-infecetd individuals (A) antigenic clusters in HA identified in FIG. 10 are shown as surface exposed residues on one HA monomer within the HA trimer structure (PDB Id-1JSM). (B) The Neuraminidase conformational epitope (NA-3676-3854) is shown on the tetrameric NA structure (PDB Id-2HTY) with the bound sialic acid.

At least, a peptide of amino acids HA 2339-2581 (SEQ ID NO:56) shows good agreement with epitope mapping using monoclonal antibodies FLA 5.10 and FLD 21.140. Peptides of amino acids HA 2376-2659 (SEQ ID NO:55) showed good correlation with antibody binding sites of monoclonal antibody FLA3.14. At least two of the peptides also map to sites that sialic acid of the receptor are thought to bind: peptide HA-2517-2538 (SEQ ID NO:60) and peptide HA-2431-2453 (SEQ ID NO:57). These antigenic clusters are shown on the crystal structure of HA as shown in FIG. 11A.

Antigenic clusters on HA2 include: amino acids HA-2682-2703 (SEQ ID NO:63); amino acids 2695-2756 (SEQ ID NO:65); amino acids HA-2703-2731 (SEQ ID NO:66); amino acids HA-2722-2762 (SEQ ID NO:70); amino acids HA-2759-2814 (SEQ ID NO:71); and amino acids 2838-2866 (SEQ ID NO:74). These antigenic clusters are shown on the crystal structure of HA as shown in FIG. 11A.

Antigenic clusters on neuraminidase include: amino acids 3676-3854, (SEQ ID NO:85); amino acids 3431-3481 (SEQ ID NO:84); 3489-3530 (SEQ ID NO:86); 3541-3576 (SEQ ID NO:88); 3639-3662 of FIG. 14; amino acids 3659-3689 (SEQ ID NO:91); and amino acids 3834-3854 (SEQ ID NO:89).

The results for other proteins encoded by the viral genome are shown in FIG. 12 a. End-point titers of individual patients and pooled sera from 20 uninfected age-matched women from Vietnam against each epitopic site were determined by ELISA against peptides derived from: PB2 (#1), PB1 (#2-3), PB1-F2 (#4-7), PA (#8), NP (#9-12), M1 (#13-16), M2e (17), M2 (#18), NS1 (#19-20), and NS2 (#21) When the peptides were analyzed by binding to individual serum samples, as shown in Table 3, other major epitopes were detected on NP, M1, and the M2 ectodomain. See Table 3

All the peptide sequences described above were obtained by affinity selection of H5N1 survivors, so any of these peptides can serve as a protective epitope. Also absence of ELISA reactivity with the uninfected Vietnam serum samples showed that these peptides can also be used for development of serodiagnosis of H5N1 infection as well as differential diagnosis of vaccine v/s infected individuals.

TABLE 3

(B) END-POINT TITER OF INDIVIDUAL POST-H5N1 EXPOSURE SERA WITH GFPDL SELECTED PEPTIDES

| | | IgG RESPONSES | | | | | |
|---|---|---|---|---|---|---|---|
| | | Viet-1 | Viet-2 | Viet-3 | Viet-4 | Viet-5 | Uninfected |
| | | Days Post-Admission | | | | | Vietnam |
| ALIGNED ID | PEPTIDE | 54 | 69 | 73 | 113 | 182 | Sera |
| 1 | PB2-344-375 | 500 | 500 | 500 | 100 | 100 | <100 |
| 2 | PB1-1348-1361 | 500 | 500 | 500 | 500 | 100 | <100 |
| 3 | PB1-1420-1437 | 500 | 500 | 500 | 500 | 100 | <100 |
| 4 | PB1-F2-1524-1598 | 500 | 500 | 500 | 500 | 100 | <100 |
| 5 | PB1-F2-1525-1572 | 500 | 500 | 500 | 100 | 100 | <100 |
| 6 | PB1-F2-1560-1592 | 500 | 100 | 500 | 500 | 100 | <100 |

TABLE 3-continued (B) END-POINT TITER OF INDIVIDUAL POST-H5N1 EXPOSURE
SERA WITH GFPDL SELECTED PEPTIDES

| | | IgG RESPONSES | | | | | |
|---|---|---|---|---|---|---|---|
| | | Viet-1 | Viet-2 | Viet-3 | Viet-4 | Viet-5 | Uninfected Vietnam |
| | | Days Post-Admission | | | | | |
| ALIGNED ID | PEPTIDE | 54 | 69 | 73 | 113 | 182 | Sera |
| 7 | PB1-F2-1570-1605 | 500 | 500 | 500 | 100 | 100 | <100 |
| 8 | PA-2202-2251 | 500 | 100 | 500 | 100 | 100 | <100 |
| 9 | NP-2906-2929 | 500 | 500 | 100 | 100 | 100 | <100 |
| 10 | NP-2955-3011 | 500 | 2500 | 100 | 12500 | 100 | 100 |
| 11 | NP-3263-3305 | 500 | 500 | 500 | 2500 | 500 | <100 |
| 12 | NP-3346-3384 | 2500 | 500 | 500 | 500 | 500 | <100 |
| 13 | M1-3866-3894 | 12500 | 12500 | 2500 | 500 | 2500 | <100 |
| 14 | M1-3859-3909 | 2500 | >12500 | 12500 | 500 | 2500 | 100 |
| 15 | M1-4040-4104 | 500 | 12500 | 100 | 2500 | 2500 | 100 |
| 16 | M1-4080-4109 | 500 | 2500 | 500 | 2500 | 2500 | <100 |
| 17 | M2e-4114-4137 | >12500 | 2500 | >12500 | 2500 | 100 | <100 |
| 18 | M2-4180-4206 | 500 | 500 | 100 | 100 | <100 | <100 |
| 19 | NS1-4235-4254 | 2500 | 2500 | 500 | 500 | 100 | <100 |
| 20 | NS1-4393-4417 | 500 | 500 | 500 | 500 | 100 | <100 |
| 21 | NS2-4467-4508 | 500 | 500 | 100 | 100 | 100 | <100 |

Example 5

Elucidation of Epitope Profile of Individuals Vaccinated with H5N1 Subunit Vaccine Pooled and individual serum samples were obtained from individuals vaccinated with H5N1 (A/Vietnam/1203/2004) subunit vaccine with or without adjuvant. The study has been described in Bernstein et al, JID; 2008:1977; 1-9. These serum samples were evaluated for epitope specificity. The adjuvants tested included alum and MF59 adjuvant.

The pooled serum was incubated with H5-HA-GFPDL. The B cell epitope profile of the phage that bound to the pooled sera was determined by isolating and sequencing clones that bound to the pooled sera. The results for HA and NA are shown in FIG. 13. Those peptide sequences delineated with unfilled squares represent peptides that adsorbed neutralizing activity of the sera. In the pre-vaccine sera, a single peptide in the HA2 ectodomain was identified after 3 rounds of affinity selection. This was unexpected as these individuals have never been vaccinated or exposed to H5N1 before in their lifetime. On homology blast search, it was found that there is only one residue change in the 73 amino acid long peptide between the HA of A/Vietnam/1203/2004 and the H1N1 (A/New Caledonia/20/99) showing 98% homology. So this peptide selection is probably due to antibodies generated following vaccination or infection due to the A/New Caledonia/20/99 strain that also cross-react with the corresponding peptide sequence in HA of A/Vietnam/1203/2004.

The results show that the sera obtained from individuals vaccinated with H5N1 subunit vaccine in MF59 adjuvant had a broader antibody response to HA1 than those vaccinated with the vaccine in alum or no adjuvant. In MF59, the neutralizing antibodies were predominantly associated with antibodies to HA1. Also a shift of antibody response was observed in individuals vaccinated with MF59 adjuvant vaccine compared to the no adjuvant or Alum adjuvant vaccine. An increase in antibody response to NA was also seen in those patients vaccinated with H5N1.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

The disclosure has been described with reference to various specific and preferred embodiments and techniques. However, it should be understood that many variations and modifications may be made while remaining within the spirit and scope of the disclosure.

TABLE 4

| Influenza Peptide Name | PEPTIDE SEQUENCE |
|---|---|
| PB2 571-596 | YNKMEFEPFQSLVPKAIKGQYSGFV |
| PB2 696-756 | LGKEDRRYGPALSINELSNLAKGEKANVLIGQGDVVLVMKRKRDSSILTDSQT ATKRIRM |

TABLE 4-continued

| Influenza Peptide Name | PEPTIDE SEQUENCE |
|---|---|
| PB1 918-948 | GLTANESGRLIDFLKDVMESMDKEEMEITT |
| PA 1720-1748 | EKPKFLPDLYDYKENRFIEIGVTRREVH |
| PA 2211-2231 | IESMIEAESSIKEKD |
| HA 2369-2424 | LVFAQKLPGNDNSAATLCLGHHAVPNRTMVKTITNDQIEVTNATELVQRGKT VESC |
| HA 2388-2408 | HAVPNGTIVKTITNDQIEV |
| HA 2391-2465 | AGPNGTIVKTITNDQIEVTNATELVLSSSTGGICDSPHQILDGENCTLINALLGD PQCDGFQNKKWDLFVERSK |
| HA 2634-2711 | SGKSSIMRSDAPIGKCNSECITPNGSIPNDKPFQNVNRITYGACPRYVKQNTLKL ATGMRNVPEKQTRGIFGAIAGFI |
| HA 2681-2717 | VKQNTLKLATGMRNVPEKQTRGIFGAIAGFIENGWE |
| HA 2772-2824 | SEVEGRIQDLEKYVEDTKIDLWSYNAELLVALENQHTIDLTDSEMNKLFERT |
| NP 2923-2941 | SGSRVDNHSLSDIKVMASQGTKRSYEQM |
| NP 2984-2997 | IQNSLTIEKMVLS |
| NP 3033-3064 | RELVLYDKKKIRRIWRQANNGDDATAGLTHIM |
| NP 3322-3363 | NTNQQRASAGQISTQPTFSVQRNLPFDKTTIMAAFTGNTEGRTSD |
| NP 3368-3392 | RAEIIRMMEGAKPEEVSFRGRGVFE |
| NP-NA 3398-3432 | PPKSDGSTSAAAAEAGVKMNPNQKIITIGSVFLTIS |
| NA 3415-3434 | PPKSDGSTRAAAAEAGVKMNPNQKIITIGSVSLTISTI |
| NA 3478-3498 | IVYLTNTTIEKEICPKLAEY |
| NA 3582-3626 | LGTKQVCIAWSSSSCHDGKAWLHVCVTGDDKNATASFIYNGRLVD |
| NA 3631-3669 | WSKEILRTQESECVCINGTCTVVMTDGSASGKADTKIL |
| NA 3754-3797 | NNEEGGHGVKGWAFDDGNDVWMGRTISEKLRSGYETFKVIEG |
| NA 3868-3881 | TYGTGSWPDGADINLMP |
| M1 3907-3943 | VETYVLSIVPSGPLKAEIAQRLEDVFAGKNTDLE |
| M1 4007-4119 | REITFHGAKEIALSYSAGALASCMGLIYNRMGAVTTESAFGLICATCEQIADSQ HKSHRQMVTTTNPLIRHENRMVLASTTAKAMEQMAGSSEQAAEAMEVASQA RQMVQAM |
| M1 4033-4084 | IYNRMGAVTTEVAFGLVCATCEQIADSQHRSHRQMVATTNPLIKHENRMVLA |
| M1 4101-4161 | AAEAMEVASQARQMVQAMRAIGTHPSSSTGLKNDLLENLRAYQKRMGVQM QRAKI |
| NS1 4291-4312 | KQVVDQELSDAPFLDRLRRDQ |
| NS1 4323-4360 | LHIKAATHVGKQIVEKILKEESDEALKMTMVSTPASRY |
| NS1 4456-4472 | PRGLEWNDNTVRVSKNLQ |
| H3-RPL-LIAV | LNPSRLEVNSGINPGPRHHGLHHARNSNRS |
| H5-HA-9-241 | LFAIVSLVKSDQICIGYHANNSTEQVDTIMEKNVTVTHAQDILEKKHNGKLCD LDGVKPLILRDCSVAGWLLGNPMCDEFINVPEWSYIVEKANPVNDLCYPGDF NDYEELKHLLSRINHFEKIQIIPKSSWSSHEASLGVSSACPYQGKSSFFRNVVWL IKKNSTYPTIKRSYNNTNQEDLLVLWGIHHPNDAAEQTKLYQNPTTYISVGTST LNQRLVPRIATRSKVNGQSGRMEFFWTILK |
| H5-HA-RPL-112 | LTAEKKGGFSS |
| H5-HA-RPL-408 | VIEPPYSWLHAP |
| H5-HA-RPL-161 | YTHMQDSRFSRL |

TABLE 4-continued

| Influenza Peptide Name | PEPTIDE SEQUENCE |
|---|---|
| H5-HA-RPL-486 | SLSPNPLIIIR |
| H5-HA-RPL-411 | SLSPKLIGSSLD |
| H5-HA-RPL-102 | LTAEKKKKKFFI |
| H5-HA-RPL-462 | SLSPKTMHHHQT |
| H5-HA-RPL-457 | FQTHMHHPFNQI |
| H5-HA-RPL-101 | LTAETQIQFFHH |
| H5-PB2-344-375 | EVLTGNLQTLKIRVHEGYEEFTMVGRRATAILR |
| H5-PB2-447-516 | QNWGIEPIDNVMGMIGILPDMTPSTEMSLRGVRVSKMGVDEYSSTERVVVSID RFLRVRDQRGNVLLSPE |
| H5-PB1-1290-1451 | TVIKNNMINNDLGPATAQMALQLFIKDYRYTYRCHRGDTQIQTRRSFELKKL WEQTRSKAGLLVSDGGPNLYNIRNLHIPEVCLKWELMDEDYQGRLCNPLNPF VSHKEIEVNNAVVMPAHGPAKSMEYDAVATTHSWIPKRNRSILNTSQRGILED EQMY |
| H5-PB1-1348-1361 | KAGLLVSDGGPNLY |
| H5-PB1-1420-1437 | DAVATTHSWIPKRNRSIL |
| H5-PB1-F2-1524-1598 | EQGQDTPWTQSTEHTNIQKRGSGQQTQRLEHPNSTRLMDHYLRIMSPVGTHK QIVYWKQWLSLKNPTQGSLKTR |
| H5-PB1-F2-1525-1572 | QGQDTPWTQSTEHTNIQKRGSGQQTQRLEHPNSTRLMDHYLRIMSPVG |
| H5-PB1-F2-1548-1608 | QTQRLEHPNSTRLMDHYLRIMSPVGTHKQIVYWKQWLSLKNPTQGSLKTRVL KRWKLFNKQ |
| H5-PB1-F2-1560-1592 | LMDHYLRIMSPVGTHKQIVYWKQWLSLKNPTQG |
| H5-PB1-F2-1570-1605 | PVGTHKQIVYWKQWLSLKNPTQGSLKTRVLKRWKLF |
| H5-PA-1852-1966 | EPNGCIEGKLSQMSKEVNARIEPFLKTTPRPLRLPDGPPCSQRSKFLLMDALKL SIEDPSHEGEGIPLYDAIKCMKTFFGWKEPNIVKPHEKGINPNYLLAWKQVLAE LQDIENE |
| H5-PA-2202-2251 | QSLQQIESMIEAESSVKEKDMTKEFFENKSETWPIGESPKGVEEGSIGKV |
| H5-HA-2365-2427 | VDTIMEKNVTVTHAQDILEKKHNGKLCDLDGVKPLILRDCSVAGWLLGNPMC DEFINVPEWS |
| H5-HA-2376-2659 | VTHAQDILEKKHNGKLCDLDGVKPLILRDCSVAGWLLGNPMCDEFINVPEWS YIVEKANPVNDLCYPGDFNDYEELKHLLSRINHFEKIQIIPKSSWSSHEASLGVS SACPYQGKSSFFRNVVWLIKKNSTYPTIKRSYNNTNQEDLLVLWGIHHPNDAA EQTKLYQNPTTYISVGTSTLNQRLVPRIATRSKVNGQSGRMEFFWTILKPNDAI NFESNGNFIAPEYAYKIVKKGDSTIMKSELEYGNCNTKCQTPMGAINSSMPFH NIHPLTIGECPKYVKSN |
| H5-HA-2339-2581 | VLLFAIVSLVKSDQICIGYHANNSTEQVDTIMEKNVTVTHAQDILEKKHNGKL CDLDGVKPLILRDCSVAGWLLGNPMCDEFINVPEWSYIVEKANPVNDLCYPG DFNDYEELKHLLSRINHFEKIQIIPKSSWSSHEASLGVSSACPYQGKSSFFRNVV WLIKKNSTYPTIKRSYNNTNQEDLLVLWGIHHPNDAAEQTKLYQNPTTYISVG TSTLNQRLVPRIATRSKVNGQSGRMEFFWT |
| H5-HA-2431-2453 | EKANPVNDLCYPGDFNDYEELKH |
| H5-HA-2436-2543 | NDYEELKHLLSRINHFEKIQIIPKSSWSSHEASLGVSSACPYQGKSSFFRNVVWL IKKNSTYPTIKRSYNNTNQEDLLVLWGIHHPNDAAEQTKLYQN |
| H5-HA-2452-2481 | KHLLSRINHFEKIQIIPKSSWSSHEASLGV |
| H5-HA-2517-2538 | TNQEDLLVLWGIHHPNDAAEQT |
| H5-HA-2520-2566 | EDLLVLWGIHHPNDAAEQTKLYQNPTTYISVGTSTLNQRLVPRIATR |
| H5-HA-2568-2649 | KVNGQSGRMEFFWTILKPNDAINFESNGNFIAPEYAYKIVKKGDSTIMKSELEY GNCNTKCQTPMGAINSSMPFHNIHPLTI |
| H5-HA-2682-2703 | LFGAIAGFIEGGWQGMVDGWYG |
| H5-HA-2686-2748 | IAGFIEGGWQGMVDGWYGYHHSNEQGSGYAADKESTQKAIDGVTNKVNSIID KMNTQFEAVGR |

TABLE 4-continued

| Influenza Peptide Name | PEPTIDE SEQUENCE |
|---|---|
| H5-HA-2695-2756 | QGMVDGWYGYHHSNEQGSGYAADKESTQKAIDGVTNKVNSIIDKMNTQFEA VGREFNNLERR |
| H5-HA-2703-2731 | GYHHSNEQGSGYAADKESTQKAIDGVTNK |
| H5-HA-2706-2808 | HSNEQGSGYAADKESTQKAIDGVTNKVNSIIDKMNTQFEAVGREFNNLERRIE NLNKKMEDGFLDVWTYNAELLVLMENERTLDFHDSNVKNLYDKVRLQLRD |
| H5-HA-2706-2843 | HSNEQGSGYAADKESTQKAIDGVTNKVNSIIDKMNTQFEAVGREFNNLERRIE NLNKKMEDGFLDVWTYNAELLVLMENERTLDFHDSNVKNLYDKVRLQLRD NAKELGNGCFEFYHKCDNECMESVRNGTYDYPQYS |
| H5-HA-2707-2753 | SNEQGSGYAADKESTQKAIDGVTNKVNSIIDKMNTQFEAVGREFNNL |
| H5-HA-2722-2762 | QKAIDGVTNKVNSIIDKMNTQFEAVGREFNNLERRIENLNK |
| H5-HA-2759-2814 | NLNKKMEDGFLDVWTYNAELLVLMENERTLDFHDSNVKNLYDKVRLQLRD NAKELG |
| H5-HA-2823-2866 | KCDNECMESVRNGTYDYPQYSEEARLKREEISGVKLESIGIYQI |
| H5-HA-2829-2864 | MESVRNGTYDYPQYSEEARLKREEISGVKLESIGIY |
| H5-HA-2838-2866 | DYPQYSEEARLKREEISGVKLESIGIYQI |
| H5-NP-2906-2929 | MASQGTKRSYEQMETGGERQNATE |
| H5-NP-2915-3011 | YEQMETGGERQNATEIRASVGRMVSGIGRFYIQMCTELKLSDYEGRLIQNSITI ERMVLSAFDERRNRYLEEHPSAGKDPKKTGGPIYRRRDGKWVR |
| H5-NP-2915-3068 | YEQMETGGERQNATEIRASVGRMVSGIGRFYIQMCTELKLSDYEGRLIQNSITI ERMVLSAFDERRNRYLEEHPSAGKDPKKTGGPIYRRRDGKWVRELILYDKEEI RRIWRQANNGEDATAGLTHLMIWHSNLNDATYQRTRALVRTGMDPRM |
| H5-NP-2939-3055 | SGIGRFYIQMCTELKLSDYEGRLIQNSITIERMVLSAFDERRNRYLEEHPSAGKD PKKTGGPIYRRRDGKWVRELILYDKEEIRRIWRQANNGEDATAGLTHLMIWH SNLNDATYQR |
| H5-NP-2955-3011 | SDYEGRLIQNSITIERMVLSAFDERRNRYLEEHPSAGKDPKKTGGPIYRRRDGK WVR |
| H5-NP-3197-3229 | EREGYSLVGIDPFRLLQNSQVFSLIRPNENPAH |
| H5-NP-3214-3261 | NSQVFSLIRPNENPAHKSQLVWMACHSAAFEDLRVSSFIRGTRVVPRG |
| H5-NP-3263-3305 | LSTRGVQIASNENMEAMDSNTLELRSRYWAIRTRSGGNTNQQR |
| H5-NP-3329-3399 | TIMAAFTGNTEGRTSDMRTEIIRMMESARPEDVSFQGRGVFELSDEKATNPIVP SFDMNNEGSYFFGDNAE |
| H5-NA-3431-3481 | QIGNMISIWVSHSIHTGNQHQSEPISNTNFLTEKAVASVKLAGNSSLCPIN |
| H5-NA-3469-3504 | VKLAGNSSLCPINGWAVYSKDNSIRIGSKGDVFVIR |
| H5-NA-3489-3530 | DNSIRIGSKGDVFVIREPFISCSHLECRTFFLTQGALLNDKH |
| H5-NA-3522-3541 | QGALLNDKHSNGTVKDRSPH |
| H5-NA-3541-3576 | HRTLMSCPVGEAPSPYNSRFESVAWSASACHDGTSW |
| H5-NA-3548-3613 | PVGEAPSPYNSRFESVAWSASACHDGTSWLTIGISGPDNGAVAVLKYNGIITDT IKSWRNNILRTQ |
| H5-NA-3618-3662 | ACVNGSCFTVMTDGPSNGQASHKIFKMEKGKVVKSVELDAPNYHY |
| H5-NA-3659-3689 | NYHYEECSCYPNAGEITCVCRDNWHGSNRPW |
| H5-NA-3676-3854 | CVCRDNWHGSNRPWVSFNQNLEYQIGYICSGVFGDNPRPNDGTGSCGPVSSN GAYGVKGFSFKYGNGVWIGRTKSTNSRSGFEMIWDPNGWTETDSSFSVKQDI VAITDWSGYSGSFVQHPELTGLDCIRPCFWVELIRGRPKESTIWTSGSSISFCGV NSDTVGWSWPDGAELPFTID |
| H5-NA-3704-3840 | CSGVFGDNPRPNDGTGSCGPVSSNGAYGVKGFSFKYGNGVWIGRTKSTNSRS GFEMIWDPNGWTETDSSFSVKQDIVAITDWSGYSGSFVQHPELTGLDCIRPCF WVELIRGRPKESTIWTSGSSISFCGVNSDTVG |

TABLE 4-continued

| Influenza Peptide Name | PEPTIDE SEQUENCE |
|---|---|
| H5-NA-3758-3809 | EMIWDPNGWTETDSSFSVKQDIVAITDWSGYSGSFVQHPELTGLDCIRPCFW |
| H5-NA-3821-3854 | TIWTSGSSISFCGVNSDTVGWSWPDGAELPFTID |
| H5-NA-3834-3854 | VNSDTVGWSWPDGAELPFTID |
| H5-M1-3859-3889 | MSLLTEVETYVLSIIPSGPLKAEIAQKLEDV |
| H5-M1-3859-4013 | MSLLTEVETYVLSIIPSGPLKAEIAQKLEDVFAGKNTDLEALMEWLKTRPILSPLTKGILGFVFTLTVPSERGLQRRRFVQNALNGNGDPNNMDRAVKLYKKLKREITFHGAKEVALSYSTGALASCMGLIYNRMGTVTTEVAFGLVCATCEQIA |
| H5-M1-3863-3909 | TEVETYVLSIIPSGPLKAEIAQKLEDVFAGKNTDLEALMEWLKTRPI |
| H5-M1-3866-3894 | ETYVLSIIPSGPLKAEIAQKLEDVFAGKN |
| H5-M1-3989-4048 | IYNRMGTVTTEVAFGLVCATCEQIADSQHRSHRQMATITNPLIRHENRMVLASTTAKAME |
| H5-M1-4002-4110 | FGLVCATCEQIADSQHRSHRQMATITNPLIRHENRMVLASTTAKAMEQMAGSSEQAAEAMEIANQARQMVQAMRTIGTHPNSSAGLRDNLLENLQAYQKRMGVQMQRFK |
| H5-M1-4040-4104 | ASTTAKAMEQMAGSSEQAAEAMEIANQARQMVQAMRTIGTHPNSSAGLRDNLLENLQAYQKRMGV |
| H5-M1-4054-4110 | SEQAAEAMEIANQARQMVQAMRTIGTHPNSSAGLRDNLLENLQAYQKRMGVQMQRFK |
| H5-M1-4080-4109 | HPNSSAGLRDNLLENLQAYQKRMGVQMQRF |
| H5-M2-4115-4137 | SLLTEVETPTRNEWECRCSDSSD |
| H5-M2-4181-4209 | VPESMREEYRQEQQSAVDVDDGHFVNIEL |
| H5-NS1-4220-4284 | SSFQVDCFLWHVRKRFADQELGDAPFLDRLRRDQKSLRGRGNTLGLDIETATRAGKQIVERILEG |
| H5-NS1-4236-4255 | ADQELGDAPFLDRLRRDQKS |
| H5-NS1-4283-4294 | EGESDKALKMPA |
| H5-NS1-4378-4397 | TGEDVKNAIGVLIGGLEWND |
| H5-NS1-4393-4428 | LEWNDNTVRVTETIQRFAWRNSDEDGRLPLPPNQKR |
| H5-NS2-4468-4509 | SLKLYRDSLGETVMRMGDFHSLQIRNGKWREQLSQKFEEIRW |
| 348-H5-HA-RPL | WTPIHLTTKVTL |
| 368-H5-HA-RPL | WSYSWFYNTSYE |
| A2.19-RPL-227 | VWNPYIWSAPFS |
| A2.19-RPL-121 | GVWPNATHFPSS |
| 21E12-RPL-315 | WWDTPHSWWTMR |
| 3F3-RPL-108 | WGLFGVSPHVQS |
| 3F3-RPL-101 | QARWPVTSPYWP |
| H5-HA-47-338 | AQDILEKKHNGKLCDLDGVKPLILRDCSVAGWLLGNPMCDEFINVPEWSYIVEKANPVNDLCYPGDFNDYEELKHLLSRINHFEKIQIIPKSSWSSHEASLGVSSACPYQGKSSFFRNVVWLIKKNSTYPTIKRSYNNTNQEDLLVLWGIHHPNDAAEQTKLYQNPTTYISVGTSTLNQRLVPRIATRSKVNGQSGRMEFFWTILKPNDAINFESNGNFIAPEYAYKIVKKGDSTIMKSELEYGNCNTKCQTPMGAINSSMPFHNIHPLTIGECPKYVKSNRLVLATGLRNS |
| H5-HA-2627-2669 | KCQTPMGAINSSMPFHNIHPLTIGECPKYVKSNRLVLATGLRN |
| H5-HA-2642-2685 | HNIHPLTIGECPKYVKSNRLVLATGLRNSPQRERRRKKRGLFGA |

TABLE 5

FREQUENCY OF SELECTED PHAGE CLONES WITH H5N1 EXPOSED SURVIVORS USING H5N1 GENE-FRAGMENT PHAGE DISPLAY LIBARIES

| Influenza Peptide Name | PEPTIDE SEQUENCE | FRE-QUENCY |
|---|---|---|
| H5-PB2-344-375 | EVLTGNLQTLKIRVHEGYEEFTMVGRRATAILR (SEQ ID NO: 42) | 9 |
| H5-PB2-447-516 | QNWGIEPIDNVMGMIGILPDMTPSTEMSLRGVRVSKMGVDEYSSTERVVVSIDRFLRVRDQRGNVLLSPE (SEQ ID NO: 43) | 2 |
| H5-PB1-1290-1451 | TVIKNNMINNDLGPATAQMALQLFIKDYRYTYRCHRGDTQIQTRRSFELKKLWEQTRSKAGLLVSDGGPNLYN IRNLHIPEVCLKWELMDEDYQGRLCNPLNPFVSHKEIEVNNAVVMPAHGPAKSMEYDAVATTHSWIPKRNRSI LNTSQRGILEDEQMY (SEQ ID NO: 44) | 2 |
| H5-PB1-1348-1361 | KAGLLVSDGGPNLY (SEQ ID NO: 45) | 7 |
| H5-PB1-1420-1437 | DAVATTHSWIPKRNRSIL (SEQ ID NO: 46) | 6 |
| H5-PB1-F2-1524-1598 | EQGQDTPWTQSTEHTNIQKRGSGQQTQRLEHPNSTRLMDHYLRIMSPVGTHKQIVYWKQWLSLKNPTQGSLKTR (SEQ ID NO: 47) | 13 |
| H5-PB1-F2-1525-1572 | QGQDTPWTQSTEHTNIQKRGSGQQTQRLEHPNSTRLMDHYLRIMSPVG (SEQ ID NO: 48) | 5 |
| H5-PB1-F2-1548-1608 | QTQRLEHPNSTRLMDHYLRIMSPVGTHKQIVYWKQWLSLKNPTQGSLKTRVLKRWKLFNKQ (SEQ ID NO: 49) | 4 |
| H5-PB1-F2-1560-1592 | LMDHYLRIMSPVGTHKQIVYWKQWLSLKNPTQG (SEQ ID NO: 50) | 6 |
| H5-PB1-F2-1570-1605 | PVGTHKQIVYWKQWLSLKNPTQGSLKTRVLKRWKLF (SEQ ID NO: 51) | 7 |
| H5-PA-1852-1966 | EPNGCIEGKLSQMSKEVNARIEPFLKTTPRPLRLPDGPPCSQRSKFLLMDALKLSIEDPSHEGEGIPLYDAIK CMKTFFGWKEPNIVKPHEKGINPNYLLAWKQVLAELQDIENE (SEQ ID NO: 52) | 3 |
| H5-PA-1904-1927 | KLSIEDPSHEGEGIPLYDAIKCMK (SEQ ID NO: 148) | 1 |
| H5-PA-1945-1973 | INPNYLLAWKQVLAELQDIENEEKIPKTK (SEQ ID NO: 149) | 1 |
| H5-PA-2202-2251 | QSLQQIESMIEAESSVKEKDMTKEFFENKSETWPIGESPKGVEEGSIGKV (SEQ ID NO: 53) | 8 |
| H5-HA-2349-2389 | KSDQICIGYHANNSTEQVDTIMEKNVTVTHAQDILEKKHNG(SEQ ID NO: 150) | 1 |
| H5-HA-2365-2427 | VDTIMEKNVTVTHAQDILEKKHNGKLCDLDGVKPLILRDCSVAGWLLGNPMCDEFINVPEWS (SEQ ID NO: 54) | 9 |
| H5-HA-2376-2659 | VTHAQDILEKKHNGKLCDLDGVKPLILRDCSVAGWLLGNPMCDEFINVPEWSYIVEKANPVNDLCYPGDFNDY EELKHLLSRINHFEKIQIIPKSSWSSHEASLGVSSACPYQGKSSFFRNVVWLIKKNSTYPTIKRSYNNTNQED LLVLWGIHHPNDAAEQTKLYQNPTTYISVGTSTLNQRLVPRIATRSKVNGQSGRMEFFWTILKPNDAINFESN GNFIAPEYAYKIVKKGDSTIMKSELEYGNCNTKCQTPMGAINSSMPFHNIHPLTIGECPKYVKSN (SEQ ID NO: 55) | 17 |
| H5-HA-2339-2581 | VLLFAIVSLVKSDQICIGYHANNSTEQVDTIMEKNVTVTHAQDILEKKHNGKLCDLDGVKPLILRDCSVAGWL LGNPMCDEFINVPEWSYIVEKANPVNDLCYPGDFNDYEELKHLLSRINHFEKIQIIPKSSWSSHEASLGVSSA CPYQGKSSFFRNVVWLIKKNSTYPTIKRSYNNTNQEDLLVLWGIHHPNDAAEQTKLYQNPTTYISVGTSTLNQ RLVPRIATRSKVNGQSGRMEFFWT (SEQ ID NO: 56) | 13 |
| H5-HA-2431-2453 | EKANPVNDLCYPGDFNDYEELKH (SEQ ID NO: 57) | 36 |
| H5-HA-2436-2543 | NDYEELKHLLSRINHFEKIQIIPKSSWSSHEASLGVSSACPYQGKSSFFRNVVWLIKKNSTYPTIKRSYNNTN QEDLLVLWGIHHPNDAAEQTKLYQN (SEQ ID NO: 58) | 3 |
| H5-HA-2452-2481 | KHLLSRINHFEKIQIIPKSSWSSHEASLGV (SEQ ID NO: 59) | 26 |
| H5-HA-2484-2514 | ACPYQGKSSFFRNVVWLIKKNSTYPTIKRSY (SEQ ID NO: 152) | 1 |
| H5-HA-2517-2538 | TNQEDLLVLWGIHHPNDAAEQT (SEQ ID NO: 60) | 16 |
| H5-HA-2520-2566 | EDLLVLWGIHHPNDAAEQTKLYQNPTTYISVGTSTLNQRLVPRIATR (SEQ ID NO: 61) | 9 |
| H5-HA-2568-2649 | KVNGQSGRMEFFWTILKPNDAINFESNGNFIAPEYAYKIVKKGDSTIMKSELEYGNCNTKCQTPMGAINSSMP FHNIHPLTI (SEQ ID NO: 62) | 4 |
| H5-HA-2603-2637 | AYKIVKKGDSTIMKSELEYGNCNTKCQTPMGAINS (SEQ ID NO: 153) | 3 |
| H5-HA-2614-2639 | IMKSELEYGNCNTKCQTPMGAINSSM (SEQ ID NO: 154) | 1 |
| H5-HA-2627-2669 | KCQTPMGAINSSMPFHNIHPLTIGECPKYVKSNRLVLATGLRN (SEQ ID NO: 155) | 17 |
| H5-HA-2632-2651 | MGAINSSMPFHNIHPLTIGE (SEQ ID NO: 156) | 2 |
| H5-HA-2642-2685 | HNIHPLTIGECPKYVKSNRLVLATGLRNSPQRERRRKKRGLFGA (SEQ ID NO: 157) | 9 |

TABLE 5-continued

FREQUENCY OF SELECTED PHAGE CLONES WITH H5N1 EXPOSED SURVIVORS USING H5N1 GENE-FRAGMENT PHAGE DISPLAY LIBARIES

| Influenza Peptide Name | PEPTIDE SEQUENCE | FREQUENCY |
|---|---|---|
| H5-HA-2648-2670 | TIGECPKYVKSNRLVLATGLRNS (SEQ ID NO: 158) | 2 |
| H5-HA-2682-2703 | LFGAIAGFIEGGWQGMVDGWYG (SEQ ID NO: 63) | 13 |
| H5-HA-2686-2748 | IAGFIEGGWQGMVDGWYGYHHSNEQGSGYAADKESTQKAIDGVTNKVNSIIDKMNTQFEAVGR (SEQ ID NO: 64) | 4 |
| H5-HA-2695-2756 | QGMVDGWYGYHHSNEQGSGYAADKESTQKAIDGVTNKVNSIIDKMNTQFEAVGREFNNLERR (SEQ ID NO: 65) | 34 |
| H5-HA-2703-2731 | GYHHSNEQGSGYAADKESTQKAIDGVTNK (SEQ ID NO: 66) | 26 |
| H5-HA-2703-2753 | GYHHSNEQGSGYAADKESTQKAIDGVTNKVNSIIDKMNTQFEAVGREFNNL (SEQ ID NO: 186) | 3 |
| H5-HA-2706-2808 | HSNEQGSGYAADKESTQKAIDGVTNKVNSIIDKMNTQFEAVGREFNNLERRIENLNKKMEDGFLDVWTYNAELLVLMENERTLDFHDSNVKNLYDKVRLQLRD (SEQ ID NO: 67) | 36 |
| H5-HA-2706-2843 | HSNEQGSGYAADKESTQKAIDGVTNKVNSIIDKMNTQFEAVGREFNNLERRIENLNKKMEDGFLDVWTYNAELLVLMENERTLDFHDSNVKNLYDKVRLQLRDNAKELGNGCFEFYHKCDNECMESVRNGTYDYPQYS (SEQ ID NO: 68) | 19 |
| H5-HA-2707-2753 | SNEQGSGYAADKESTQKAIDGVTNKVNSIIDKMNTQFEAVGREFNNL (SEQ ID NO: 69) | 17 |
| H5-HA-2707-2786 | SNEQGSGYAADKESTQKAIDGVTNKVNSIIDKMNTQFEAVGREFNNLERRIENLNKKMEDGFLDVWTYNAELLVLMENER (SEQ ID NO: 159) | 4 |
| H5-HA-2709-2727 | EQGSGYAADKESTQKAIDG (SEQ ID NO: 160) | 1 |
| H5-HA-2711-2730 | GSGYAADKESTQKAIDGVTN (SEQ ID NO: 161) | 6 |
| H5-HA-2716-2791 | ADKESTQKAIDGVTNKVNSIIDKMNTQFEAVGREFNNLERRIENLNKKMEDGFLDVWTYNAELLVLMENERTLDFH (SEQ ID NO: 162) | 3 |
| H5-HA-2722-2749 | QKAIDGVTNKVNSIIDKMNTQFEAVGRE (SEQ ID NO: 163) | 8 |
| H5-HA-2724-2756 | AIDGVTNKVNSIIDKMNTQFEAVGREFNNLERR (SEQ ID NO: 164) | 12 |
| H5-HA-2722-2762 | QKAIDGVTNKVNSIIDKMNTQFEAVGREFNNLERRIENLNK (SEQ ID NO: 70) | 9 |
| H5-HA-2729-2750 | TNKVNSIIDKMNTQFEAVGREF (SEQ ID NO: 165) | 5 |
| H5-HA-2759-2814 | NLNKKMEDGFLDVWTYNAELLVLMENERTLDFHDSNVKNLYDKVRLQLRDNAKELG (SEQ ID NO: 71) | 54 |
| H5-HA-2805-2860 | QLRDNAKELGNGCFEFYHKCDNECMESVRNGTYDYPQYSEEARLKREEISGVKLES (SEQ ID NO: 166) | 2 |
| H5-HA-2805-2828 | QLRDNAKELGNGCFEFYHKCDNEC (SEQ ID NO: 167) | 1 |
| H5-HA-2823-2866 | KCDNECMESVRNGTYDYPQYSEEARLKREEISGVKLESIGIYQI (SEQ ID NO: 72) | 172 |
| H5-HA-2829-2864 | MESVRNGTYDYPQYSEEARLKREEISGVKLESIGIY (SEQ ID NO: 73) | 32 |
| H5-HA-2838-2866 | DYPQYSEEARLKREEISGVKLESIGIYQI (SEQ ID NO: 74) | 154 |
| H5-NP-2906-2929 | MASQGTKRSYEQMETGGERQNATE (SEQ ID NO: 75) | 8 |
| H5-NP-2915-3011 | YEQMETGGERQNATEIRASVGRMVSGIGRFYIQMCTELKLSDYEGRLIQNSITIERMVLSAFDERRNRYLEEHPSAGKDPKKTGGPIYRRRDGKWVR (SEQ ID NO: 76) | 13 |
| H5-NP-2915-3068 | YEQMETGGERQNATEIRASVGRMVSGIGRFYIQMCTELKLSDYEGRLIQNSITIERMVLSAFDERRNRYLEEHPSAGKDPKKTGGPIYRRRDGKWVRELILYDKEEIRRIWRQANNGEDATAGLTHLMIWHSNLNDATYQRTRALVRTGMDPRM (SEQ ID NO: 77) | 3 |
| H5-NP-2939-3055 | SGIGRFYIQMCTELKLSDYEGRLIQNSITIERMVLSAFDERRNRYLEEHPSAGKDPKKTGGPIYRRRDGKWVRELILYDKEEIRRIWRQANNGEDATAGLTHLMIWHSNLNDATYQR (SEQ ID NO: 78) | 6 |
| H5-NP-2955-3011 | SDYEGRLIQNSITIERMVLSAFDERRNRYLEEHPSAGKDPKKTGGPIYRRRDGRWVR (SEQ ID NO: 79) | 26 |
| H5-NP-2964-3022 | NSITIERMVLSAFDERRNRYLEEHPSAGKDPKKTGGPIYRRRDGKWVRELILYDKEEIR (SEQ ID NO: 168) | 11 |
| H5-NP-3197-3229 | EREGYSLVGIDPFRLLQNSQVFSLIRPNENPAH (SEQ ID NO: 80) | 2 |
| H5-NP-3214-3261 | NSQVFSLIRPNENPAHKSQLVWMACHSAAFEDLRVSSFIRGTRVVPRG (SEQ ID NO: 81) | 3 |
| H5-NP-3263-3305 | LSTRGVQIASNENMEAMDSNTLELRSRYWAIRTRSGGNTNOQR (SEQ ID NO: 82) | 8 |

TABLE 5-continued

FREQUENCY OF SELECTED PHAGE CLONES WITH H5N1 EXPOSED SURVIVORS USING H5N1 GENE-FRAGMENT PHAGE DISPLAY LIBARIES

| Influenza Peptide Name | PEPTIDE SEQUENCE | FRE-QUENCY |
|---|---|---|
| H5-NP-3329-3399 | TIMAAFTGNTEGRTSDMRTEIIRMMESARPEDVSFQGRGVFELSDEKATNPIVPSFDMNNEGSYFFGDNAE (SEQ ID NO: 83) | 2 |
| H5-NP-3347-3385 | TEIIRMMESARPEDVSFQGRGVFELSDEKATNPIVPSFD (SEQ ID NO: 169) | 9 |
| H5-NA-3431-3481 | QIGNMISIWVSHSIHTGNQHQSEPISNTNFLTEKAVASVKLAGNSSLCPIN (SEQ ID NO: 84) | 7 |
| H5-NA-3453-3480 | EPISNTNFLTEKAVASVKLAGNSSLCPI (SEQ ID NO: 170) | 3 |
| H5-NA-3469-3504 | VKLAGNSSLCPINGWAVYSKDNSIRIGSKGDVFVIR (SEQ ID NO: 85) | 2 |
| H5-NA-3489-3530 | DNSIRIGSKGDVFVIREPFISCSHLECRTFFLTQGALLNDKH (SEQ ID NO: 86) | 11 |
| H5-NA-3522-3541 | QGALLNDKHSNGTVKDRSPH (SEQ ID NO: 87) | 1 |
| H5-NA-3541-3576 | HRTLMSCPVGEAPSPYNSRFESVAWSASACHDGTSW (SEQ ID NO: 88) | 9 |
| H5-NA-3548-3613 | PVGEAPSPYNSRFESVAWSASACHDGTSWLTIGISGPDNGAVAVLKYNGIITDTIKSWRNNILRTQ (SEQ ID NO: 89) | 1 |
| H5-NA-3578-3606 | TIGISGPDNGAVAVLKYNGIITDTIKSWR (SEQ ID NO: 171) | 2 |
| H5-NA-3618-3650 | ACVNGSCFTVMTDGPSNGQASHKIFKMEKGKVV (SEQ ID NO: 172) | 1 |
| H5-NA-3618-3662 | ACVNGSCFTVMTDGPSNGQASHKIFKMEKGKVVKSVELDAPNYHY (SEQ ID NO: 90) | 4 |
| H5-NA-3638-3662 | HKIFKMEKGKVVKSVELDAPNYHY (SEQ ID NO: 173) | 8 |
| H5-NA-3659-3689 | NYHYEECSCYPNAGEITCVCRDNWHGSNRPW (SEQ ID NO: 91) | 9 |
| H5-NA-3676-3854 | CVCRDNWHGSNRPWVSFNQNLEYQIGYICSGVFGDNPRPNDGTGSCGPVSSNGAYGVKGFSFKYGNGVWIGRTKSTNSRSGFEMIWDPNGWTETDSSFSVKQDIVAITDWSGYSGSFVQHPELTGLDCIRPCFWVELIRGRPKESTIWTSGSSISFCGVNSDTVGWSWPDGAELPFTID (SEQ ID NO: 92) | 39 |
| H5-NA-3703-3723 | ICSGVFGDNPRPNDGTGSCGP (SEQ ID NO: 174) | 2 |
| H5-NA-3704-3840 | CSGVFGDNPRPNDGTGSCGPVSSNGAYGVKGFSFKYGNGVWIGRTKSTNSRSGFEMIWDPNGWTETDSSFSVKQDIVAITDWSGYSGSFVQHPELTGLDCIRPCFWVELIRGRPKESTIWTSGSSISFCGVNSDTVG (SEQ ID NO: 93) | 23 |
| H5-NA-3758-3809 | EMIWDPNGWTETDSSFSVKQDIVAITDWSGYSGSFVQHPELTGLDCIRPCFW (SEQ ID NO: 94) | 2 |
| H5-NA-3821-3854 | TIWTSGSSISFCGVNSDTVGWSWPDGAELPFTID (SEQ ID NO: 95) | 4 |
| H5-NA-3834-3854 | VNSDTVGWSWPDGAELPFTID (SEQ ID NO: 96) | 19 |
| H5-M1-3859-3889 | MSLLTEVETYVLSIIPSGPLKAEIAQKLEDV (SEQ ID NO: 97) | 65 |
| H5-M1-3859-4013 | MSLLTEVETYVLSIIPSGPLKAEIAQKLEDVFAGKNTDLEALMEWLKTRPILSPLTKGILGFVFTLTVPSERGLQRRRFVQNALNGNGDPNNMDRAVKLYKKLKREITFHGAKEVALSYSTGALASCMGLIYNRMGTVTTEVAFGLVCATCEQIA (SEQ ID NO: 98) | 2 |
| H5-M1-3863-3909 | TEVETYVLSIIPSGPLKAEIAQKLEDVFAGKNTDLEALMEWLKTRPI (SEQ ID NO: 99) | 35 |
| H5-M1-3866-3894 | ETYVLSIIPSGPLKAEIAQKLEDVFAGKN (SEQ ID NO: 100) | 102 |
| H5-M1-3989-4048 | IYNRMGTVTTEVAFGLVCATCEQIADSQHRSHRQMATITNPLIRHENRMVLASTTAKAME (SEQ ID NO: 101) | 3 |
| H5-M1-4002-4110 | FGLVCATCEQIADSQHRSHRQMATITNPLIRHENRMVLASTTAKAMEQMAGSSEQAAEAMEIANQARQMVQAMRTIGTHPNSSAGLRDNLLENLQAYQKRMGVQMQRFK (SEQ ID NO: 102) | 10 |
| H5-M1-4012-4055 | IADSQHRSHRQMATITNPLIRHENRMVLASTTAKAMEQMAGSSE (SEQ ID NO: 175) | 5 |
| H5-M1-4040-4104 | ASTTAKAMEQMAGSSEQAAEAMEIANQARQMVQAMRTIGTHPNSSAGLRDNLLENLQAYQRMGV (SEQ ID NO: 103) | 174 |
| H5-M1-4050-4078 | MAGSSEQAAEAMEIANQARQMVQAMRTIG (SEQ ID NO: 176) | 2 |
| H5-M1-4054-4110 | SEQAAEAMEIANQARQMVQAMRTIGTHPNSSAGLRDNLLENLQAYQKRMGVQMQRFK (SEQ ID NO: 104) | 88 |
| H5-M1-4080-4109 | HPNSSAGLRDNLLENLQAYQKRMGVQMQRF (SEQ ID NO: 105) | 45 |
| H5-M2-4115-4123 | SLLTEVETP (SEQ ID NO: 187) | 37 |

TABLE 5-continued

FREQUENCY OF SELECTED PHAGE CLONES WITH H5N1 EXPOSED SURVIVORS USING H5N1 GENE-FRAGMENT PHAGE DISPLAY LIBRARIES

| Influenza Peptide Name | PEPTIDE SEQUENCE | FREQUENCY |
|---|---|---|
| H5-M2-4124-4138 | TRNEWECRCSDSSDP (SEQ ID NO: 188) | 29 |
| H5-M2-4181-4209 | VPESMREEYRQEQQSAVDVDDGHFVNIEL (SEQ ID NO: 107) | 17 |
| H5-NS1-4220-4284 | SSFQVDCFLWHVRKRFADQELGDAPFLDRLRRDQKSLRGRGNTLGLDIETATRAGKQIVERILEG (SEQ ID NO: 108) | 10 |
| H5-NS1-4236-4255 | ADQELGDAPFLDRLRRDQKS (SEQ ID NO: 109) | 6 |
| H5-NS1-4283-4294 | EGESDKALKMPA (SEQ ID NO: 110) | 1 |
| H5-NS1-4378-4397 | TGEDVKNAIGVLIGGLEWND (SEQ ID NO: 111) | 1 |
| H5-NS1-4393-4428 | LEWNDNTVRVTETIQRFAWRNSDEDGRLPLPPNQKR (SEQ ID NO: 112) | 5 |
| H5-NS2-4468-4509 | SLKLYRDSLGETVMRMGDFHSLQIRNGKWREQLSQKFEEIRW (SEQ ID NO: 113) | 5 |

TABLE 6

(SEQ ID NOS: 189-225)
Positions from 1 till 60

| Consensus sequence | ICKMEKIVLLLAIVSLVKSDQICIGYHANNSTEQVDTIMEKNVTVTHAQDILEKTHNGKL |
|---|---|
| ABD16284 A/Thailand/NK165/2005 (H5N1) | -----R....F................................................ |
| ABE01046 A/Egypt/2782-NAMRU3/2006 (H5N1) | ------------------------------------------------------------ |
| ABI36040 A/Indonesia/CDC184/2005 (H5N1) | ------------------------------------------------------------ |
| ABI36041 A/Indonesia/CDC194P/2005 (H5N1) | ------------------------------------------------------------ |
| ABI36044 A/Indonesia/CDC292N/2005 (H5N1) | ------------------------------------------------------------ |
| ABI36045 A/Indonesia/CDC292T/2005 (H5N1) | ------------------------------------------------------------ |
| ABI36046 A/Indonesia/CDC326N/2006 (H5N1) | ------------------------------------------------------------ |
| ABI36047 A/Indonesia/CDC326N2/2006 (H5N1) | ------------------------------------------------------------ |
| ABI36049 A/Indonesia/CDC326T/2006 (H5N1) | ------------------------------------------------------------ |
| ABI36056 A/Indonesia/CDC370T/2006 (H5N1) | ------------------------------------------------------------ |
| ABI36057 A/Indonesia/CDC390/2006 (H5N1) | ------------------------------------------------------------ |
| ABM90544 A/Indonesia/CDC1047S/2007 (H5N1) | ---........S................................................ |
| ABU53968 A/Egypt/2629-NAMRU3/2007 (H5N1) | ------------------------------------------------------------ |
| ABU53969 A/Egypt/2630-NAMRU3/2007 (H5N1) | ------------------------------------------------------------ |
| ABU53970 A/Egypt/2631-NAMRU3/2007 (H5N1) | ------------------------------------------------------------ |
| ABU53971 A/Egypt/2750-NAMRU3/2007 (H5N1) | ------------------------------------------------------------ |
| ABW74701 A/Indonesia/TLL001/2006 (H5N1) | ---......................................................... |
| ABW74704 A/Indonesia/TLL004/2006 (H5N1) | ---......................................................... |
| ABW74706 A/Indonesia/TLL006/2006 (H5N1) | ---......................................................... |
| ABW74707 A/Indonesia/TLL007/2006 (H5N1) | ---......................................................... |
| AAD52043 A/Hong Kong/485/97 (H5N1) | ---..........T.........................................R...... |
| ABI36198 A/Indonesia/CDC523/2006 (H5N1) | ---......................................................... |
| AAF74330 A/Hong Kong/483/97 (H5N1) | ---..........T.........................................R...... |
| AAF74331 A/Hong Kong/486/97 (H5N1) | ---..........T.........................................R...... |

TABLE 6-continued

| | |
|---|---|
| ABC72655 A/Thailand/676/2005 (H5N1) | ---.......F............................................ |
| ABE97626 A/Vietnam/CL17/2004 (H5N1) | -------------------------------------------------------- |
| ABE97633 A/Vietnam/CL119/2005 (H5N1) | ---.......F............................................ |

| Positions from 61 till 120 | |
|---|---|
| Consensus sequence | C DLDGVKPLILRDCSVAGWLLGNPMCDEFINVPEWSYIVEKANPANDLCYPGNFNDYEEL |
| ABD16284 A/Thailand/NK165/2005 (H5N1) | . .......................................P..........D....... |
| ABE01046 A/Egypt/2782-NAMRU3/2006 (H5N1) | . ...................................L.........I............ |
| A3I36040 A/Indonesia/CDC184/2005 (H5N1) | . ...................................T.........S............ |
| ABI36041 A/Indonesia/CDC194P/2005 (H5N1) | . ...................................T.G.......S............ |
| ABI36044 A/Indonesia/CDC292N/2005 (H5N1) | . ...................................T.........S............ |
| ABI36045 A/Indonesia/CDC292T/2005 (H5N1) | . ...................................T.........S............ |
| ABI36046 A/Indonesia/CDC326N/2006 (H5N1) | . ...................................T.........S............ |
| A5I36047 A/Indonesia/CDC326N2/2006 (H5N1) | . ...................................T.........S............ |
| ABI36049 A/Indonesia/CDC326T/2006 (H5N1) | . ...................................T.........S............ |
| ABI36056 A/Indonesia/CDC370T/2006 (H5N1) | . ...........K.......................T.........S............ |
| ABI36057 A/Indonesia/CDC390/2006 (H5N1) | . ...........K.......................T.........S............ |
| ABM90544 A/Indonesia/CDC1047S/2007 (H5N1) | . ...........K.......................T.........S............ |
| ABU53968 A/Egypt/2629-NAMRU3/2007 (H5N1) | . N.................................L.........I............ |
| ABU53969 A/Egypt/2630-NAMRU3/2007 (H5N1) | . ...................................L.........I............ |
| ABU53970 A/Egypt/2631-NAMRU3/2007 (H5N1) | . N.................................L.........I............ |
| ABU53971 A/Egypt/2750-NAMRU3/2007 (H5N1) | . ...................................L.........I.......D.... |
| ABW74701 A/Indonesia/TLL001/2006 (H5N1) | . ...................................T.........S............ |
| ABW74704 A/Indonesia/TLL004/2006 (H5N1) | . ......................T............T.........S............ |
| ABW74706 A/Indonesia/TLL006/2006 (H5N1) | . ...................................T.........S............ |
| ABW74707 A/Indonesia/TLL007/2006 (H5N1) | . ...................................T.........S............ |
| AAD52043 A/Hong Kong/485/97 (H5N1) | . ..N...............................S............ |
| ABI36198 A/Indonesia/CDC523/2006 (H5N1) | . ...................................T.........S............ |
| AAC32099 A/Hong Kong/483/97 (H5N1) | . ..N...............................S............ |
| AAC40508 A/Hong Kong/156/97 (H5N1) | . ..N...............................S............ |
| AAD21153 A/Hong Kong/486/97 (H5N1) | . ..N...............................S............ |
| ABE97624 A/Vietnam/CL01/2004 (H5N1) | . ............................................V.......D....... |
| ABE97628 A/Vietnam/CL26/2004 (H5N1) | . ............................................V.......D....... |
| ABE97629 A/Vietnam/CL36/2004 (H5N1) | . ............................................V.......D....... |
| ABE97630 A/Vietnam/CL100/2004 (H5N1) | . ...........K................................D.V........... |
| ABE97631 A/Vietnam/CL105/2005 (H5N1) | . ............................................V..V.......V.... |

| Positions from 121 till 180 | |
|---|---|
| Consensus sequence | KHLLSRINHFEKIAQIIPKSSWSDHEASSGVSSACPYQGRSSFFRNVVWLIKKNSTYPTI |
| ABD16284 A/Thailand/NK165/2005 (H5N1) | ................-...........S....V..........K.................... |
| ABE01046 A/Egypt/2782-NAMRU3/2006 (H5N1) | ................-..........................................DNA.... |
| ABI36040 A/Indonesia/CDC184/2005 (H5N1) | ................-..........................L.SP................. |

TABLE 6-continued

| | |
|---|---|
| ABI36041 A/Indonesia/CDC194P/2005 (H5N1) | ..............-..........L.SP............... |
| ABI36044 A/Indonesia/CDC292N/2005 (H5N1) | ..............-..........L.SP............... |
| ABI36045 A/Indonesia/CDC292T/2005 (H5N1) | ..............-..........L.SP............... |
| ABI36046 A/Indonesia/CDC326N/2006 (H5N1) | ..............-..........L.SP............... |
| ABI36047 A/Indonesia/CDC326N2/2006 (H5N1) | ..............-..........L.SP............... |
| ABI36049 A/Indonesia/CDC326T/2006 (H5N1) | ..............-..........L.SP............... |
| ABI36056 A/Indonesia/CDC370T/2006 (H5N1) | ..............-..........L.SP............... |
| ABI36057 A/Indonesia/CDC390/2006 (H5N1) | ..............-..........L.SP............... |
| ABM90544 A/Indonesia/CDC1047S/2007 (H5N1) | ..............-..........L.SP............... |
| ABU53968 A/Egypt/2629-NAMRU3/2007 (H5N1) | ..............-.....N....-............T..DNA.... |
| ABU53969 A/Egypt/2630-NAMRU3/2007 (H5N1) | ..............-..........................DNA.... |
| ABU53970 A/Egypt/2631-NAMRU3/2007 (H5N1) | ..............-.....N....-............T..DNA.... |
| ABU53971 A/Egypt/2750-NAMRU3/2007 (H5N1) | ..............-...........................NA.... |
| ABW74701 A/Indonesia/TLL001/2006 (H5N1) | ..............-..........L.S................ |
| ABW74704 A/Indonesia/TLL004/2006 (H5N1) | ..............-..........L.SP.....A......... |
| ABW74706 A/Indonesia/TLL006/2006(H5N1) | ..............-..........L.SP............... |
| ABW74707 A/Indonesia/TLL007/2006(H5N1) | ..............-..........L.SP............... |
| AAD52043 A/Hong Kong/485/97(H5N1) | ................-.......N.D....L...........S.... |
| ABI36198 A/Indonesia/CDC523/2006(H5N1) | ..............-..........L.SP............... |
| AAC32099 A/Hong Kong/483/97(H5N1) | .......S......-.......N.D....L.K............ |
| AAC40508 A/Hong Kong/156/97(H5N1) | ..............-.......N.D....L..........A.... |
| AAD21153 A/Hong Kong/486/97(H5N1) | ..............-.......N.D....L..........A.... |
| ABE97625 A/Vietnam/CL02/2004(H5N1) | ..............-........S....L.......E....... |
| ABE97627 A/Vietnam/CL20/2004(H5N1) | ..............-........S....L.......K....... |
| ABE97632 A/Vietnam/CL115/2005(H5N1) | ..............-........S....L...A......K....... |

| Positions from 181 till 240 | |
|---|---|
| Consensus sequence | KRSYNNTNQEDLLVLWGIHHPNDAAEQTRLYQNPTTYISVGTSTLNQRLVPKIATRSKVN |
| ABD16284 A/Thailand/NK165/2005(H5N1) | ...........................K.................R....... |
| ABE01046 A/Egypt/2782-NAMRU3/2006(H5N1) | ...................................................... |
| ABI36040 A/Indonesia/CDC184/2005(H5N1) | .K..............G.................I.................. |
| ABI36041 A/Indonesia/CDC194P/2005(H5N1) | .K.................................I.................. |
| ABI36044 A/Indonesia/CDC292N/2005(H5N1) | .K.................................I.................. |
| ABI36045 A/Indonesia/CDC292T/2005(H5N1) | .K.................................I.................. |
| ABI36046 A/Indonesia/CDC326N/2006(H5N1) | .K.................................I.................. |
| ABI36047 A/Indonesia/CDC326N2/2006(H5N1) | .K.................................I.................. |
| ABI36049 A/Indonesia/CDC326T/2006(H5N1) | .K.................................I.................. |
| ABI36056 A/Indonesia/CDC370T/2006(H5N1) | .K.................................I.................. |
| ABI36057 A/Indonesia/CDC390/2006(H5N1) | .E.................................I.................. |
| ABM90544 A/Indonesia/CDC1047S/2007(H5N1) | .K............NEE..................I.................. |
| ABU53968 A/Egypt/2629-NAMRU3/2007(H5N1) | |

TABLE 6-continued

| | |
|---|---|
| ABU53969 A/Egypt/2630-NAMRU3/2007(H5N1) | ................................................................ |
| ABU53970 A/Egypt/2631-NAMRU3/2007(H5N1) | ................................................................ |
| ABU53971 A/Egypt/2750-NAMRU3/2007(H5N1) | ................................................................ |
| ABW74701 A/Indonesia/TLL001/2006(H5N1) | .K..........................I................................... |
| ABW74704 A/Indonesia/TLL004/2006(H5N1) | .K..........................I................................... |
| ABW74706 A/Indonesia/TLL006/2006(H5N1) | .K..........................I................................... |
| ABW74707 A/Indonesia/TLL007/2006(H5N1) | .K..........................I............M...................... |
| AAD52043 A/Hong Kong/485/97(H5N1) | ..................................................E....P........ |
| ABI36198 A/Indonesia/CDC523/2006(H5N1) | .K................N.........I................................... |
| ABE97626 A/Vietnam/CL17/2004(H5N1) | ..............M...........K...............R..................... |
| ABE97633 A/Vietnam/CL119/2005(H5N1) | ..............M...........K...............R..................... |
| AAC32099 A/Hong Kong/483/97(H5N1) | ...........................K......................E....P........ |
| AAC40508 A/Hong Kong/156/97(H5N1) | ...............V...........K......................E....P........ |
| AAD21153 A/Hong Kong/486/97(H5N1) | ...........................K......................E....P........ |
| ABE97627 A/Vietnam/CL20/2004(H5N1) | ..............M...........K...............R..................... |
| ABE97632 A/Vietnam/CL115/2005(H5N1) | ..............M..........AK...............R..................... |
| ABE97634 A/Vietnam/CL2009/2005(H5N1) | ..............M..........AK...............R..................... |

| Positions from 241 till 300 | |
|---|---|
| Consensus sequence | GQSGRMEFFWTILKPNDAINFESNGNFIAPEYAYKIVKKGDSTIMKSELEYGNCNTPKCQ |
| ABD16284 A/Thailand/NK165/2005(H5N1) | ........................................................-... |
| ABE01046 A/Egypt/2782-NAMRU3/2006(H5N1) | ............S...............N................................ |
| ABI36040 A/Indonesia/CDC184/2005(H5N1) | ..........................................A.................-... |
| ABI36041 A/Indonesia/CDC194P/2005(H5N1) | ..........................................A.................-... |
| ABI36044 A/Indonesia/CDC292N/2005(H5N1) | ..............N...........................A..................... |
| ABI36045 A/Indonesia/CDC292T/2005(H5N1) | ..............N...........................A..................... |
| ABI36046 A/Indonesia/CDC326N/2006(H5N1) | ..............N...........................A.................-... |
| ABI36047 A/Indonesia/CDC326N2/2006(H5N1) | ..............N...........................A.................-... |
| ABI36049 A/Indonesia/CDC326T/2006(H5N1) | ..............N...........................A.................-... |
| ABI36056 A/Indonesia/CDC370T/2006(H5N1) | ...........................................A.................... |
| ABI36057 A/Indonesia/CDC390/2006(H5N1) | ...........................................A.................... |
| ABM90544 A/Indonesia/CDC1047S/2007(H5N1) | ...........................................A.......S....-... |
| ABU53968 A/Egypt/2629-NAMRU3/2007(H5N1) | ............S...............N............................-... |
| ABU53969 A/Egypt/2630-NAMRU3/2007(H5N1) | ............S...............N............................-... |
| ABU53970 A/Egypt/2631-NAMRU3/2007(H5N1) | ............S...............N............................-... |
| ABU53971 A/Egypt/2750-NAMRU3/2007(H5N1) | ............S.............................................-... |
| ABW74701 A/Indonesia/TLL001/2006(H5N1) | ...........................................A.................... |
| ABW74704 A/Indonesia/TLL004/2006(H5N1) | ...........................................A.................... |
| ABW74706 A/Indonesia/TLL006/2006(H5N1) | ...........................................A.................... |
| ABW74707 A/Indonesia/TLL007/2006(H5N1) | ...........................................A.................... |
| AAD52043 A/Hong Kong/485/97(H5N1) | .............................................................. |

TABLE 6-continued

| | |
|---|---|
| ABI36198 A/Indonesia/CDC523/2006(H5N1) | ................................................A...........-... |
| ABE97626 A/Vietnam/CL17/2004(H5N1) | ..............................................................-... |
| ABE97633 A/Vietnam/CL119/2005(H5N1) | ..............................................................-... |
| AAC32099 A/Hong Kong/483/97(H5N1) | .....I........................................................-... |
| AAC40508 A/Hong Kong/156/97(H5N1) | ..............................................................-... |
| AAD21153 A/Hong Kong/486/97(H5N1) | ..............................................................-... |
| ABE97625 A/Vietnam/CL02/2004(H5N1) | ..............................................................-... |
| ABE97627 A/Vietnam/CL20/2004(H5N1) | ..............................................................-... |
| ABE97632 A/Vietnam/CL115/2005(H5N1) | ..............................................................-... |

Positions from 301 till 360

| Consensus sequence | TPMGAIGAINSSMPFHNIHPLTIGECPKYVKSNRLVLATGLRNSPQRERRRKKRGLFGAI |
|---|---|
| ABD16284 A/Thailand/NK165/2005(H5N1) | ...----.....................................K.............. |
| ABE01046 A/Egypt/2782-NAMRU3/2006(H5N1) | ..I----..................I................G................ |
| ABI36040 A/Indonesia/CDC184/2005(H5N1) | ...----...........................................S........ |
| ABI36041 A/Indonesia/CDC194P/2005(H5N1) | ...----...........................................S........ |
| ABI36044 A/Indonesia/CDC292N/2005(H5N1) | ...----...........................................S........ |
| ABI36045 A/Indonesia/CDC292T/2005(H5N1) | ...----...........................................S........ |
| ABI36046 A/Indonesia/CDC326N/2006(H5N1) | ...----...........................................S........ |
| ABI36047 A/Indonesia/CDC326N2/2006(H5N1) | ...----...........................................S........ |
| ABI36049 A/Indonesia/CDC326T/2006(H5N1) | ...----...........................................S........ |
| ABI36056 A/Indonesia/CDC370T/2006(H5N1) | ...----...........................................S........ |
| ABI36057 A/Indonesia/CDC390/2006(H5N1) | ...----.........................K.................S........ |
| ABM90544 A/Indonesia/CDC1047S/2007(H5N1) | ...----.................S..........................S........ |
| ABU53968 A/Egypt/2629-NAMRU3/2007(H5N1) | ..I----....................................G................ |
| ABU53969 A/Egypt/2630-NAMRU3/2007(H5N1) | ..I----....................................G................ |
| ABU53970 A/Egypt/2631-NAMRU3/2007(H5N1) | ..I----....................................G................ |
| ABU53971 A/Egypt/2750-NAMRU3/2007(H5N1) | ..I----....................................G................ |
| ABW74701 A/Indonesia/TLL001/2006(H5N1) | ...----..............T..............................S........ |
| ABW74704 A/Indonesia/TLL004/2006(H5N1) | ...----...........................................S........ |
| ABW74706 A/Indonesia/TLL006/2006(H5N1) | ...----...........................................S........ |
| ABW74707 A/Indonesia/TLL007/2006(H5N1) | ...----...........................................S........ |
| AAD52043 A/Hong Kong/485/97(H5N1) | ...----..............................T...................... |
| ABI36198 A/Indonesia/CDC523/2006(H5N1) | ...----...........................................S........ |
| AAF74330 A/Hong Kong/483/97(H5N1) | ...----....................................A................ |
| AAF74331 A/Hong Kong/486/97(H5N1) | ...----..............................T...................... |
| ABC72655 A/Thailand/676/2005(H5N1) | ...----.....................................K.............. |
| ABE97626 A/Vietnam/CL17/2004(H5N1) | ...----...................................................... |
| ABE97633 A/Vietnam/CL119/2005(H5N1) | ...----...................................................... |

TABLE 6-continued

Positions from 361 till 420

| | |
|---|---|
| Consensus sequence | AGFIEGGWQGMVDGWYGYHHSNEQGSGYAADKESTQKAIDGVTNKVNSIIDKMNTQFEAV |
| ABD16284 A/Thailand/NK165/2005(H5N1) | ............................................................ |
| ABE01046 A/Egypt/2782-NAMRU3/2006(H5N1) | ............................................................ |
| ABI36040 A/Indonesia/CDC184/2005(H5N1) | ..................................................R......... |
| ABI36041 A/Indonesia/CDC194P/2005(H5N1) | ............................................................ |
| ABI36044 A/Indonesia/CDC292N/2005(H5N1) | ............................................................ |
| ABI36045 A/Indonesia/CDC292T/2005(H5N1) | ............................................................ |
| ABI36046 A/Indonesia/CDC326N/2006(H5N1) | ............................................................ |
| ABI36047 A/Indonesia/CDC326N2/2006(H5N1) | ............................................................ |
| ABI36049 A/Indonesia/CDC326T/2006(H5N1) | ............................................................ |
| ABI36056 A/Indonesia/CDC370T/2006(H5N1) | ............................................................ |
| ABI36057 A/Indonesia/CDC390/2006(H5N1) | ............................................................ |
| ABM90544 A/Indonesia/CDC1047S/2007(H5N1) | ............................................................ |
| ABU53968 A/Egypt/2629-NAMRU3/2007(H5N1) | ............................................................ |
| ABU53969 A/Egypt/2630-NAMRU3/2007(H5N1) | ............................................................ |
| ABU53970 A/Egypt/2631-NAMRU3/2007(H5N1) | ............................................................ |
| ABU53971 A/Egypt/2750-NAMRU3/2007(H5N1) | ....................................................N....... |
| ABW74701 A/Indonesia/TLL001/2006(H5N1) | ............................................................ |
| ABW74704 A/Indonesia/TLL004/2006(H5N1) | ............................................................ |
| ABW74706 A/Indonesia/TLL006/2006(H5N1) | ............................................................ |
| ABW74707 A/Indonesia/TLL007/2006(H5N1) | ............................................................ |
| AAD52043 A/Hong Kong/485/97(H5N1) | ......................Q.............................N....... |
| ABI36198 A/Indonesia/CDC523/2006(H5N1) | ............................................................ |
| AAF74330 A/Hong Kong/483/97(H5N1) | ......................Q.............................N....... |
| AAF74331 A/Hong Kong/486/97(H5N1) | ....................................................N....... |
| ABC72655 A/Thailand/676/2005(H5N1) | ............................................................ |
| ABE97626 A/Vietnam/CL17/2004(H5N1) | ............................................................ |
| ABE97633 A/Vietnam/CL119/2005(H5N1) | ............................................................ |

Positions from 421 till 480

| | |
|---|---|
| Consensus sequence | GREFNNLERRIENLNKKMEDGFLDVWTYNAELLVLMENERTLDFHDSNVKNLYDKVRLQL |
| ABD16284 A/Thailand/NK165/2005(H5N1) | ............................................................ |
| ABE01046 A/Egypt/2782-NAMRU3/2006(H5N1) | ............................................................ |
| ABI36040 A/Indonesia/CDC184/2005(H5N1) | ............................................................ |
| ABI36041 A/Indonesia/CDC194P/2005(H5N1) | ............................................................ |
| ABI36044 A/Indonesia/CDC292N/2005(H5N1) | ............................................................ |
| ABI36045 A/Indonesia/CDC292T/2005(H5N1) | ............................................................ |
| ABI36046 A/Indonesia/CDC326N/2006(H5N1) | ............................................................ |
| ABI36047 A/Indonesia/CDC326N2/2006(H5N1) | ............................................................ |
| ABI36049 A/Indonesia/CDC326T/2006(H5N1) | ............................................................ |

TABLE 6-continued

| | |
|---|---|
| ABI36056 A/Indonesia/CDC370T/2006(H5N1) | .....S...................................................... |
| ABI36057 A/Indonesia/CDC390/2006(H5N1) | ............................................................ |
| ABM90544 A/Indonesia/CDC1047S/2007(H5N1) | ............................................................ |
| ABU53968 A/Egypt/2629-NAMRU3/2007(H5N1) | ............................................................ |
| ABU53969 A/Egypt/2630-NAMRU3/2007(H5N1) | ............................................................ |
| ABU53970 A/Egypt/2631-NAMRU3/2007(H5N1) | ............................................................ |
| ABU53971 A/Egypt/2750-NAMRU3/2007(H5N1) | ............................................................ |
| ABW74701 A/Indonesia/TLL001/2006(H5N1) | ............................................................ |
| ABW74704 A/Indonesia/TLL004/2006(H5N1) | ............................................................ |
| ABW74706 A/Indonesia/TLL006/2006(H5N1) | ............................................................ |
| ABW74707 A/Indonesia/TLL007/2006(H5N1) | ............................................................ |
| AAD52043 A/Hong Kong/485/97(H5N1) | ............................................................ |
| ABI36198 A/Indonesia/CDC523/2006(H5N1) | ............................................................ |
| AAF74330 A/Hong Kong/483/97(H5N1) | ............................................................ |
| AAF74331 A/Hong Kong/486/97(H5N1) | ............................................................ |
| ABC72655 A/Thailand/676/2005(H5N1) | ............................................................ |
| ABE97626 A/Vietnam/CL17/2004(H5N1) | ............................................................ |
| ABE97633 A/Vietnam/CL119/2005(H5N1) | ............................................................ |

| Positions from 481 till 540 | |
|---|---|
| Consensus sequence | RDNAKELGNGCFEFYHKCDNECMESVRNGTYDYPQYSEEARLKREEISGVKLESIGTYQI |
| ABD16284 A/Thailand/NK165/2005(H5N1) | ........................................................I... |
| ABE01046 A/Egypt/2782-NAMRU3/2006(H5N1) | ...............R............................................ |
| ABI36040 A/Indonesia/CDC184/2005(H5N1) | .......................I.....N.............................. |
| ABI36041 A/Indonesia/CDC194P/2005(H5N1) | .......................I.....N.............................. |
| ABI36044 A/Indonesia/CDC292N/2005(H5N1) | .......................I.....N.............................. |
| ABI36045 A/Indonesia/CDC292T/2005(H5N1) | .......................I.....N.............................. |
| ABI36046 A/Indonesia/CDC326N/2006(H5N1) | .......................I.....N.............................. |
| ABI36047 A/Indonesia/CDC326N2/2006(H5N1) | .......................I.....N.............................. |
| ABI36049 A/Indonesia/CDC326T/2006(H5N1) | .......................I.....N.............................. |
| ABI36056 A/Indonesia/CDC370T/2006(H5N1) | .......................I.....N.............................. |
| ABI36057 A/Indonesia/CDC390/2006(H5N1) | .......................I.....N.............................. |
| ABM90544 A/Indonesia/CDC1047S/2007(H5N1) | .......................I.....N.............................. |
| ABU53968 A/Egypt/2629-NAMRU3/2007(H5N1) | ...............R............................................ |
| ABU53969 A/Egypt/2630-NAMRU3/2007(H5N1) | ...............R............................................ |
| ABU53970 A/Egypt/2631-NAMRU3/2007(H5N1) | ...............R............................................ |
| ABU53971 A/Egypt/2750-NAMRU3/2007(H5N1) | ...............R........................................I... |
| ABW74701 A/Indonesia/TLL001/2006(H5N1) | ....................I..I.....N.............................. |
| ABW74704 A/Indonesia/TLL004/2006(H5N1) | .......................I.....N.............................. |
| ABW74706 A/Indonesia/TLL006/2006(H5N1) | .......................I.....N.............................. |
| ABW74707 A/Indonesia/TLL007/2006(H5N1) | .......................I.....N.............................. |

TABLE 6-continued

| | |
|---|---|
| AAD52043 A/Hong Kong/485/97(H5N1) | ...........................K...............N...........M..... |
| ABI36198 A/Indonesia/CDC523/2006(H5N1) | ...........................I.....N........................... |
| AAF74330 A/Hong Kong/483/97(H5N1) | ...........................K...............N...........M..... |
| AAF74331 A/Hong Kong/486/97(H5N1) | ...........................K...............N...........M..... |
| ABC72655 A/Thailand/676/2005(H5N1) | .............................................................I... |
| ABE97626 A/Vietnam/CL17/2004(H5N1) | .............................................................I... |
| ABE97633 A/Vietnam/CL119/2005(H5N1) | .............................................................I... |

Positions from 541 till 583

| Consensus sequence | LSIYSTVASSLALAIMVAGLSLWMCSNGSLQCRICIKFCEDRL |
|---|---|
| ABD16284 A/Thailand/NK165/2005(H5N1) | .......................................LES.-- |
| ABE01046 A/Egypt/2782-NAMRU3/2006(H5N1) | .....................F.............----------- |
| ABI36040 A/Indonesia/CDC184/2005(H5N1) | ................M...................------- |
| ABI36041 A/Indonesia/CDC194P/2005(H5N1) | ................M...................------- |
| ABI36044 A/Indonesia/CDC292N/2005(H5N1) | ................M...................------- |
| ABI36045 A/Indonesia/CDC292T/2005(H5N1) | ................M...................------- |
| ABI36046 A/Indonesia/CDC326N/2006(H5N1) | ................M...................------- |
| ABI36047 A/Indonesia/CDC326N2/2006(H5N1) | ................M...................------- |
| ABI36049 A/Indonesia/CDC326T/2006(H5N1) | ................M...................------- |
| ABI36056 A/Indonesia/CDC370T/2006(H5N1) | ................I...................------- |
| ABI36057 A/Indonesia/CDC390/2006(H5N1) | ................I...................------- |
| ABM90544 A/Indonesia/CDC1047S/2007(H5N1) | ................I...................------- |
| ABU53968 A/Egypt/2629-NAMRU3/2007(H5N1) | .....................F.............---------- |
| ABU53969 A/Egypt/2630-NAMRU3/2007(H5N1) | .....................F.............---------- |
| ABU53970 A/Egypt/2631-NAMRU3/2007(H5N1) | .....................F.............---------- |
| ABU53971 A/Egypt/2750-NAMRU3/2007(H5N1) | .....................F.............---------- |
| ABW74701 A/Indonesia/TLL001/2006(H5N1) | ................M...................------- |
| ABW74704 A/Indonesia/TLL004/2006(H5N1) | ................I...................------- |
| ABW74706 A/Indonesia/TLL006/2006(H5N1) | ................M...................------- |
| ABW74707 A/Indonesia/TLL007/2006(H5N1) | ................I...................------- |
| AAD52043 A/Hong Kong/485/97(H5N1) | ...................................-------------------- |
| ABI36198 A/Indonesia/CDC523/2006(H5N1) | ................I...................------- |
| AAF74330 A/Hong Kong/483/97(H5N1) | ..L................................-------------------- |
| AAF74331 A/Hong Kong/486/97(H5N1) | ...................................-------------------- |
| ABC72655 A/Thailand/676/2005(H5N1) | ...................................------- |
| ABE97626 A/Vietnam/CL17/2004(H5N1) | ...................................-------------------- |
| ABE97633 A/Vietnam/CL119/2005(H5N1) | ...................................----------- |

TABLE 7

(SEQ ID NOS: 226-244)

Positions from 1 till 60

| | Consensus sequence | IFLREQKQEFKMNPNQKIITIGSICMVIGIVSLMLQIGNMDISIWGVSHSIQTGNQHQAE |
|---|---|---|
| ABC72646 | A/Thailand/676/2005(H5N1) | -----------....K.........T.M.........L-....-....H....QK.. |
| ABI36200 | A/Indonesia/CDC523/2006(H5N1) | -----------..................-...-....K....... |
| ABI36347 | A/Indonesia/CDC624/2006(H5N1) | -----------..................-...-....V....... |
| ABI36380 | A/Indonesia/CDC634/2006(H5N1) | -----------..................-...-....T.K..... |
| ABI49409 | A/Indonesia/CDC742/2006(H5N1) | -----------....R.........M.................... |
| ABJ98530 | A/Thailand/RPNP/2005(H5N1) | -------.......K.........T.M.........L-....-L.R..H....QK.. |
| ABM90513 | A/Indonesia/CDC1046/2007(H5N1) | -----------..................-...-............ |
| ABU80632 | A/Anhui/T2/2006(H5N1) | --------------------------------------...R... |
| AAC32089 | A/Hong Kong/156/97(H5N1) | -----------......V..I........I-..V.-....I...WHPN.P. |
| AAD16788 | A/Hong Kong/486/97(H5N1) | -----------......V..IN.......T-..V.-....I.K.WHPN.P. |
| AAD16799 | A/Hong Kong/514/97(H5N1) | -----------......V..I........I-..V.-....I...WHPN.P. |
| AAS89006 | A/Thailand/4(SP-528)/2004(H5N1) | -----------....K.........T.M.........L-.....H.....K.. |
| AAV73978 | A/Viet Nam/DN-33/2004(H5N1) | ------------------------------------------------------------ |
| AAZ72720 | A/Viet Nam/BL-014/2005(H5N1) | ------------------T........V...-....H........ |
| AAZ72721 | A/Viet Nam/DT-036/2005(H5N1) | ------------------T........V............N..... |
| ABI34143 | A/Guangzhou/1/2006(H5N1) | --------------------------------------------VG |
| ABI36014 | A/Indonesia/CDC7/2005(H5N1) | -----------..................-...-............ |
| ABI36084 | A/Indonesia/CDC292N/2005(H5N1) | -----------..................-...-............ |

Positions from 61 till 120

| | Consensus sequence | PCNQSIITYENNTWVNQTYVNISNTNFLTEKAVASVTLAGNSSLCPIRGWAVYSKDNSIR |
|---|---|---|
| ABC72646 | A/Thailand/676/2005(H5N1) | .-------------------.............K.........N............ |
| ABI36200 | A/Indonesia/CDC523/2006(H5N1) | S-------------------.............P.........H....N.. |
| ABI36347 | A/Indonesia/CDC624/2006(H5N1) | S-------------------.............P.........H....N.. |
| ABI36380 | A/Indonesia/CDC634/2006(H5N1) | S-------------------.............P.........H....N.. |
| ABI49409 | A/Indonesia/CDC742/2006(H5N1) | S-------------------.............P.........H....N.. |
| ABJ98530 | A/Thailand/RPNP/2005(H5N1) | .-------------------.............K.........N............ |
| ABM90513 | A/Indonesia/CDC1046/2007(H5N1) | S-------------------.............P.....V...H....N.. |
| ABU80632 | A/Anhui/T2/2006(H5N1) | .--------------------V...K..................S...H.. |
| AAC32089 | A/Hong Kong/156/97(H5N1) | .-------------------NQSI..Y..Q.A.............S...I.. |
| AAD16788 | A/Hong Kong/486/97(H5N1) | .-------------------NQSI..Y..Q.A.............S...I.. |
| AAD16799 | A/Hong Kong/514/97(H5N1) | .-------------------NQSI..Y..Q.A.............S...I....K... |
| AAS89006 | A/Thailand/4(SP-528)/2004(H5N1) | .-------------------.............K.........N............ |
| AAV73978 | A/Viet Nam/DN-33/2004(H5N1) | ------------------------------------------------------------ |
| AAZ72720 | A/Viet Nam/BL-014/2005(H5N1) | .-------------------.............K.........N............ |
| AAZ72721 | A/Viet Nam/DT-036/2005(H5N1) | .-------------------........A....K.........N............ |
| ABI34143 | A/Guangzhou/1/2006(H5N1) | .-----------------------------------................H....... |
| ABI36014 | A/Indonesia/CDC7/2005(H5N1) | S-------------------.............P.........H....N.. |

TABLE 7-continued

| ABI36084 | A/Indonesia/CDC292N/2005(H5N1) | S---------------------.....P.......................H....N.. |

| Positions from 121 till 180 |||
|---|---|---|
| | Consensus sequence | IGSKGDVFVIREPFISCSHLECRTFFLTQGALLNDKHSNGTVKDRSPHRTLMSCPVGEAP |
| ABC72646 | A/Thailand/676/2005(H5N1) | ...........................................S............... |
| ABI36200 | A/Indonesia/CDC523/2006(H5N1) | ............................................................ |
| ABI36347 | A/Indonesia/CDC624/2006(H5N1) | ............................................................ |
| ABI36380 | A/Indonesia/CDC634/2006(H5N1) | ............................................................ |
| ABI49409 | A/Indonesia/CDC742/2006(H5N1) | ............................................................ |
| ABJ98530 | A/Thailand/RPNP/2005(H5N1) | ...........................................S............... |
| ABM90513 | A/Indonesia/CDC1046/2007(H5N1) | ............................................................ |
| ABU80632 | A/Anhui/T2/2006(H5N1) | ............................................................ |
| AAC32089 | A/Hong Kong/156/97(H5N1) | .......................................Y.................. |
| AAD16788 | A/Hong Kong/486/97(H5N1) | ...................K...................Y.................. |
| AAD16799 | A/Hong Kong/514/97(H5N1) | .......................................YG.........T. |
| AAS89006 | A/Thailand/4(SP-528)/2004(H5N1) | ............................................................ |
| AAV73978 | A/Viet Nam/DN-33/2004(H5N1) | ------------------------------------------------------------ |
| AAZ72720 | A/Viet Nam/BL-014/2005(H5N1) | ............................................................ |
| AAZ72721 | A/Viet Nam/DT-036/2005(H5N1) | ............................................................ |
| ABI34143 | A/Guangzhou/1/2006(H5N1) | ............................................................ |
| ABI36014 | A/Indonesia/CDC7/2005(H5N1) | ............................................................ |
| ABI36084 | A/Indonesia/CDC292N/2005(H5N1) | ............................................................ |

| Positions from 181 till 240 |||
|---|---|---|
| | Consensus sequence | SPYNSRFESVAWSASACHDGTSWLTIGISGPDNGAVAVLKYNGIITDTIKSWRNNILRTQ |
| ABC72646 | A/Thailand/676/2005(H5N1) | ..............................S............................ |
| ABI36200 | A/Indonesia/CDC523/2006(H5N1) | ..............................E............................ |
| ABI36347 | A/Indonesia/CDC624/2006(H5N1) | ..............................E............................ |
| ABI36380 | A/Indonesia/CDC634/2006(H5N1) | ..............................E............................ |
| ABI49409 | A/Indonesia/CDC742/2006(H5N1) | ..............................E............................ |
| ABJ98530 | A/Thailand/RPNP/2005(H5N1) | ..............................S..................T.... |
| ABM90513 | A/Indonesia/CDC1046/2007(H5N1) | ..............................E............................ |
| ABU80632 | A/Anhui/T2/2006(H5N1) | ............................................................ |
| AAC32089 | A/Hong Kong/156/97(H5N1) | ....................I....................................... |
| AAD16788 | A/Hong Kong/486/97(H5N1) | ....................I.............................T.... |
| AAD16799 | A/Hong Kong/514/97(H5N1) | ..................SI..............................M.........K...... |
| AAS89006 | A/Thailand/4(SP-528)/2004(H5N1) | ............................................................ |
| AAV73978 | A/Viet Nam/DN-33/2004(H5N1) | ----------L................................................. |
| AAZ72720 | A/Viet Nam/BL-014/2005(H5N1) | ............................................................ |
| AAZ72721 | A/Viet Nam/DT-036/2005(H5N1) | ............................................................ |
| ABI34143 | A/Guangzhou/1/2006(H5N1) | ..............................................M............ |
| ABI36014 | A/Indonesia/CDC7/2005(H5N1) | ..............................E............................ |

TABLE 7-continued

| ABI36084 | A/Indonesia/CDC292N/2005(H5N1) | ................................E......................... |

Positions from 241 till 300

| | Consensus sequence | ESECACVNGSCFTVMTDGPSNGQASYKIFKMGEKGKVVKSVELDAPNYHYEECSCYPDAG |
|---|---|---|
| ABC72646 | A/Thailand/676/2005(H5N1) | ........................H.....-D........................... |
| ABI36200 | A/Indonesia/CDC523/2006(H5N1) | .........................................-................. |
| ABI36347 | A/Indonesia/CDC624/2006(H5N1) | .........................................-................. |
| ABI36380 | A/Indonesia/CDC634/2006(H5N1) | .........................................-................. |
| ABI49409 | A/Indonesia/CDC742/2006(H5N1) | .........................................-.........V....... |
| ABJ98530 | A/Thailand/RPNP/2005(H5N1) | ........................H....W-K...WLNQSQ................... |
| ABM90513 | A/Indonesia/CDC1046/2007(H5N1) | .........................................-................. |
| ABU80632 | A/Anhui/T2/2006(H5N1) | .........................................-..............D.. |
| AAC32089 | A/Hong Kong/156/97(H5N1) | .....................E........I-...R......N................ |
| AAD16788 | A/Hong Kong/486/97(H5N1) | .....................E........I-...R......N................ |
| AAD16799 | A/Hong Kong/514/97(H5N1) | .....................E........I-...R......N................ |
| AAS89006 | A/Thailand/4(SP-528)/2004(H5N1) | ........................H................-................. |
| AAV73978 | A/Viet Nam/DN-33/2004(H5N1) | ........................H................-................. |
| AAZ72720 | A/Viet Nam/BL-014/2005(H5N1) | ........................H................-................. |
| AAZ72721 | A/Viet Nam/DT-036/2005(H5N1) | ........................H................-................. |
| ABI34143 | A/Guangzhou/1/2006(H5N1) | ....V......................................-................ |
| ABI36014 | A/Indonesia/CDC7/2005(H5N1) | .........................................-................. |
| ABI36084 | A/Indonesia/CDC292N/2005(H5N1) | .........................................-................. |

Positions from 301 till 360

| | Consensus sequence | EITCVCRDNWHGSNRPWVSFNQNLEYQIGYICSGVFGDNPRPNDGTGSCGPVSPNGAYGV |
|---|---|---|
| ABC72646 | A/Thailand/676/2005(H5N1) | ..........................................T.........S..T... |
| ABI36200 | A/Indonesia/CDC523/2006(H5N1) | ....................................................M....... |
| ABI36347 | A/Indonesia/CDC624/2006(H5N1) | ....................................................M....... |
| ABI36380 | A/Indonesia/CDC634/2006(H5N1) | ...............................I....................MF...... |
| ABI49409 | A/Indonesia/CDC742/2006(H5N1) | ....................................................M....... |
| ABJ98530 | A/Thailand/RPNP/2005(H5N1) | .................G........................T.........S..T... |
| ABM90513 | A/Indonesia/CDC1046/2007(H5N1) | ....................................................M....... |
| ABU80632 | A/Anhui/T2/2006(H5N1) | ............................................................ |
| AAC32089 | A/Hong Kong/156/97(H5N1) | ..........................................S.........L...... |
| AAD16788 | A/Hong Kong/486/97(H5N1) | ..........................................S.........L...... |
| AAD16799 | A/Hong Kong/514/97(H5N1) | ..........................................S.........L...... |
| AAS89006 | A/Thailand/4(SP-528)/2004(H5N1) | ..........................................................S...... |
| AAV73978 | A/Viet Nam/DN-33/2004(H5N1) | ..........................................................S...... |
| AAZ72720 | A/Viet Nam/BL-014/2005(H5N1) | ..........................................................S...... |
| AAZ72721 | A/Viet Nam/DT-036/2005(H5N1) | ..........................................T.............S...... |
| ABI34143 | A/Guangzhou/1/2006(H5N1) | ............................................................ |
| ABI36014 | A/Indonesia/CDC7/2005(H5N1) | ....................................................M....... |

TABLE 7-continued

| | | |
|---|---|---|
| ABI36084 | A/Indonesia/CDC292N/2005(H5N1) | ................................................M........ |

| Positions from 361 till 420 | | |
|---|---|---|
| | Consensus sequence | KGFSFKYGNGVWIGRTKSTNSRSGFEMIWDPNGWTETDSSFSVKQDIVAITDWSGYSGSF |
| ABC72646 | A/Thailand/676/2005(H5N1) | ............................................................ |
| ABI36200 | A/Indonesia/CDC523/2006(H5N1) | ..................................G......................... |
| ABI36347 | A/Indonesia/CDC624/2006(H5N1) | ..................................G......................... |
| ABI36380 | A/Indonesia/CDC634/2006(H5N1) | ..................................G......................... |
| ABI49409 | A/Indonesia/CDC742/2006(H5N1) | ..................................G......................... |
| ABJ98530 | A/Thailand/RPNP/2005(H5N1) | ............................................................ |
| ABM90513 | A/Indonesia/CDC1046/2007(H5N1) | ..................................G......................... |
| ABU80632 | A/Anhui/T2/2006(H5N1) | ..................................G......................... |
| AAC32089 | A/Hong Kong/156/97(H5N1) | ....................S...................L....I.............. |
| AAD16788 | A/Hong Kong/486/97(H5N1) | ....................S...................L....I.............. |
| AAD16799 | A/Hong Kong/514/97(H5N1) | ....................S...................L....I.............. |
| AAS89006 | A/Thailand/4(SP-528)/2004(H5N1) | ............................................................ |
| AAV73978 | A/Viet Nam/DN-33/2004(H5N1) | ....................--------------------------------------- |
| AAZ72720 | A/Viet Nam/BL-014/2005(H5N1) | ............................................................ |
| AAZ72721 | A/Viet Nam/DT-036/2005(H5N1) | ............................................................ |
| ABI34143 | A/Guangzhou/1/2006(H5N1) | ...............PS............................................ |
| ABI36014 | A/Indonesia/CDC7/2005(H5N1) | ..................................G......................... |
| ABI36084 | A/Indonesia/CDC292N/2005(H5N1) | ..................................G...............N........ |

| Positions from 421 till 480 | | |
|---|---|---|
| | Consensus sequence | VQHPELTGLDCIRPCFWVELIRGRPKESTIWTSGSSISFCGVNSDTVGWSWPDGAELPFT |
| ABC72646 | A/Thailand/676/2005(H5N1) | ............................................................ |
| ABI36200 | A/Indonesia/CDC523/2006(H5N1) | .......................................S.................... |
| ABI36347 | A/Indonesia/CDC624/2006(H5N1) | .......................................S.................... |
| ABI36380 | A/Indonesia/CDC634/2006(H5N1) | .......................................S.................... |
| ABI49409 | A/Indonesia/CDC742/2006(H5N1) | ......................................AS.................... |
| ABJ98530 | A/Thailand/RPNP/2005(H5N1) | .........N...........................G...-------- |
| ABM90513 | A/Indonesia/CDC1046/2007(H5N1) | .......................................S.................... |
| ABU80632 | A/Anhui/T2/2006(H5N1) | .........-------------------------------------------------- |
| AAC32089 | A/Hong Kong/156/97(H5N1) | I........N.M...............K................................ |
| AAD16788 | A/Hong Kong/486/97(H5N1) | I........N.M...............K.......................D........ |
| AAD16799 | A/Hong Kong/514/97(H5N1) | I........N.M...............K.......D...........D............ |
| AAS89006 | A/Thailand/4(SP-528)/2004(H5N1) | ............................................................ |
| AAV73978 | A/Viet Nam/DN-33/2004(H5N1) | ------------------------------------------------------------ |
| AAZ72720 | A/Viet Nam/BL-014/2005(H5N1) | ..............................................T............. |
| AAZ72721 | A/Viet Nam/DT-036/2005(H5N1) | ............................................................ |
| ABI34143 | A/Guangzhou/1/2006(H5N1) | .......................................S..........----- |
| ABI36014 | A/Indonesia/CDC7/2005(H5N1) | .......................................S.....D....-- |

TABLE 7-continued

| ABI36084 | A/Indonesia/CDC292N/2005(H5N1) | ................................S.....D....-- |

| | Positions from 481 till 484 | |
|---|---|---|
| | Consensus sequence | IDKY |

| ABC72646 | A/Thailand/676/2005(H5N1) | ...- |
| ABI36200 | A/Indonesia/CDC523/2006(H5N1) | ...- |
| ABI36347 | A/Indonesia/CDC524/2006(H5N1) | ...- |
| ABI36380 | A/Indonesia/CDC634/2006(H5N1) | ...- |
| ABI49409 | A/Indonesia/CDC742/2006(H5N1) | ...- |
| ABJ98530 | A/Thailand/RPNP/2005(H5N1) | ---- |
| ABM90513 | A/Indonesia/CDC1046/2007(H5N1) | ...- |
| ABU80632 | A/Anhui/T2/2006(H5N1) | ---- |
| AAC32089 | A/Hong Kong/156/97(H5N1) | ...- |
| AAD16788 | A/Hong Kong/486/97(H5N1) | ...- |
| AAD16799 | A/Hong Kong/514/97(H5N1) | ...- |
| AAS89006 | A/Thailand/4(SP-528)/2004(H5N1) | ...- |
| AAV73978 | A/Viet Nam/DN-33/2004(H5N1) | ---- |
| AAZ72720 | A/Viet Nam/BL-014/2005(H5N1) | ...- |
| AAZ72721 | A/Viet Nam/DT-036/2005(H5N1) | ...- |
| ABI34143 | A/Guangzhou/1/2006(H5N1) | ---- |
| ABI36014 | A/Indonesia/CDC7/2005(H5N1) | ---- |
| ABI36084 | A/Indonesia/CDC292N/2005(H5N1) | ---- |

---

SEQUENCE LISTING

<160> NUMBER OF SEQ ID NOS: 244

<210> SEQ ID NO 1
<211> LENGTH: 25
<212> TYPE: PRT
<213> ORGANISM: Influenza A virus

<400> SEQUENCE: 1

Tyr Asn Lys Met Glu Phe Glu Pro Phe Gln Ser Leu Val Pro Lys Ala
 1               5                  10                  15

Ile Lys Gly Gln Tyr Ser Gly Phe Val
            20                  25

<210> SEQ ID NO 2
<211> LENGTH: 60
<212> TYPE: PRT
<213> ORGANISM: Influenza A virus

<400> SEQUENCE: 2

Leu Gly Lys Glu Asp Arg Arg Tyr Gly Pro Ala Leu Ser Ile Asn Glu
 1               5                  10                  15

Leu Ser Asn Leu Ala Lys Gly Glu Lys Ala Asn Val Leu Ile Gly Gln
            20                  25                  30

Gly Asp Val Val Leu Val Met Lys Arg Lys Arg Asp Ser Ser Ile Leu
        35                  40                  45

```
Thr Asp Ser Gln Thr Ala Thr Lys Arg Ile Arg Met
    50                  55                  60

<210> SEQ ID NO 3
<211> LENGTH: 30
<212> TYPE: PRT
<213> ORGANISM: Influenza A virus

<400> SEQUENCE: 3

Gly Leu Thr Ala Asn Glu Ser Gly Arg Leu Ile Asp Phe Leu Lys Asp
 1               5                  10                  15

Val Met Glu Ser Met Asp Lys Glu Glu Met Glu Ile Thr Thr
            20                  25                  30

<210> SEQ ID NO 4
<211> LENGTH: 28
<212> TYPE: PRT
<213> ORGANISM: Influenza A virus

<400> SEQUENCE: 4

Glu Lys Pro Lys Phe Leu Pro Asp Leu Tyr Asp Tyr Lys Glu Asn Arg
 1               5                  10                  15

Phe Ile Glu Ile Gly Val Thr Arg Arg Glu Val His
            20                  25

<210> SEQ ID NO 5
<211> LENGTH: 15
<212> TYPE: PRT
<213> ORGANISM: Influenza A virus

<400> SEQUENCE: 5

Ile Glu Ser Met Ile Glu Ala Glu Ser Ser Ile Lys Glu Lys Asp
 1               5                  10                  15

<210> SEQ ID NO 6
<211> LENGTH: 56
<212> TYPE: PRT
<213> ORGANISM: Influenza A virus

<400> SEQUENCE: 6

Leu Val Phe Ala Gln Lys Leu Pro Gly Asn Asp Asn Ser Ala Ala Thr
 1               5                  10                  15

Leu Cys Leu Gly His His Ala Val Pro Asn Arg Thr Met Val Lys Thr
            20                  25                  30

Ile Thr Asn Asp Gln Ile Glu Val Thr Asn Ala Thr Glu Leu Val Gln
        35                  40                  45

Arg Gly Lys Thr Val Glu Ser Cys
    50                  55

<210> SEQ ID NO 7
<211> LENGTH: 19
<212> TYPE: PRT
<213> ORGANISM: Influenza A virus

<400> SEQUENCE: 7

His Ala Val Pro Asn Gly Thr Ile Val Lys Thr Ile Thr Asn Asp Gln
 1               5                  10                  15

Ile Glu Val

<210> SEQ ID NO 8
<211> LENGTH: 74
```

```
<212> TYPE: PRT
<213> ORGANISM: Influenza A virus

<400> SEQUENCE: 8

Ala Gly Pro Asn Gly Thr Ile Val Lys Thr Ile Thr Asn Asp Gln Ile
 1               5                  10                  15

Glu Val Thr Asn Ala Thr Glu Leu Val Leu Ser Ser Ser Thr Gly Gly
             20                  25                  30

Ile Cys Asp Ser Pro His Gln Ile Leu Asp Gly Glu Asn Cys Thr Leu
         35                  40                  45

Ile Asn Ala Leu Leu Gly Asp Pro Gln Cys Asp Gly Phe Gln Asn Lys
     50                  55                  60

Lys Trp Asp Leu Phe Val Glu Arg Ser Lys
 65                  70

<210> SEQ ID NO 9
<211> LENGTH: 78
<212> TYPE: PRT
<213> ORGANISM: Influenza A virus

<400> SEQUENCE: 9

Ser Gly Lys Ser Ser Ile Met Arg Ser Asp Ala Pro Ile Gly Lys Cys
 1               5                  10                  15

Asn Ser Glu Cys Ile Thr Pro Asn Gly Ser Ile Pro Asn Asp Lys Pro
             20                  25                  30

Phe Gln Asn Val Asn Arg Ile Thr Tyr Gly Ala Cys Pro Arg Tyr Val
         35                  40                  45

Lys Gln Asn Thr Leu Lys Leu Ala Thr Gly Met Arg Asn Val Pro Glu
     50                  55                  60

Lys Gln Thr Arg Gly Ile Phe Gly Ala Ile Ala Gly Phe Ile
 65                  70                  75

<210> SEQ ID NO 10
<211> LENGTH: 36
<212> TYPE: PRT
<213> ORGANISM: Influenza A virus

<400> SEQUENCE: 10

Val Lys Gln Asn Thr Leu Lys Leu Ala Thr Gly Met Arg Asn Val Pro
 1               5                  10                  15

Glu Lys Gln Thr Arg Gly Ile Phe Gly Ala Ile Ala Gly Phe Ile Glu
             20                  25                  30

Asn Gly Trp Glu
         35

<210> SEQ ID NO 11
<211> LENGTH: 52
<212> TYPE: PRT
<213> ORGANISM: Influenza A virus

<400> SEQUENCE: 11

Ser Glu Val Glu Gly Arg Ile Gln Asp Leu Glu Lys Tyr Val Glu Asp
 1               5                  10                  15

Thr Lys Ile Asp Leu Trp Ser Tyr Asn Ala Glu Leu Leu Val Ala Leu
             20                  25                  30

Glu Asn Gln His Thr Ile Asp Leu Thr Asp Ser Glu Met Asn Lys Leu
         35                  40                  45

Phe Glu Arg Thr
     50
```

<210> SEQ ID NO 12
<211> LENGTH: 28
<212> TYPE: PRT
<213> ORGANISM: Influenza A virus

<400> SEQUENCE: 12

```
Ser Gly Ser Arg Val Asp Asn His Ser Leu Ser Asp Ile Lys Val Met
 1               5                  10                  15

Ala Ser Gln Gly Thr Lys Arg Ser Tyr Glu Gln Met
            20                  25
```

<210> SEQ ID NO 13
<211> LENGTH: 13
<212> TYPE: PRT
<213> ORGANISM: Influenza A virus

<400> SEQUENCE: 13

```
Ile Gln Asn Ser Leu Thr Ile Glu Lys Met Val Leu Ser
 1               5                  10
```

<210> SEQ ID NO 14
<211> LENGTH: 32
<212> TYPE: PRT
<213> ORGANISM: Influenza A virus

<400> SEQUENCE: 14

```
Arg Glu Leu Val Leu Tyr Asp Lys Lys Lys Ile Arg Arg Ile Trp Arg
 1               5                  10                  15

Gln Ala Asn Asn Gly Asp Asp Ala Thr Ala Gly Leu Thr His Ile Met
            20                  25                  30
```

<210> SEQ ID NO 15
<211> LENGTH: 45
<212> TYPE: PRT
<213> ORGANISM: Influenza A virus

<400> SEQUENCE: 15

```
Asn Thr Asn Gln Gln Arg Ala Ser Ala Gly Gln Ile Ser Thr Gln Pro
 1               5                  10                  15

Thr Phe Ser Val Gln Arg Asn Leu Pro Phe Asp Lys Thr Thr Ile Met
            20                  25                  30

Ala Ala Phe Thr Gly Asn Thr Glu Gly Arg Thr Ser Asp
        35                  40                  45
```

<210> SEQ ID NO 16
<211> LENGTH: 25
<212> TYPE: PRT
<213> ORGANISM: Influenza A virus

<400> SEQUENCE: 16

```
Arg Ala Glu Ile Ile Arg Met Met Glu Gly Ala Lys Pro Glu Glu Val
 1               5                  10                  15

Ser Phe Arg Gly Arg Gly Val Phe Glu
            20                  25
```

<210> SEQ ID NO 17
<211> LENGTH: 36
<212> TYPE: PRT
<213> ORGANISM: Influenza A virus

<400> SEQUENCE: 17

```
Pro Pro Lys Ser Asp Gly Ser Thr Ala Ala Ala Glu Ala Gly
1               5                   10                  15

Val Lys Met Asn Pro Asn Gln Lys Ile Ile Thr Ile Gly Ser Val Phe
            20                  25                  30

Leu Thr Ile Ser
            35
```

```
<210> SEQ ID NO 18
<211> LENGTH: 38
<212> TYPE: PRT
<213> ORGANISM: Influenza A virus

<400> SEQUENCE: 18

Pro Pro Lys Ser Asp Gly Ser Thr Arg Ala Ala Ala Glu Ala Gly
1               5                   10                  15

Val Lys Met Asn Pro Asn Gln Lys Ile Ile Thr Ile Gly Ser Val Ser
            20                  25                  30

Leu Thr Ile Ser Thr Ile
            35
```

```
<210> SEQ ID NO 19
<211> LENGTH: 20
<212> TYPE: PRT
<213> ORGANISM: Influenza A virus

<400> SEQUENCE: 19

Ile Val Tyr Leu Thr Asn Thr Thr Ile Glu Lys Glu Ile Cys Pro Lys
1               5                   10                  15

Leu Ala Glu Tyr
            20
```

```
<210> SEQ ID NO 20
<211> LENGTH: 45
<212> TYPE: PRT
<213> ORGANISM: Influenza A virus

<400> SEQUENCE: 20

Leu Gly Thr Lys Gln Val Cys Ile Ala Trp Ser Ser Ser Ser Cys His
1               5                   10                  15

Asp Gly Lys Ala Trp Leu His Val Cys Val Thr Gly Asp Asp Lys Asn
            20                  25                  30

Ala Thr Ala Ser Phe Ile Tyr Asn Gly Arg Leu Val Asp
            35                  40                  45
```

```
<210> SEQ ID NO 21
<211> LENGTH: 38
<212> TYPE: PRT
<213> ORGANISM: Influenza A virus

<400> SEQUENCE: 21

Trp Ser Lys Glu Ile Leu Arg Thr Gln Glu Ser Glu Cys Val Cys Ile
1               5                   10                  15

Asn Gly Thr Cys Thr Val Val Met Thr Asp Gly Ser Ala Ser Gly Lys
            20                  25                  30

Ala Asp Thr Lys Ile Leu
            35
```

```
<210> SEQ ID NO 22
<211> LENGTH: 42
<212> TYPE: PRT
<213> ORGANISM: Influenza A virus
```

```
<400> SEQUENCE: 22

Asn Asn Glu Glu Gly Gly His Gly Val Lys Gly Trp Ala Phe Asp Asp
 1               5                  10                  15

Gly Asn Asp Val Trp Met Gly Arg Thr Ile Ser Glu Lys Leu Arg Ser
                20                  25                  30

Gly Tyr Glu Thr Phe Lys Val Ile Glu Gly
            35                  40

<210> SEQ ID NO 23
<211> LENGTH: 17
<212> TYPE: PRT
<213> ORGANISM: Influenza A virus

<400> SEQUENCE: 23

Thr Tyr Gly Thr Gly Ser Trp Pro Asp Gly Ala Asp Ile Asn Leu Met
 1               5                  10                  15

Pro

<210> SEQ ID NO 24
<211> LENGTH: 34
<212> TYPE: PRT
<213> ORGANISM: Influenza A virus

<400> SEQUENCE: 24

Val Glu Thr Tyr Val Leu Ser Ile Val Pro Ser Gly Pro Leu Lys Ala
 1               5                  10                  15

Glu Ile Ala Gln Arg Leu Glu Asp Val Phe Ala Gly Lys Asn Thr Asp
                20                  25                  30

Leu Glu

<210> SEQ ID NO 25
<211> LENGTH: 112
<212> TYPE: PRT
<213> ORGANISM: Influenza A virus

<400> SEQUENCE: 25

Arg Glu Ile Thr Phe His Gly Ala Lys Glu Ile Ala Leu Ser Tyr Ser
 1               5                  10                  15

Ala Gly Ala Leu Ala Ser Cys Met Gly Leu Ile Tyr Asn Arg Met Gly
                20                  25                  30

Ala Val Thr Thr Glu Ser Ala Phe Gly Leu Ile Cys Ala Thr Cys Glu
            35                  40                  45

Gln Ile Ala Asp Ser Gln His Lys Ser His Arg Gln Met Val Thr Thr
        50                  55                  60

Thr Asn Pro Leu Ile Arg His Glu Asn Arg Met Val Leu Ala Ser Thr
 65                 70                  75                  80

Thr Ala Lys Ala Met Glu Gln Met Ala Gly Ser Ser Glu Gln Ala Ala
                85                  90                  95

Glu Ala Met Glu Val Ala Ser Gln Ala Arg Gln Met Val Gln Ala Met
            100                 105                 110

<210> SEQ ID NO 26
<211> LENGTH: 52
<212> TYPE: PRT
<213> ORGANISM: Influenza A virus

<400> SEQUENCE: 26

Ile Tyr Asn Arg Met Gly Ala Val Thr Thr Glu Val Ala Phe Gly Leu
 1               5                  10                  15
```

-continued

```
 1               5                  10                  15

Val Cys Ala Thr Cys Glu Gln Ile Ala Asp Ser Gln His Arg Ser His
            20                  25                  30

Arg Gln Met Val Ala Thr Thr Asn Pro Leu Ile Lys His Glu Asn Arg
        35                  40                  45

Met Val Leu Ala
    50

<210> SEQ ID NO 27
<211> LENGTH: 55
<212> TYPE: PRT
<213> ORGANISM: Influenza A virus

<400> SEQUENCE: 27

Ala Ala Glu Ala Met Glu Val Ala Ser Gln Ala Arg Gln Met Val Gln
 1               5                  10                  15

Ala Met Arg Ala Ile Gly Thr His Pro Ser Ser Ser Thr Gly Leu Lys
            20                  25                  30

Asn Asp Leu Leu Glu Asn Leu Arg Ala Tyr Gln Lys Arg Met Gly Val
        35                  40                  45

Gln Met Gln Arg Ala Lys Ile
    50                  55

<210> SEQ ID NO 28
<211> LENGTH: 21
<212> TYPE: PRT
<213> ORGANISM: Influenza A virus

<400> SEQUENCE: 28

Lys Gln Val Val Asp Gln Glu Leu Ser Asp Ala Pro Phe Leu Asp Arg
 1               5                  10                  15

Leu Arg Arg Asp Gln
            20

<210> SEQ ID NO 29
<211> LENGTH: 38
<212> TYPE: PRT
<213> ORGANISM: Influenza A virus

<400> SEQUENCE: 29

Leu His Ile Lys Ala Ala Thr His Val Gly Lys Gln Ile Val Glu Lys
 1               5                  10                  15

Ile Leu Lys Glu Glu Ser Asp Glu Ala Leu Lys Met Thr Met Val Ser
            20                  25                  30

Thr Pro Ala Ser Arg Tyr
        35

<210> SEQ ID NO 30
<211> LENGTH: 18
<212> TYPE: PRT
<213> ORGANISM: Influenza A virus

<400> SEQUENCE: 30

Pro Arg Gly Leu Glu Trp Asn Asp Asn Thr Val Arg Val Ser Lys Asn
 1               5                  10                  15

Leu Gln

<210> SEQ ID NO 31
<211> LENGTH: 30
<212> TYPE: PRT
```

<213> ORGANISM: Influenza A virus

<400> SEQUENCE: 31

Leu Asn Pro Ser Arg Leu Glu Val Asn Ser Gly Ile Asn Pro Gly Pro
1               5                   10                  15
Arg His His Gly Leu His His Ala Arg Asn Ser Asn Arg Ser
            20                  25                  30

<210> SEQ ID NO 32
<211> LENGTH: 244
<212> TYPE: PRT
<213> ORGANISM: Influenza A virus

<400> SEQUENCE: 32

Leu Phe Ala Ile Val Ser Leu Val Lys Ser Asp Gln Ile Cys Ile Gly
1               5                   10                  15
Tyr His Ala Asn Asn Ser Thr Glu Gln Val Asp Thr Ile Met Glu Lys
            20                  25                  30
Asn Val Thr Val Thr His Ala Gln Asp Ile Leu Glu Lys Lys His Asn
        35                  40                  45
Gly Lys Leu Cys Asp Leu Asp Gly Val Lys Pro Leu Ile Leu Arg Asp
50                  55                  60
Cys Ser Val Ala Gly Trp Leu Leu Gly Asn Pro Met Cys Asp Glu Phe
65                  70                  75                  80
Ile Asn Val Pro Glu Trp Ser Tyr Ile Val Glu Lys Ala Asn Pro Val
                85                  90                  95
Asn Asp Leu Cys Tyr Pro Gly Asp Phe Asn Asp Tyr Glu Glu Leu Lys
            100                 105                 110
His Leu Leu Ser Arg Ile Asn His Phe Glu Lys Ile Gln Ile Ile Pro
        115                 120                 125
Lys Ser Ser Trp Ser Ser His Glu Ala Ser Leu Gly Val Ser Ser Ala
130                 135                 140
Cys Pro Tyr Gln Gly Lys Ser Ser Phe Phe Arg Asn Val Val Trp Leu
145                 150                 155                 160
Ile Lys Lys Asn Ser Thr Tyr Pro Thr Ile Lys Arg Ser Tyr Asn Asn
                165                 170                 175
Thr Asn Gln Glu Asp Leu Leu Val Leu Trp Gly Ile His His Pro Asn
            180                 185                 190
Asp Ala Ala Glu Gln Thr Lys Leu Tyr Gln Asn Pro Thr Thr Tyr Ile
        195                 200                 205
Ser Val Gly Thr Ser Thr Leu Asn Gln Arg Leu Val Pro Arg Ile Ala
    210                 215                 220
Thr Arg Ser Lys Val Asn Gly Gln Ser Gly Arg Met Glu Phe Phe Trp
225                 230                 235                 240
Thr Ile Leu Lys

<210> SEQ ID NO 33
<211> LENGTH: 11
<212> TYPE: PRT
<213> ORGANISM: Influenza A virus

<400> SEQUENCE: 33

Leu Thr Ala Glu Lys Lys Gly Gly Phe Ser Ser
1               5                   10

<210> SEQ ID NO 34
<211> LENGTH: 12

```
<212> TYPE: PRT
<213> ORGANISM: Influenza A virus

<400> SEQUENCE: 34

Val Ile Glu Pro Pro Tyr Ser Trp Leu His Ala Pro
 1               5                  10

<210> SEQ ID NO 35
<211> LENGTH: 12
<212> TYPE: PRT
<213> ORGANISM: Influenza A virus

<400> SEQUENCE: 35

Tyr Thr His Met Gln Asp Ser Arg Phe Ser Arg Leu
 1               5                  10

<210> SEQ ID NO 36
<211> LENGTH: 11
<212> TYPE: PRT
<213> ORGANISM: Influenza A virus

<400> SEQUENCE: 36

Ser Leu Ser Pro Asn Pro Leu Ile Ile Ile Arg
 1               5                  10

<210> SEQ ID NO 37
<211> LENGTH: 12
<212> TYPE: PRT
<213> ORGANISM: Influenza A virus

<400> SEQUENCE: 37

Ser Leu Ser Pro Lys Leu Ile Gly Ser Ser Leu Asp
 1               5                  10

<210> SEQ ID NO 38
<211> LENGTH: 12
<212> TYPE: PRT
<213> ORGANISM: Influenza A virus

<400> SEQUENCE: 38

Leu Thr Ala Glu Lys Lys Lys Lys Phe Phe Ile
 1               5                  10

<210> SEQ ID NO 39
<211> LENGTH: 12
<212> TYPE: PRT
<213> ORGANISM: Influenza A virus

<400> SEQUENCE: 39

Ser Leu Ser Pro Lys Thr Met His His His Gln Thr
 1               5                  10

<210> SEQ ID NO 40
<211> LENGTH: 12
<212> TYPE: PRT
<213> ORGANISM: Influenza A virus

<400> SEQUENCE: 40

Phe Gln Thr His Met His His Pro Phe Asn Gln Ile
 1               5                  10

<210> SEQ ID NO 41
<211> LENGTH: 12
<212> TYPE: PRT
<213> ORGANISM: Influenza A virus
```

<400> SEQUENCE: 41

Leu Thr Ala Glu Thr Gln Ile Gln Phe Phe His His
1               5                   10

<210> SEQ ID NO 42
<211> LENGTH: 33
<212> TYPE: PRT
<213> ORGANISM: Influenza A virus

<400> SEQUENCE: 42

Glu Val Leu Thr Gly Asn Leu Gln Thr Leu Lys Ile Arg Val His Glu
1               5                   10                  15

Gly Tyr Glu Glu Phe Thr Met Val Gly Arg Arg Ala Thr Ala Ile Leu
            20                  25                  30

Arg

<210> SEQ ID NO 43
<211> LENGTH: 70
<212> TYPE: PRT
<213> ORGANISM: Influenza A virus

<400> SEQUENCE: 43

Gln Asn Trp Gly Ile Glu Pro Ile Asp Asn Val Met Gly Met Ile Gly
1               5                   10                  15

Ile Leu Pro Asp Met Thr Pro Ser Thr Glu Met Ser Leu Arg Gly Val
            20                  25                  30

Arg Val Ser Lys Met Gly Val Asp Glu Tyr Ser Ser Thr Glu Arg Val
        35                  40                  45

Val Val Ser Ile Asp Arg Phe Leu Arg Val Arg Asp Gln Arg Gly Asn
    50                  55                  60

Val Leu Leu Ser Pro Glu
65                  70

<210> SEQ ID NO 44
<211> LENGTH: 161
<212> TYPE: PRT
<213> ORGANISM: Influenza A virus

<400> SEQUENCE: 44

Thr Val Ile Lys Asn Asn Met Ile Asn Asn Asp Leu Gly Pro Ala Thr
1               5                   10                  15

Ala Gln Met Ala Leu Gln Leu Phe Ile Lys Asp Tyr Arg Tyr Thr Tyr
            20                  25                  30

Arg Cys His Arg Gly Asp Thr Gln Ile Gln Thr Arg Arg Ser Phe Glu
        35                  40                  45

Leu Lys Lys Leu Trp Glu Gln Thr Arg Ser Lys Ala Gly Leu Leu Val
    50                  55                  60

Ser Asp Gly Gly Pro Asn Leu Tyr Asn Ile Arg Asn Leu His Ile Pro
65                  70                  75                  80

Glu Val Cys Leu Lys Trp Glu Leu Met Asp Glu Asp Tyr Gln Gly Arg
                85                  90                  95

Leu Cys Asn Pro Leu Asn Pro Phe Val Ser His Lys Glu Ile Glu Val
            100                 105                 110

Asn Asn Ala Val Val Met Pro Ala His Gly Pro Ala Lys Ser Met Glu
        115                 120                 125

Tyr Asp Ala Val Ala Thr Thr His Ser Trp Ile Pro Lys Arg Asn Arg
    130                 135                 140

Ser Ile Leu Asn Thr Ser Gln Arg Gly Ile Leu Glu Asp Glu Gln Met
145                 150                 155                 160

Tyr

<210> SEQ ID NO 45
<211> LENGTH: 14
<212> TYPE: PRT
<213> ORGANISM: Influenza A virus

<400> SEQUENCE: 45

Lys Ala Gly Leu Leu Val Ser Asp Gly Gly Pro Asn Leu Tyr
1               5                   10

<210> SEQ ID NO 46
<211> LENGTH: 18
<212> TYPE: PRT
<213> ORGANISM: Influenza A virus

<400> SEQUENCE: 46

Asp Ala Val Ala Thr Thr His Ser Trp Ile Pro Lys Arg Asn Arg Ser
1               5                   10                  15

Ile Leu

<210> SEQ ID NO 47
<211> LENGTH: 74
<212> TYPE: PRT
<213> ORGANISM: Influenza A virus

<400> SEQUENCE: 47

Glu Gln Gly Gln Asp Thr Pro Trp Thr Gln Ser Thr Glu His Thr Asn
1               5                   10                  15

Ile Gln Lys Arg Gly Ser Gly Gln Gln Thr Gln Arg Leu Glu His Pro
            20                  25                  30

Asn Ser Thr Arg Leu Met Asp His Tyr Leu Arg Ile Met Ser Pro Val
        35                  40                  45

Gly Thr His Lys Gln Ile Val Tyr Trp Lys Gly Trp Leu Ser Leu Lys
    50                  55                  60

Asn Pro Thr Gln Gly Ser Leu Lys Thr Arg
65                  70

<210> SEQ ID NO 48
<211> LENGTH: 48
<212> TYPE: PRT
<213> ORGANISM: Influenza A virus

<400> SEQUENCE: 48

Gln Gly Gln Asp Thr Pro Trp Thr Gln Ser Thr Glu His Thr Asn Ile
1               5                   10                  15

Gln Lys Arg Gly Ser Gly Gln Gln Thr Gln Arg Leu Glu His Pro Asn
            20                  25                  30

Ser Thr Arg Leu Met Asp His Tyr Leu Arg Ile Met Ser Pro Val Gly
        35                  40                  45

<210> SEQ ID NO 49
<211> LENGTH: 61
<212> TYPE: PRT
<213> ORGANISM: Influenza A virus

<400> SEQUENCE: 49

Gln Thr Gln Arg Leu Glu His Pro Asn Ser Thr Arg Leu Met Asp His

```
            1               5                  10                 15
Tyr Leu Arg Ile Met Ser Pro Val Gly Thr His Lys Gln Ile Val Tyr
                    20                  25                  30

Trp Lys Gln Trp Leu Ser Leu Lys Asn Pro Thr Gln Gly Ser Leu Lys
            35                  40                  45

Thr Arg Val Leu Lys Arg Trp Lys Leu Phe Asn Lys Gln
 50                  55                  60

<210> SEQ ID NO 50
<211> LENGTH: 33
<212> TYPE: PRT
<213> ORGANISM: Influenza A virus

<400> SEQUENCE: 50

Leu Met Asp His Tyr Leu Arg Ile Met Ser Pro Val Gly Thr His Lys
 1               5                  10                  15

Gln Ile Val Tyr Trp Lys Gln Trp Leu Ser Leu Lys Asn Pro Thr Gln
                20                  25                  30

Gly

<210> SEQ ID NO 51
<211> LENGTH: 36
<212> TYPE: PRT
<213> ORGANISM: Influenza A virus

<400> SEQUENCE: 51

Pro Val Gly Thr His Lys Gln Ile Val Tyr Trp Lys Gln Trp Leu Ser
 1               5                  10                  15

Leu Lys Asn Pro Thr Gln Gly Ser Leu Lys Thr Arg Val Leu Lys Arg
                20                  25                  30

Trp Lys Leu Phe
            35

<210> SEQ ID NO 52
<211> LENGTH: 115
<212> TYPE: PRT
<213> ORGANISM: Influenza A virus

<400> SEQUENCE: 52

Glu Pro Asn Gly Cys Ile Glu Gly Lys Leu Ser Gln Met Ser Lys Glu
 1               5                  10                  15

Val Asn Ala Arg Ile Glu Pro Phe Leu Lys Thr Thr Pro Arg Pro Leu
                20                  25                  30

Arg Leu Pro Asp Gly Pro Pro Cys Ser Gln Arg Ser Lys Phe Leu Leu
            35                  40                  45

Met Asp Ala Leu Lys Leu Ser Ile Glu Asp Pro Ser His Glu Gly Glu
 50                  55                  60

Gly Ile Pro Leu Tyr Asp Ala Ile Lys Cys Met Lys Thr Phe Phe Gly
 65                  70                  75                  80

Trp Lys Glu Pro Asn Ile Val Lys Pro His Glu Lys Gly Ile Asn Pro
                85                  90                  95

Asn Tyr Leu Leu Ala Trp Lys Gln Val Leu Ala Glu Leu Gln Asp Ile
                100                 105                 110

Glu Asn Glu
    115

<210> SEQ ID NO 53
<211> LENGTH: 50
```

```
<212> TYPE: PRT
<213> ORGANISM: Influenza A virus

<400> SEQUENCE: 53

Gln Ser Leu Gln Gln Ile Glu Ser Met Ile Glu Ala Glu Ser Ser Val
 1               5                   10                  15

Lys Glu Lys Asp Met Thr Lys Glu Phe Phe Glu Asn Lys Ser Glu Thr
            20                  25                  30

Trp Pro Ile Gly Glu Ser Pro Lys Gly Val Glu Glu Gly Ser Ile Gly
        35                  40                  45

Lys Val
    50

<210> SEQ ID NO 54
<211> LENGTH: 62
<212> TYPE: PRT
<213> ORGANISM: Influenza A virus

<400> SEQUENCE: 54

Val Asp Thr Ile Met Glu Lys Asn Val Thr Val Thr His Ala Gln Asp
 1               5                   10                  15

Ile Leu Glu Lys Lys His Asn Gly Lys Leu Cys Asp Leu Asp Gly Val
            20                  25                  30

Lys Pro Leu Ile Leu Arg Asp Cys Ser Val Ala Gly Trp Leu Leu Gly
        35                  40                  45

Asn Pro Met Cys Asp Glu Phe Ile Asn Val Pro Glu Trp Ser
    50                  55                  60

<210> SEQ ID NO 55
<211> LENGTH: 284
<212> TYPE: PRT
<213> ORGANISM: Influenza A virus

<400> SEQUENCE: 55

Val Thr His Ala Gln Asp Ile Leu Glu Lys Lys His Asn Gly Lys Leu
 1               5                   10                  15

Cys Asp Leu Asp Gly Val Lys Pro Leu Ile Leu Arg Asp Cys Ser Val
            20                  25                  30

Ala Gly Trp Leu Leu Gly Asn Pro Met Cys Asp Glu Phe Ile Asn Val
        35                  40                  45

Pro Glu Trp Ser Tyr Ile Val Glu Lys Ala Asn Pro Val Asn Asp Leu
    50                  55                  60

Cys Tyr Pro Gly Asp Phe Asn Asp Tyr Glu Glu Leu Lys His Leu Leu
65                  70                  75                  80

Ser Arg Ile Asn His Phe Glu Lys Ile Gln Ile Ile Pro Lys Ser Ser
                85                  90                  95

Trp Ser Ser His Glu Ala Ser Leu Gly Val Ser Ser Ala Cys Pro Tyr
            100                 105                 110

Gln Gly Lys Ser Ser Phe Phe Arg Asn Val Val Trp Leu Ile Lys Lys
        115                 120                 125

Asn Ser Thr Tyr Pro Thr Ile Lys Arg Ser Tyr Asn Asn Thr Asn Gln
    130                 135                 140

Glu Asp Leu Leu Val Leu Trp Gly Ile His His Pro Asn Asp Ala Ala
145                 150                 155                 160

Glu Gln Thr Lys Leu Tyr Gln Asn Pro Thr Thr Tyr Ile Ser Val Gly
                165                 170                 175

Thr Ser Thr Leu Asn Gln Arg Leu Val Pro Arg Ile Ala Thr Arg Ser
```

```
                180                 185                 190
Lys Val Asn Gly Gln Ser Gly Arg Met Glu Phe Phe Trp Thr Ile Leu
            195                 200                 205
Lys Pro Asn Asp Ala Ile Asn Phe Glu Ser Asn Gly Asn Phe Ile Ala
        210                 215                 220
Pro Glu Tyr Ala Tyr Lys Ile Val Lys Lys Gly Asp Ser Thr Ile Met
225                 230                 235                 240
Lys Ser Glu Leu Glu Tyr Gly Asn Cys Asn Thr Lys Cys Gln Thr Pro
                245                 250                 255
Met Gly Ala Ile Asn Ser Ser Met Pro Phe His Asn Ile His Pro Leu
            260                 265                 270
Thr Ile Gly Glu Cys Pro Lys Tyr Val Lys Ser Asn
            275                 280

<210> SEQ ID NO 56
<211> LENGTH: 243
<212> TYPE: PRT
<213> ORGANISM: Influenza A virus

<400> SEQUENCE: 56

Val Leu Leu Phe Ala Ile Val Ser Leu Val Lys Ser Asp Gln Ile Cys
1               5                   10                  15
Ile Gly Tyr His Ala Asn Asn Ser Thr Glu Gln Val Asp Thr Ile Met
            20                  25                  30
Glu Lys Asn Val Thr Val Thr His Ala Gln Asp Ile Leu Glu Lys Lys
        35                  40                  45
His Asn Gly Lys Leu Cys Asp Leu Asp Gly Val Lys Pro Leu Ile Leu
    50                  55                  60
Arg Asp Cys Ser Val Ala Gly Trp Leu Leu Gly Asn Pro Met Cys Asp
65                  70                  75                  80
Glu Phe Ile Asn Val Pro Glu Trp Ser Tyr Ile Val Glu Lys Ala Asn
                85                  90                  95
Pro Val Asn Asp Leu Cys Tyr Pro Gly Asp Phe Asn Asp Tyr Glu Glu
            100                 105                 110
Leu Lys His Leu Leu Ser Arg Ile Asn His Phe Glu Lys Ile Gln Ile
        115                 120                 125
Ile Pro Lys Ser Ser Trp Ser Ser His Glu Ala Ser Leu Gly Val Ser
    130                 135                 140
Ser Ala Cys Pro Tyr Gln Gly Lys Ser Ser Phe Phe Arg Asn Val Val
145                 150                 155                 160
Trp Leu Ile Lys Lys Asn Ser Thr Tyr Pro Thr Ile Lys Arg Ser Tyr
                165                 170                 175
Asn Asn Thr Asn Gln Glu Asp Leu Leu Val Leu Trp Gly Ile His His
            180                 185                 190
Pro Asn Asp Ala Ala Glu Gln Thr Lys Leu Tyr Gln Asn Pro Thr Thr
        195                 200                 205
Tyr Ile Ser Val Gly Thr Ser Thr Leu Asn Gln Arg Leu Val Pro Arg
    210                 215                 220
Ile Ala Thr Arg Ser Lys Val Asn Gly Gln Ser Gly Arg Met Glu Phe
225                 230                 235                 240
Phe Trp Thr

<210> SEQ ID NO 57
<211> LENGTH: 23
<212> TYPE: PRT
```

<213> ORGANISM: Influenza A virus

<400> SEQUENCE: 57

Glu Lys Ala Asn Pro Val Asn Asp Leu Cys Tyr Pro Gly Asp Phe Asn
1 5 10 15

Asp Tyr Glu Glu Leu Lys His
20

<210> SEQ ID NO 58
<211> LENGTH: 98
<212> TYPE: PRT
<213> ORGANISM: Influenza A virus

<400> SEQUENCE: 58

Asn Asp Tyr Glu Glu Leu Lys His Leu Leu Ser Arg Ile Asn His Phe
1 5 10 15

Glu Lys Ile Gln Ile Ile Pro Lys Ser Ser Trp Ser Ser His Glu Ala
20 25 30

Ser Leu Gly Val Ser Ser Ala Cys Pro Tyr Gln Gly Lys Ser Ser Phe
35 40 45

Phe Arg Asn Val Val Trp Leu Ile Lys Lys Asn Ser Thr Tyr Pro Thr
50 55 60

Ile Lys Arg Ser Tyr Asn Asn Thr Asn Gln Glu Asp Leu Leu Val Leu
65 70 75 80

Trp Gly Ile His His Pro Asn Asp Ala Ala Glu Gln Thr Lys Leu Tyr
85 90 95

Gln Asn

<210> SEQ ID NO 59
<211> LENGTH: 30
<212> TYPE: PRT
<213> ORGANISM: Influenza A virus

<400> SEQUENCE: 59

Lys His Leu Leu Ser Arg Ile Asn His Phe Glu Lys Ile Gln Ile Ile
1 5 10 15

Pro Lys Ser Ser Trp Ser Ser His Glu Ala Ser Leu Gly Val
20 25 30

<210> SEQ ID NO 60
<211> LENGTH: 22
<212> TYPE: PRT
<213> ORGANISM: Influenza A virus

<400> SEQUENCE: 60

Thr Asn Gln Glu Asp Leu Leu Val Leu Trp Gly Ile His His Pro Asn
1 5 10 15

Asp Ala Ala Glu Gln Thr
20

<210> SEQ ID NO 61
<211> LENGTH: 47
<212> TYPE: PRT
<213> ORGANISM: Influenza A virus

<400> SEQUENCE: 61

Glu Asp Leu Leu Val Leu Trp Gly Ile His His Pro Asn Asp Ala Ala
1 5 10 15

Glu Gln Thr Lys Leu Tyr Gln Asn Pro Thr Thr Tyr Ile Ser Val Gly
20 25 30

```
Thr Ser Thr Leu Asn Gln Arg Leu Val Pro Arg Ile Ala Thr Arg
        35                  40                  45

<210> SEQ ID NO 62
<211> LENGTH: 82
<212> TYPE: PRT
<213> ORGANISM: Influenza A virus

<400> SEQUENCE: 62

Lys Val Asn Gly Gln Ser Gly Arg Met Glu Phe Phe Trp Thr Ile Leu
  1               5                  10                  15

Lys Pro Asn Asp Ala Ile Asn Phe Glu Ser Asn Gly Asn Phe Ile Ala
             20                  25                  30

Pro Glu Tyr Ala Tyr Lys Ile Val Lys Lys Gly Asp Ser Thr Ile Met
         35                  40                  45

Lys Ser Glu Leu Glu Tyr Gly Asn Cys Asn Thr Lys Cys Gln Thr Pro
     50                  55                  60

Met Gly Ala Ile Asn Ser Ser Met Pro Phe His Asn Ile His Pro Leu
 65                  70                  75                  80

Thr Ile

<210> SEQ ID NO 63
<211> LENGTH: 22
<212> TYPE: PRT
<213> ORGANISM: Influenza A virus

<400> SEQUENCE: 63

Leu Phe Gly Ala Ile Ala Gly Phe Ile Glu Gly Gly Trp Gln Gly Met
  1               5                  10                  15

Val Asp Gly Trp Tyr Gly
             20

<210> SEQ ID NO 64
<211> LENGTH: 63
<212> TYPE: PRT
<213> ORGANISM: Influenza A virus

<400> SEQUENCE: 64

Ile Ala Gly Phe Ile Glu Gly Gly Trp Gln Gly Met Val Asp Gly Trp
  1               5                  10                  15

Tyr Gly Tyr His His Ser Asn Glu Gln Gly Ser Gly Tyr Ala Ala Asp
             20                  25                  30

Lys Glu Ser Thr Gln Lys Ala Ile Asp Gly Val Thr Asn Lys Val Asn
         35                  40                  45

Ser Ile Ile Asp Lys Met Asn Thr Gln Phe Glu Ala Val Gly Arg
     50                  55                  60

<210> SEQ ID NO 65
<211> LENGTH: 62
<212> TYPE: PRT
<213> ORGANISM: Influenza A virus

<400> SEQUENCE: 65

Gln Gly Met Val Asp Gly Trp Tyr Gly Tyr His His Ser Asn Glu Gln
  1               5                  10                  15

Gly Ser Gly Tyr Ala Ala Asp Lys Glu Ser Thr Gln Lys Ala Ile Asp
             20                  25                  30

Gly Val Thr Asn Lys Val Asn Ser Ile Ile Asp Lys Met Asn Thr Gln
         35                  40                  45
```

Phe Glu Ala Val Gly Arg Glu Phe Asn Asn Leu Glu Arg Arg
            50                  55                  60

<210> SEQ ID NO 66
<211> LENGTH: 29
<212> TYPE: PRT
<213> ORGANISM: Influenza A virus

<400> SEQUENCE: 66

Gly Tyr His His Ser Asn Glu Gln Gly Ser Gly Tyr Ala Ala Asp Lys
  1               5                  10                  15

Glu Ser Thr Gln Lys Ala Ile Asp Gly Val Thr Asn Lys
             20                  25

<210> SEQ ID NO 67
<211> LENGTH: 103
<212> TYPE: PRT
<213> ORGANISM: Influenza A virus

<400> SEQUENCE: 67

His Ser Asn Glu Gln Gly Ser Gly Tyr Ala Ala Asp Lys Glu Ser Thr
  1

```
Asn Gly Thr Tyr Asp Tyr Pro Gln Tyr Ser
    130                 135
```

<210> SEQ ID NO 69
<211> LENGTH: 47
<212> TYPE: PRT
<213> ORGANISM: Influenza A virus

<400> SEQUENCE: 69

```
Ser Asn Glu Gln Gly Ser Gly Tyr Ala Ala Asp Lys Glu Ser Thr Gln
 1               5                  10                  15

Lys Ala Ile Asp Gly Val Thr Asn Lys Val Asn Ser Ile Ile Asp Lys
            20                  25                  30

Met Asn Thr Gln Phe Glu Ala Val Gly Arg Glu Phe Asn Asn Leu
        35                  40                  45
```

<210> SEQ ID NO 70
<211> LENGTH: 41
<212> TYPE: PRT
<213> ORGANISM: Influenza A virus

<400> SEQUENCE: 70

```
Gln Lys Ala Ile Asp Gly Val

```
<400> SEQUENCE: 73

Met Glu Ser Val Arg Asn Gly Thr Tyr Asp Tyr Pro Gln Tyr Ser Glu
1               5                   10                  15

Glu Ala Arg Leu Lys Arg Glu Glu Ile Ser Gly Val Lys Leu Glu Ser
            20                  25                  30

Ile Gly Ile Tyr
        35

<210> SEQ ID NO 74
<211> LENGTH: 29
<212> TYPE: PRT
<213> ORGANISM: Influenza A virus

<400> SEQUENCE: 74

Asp Tyr Pro Gln Tyr Ser Glu Glu Ala Arg Leu Lys Arg Glu Glu Ile
1               5                   10                  15

Ser Gly Val Lys Leu Glu Ser Ile Gly Ile Tyr Gln Ile
            20                  25

<210> SEQ ID NO 75
<211> LENGTH: 24
<212> TYPE: PRT
<213> ORGANISM: Influenza A virus

<400> SEQUENCE: 75

Met Ala Ser Gln Gly Thr Lys Arg Ser Tyr Glu Gln Met Glu Thr Gly
1               5                   10                  15

Gly Glu Arg Gln Asn Ala Thr Glu
            20

<210> SEQ ID NO 76
<211> LENGTH: 97
<212> TYPE: PRT
<213> ORGANISM: Influenza A virus

<400> SEQUENCE: 76

Tyr Glu Gln Met Glu Thr Gly Gly Glu Arg Gln Asn Ala Thr Glu Ile
1               5                   10                  15

Arg Ala Ser Val Gly Arg Met Val Ser Gly Ile Gly Arg Phe Tyr Ile
            20                  25                  30

Gln Met Cys Thr Glu Leu Lys Leu Ser Asp Tyr Glu Gly Arg Leu Ile
        35                  40                  45

Gln Asn Ser Ile Thr Ile Glu Arg Met Val Leu Ser Ala Phe Asp Glu
    50                  55                  60

Arg Arg Asn Arg Tyr Leu Glu Glu His Pro Ser Ala Gly Lys Asp Pro
65                  70                  75                  80

Lys Lys Thr Gly Gly Pro Ile Tyr Arg Arg Arg Asp Gly Lys Trp Val
                85                  90                  95

Arg

<210> SEQ ID NO 77
<211> LENGTH: 154
<212> TYPE: PRT
<213> ORGANISM: Influenza A virus

<400> SEQUENCE: 77

Tyr Glu Gln Met Glu Thr Gly Gly Glu Arg Gln Asn Ala Thr Glu Ile
1               5                   10                  15
```

```
Arg Ala Ser Val Gly Arg Met Val Ser Gly Ile Gly Arg Phe Tyr Ile
            20                  25                  30

Gln Met Cys Thr Glu Leu Lys Leu Ser Asp Tyr Glu Gly Arg Leu Ile
        35                  40                  45

Gln Asn Ser Ile Thr Ile Glu Arg Met Val Leu Ser Ala Phe Asp Glu
    50                  55                  60

Arg Arg Asn Arg Tyr Leu Glu Glu His Pro Ser Ala Gly Lys Asp Pro
65                  70                  75                  80

Lys Lys Thr Gly Gly Pro Ile Tyr Arg Arg Arg Asp Gly Lys Trp Val
                85                  90                  95

Arg Glu Leu Ile Leu Tyr Asp Lys Glu Glu Ile Arg Arg Ile Trp Arg
            100                 105                 110

Gln Ala Asn Asn Gly Glu Asp Ala Thr Ala Gly Leu Thr His Leu Met
        115                 120                 125

Ile Trp His Ser Asn Leu Asn Asp Ala Thr Tyr Gln Arg Thr Arg Ala
    130                 135                 140

Leu Val Arg Thr Gly Met Asp Pro Arg Met
145                 150

<210> SEQ ID NO 78
<211> LENGTH: 117
<212> TYPE: PRT
<213> ORGANISM: Influenza A virus

<400> SEQUENCE: 78

Ser Gly Ile Gly Arg Phe Tyr Ile Gln Met Cys Thr Glu Leu Lys Leu
1               5                   10                  15

Ser Asp Tyr Glu Gly Arg Leu Ile Gln Asn Ser Ile Thr Ile Glu Arg
            20                  25                  30

Met Val Leu Ser Ala Phe Asp Glu Arg Arg Asn Arg Tyr Leu Glu Glu
        35                  40                  45

His Pro Ser Ala Gly Lys Asp Pro Lys Lys Thr Gly Gly Pro Ile Tyr
    50                  55                  60

Arg Arg Arg Asp Gly Lys Trp Val Arg Glu Leu Ile Leu Tyr Asp Lys
65                  70                  75                  80

Glu Glu Ile Arg Arg Ile Trp Arg Gln Ala Asn Asn Gly Glu Asp Ala
                85                  90                  95

Thr Ala Gly Leu Thr His Leu Met Ile Trp His Ser Asn Leu Asn Asp
            100                 105                 110

Ala Thr Tyr Gln Arg
        115

<210> SEQ ID NO 79
<211> LENGTH: 57
<212> TYPE: PRT
<213> ORGANISM: Influenza A virus

<400> SEQUENCE: 79

Ser Asp Tyr Glu Gly Arg Leu Ile Gln Asn Ser Ile Thr Ile Glu Arg
1               5                   10                  15

Met Val Leu Ser Ala Phe Asp Glu Arg Arg Asn Arg Tyr Leu Glu Glu
            20                  25                  30

His Pro Ser Ala Gly Lys Asp Pro Lys Lys Thr Gly Gly Pro Ile Tyr
        35                  40                  45

Arg Arg Arg Asp Gly Lys Trp Val Arg
50                  55
```

-continued

<210> SEQ ID NO 80
<211> LENGTH: 33
<212> TYPE: PRT
<213> ORGANISM: Influenza A virus

<400> SEQUENCE: 80

```
Glu Arg Glu Gly Tyr Ser Leu Val Gly Ile Asp Pro Phe Arg Leu Leu
 1               5                  10                  15

Gln Asn Ser Gln Val Phe Ser Leu Ile Arg Pro Asn Glu Asn Pro Ala
            20                  25                  30

His
```

<210> SEQ ID NO 81
<211> LENGTH: 48
<212> TYPE: PRT
<213> ORGANISM: Influenza A virus

<400> SEQUENCE: 81

```
Asn Ser Gln Val Phe Ser Leu Ile Arg Pro Asn Glu Asn Pro Ala His
 1               5                  10                  15

Lys Ser Gln Leu Val Trp Met Ala Cys His Ser Ala Ala Phe Glu Asp
            20                  25                  30

Leu Arg Val Ser Ser Phe Ile Arg Gly Thr Arg Val Val Pro Arg Gly
        35                  40                  45
```

<210> SEQ ID NO 82
<211> LENGTH: 43
<212> TYPE: PRT
<213> ORGANISM: Influenza A virus

<400> SEQUENCE: 82

```
Leu Ser Thr Arg Gly Val Gln Ile Ala Ser Asn Glu Asn Met Glu Ala
 1               5                  10                  15

Met Asp Ser Asn Thr Leu Glu Leu Arg Ser Arg Tyr Trp Ala Ile Arg
            20                  25                  30

Thr Arg Ser Gly Gly Asn Thr Asn Gln Gln Arg
        35                  40
```

<210> SEQ ID NO 83
<211> LENGTH: 71
<212> TYPE: PRT
<213> ORGANISM: Influenza A virus

<400> SEQUENCE: 83

```
Thr Ile Met Ala Ala Phe Thr Gly Asn Thr Glu Gly Arg Thr Ser Asp
 1               5                  10                  15

Met Arg Thr Glu Ile Ile Arg Met Met Glu Ser Ala Arg Pro Glu Asp
            20                  25                  30

Val Ser Phe Gln Gly Arg Gly Val Phe Glu Leu Ser Asp Glu Lys Ala
        35                  40                  45

Thr Asn Pro Ile Val Pro Ser Phe Asp Met Asn Asn Glu Gly Ser Tyr
    50                  55                  60

Phe Phe Gly Asp Asn Ala Glu
65                  70
```

<210> SEQ ID NO 84
<211> LENGTH: 51
<212> TYPE: PRT
<213> ORGANISM: Influenza A virus

```
<400> SEQUENCE: 84

Gln Ile Gly Asn Met Ile Ser Ile Trp Val Ser His Ser Ile His Thr
1               5                   10                  15

Gly Asn Gln His Gln Ser Glu Pro Ile Ser Asn Thr Asn Phe Leu Thr
            20                  25                  30

Glu Lys Ala Val Ala Ser Val Lys Leu Ala Gly Asn Ser Ser Leu Cys
        35                  40                  45

Pro Ile Asn
    50

<210> SEQ ID NO 85
<211> LENGTH: 36
<212> TYPE: PRT
<213> ORGANISM: Influenza A virus

<400> SEQUENCE: 85

Val Lys Leu Ala Gly Asn Ser Ser Leu Cys Pro Ile Asn Gly Trp Ala
1               5                   10                  15

Val Tyr Ser Lys Asp Asn Ser Ile Arg Ile Gly Ser Lys Gly Asp Val
            20                  25                  30

Phe Val Ile Arg
        35

<210> SEQ ID NO 86
<211> LENGTH: 42
<212> TYPE: PRT
<213> ORGANISM: Influenza A virus

<400> SEQUENCE: 86

Asp Asn Ser Ile Arg Ile Gly Ser Lys Gly Asp Val Phe Val Ile Arg
1               5                   10                  15

Glu Pro Phe Ile Ser Cys Ser His Leu Glu Cys Arg Thr Phe Phe Leu
            20                  25                  30

Thr Gln Gly Ala Leu Leu Asn Asp Lys His
        35                  40

<210> SEQ ID NO 87
<211> LENGTH: 20
<212> TYPE: PRT
<213> ORGANISM: Influenza A virus

<400> SEQUENCE: 87

Gln Gly Ala Leu Leu Asn Asp Lys His Ser Asn Gly Thr Val Lys Asp
1               5                   10                  15

Arg Ser Pro His
    20

<210> SEQ ID NO 88
<211> LENGTH: 36
<212> TYPE: PRT
<213> ORGANISM: Influenza A virus

<400> SEQUENCE: 88

His Arg Thr Leu Met Ser Cys Pro Val Gly Glu Ala Pro Ser Pro Tyr
1               5                   10                  15

Asn Ser Arg Phe Glu Ser Val Ala Trp Ser Ala Ser Ala Cys His Asp
            20                  25                  30

Gly Thr Ser Trp
        35
```

<210> SEQ ID NO 89
<211> LENGTH: 66
<212> TYPE: PRT
<213> ORGANISM: Influenza A virus

<400> SEQUENCE: 89

```
Pro Val Gly Glu Ala Pro Ser Pro Tyr Asn Ser Arg Phe Glu Ser Val
1               5                   10                  15
Ala Trp Ser Ala Ser Ala Cys His Asp Gly Thr Ser Trp Leu Thr Ile
            20                  25                  30
Gly Ile Ser Gly Pro Asp Asn Gly Ala Val Ala Val Leu Lys Tyr Asn
        35                  40                  45
Gly Ile Ile Thr Asp Thr Ile Lys Ser Trp Arg Asn Asn Ile Leu Arg
    50                  55                  60
Thr Gln
65
```

<210> SEQ ID NO 90
<211> LENGTH: 45
<212> TYPE: PRT
<213> ORGANISM: Influenza A virus

<400> SEQUENCE: 90

```
Ala Cys Val Asn Gly Ser Cys Phe Thr Val Met Thr Asp Gly Pro Ser
1               5                   10                  15
Asn Gly Gln Ala Ser His Lys Ile Phe Lys Met Glu Lys Gly Lys Val
            20                  25                  30
Val Lys Ser Val Glu Leu Asp Ala Pro Asn Tyr His Tyr
        35                  40                  45
```

<210> SEQ ID NO 91
<211> LENGTH: 31
<212> TYPE: PRT
<213> ORGANISM: Influenza A virus

<400> SEQUENCE: 91

```
Asn Tyr His Tyr Glu Glu Cys Ser Cys Tyr Pro Asn Ala Gly Glu Ile
1               5                   10                  15
Thr Cys Val Cys Arg Asp Asn Trp His Gly Ser Asn Arg Pro Trp
            20                  25                  30
```

<210> SEQ ID NO 92
<211> LENGTH: 179
<212> TYPE: PRT
<213> ORGANISM: Influenza A virus

<400> SEQUENCE: 92

```
Cys Val Cys Arg Asp Asn Trp His Gly Ser Asn Arg Pro Trp Val Ser
1               5                   10                  15
Phe Asn Gln Asn Leu Glu Tyr Gln Ile Gly Tyr Ile Cys Ser Gly Val
            20                  25                  30
Phe Gly Asp Asn Pro Arg Pro Asn Asp Gly Thr Gly Ser Cys Gly Pro
        35                  40                  45
Val Ser Ser Asn Gly Ala Tyr Gly Val Lys Gly Phe Ser Phe Lys Tyr
    50                  55                  60
Gly Asn Gly Val Trp Ile Gly Arg Thr Lys Ser Thr Asn Ser Arg Ser
65                  70                  75                  80
Gly Phe Glu Met Ile Trp Asp Pro Asn Gly Trp Thr Glu Thr Asp Ser
                85                  90                  95
```

```
Ser Phe Ser Val Lys Gln Asp Ile Val Ala Ile Thr Asp Trp Ser Gly
            100                 105                 110

Tyr Ser Gly Ser Phe Val Gln His Pro Glu Leu Thr Gly Leu Asp Cys
        115                 120                 125

Ile Arg Pro Cys Phe Trp Val Glu Leu Ile Arg Gly Arg Pro Lys Glu
    130                 135                 140

Ser Thr Ile Trp Thr Ser Gly Ser Ser Ile Ser Phe Cys Gly Val Asn
145                 150                 155                 160

Ser Asp Thr Val Gly Trp Ser Trp Pro Asp Gly Ala Glu Leu Pro Phe
                165                 170                 175

Thr Ile Asp

<210> SEQ ID NO 93
<211> LENGTH: 137
<212> TYPE: PRT
<213> ORGANISM: Influenza A virus

<400> SEQUENCE: 93

Cys Ser Gly Val Phe Gly Asp Asn Pro Arg Pro Asn Asp Gly Thr Gly
1               5                   10                  15

Ser Cys Gly Pro Val Ser Ser Asn Gly Ala Tyr Gly Val Lys Gly Phe
            20                  25                  30

Ser Phe Lys Tyr Gly Asn Gly Val Trp Ile Gly Arg Thr Lys Ser Thr
        35                  40                  45

Asn Ser Arg Ser Gly Phe Glu Met Ile Trp Asp Pro Asn Gly Trp Thr
    50                  55                  60

Glu Thr Asp Ser Ser Phe Ser Val Lys Gln Asp Ile Val Ala Ile Thr
65                  70                  75                  80

Asp Trp Ser Gly Tyr Ser Gly Ser Phe Val Gln His Pro Glu Leu Thr
                85                  90                  95

Gly Leu Asp Cys Ile Arg Pro Cys Phe Trp Val Glu Leu Ile Arg Gly
            100                 105                 110

Arg Pro Lys Glu Ser Thr Ile Trp Thr Ser Gly Ser Ser Ile Ser Phe
        115                 120                 125

Cys Gly Val Asn Ser Asp Thr Val Gly
        130                 135

<210> SEQ ID NO 94
<211> LENGTH: 52
<212> TYPE: PRT
<213> ORGANISM: Influenza A virus

<400> SEQUENCE: 94

Glu Met Ile Trp Asp Pro Asn Gly Trp Thr Glu Thr Asp Ser Ser Phe
1               5                   10                  15

Ser Val Lys Gln Asp Ile Val Ala Ile Thr Asp Trp Ser Gly Tyr Ser
            20                  25                  30

Gly Ser Phe Val Gln His Pro Glu Leu Thr Gly Leu Asp Cys Ile Arg
        35                  40                  45

Pro Cys Phe Trp
    50

<210> SEQ ID NO 95
<211> LENGTH: 34
<212> TYPE: PRT
<213> ORGANISM: Influenza A virus
```

```
<400> SEQUENCE: 95

Thr Ile Trp Thr Ser Gly Ser Ser Ile Ser Phe Cys Gly Val Asn Ser
1               5                   10                  15

Asp Thr Val Gly Trp Ser Trp Pro Asp Gly Ala Glu Leu Pro Phe Thr
            20                  25                  30

Ile Asp

<210> SEQ ID NO 96
<211> LENGTH: 21
<212> TYPE: PRT
<213> ORGANISM: Influenza A virus

<400> SEQUENCE: 96

Val Asn Ser Asp Thr Val Gly Trp Ser Trp Pro Asp Gly Ala Glu Leu
1               5                   10                  15

Pro Phe Thr Ile Asp
            20

<210> SEQ ID NO 97
<211> LENGTH: 31
<212> TYPE: PRT
<213> ORGANISM: Influenza A virus

<400> SEQUENCE: 97

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val
            20                  25                  30

<210> SEQ ID NO 98
<211> LENGTH: 155
<212> TYPE: PRT
<213> ORGANISM: Influenza A virus

<400> SEQUENCE: 98

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala
145                 150                 155

<210> SEQ ID NO 99
<211> LENGTH: 47
```

```
<212> TYPE: PRT
<213> ORGANISM: Influenza A virus

<400> SEQUENCE: 99

Thr Glu Val Glu Thr Tyr Val Leu Ser Ile Ile Pro Ser Gly Pro Leu
 1               5                  10                  15

Lys Ala Glu Ile Ala Gln Lys Leu Glu Asp Val Phe Ala Gly Lys Asn
            20                  25                  30

Thr Asp Leu Glu Ala Leu Met Glu Trp Leu Lys Thr Arg Pro Ile
        35                  40                  45

<210> SEQ ID NO 100
<211> LENGTH: 29
<212> TYPE: PRT
<213> ORGANISM: Influenza A virus

<400> SEQUENCE: 100

Glu Thr Tyr Val Leu Ser Ile Ile Pro Ser Gly Pro Leu Lys Ala Glu
 1               5                  10                  15

Ile Ala Gln Lys Leu Glu Asp Val Phe Ala Gly Lys Asn
            20                  25

<210> SEQ ID NO 101
<211> LENGTH: 60
<212> TYPE: PRT
<213> ORGANISM: Influenza A virus

<400> SEQUENCE: 101

Ile Tyr Asn Arg Met Gly Thr Val Thr Thr Glu Val Ala Phe Gly Leu
 1               5                  10                  15

Val Cys Ala Thr Cys Glu Gln Ile Ala Asp Ser Gln His Arg Ser His
            20                  25                  30

Arg Gln Met Ala Thr Ile Thr Asn Pro Leu Ile Arg His Glu Asn Arg
        35                  40                  45

Met Val Leu Ala Ser Thr Thr Ala Lys Ala Met Glu
    50                  55                  60

<210> SEQ ID NO 102
<211> LENGTH: 109
<212> TYPE: PRT
<213> ORGANISM: Influenza A virus

<400> SEQUENCE: 102

Phe Gly Leu Val Cys Ala Thr Cys Glu Gln Ile Ala Asp Ser Gln His
 1               5                  10                  15

Arg Ser His Arg Gln Met Ala Thr Ile Thr Asn Pro Leu Ile Arg His
            20                  25                  30

Glu Asn Arg Met Val Leu Ala Ser Thr Thr Ala Lys Ala Met Glu Gln
        35                  40                  45

Met Ala Gly Ser Ser Glu Gln Ala Ala Glu Ala Met Glu Ile Ala Asn
    50                  55                  60

Gln Ala Arg Gln Met Val Gln Ala Met Arg Thr Ile Gly Thr His Pro
65                  70                  75                  80

Asn Ser Ser Ala Gly Leu Arg Asp Asn Leu Leu Glu Asn Leu Gln Ala
                85                  90                  95

Tyr Gln Lys Arg Met Gly Val Gln Met Gln Arg Phe Lys
            100                 105

<210> SEQ ID NO 103
```

```
<211> LENGTH: 65
<212> TYPE: PRT
<213> ORGANISM: Influenza A virus

<400> SEQUENCE: 103

Ala Ser Thr Thr Ala Lys Ala Met Glu Gln Met Ala Gly Ser Ser Glu
1               5                   10                  15

Gln Ala Ala Glu Ala Met Glu Ile Ala Asn Gln Ala Arg Gln Met Val
            20                  25                  30

Gln Ala Met Arg Thr Ile Gly Thr His Pro Asn Ser Ser Ala Gly Leu
        35                  40                  45

Arg Asp Asn Leu Leu Glu Asn Leu Gln Ala Tyr Gln Lys Arg Met Gly
    50                  55                  60

Val
65

<210> SEQ ID NO 104
<211> LENGTH: 57
<212> TYPE: PRT
<213> ORGANISM: Influenza A virus

<400> SEQUENCE: 104

Ser Glu Gln Ala Ala Glu Ala Met Glu Ile Ala Asn Gln Ala Arg Gln
1               5                   10                  15

Met Val Gln Ala Met Arg Thr Ile Gly Thr His Pro Asn Ser Ser Ala
            20                  25                  30

Gly Leu Arg Asp Asn Leu Leu Glu Asn Leu Gln Ala Tyr Gln Lys Arg
        35                  40                  45

Met Gly Val Gln Met Gln Arg Phe Lys
    50                  55

<210> SEQ ID NO 105
<211> LENGTH: 30
<212> TYPE: PRT
<213> ORGANISM: Influenza A virus

<400> SEQUENCE: 105

His Pro Asn Ser Ser Ala Gly Leu Arg Asp Asn Leu Leu Glu Asn Leu
1               5                   10                  15

Gln Ala Tyr Gln Lys Arg Met Gly Val Gln Met Gln Arg Phe
            20                  25                  30

<210> SEQ ID NO 106
<211> LENGTH: 23
<212> TYPE: PRT
<213> ORGANISM: Influenza A virus

<400> SEQUENCE: 106

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 107
<211> LENGTH: 29
<212> TYPE: PRT
<213> ORGANISM: Influenza A virus

<400> SEQUENCE: 107

Val Pro Glu Ser Met Arg Glu Glu Tyr Arg Gln Glu Gln Gln Ser Ala
1               5                   10                  15
```

Val Asp Val Asp Asp Gly His Phe Val Asn Ile Glu Leu
            20                  25

<210> SEQ ID NO 108
<211> LENGTH: 65
<212> TYPE: PRT
<213> ORGANISM: Influenza A virus

<400> SEQUENCE: 108

Ser Ser Phe Gln Val Asp Cys Phe Leu Trp His Val Arg Lys Arg Phe
1               5                   10                  15

Ala Asp Gln Glu Leu Gly Asp Ala Pro Phe Leu Asp Arg Leu Arg Arg
            20                  25                  30

Asp Gln Lys Ser Leu Arg Gly Arg Gly Asn Thr Leu Gly Leu Asp Ile
        35                  40                  45

Glu Thr Ala Thr Arg Ala Gly Lys Gln Ile Val Glu Arg Ile Leu Glu
    50                  55                  60

Gly
65

<210> SEQ ID NO 109
<211> LENGTH: 20
<212> TYPE: PRT
<213> ORGANISM: Influenza A virus

<400> SEQUENCE: 109

Ala Asp Gln Glu Leu Gly Asp Ala Pro Phe Leu Asp Arg Leu Arg Arg
1               5                   10                  15

Asp Gln Lys Ser
            20

<210> SEQ ID NO 110
<211> LENGTH: 12
<212> TYPE: PRT
<213> ORGANISM: Influenza A virus

<400> SEQUENCE: 110

Glu Gly Glu Ser Asp Lys Ala Leu Lys Met Pro Ala
1               5                   10

<210> SEQ ID NO 111
<211> LENGTH: 20
<212> TYPE: PRT
<213> ORGANISM: Influenza A virus

<400> SEQUENCE: 111

Thr Gly Glu Asp Val Lys Asn Ala Ile Gly Val Leu Ile Gly Gly Leu
1               5                   10                  15

Glu Trp Asn Asp
            20

<210> SEQ ID NO 112
<211> LENGTH: 36
<212> TYPE: PRT
<213> ORGANISM: Influenza A virus

<400> SEQUENCE: 112

Leu Glu Trp Asn Asp Asn Thr Val Arg Val Thr Glu Thr Ile Gln Arg
1               5                   10                  15

Phe Ala Trp Arg Asn Ser Asp Glu Asp Gly Arg Leu Pro Leu Pro Pro
            20                  25                  30

Asn Gln Lys Arg
        35

<210> SEQ ID NO 113
<211> LENGTH: 42
<212> TYPE: PRT
<213> ORGANISM: Influenza A virus

<400> SEQUENCE: 113

Ser Leu Lys Leu Tyr Arg Asp Ser Leu Gly Glu Thr Val Met Arg Met
1               5                   10                  15

Gly Asp Phe His Ser Leu Gln Ile Arg Asn Gly Lys Trp Arg Glu Gln
            20                  25                  30

Leu Ser Gln Lys Phe Glu Glu Ile Arg Trp
        35                  40

<210> SEQ ID NO 114
<211> LENGTH: 12
<212> TYPE: PRT
<213> ORGANISM: Influenza A virus

<400> SEQUENCE: 114

Trp Thr Pro Ile His Leu Thr Thr Lys Val Thr Leu
1               5                   10

<210> SEQ ID NO 115
<211> LENGTH: 12
<212> TYPE: PRT
<213> ORGANISM: Influenza A virus

<400> SEQUENCE: 115

Trp Ser Tyr Ser Trp Phe Tyr Asn Thr Ser Tyr Glu
1 5 10

<210> SEQ ID NO 116
<211> LENGTH: 12
<212> TYPE: PRT
<213> ORGANISM: Influenza A virus

<400> SEQUENCE: 116

Val Trp Asn Pro Tyr Ile Trp Ser Ala Pro Phe Ser
1 5 10

<210> SEQ ID NO 117
<211> LENGTH: 12
<212> TYPE: PRT
<213> ORGANISM: Influenza A virus

<400> SEQUENCE: 117

Gly Val Trp Pro Asn Ala Thr His Phe Pro Ser Ser
1 5 10

<210> SEQ ID NO 118
<211> LENGTH: 12
<212> TYPE: PRT
<213> ORGANISM: Influenza A virus

<400> SEQUENCE: 118

Trp Trp Asp Thr Pro His Ser Trp Trp Thr Met Arg
1 5 10

<210> SEQ ID NO 119
<211> LENGTH: 12

<212> TYPE: PRT
<213> ORGANISM: Influenza A virus

<400> SEQUENCE: 119

```
Trp Gly Leu Phe Gly Val Ser Pro His Val Gln Ser
 1              5                   10
```

<210> SEQ ID NO 120
<211> LENGTH: 12
<212> TYPE: PRT
<213> ORGANISM: Influenza A virus

<400> SEQUENCE: 120

```
Gln Ala Arg Trp Pro Val Thr Ser Pro Tyr Trp Pro
 1              5                   10
```

<210> SEQ ID NO 121
<211> LENGTH: 292
<212> TYPE: PRT
<213> ORGANISM: Influenza A virus

<400> SEQUENCE: 121

```
Ala Gln Asp Ile Leu Glu Lys Lys His Asn Gly Lys Leu Cys Asp Leu
 1              5                   10                  15

Asp Gly Val Lys Pro Leu Ile Leu Arg Asp Cys Ser Val Ala Gly Trp
            20                  25                  30

Leu Leu Gly Asn Pro Met Cys Asp Glu Phe Ile Asn Val Pro Glu Trp
        35                  40                  45

Ser Tyr Ile Val Glu Lys Ala Asn Pro Val Asn Asp Leu Cys Tyr Pro
    50                  55                  60

Gly Asp Phe Asn Asp Tyr Glu Glu Leu Lys His Leu Leu Ser Arg Ile
65                  70                  75                  80

Asn His Phe Glu Lys Ile Gln Ile Ile Pro Lys Ser Ser Trp Ser Ser
                85                  90                  95

His Glu Ala Ser Leu Gly Val Ser Ser Ala Cys Pro Tyr Gln Gly Lys
            100                 105                 110

Ser Ser Phe Phe Arg Asn Val Val Trp Leu Ile Lys Lys Asn Ser Thr
        115                 120                 125

Tyr Pro Thr Ile Lys Arg Ser Tyr Asn Asn Thr Asn Gln Glu Asp Leu
    130                 135                 140

Leu Val Leu Trp Gly Ile His His Pro Asn Asp Ala Ala Glu Gln Thr
145                 150                 155                 160

Lys Leu Tyr Gln Asn Pro Thr Thr Tyr Ile Ser Val Gly Thr Ser Thr
                165                 170                 175

Leu Asn Gln Arg Leu Val Pro Arg Ile Ala Thr Arg Ser Lys Val Asn
            180                 185                 190

Gly Gln Ser Gly Arg Met Glu Phe Phe Trp Thr Ile Leu Lys Pro Asn
        195                 200                 205

Asp Ala Ile Asn Phe Glu Ser Asn Gly Asn Phe Ile Ala Pro Glu Tyr
    210                 215                 220

Ala Tyr Lys Ile Val Lys Lys Gly Asp Ser Thr Ile Met Lys Ser Glu
225                 230                 235                 240

Leu Glu Tyr Gly Asn Cys Asn Thr Lys Cys Gln Thr Pro Met Gly Ala
                245                 250                 255

Ile Asn Ser Ser Met Pro Phe His Asn Ile His Pro Leu Thr Ile Gly
            260                 265                 270

Glu Cys Pro Lys Tyr Val Lys Ser Asn Arg Leu Val Leu Ala Thr Gly
```

```
                275                 280                 285

Leu Arg Asn Ser
    290

<210> SEQ ID NO 122
<211> LENGTH: 43
<212> TYPE: PRT
<213> ORGANISM: Influenza A virus

<400> SEQUENCE: 122

Lys Cys Gln Thr Pro Met Gly Ala Ile Asn Ser Ser Met Pro Phe His
1               5                   10                  15

Asn Ile His Pro Leu Thr Ile Gly Glu Cys Pro Lys Tyr Val Lys Ser
            20                  25                  30

Asn Arg Leu Val Leu Ala Thr Gly Leu Arg Asn
        35                  40

<210> SEQ ID NO 123
<211> LENGTH: 44
<212> TYPE: PRT
<213> ORGANISM: Influenza A virus

<400> SEQUENCE: 123

His Asn Ile His Pro Leu Thr Ile Gly Glu Cys Pro Lys Tyr Val Lys
1               5                   10                  15

Ser Asn Arg Leu Val Leu Ala Thr Gly Leu Arg Asn Ser Pro Gln Arg
            20                  25                  30

Glu Arg Arg Arg Lys Lys Arg Gly Leu Phe Gly Ala
        35                  40

<210> SEQ ID NO 124

<400> SEQUENCE: 124

000

<210> SEQ ID NO 125
<211> LENGTH: 759
<212> TYPE: PRT
<213> ORGANISM: Influenza A virus
<220> FEATURE:
<223> OTHER INFORMATION: influenza A virus serotype H5N1 strain A/Viet
      Nam/1203/2004 basic polymerase B2 (PB2)

<400> SEQUENCE: 125

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Ile
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Ala Thr Ser Ala Val His Tyr Pro
            100                 105                 110

Lys Val Tyr Lys Thr Tyr Phe Glu Lys Val Glu Arg Leu Lys His Gly
```

-continued

```
            115                 120                 125
Thr Phe Gly Pro Val His Phe Arg Asn Gln Val Lys Ile Arg Arg
130                 135                 140
Val Asp Ile Asn Pro Gly His Ala Asp Leu Ser Ala Lys Glu Ala Gln
145                 150                 155                 160
Asp Val Ile Met Glu Val Val Phe Pro Asn Glu Val Gly Ala Arg Ile
                    165                 170                 175
Leu Thr Ser Glu Ser Gln Leu Thr Ile Thr Lys Glu Lys Lys Glu Glu
                    180                 185                 190
Leu Gln Asp Cys Lys Ile Ala Pro Leu Met Val Ala Tyr Met Leu Glu
                    195                 200                 205
Arg Glu Leu Val Arg Lys Thr Arg Phe Leu Pro Val Ala Gly Gly Thr
210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Val Arg Asn Asp Asp Val Asp
                    245                 250                 255
Gln Ser Leu Ile Ile Ala Ala Arg Asn Ile Val Arg Arg Ala Thr Val
                    260                 265                 270
Ser Ala Asp Pro Leu Ala Ser Leu Leu Glu Met Cys His Ser Thr Gln
                    275                 280                 285
Ile Gly Gly Ile Arg Met Val Asp Ile Leu Arg Gln Asn Pro Thr Glu
290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                    325                 330                 335
Ser Val Lys Lys Glu Glu Glu Val Leu Thr Gly Asn Leu Gln Thr Leu
                    340                 345                 350
Lys Ile Arg Val His Glu Gly Tyr Glu Glu Phe Thr Met Val Gly Arg
                    355                 360                 365
Arg Ala Thr Ala Ile Leu Arg Lys Ala Thr Arg Arg Leu Ile Gln Leu
370                 375                 380
Ile Val Ser Gly Arg Asp Gln Gln Ser Ile Ala Glu Ala Ile Ile Val
385                 390                 395                 400
Ala Met Val Phe Ser Gln Glu Asp Cys Met Ile Lys Ala Val Arg Gly
                    405                 410                 415
Asp Leu Asn Phe Val Asn Arg Ala Asn Gln Arg Leu Asn Pro Met His
                    420                 425                 430
Gln Leu Leu Arg His Phe Gln Lys Asp Ala Lys Val Leu Phe Gln Asn
                    435                 440                 445
Trp Gly Ile Glu Pro Ile Asp Asn Val Met Gly Met Ile Gly Ile Leu
                    450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val
                    485                 490                 495
Ser Ile Asp Arg Phe Leu Arg Val Arg Asp Gln Arg Gly Asn Val Leu
                    500                 505                 510
Leu Ser Pro Glu Glu Val Ser Glu Thr Gln Gly Thr Glu Lys Leu Thr
                    515                 520                 525
Ile Thr Tyr Ser Ser Ser Met Met Trp Glu Ile Asn Gly Pro Glu Ser
530                 535                 540
```

```
Val Leu Val Asn Thr Tyr Gln Trp Ile Ile Arg Asn Trp Glu Thr Val
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Ala Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 126
<211> LENGTH: 847
<212> TYPE: PRT
<213> ORGANISM: Influenza A virus
<220> FEATURE:
<223> OTHER INFORMATION: influenza A virus serotype H5N1 strain A/Viet
      Nam/1203/2004 basic polymerase B1 (PB1)

<400> SEQUENCE: 126

Met Asp Val Asn Pro Thr Leu Leu Phe Leu Lys Val Pro Val Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ile Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
```

-continued

```
            130                 135                 140
Asn Thr Ile Glu Ile Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Arg Lys
            195                 200                 205

Lys Gln Arg Leu Asn Lys Lys Ser Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
            355                 360                 365

Pro Ala Glu Met Leu Ala Asn Ile Asp Leu Lys Tyr Phe Asn Glu Leu
        370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr His Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560
```

Cys His Arg Gly Asp Thr Gln Ile Gln Thr Arg Arg Ser Phe Glu Leu
            565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
            645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
            725                 730                 735

Lys Glu Glu Phe Ala Glu Ile Met Lys Ile Cys Ser Thr Ile Glu Glu
            740                 745                 750

Leu Arg Arg Gln Lys Met Glu Gln Gly Gln Asp Thr Pro Trp Thr Gln
            755                 760                 765

Ser Thr Glu His Thr Asn Ile Gln Lys Arg Gly Ser Gly Gln Gln Thr
770                 775                 780

Gln Arg Leu Glu His Pro Asn Ser Thr Arg Leu Met Asp His Tyr Leu
785                 790                 795                 800

Arg Ile Met Ser Pro Val Gly Thr His Lys Gln Ile Val Tyr Trp Lys
            805                 810                 815

Gln Trp Leu Ser Leu Lys Asn Pro Thr Gln Gly Ser Leu Lys Thr Arg
            820                 825                 830

Val Leu Lys Arg Trp Lys Leu Phe Asn Lys Gln Glu Trp Ile Asn
            835                 840                 845

<210> SEQ ID NO 127
<211> LENGTH: 90
<212> TYPE: PRT
<213> ORGANISM: Influenza A virus
<220> FEATURE:
<223> OTHER INFORMATION: influenza A virus serotype H5N1 strain A/Viet
      Nam/1203/2004 basic polymerase frame 2 (PB1-F2)

<400> SEQUENCE: 127

Met Glu Gln Gly Gln Asp Thr Pro Trp Thr Gln Ser Thr Glu His Thr
1               5                   10                  15

Asn Ile Gln Lys Arg Gly Ser Gly Gln Gln Thr Gln Arg Leu Glu His
            20                  25                  30

Pro Asn Ser Thr Arg Leu Met Asp His Tyr Leu Arg Ile Met Ser Pro
        35                  40                  45

Val Gly Thr His Lys Gln Ile Val Tyr Trp Lys Gln Trp Leu Ser Leu
    50                  55                  60

Lys Asn Pro Thr Gln Gly Ser Leu Lys Thr Arg Val Leu Lys Arg Trp

```
                65                  70                  75                  80
Lys Leu Phe Asn Lys Gln Glu Trp Ile Asn
                    85                  90

<210> SEQ ID NO 128
<211> LENGTH: 716
<212> TYPE: PRT
<213> ORGANISM: Influenza A virus
<220> FEATURE:
<223> OTHER INFORMATION: influenza A virus serotype H5N1 strain A/Viet
      Nam/1203/2004 acidic polymerase (PA)

<400> SEQUENCE: 128

Met Glu Asp Phe Val Arg Gln Cys Phe Asn Pro Met Ile Val Glu Leu
 1               5                  10                  15

Ala Glu Lys Ala Met Lys Glu Tyr Gly Glu Asp Pro Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asp Glu Arg Ser Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Thr Tyr Tyr Leu Glu Lys Ala Asn Lys Ile Lys Ser Glu Glu Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Leu
                325                 330                 335
```

Ala Trp Lys Gln Val Leu Ala Glu Leu Gln Asp Ile Glu Asn Glu Glu
                340                 345                 350

Lys Ile Pro Lys Thr Lys Asn Met Lys Thr Ser Gln Leu Lys Trp
        355                 360                 365

Ala Leu Gly Glu Asn Met Ala Pro Glu Lys Val Asp Phe Glu Asp Cys
        370                 375                 380

Lys Asp Val Ser Asp Leu Arg Gln Tyr Asp Ser Asp Glu Pro Glu Ser
385                 390                 395                 400

Arg Ser Leu Ala Ser Trp Ile Gln Ser Glu Phe Asn Lys Ala Cys Glu
                405                 410                 415

Leu Thr Asp Ser Ile Trp Ile Glu Leu Asp Glu Ile Gly Glu Asp Val
                420                 425                 430

Ala Pro Ile Glu His Ile Ala Ser Met Arg Arg Asn Tyr Phe Thr Ala
                435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
                515                 520                 525

Asp Pro Arg Leu Glu Pro His Lys Trp Glu Lys Tyr Cys Val Leu Glu
530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
        580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
        610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Ala Gln Ala Leu
                660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
        690                 695                 700

Ser Trp Phe Asn Ser Phe Leu Ala His Ala Leu Lys
705                 710                 715

<210> SEQ ID NO 129
<211> LENGTH: 568
<212> TYPE: PRT
<213> ORGANISM: Influenza A virus
<220> FEATURE:
<223> OTHER INFORMATION: influenza A virus serotype H5N1 strain A/Viet Nam/1203/2004 haemagglutinin (HA)

<400> SEQUENCE: 129

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400
```

```
Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 130
<211> LENGTH: 498
<212> TYPE: PRT
<213> ORGANISM: Influenza A virus
<220> FEATURE:
<223> OTHER INFORMATION: influenza A virus serotype H5N1 strain A/Viet
      Nam/1203/2004 nucleoprotein (NP)

<400> SEQUENCE: 130

Met Ala Ser Gln Gly Thr Lys Arg Ser Tyr Glu Gln Met Glu Thr Gly
  1               5                  10                  15

Gly Glu Arg Gln Asn Ala Thr Glu Ile Arg Ala Ser Val Gly Arg Met
             20                  25                  30

Val Ser Gly Ile Gly Arg Phe Tyr Ile Gln Met Cys Thr Glu Leu Lys
         35                  40                  45

Leu Ser Asp Tyr Glu Gly Arg Leu Ile Gln Asn Ser Ile Thr Ile Glu
     50                  55                  60

Arg Met Val Leu Ser Ala Phe Asp Glu Arg Arg Asn Arg Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190
```

-continued

```
Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Ala Ser Gly
            275                 280                 285

Tyr Asp Phe Glu Arg Glu Gly Tyr Ser Leu Val Gly Ile Asp Pro Phe
        290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Ala Met Asp Ser Asn Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
                420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
        450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn
```

<210> SEQ ID NO 131
<211> LENGTH: 449
<212> TYPE: PRT
<213> ORGANISM: Influenza A virus
<220> FEATURE:
<223> OTHER INFORMATION: influenza A virus serotype H5N1 strain A/Viet
     Nam/1203/2004 neuraminidase (NA)

<400> SEQUENCE: 131

```
Met Asn Pro Asn Gln Lys Ile Ile Thr Ile Gly Ser Ile Cys Met Val
 1               5                  10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45
```

-continued

```
Ile Ser Asn Thr Asn Phe Leu Thr Glu Lys Ala Val Ala Ser Val Lys
 50                  55                  60
Leu Ala Gly Asn Ser Ser Leu Cys Pro Ile Asn Gly Trp Ala Val Tyr
 65                  70                  75                  80
Ser Lys Asp Asn Ser Ile Arg Ile Gly Ser Lys Gly Asp Val Phe Val
                 85                  90                  95
Ile Arg Glu Pro Phe Ile Ser Cys Ser His Leu Glu Cys Arg Thr Phe
                100                 105                 110
Phe Leu Thr Gln Gly Ala Leu Leu Asn Asp Lys His Ser Asn Gly Thr
            115                 120                 125
Val Lys Asp Arg Ser Pro His Arg Thr Leu Met Ser Cys Pro Val Gly
130                 135                 140
Glu Ala Pro Ser Pro Tyr Asn Ser Arg Phe Glu Ser Val Ala Trp Ser
145                 150                 155                 160
Ala Ser Ala Cys His Asp Gly Thr Ser Trp Leu Thr Ile Gly Ile Ser
                165                 170                 175
Gly Pro Asp Asn Gly Ala Val Ala Val Leu Lys Tyr Asn Gly Ile Ile
            180                 185                 190
Thr Asp Thr Ile Lys Ser Trp Arg Asn Asn Ile Leu Arg Thr Gln Glu
        195                 200                 205
Ser Glu Cys Ala Cys Val Asn Gly Ser Cys Phe Thr Val Met Thr Asp
210                 215                 220
Gly Pro Ser Asn Gly Gln Ala Ser His Lys Ile Phe Lys Met Glu Lys
225                 230                 235                 240
Gly Lys Val Val Lys Ser Val Glu Leu Asp Ala Pro Asn Tyr His Tyr
                245                 250                 255
Glu Glu Cys Ser Cys Tyr Pro Asn Ala Gly Glu Ile Thr Cys Val Cys
            260                 265                 270
Arg Asp Asn Trp His Gly Ser Asn Arg Pro Trp Val Ser Phe Asn Gln
        275                 280                 285
Asn Leu Glu Tyr Gln Ile Gly Tyr Ile Cys Ser Gly Val Phe Gly Asp
290                 295                 300
Asn Pro Arg Pro Asn Asp Gly Thr Gly Ser Cys Gly Pro Val Ser Ser
305                 310                 315                 320
Asn Gly Ala Tyr Gly Val Lys Gly Phe Ser Phe Lys Tyr Gly Asn Gly
                325                 330                 335
Val Trp Ile Gly Arg Thr Lys Ser Thr Asn Ser Arg Ser Gly Phe Glu
            340                 345                 350
Met Ile Trp Asp Pro Asn Gly Trp Thr Glu Thr Asp Ser Ser Phe Ser
        355                 360                 365
Val Lys Gln Asp Ile Val Ala Ile Thr Asp Trp Ser Gly Tyr Ser Gly
370                 375                 380
Ser Phe Val Gln His Pro Glu Leu Thr Gly Leu Asp Cys Ile Arg Pro
385                 390                 395                 400
Cys Phe Trp Val Glu Leu Ile Arg Gly Arg Pro Lys Glu Ser Thr Ile
                405                 410                 415
Trp Thr Ser Gly Ser Ser Ile Ser Phe Cys Gly Val Asn Ser Asp Thr
            420                 425                 430
Val Gly Trp Ser Trp Pro Asp Gly Ala Glu Leu Pro Phe Thr Ile Asp
        435                 440                 445
Lys
```

<210> SEQ ID NO 132
<211> LENGTH: 252
<212> TYPE: PRT
<213> ORGANISM: Influenza A virus
<220> FEATURE:
<223> OTHER INFORMATION: influenza A virus serotype H5N1 strain A/Viet
      Nam/1203/2004 matrix protein 1 (M1)

<400> SEQUENCE: 132

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250

<210> SEQ ID NO 133
<211> LENGTH: 97
<212> TYPE: PRT
<213> ORGANISM: Influenza A virus
<220> FEATURE:
<223> OTHER INFORMATION: influenza A virus serotype H5N1 strain A/Viet
      Nam/1203/2004 matrix protein 2 (M2)

<400> SEQUENCE: 133

Met Ser Leu Leu Thr Glu Val Glu Thr Pro Thr Arg Asn Glu Trp Glu
1               5                   10                  15

Cys Arg Cys Ser Asp Ser Ser Asp Pro Ile Val Val Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Leu Lys Tyr Gly Leu Lys Arg Gly Pro Ala

```
                  50                  55                  60

Thr Ala Gly Val Pro Glu Ser Met Arg Glu Glu Tyr Arg Gln Glu Gln
 65                  70                  75                  80

Gln Ser Ala Val Asp Val Asp Gly His Phe Val Asn Ile Glu Leu
                 85                  90                  95

Glu

<210> SEQ ID NO 134
<211> LENGTH: 215
<212> TYPE: PRT
<213> ORGANISM: Influenza A virus
<220> FEATURE:
<223> OTHER INFORMATION: influenza A virus serotype H5N1 strain A/Viet
      Nam/1203/2004 non-structural protein 1 (NS1)

<400> SEQUENCE: 134

Met Asp Ser Asn Thr Val Ser Ser Phe Gln Val Asp Cys Phe Leu Trp
  1               5                  10                  15

His Val Arg Lys Arg Phe Ala Asp Gln Glu Leu Gly Asp Ala Pro Phe
                 20                  25                  30

Leu Asp Arg Leu Arg Arg Asp Gln Lys Ser Leu Arg Gly Arg Gly Asn
             35                  40                  45

Thr Leu Gly Leu Asp Ile Glu Thr Ala Thr Arg Ala Gly Lys Gln Ile
 50                  55                  60

Val Glu Arg Ile Leu Glu Gly Glu Ser Asp Lys Ala Leu Lys Met Pro
 65                  70                  75                  80

Ala Ser Arg Tyr Leu Thr Asp Met Thr Leu Glu Glu Met Ser Arg Asp
                 85                  90                  95

Trp Phe Met Leu Met Pro Lys Gln Lys Val Ala Gly Ser Leu Cys Ile
                100                 105                 110

Lys Met Asp Gln Ala Ile Met Asp Lys Thr Ile Ile Leu Lys Ala Asn
            115                 120                 125

Phe Ser Val Ile Phe Asp Arg Leu Glu Thr Leu Ile Leu Leu Arg Ala
        130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Leu Pro
        195                 200                 205

Leu Pro Pro Asn Gln Lys Arg
    210                 215

<210> SEQ ID NO 135
<211> LENGTH: 121
<212> TYPE: PRT
<213> ORGANISM: Influenza A virus
<220> FEATURE:
<223> OTHER INFORMATION: influenza A virus serotype H5N1 strain A/Viet
      Nam/1203/2004 non-structural protein 2 (NS2)

<400> SEQUENCE: 135

Met Asp Ser Asn Thr Val Ser Ser Phe Gln Asp Ile Leu Val Arg Met
  1               5                  10                  15

Ser Lys Met Gln Leu Ala Ser Ser Ser Glu Asp Leu Asn Gly Met Ile
                 20                  25                  30
```

```
Thr Gln Phe Glu Ser Leu Lys Leu Tyr Arg Asp Ser Leu Gly Glu Thr
            35                  40                  45

Val Met Arg Met Gly Asp Phe His Ser Leu Gln Ile Arg Asn Gly Lys
 50                  55                  60

Trp Arg Glu Gln Leu Ser Gln Lys Phe Glu Ile Arg Trp Leu Ile
 65                  70                  75                  80

Glu Glu Val Arg His Arg Leu Lys Ile Thr Glu Asn Ser Phe Glu Gln
                    85                  90                  95

Ile Thr Phe Met Gln Ala Leu Gln Leu Leu Glu Val Glu Gln Glu
                    100                 105                 110

Ile Arg Ala Phe Ser Phe Gln Leu Ile
                    115                 120
```

<210> SEQ ID NO 136

<400> SEQUENCE: 136

000

<210> SEQ ID NO 137
<211> LENGTH: 761
<212> TYPE: PRT
<213> ORGANISM: Influenza A virus
<220> FEATURE:
<223> OTHER INFORMATION: influenza A virus serotype H3N2 strain
    A/California/7/2004 basic polymerase B2 (PB2)

<400> SEQUENCE: 137

```
Met Glu Arg Ile Lys Glu Leu Arg Asn Leu Met Ser Gln Ser Arg Thr
 1               5                  10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ser Leu Arg Met Lys
            35                  40                  45

Trp Met Met Ala Met Lys Tyr Pro Ile Thr Ala Asp Lys Arg Ile Thr
 50                  55                  60

Glu Met Val Pro Glu Arg Asn Glu Gln Gly Gln Thr Leu Trp Ser Lys
 65                  70                  75                  80

Met Ser Asp Ala Gly Ser Asp Arg Val Met Val Ser Pro Leu Ala Val
                    85                  90                  95

Thr Trp Trp Asn Arg Asn Gly Pro Val Thr Ser Thr Val His Tyr Pro
                    100                 105                 110

Lys Val Tyr Lys Thr Tyr Phe Asp Lys Val Glu Arg Leu Lys His Gly
                    115                 120                 125

Thr Phe Gly Pro Val His Phe Arg Asn Gln Val Lys Ile Arg Arg Arg
            130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                    165                 170                 175

Leu Thr Ser Glu Ser Gln Leu Thr Ile Thr Lys Glu Lys Lys Glu Glu
                    180                 185                 190

Leu Arg Asp Cys Lys Ile Ser Pro Leu Met Val Ala Tyr Met Leu Glu
                    195                 200                 205

Arg Glu Leu Val Arg Lys Thr Arg Phe Leu Pro Val Ala Gly Gly Thr
            210                 215                 220
```

-continued

```
Ser Ser Ile Tyr Ile Glu Val Leu His Leu Thr Gln Gly Thr Cys Trp
225                 230                 235                 240

Glu Gln Met Tyr Thr Pro Val Arg Ser Glu Asp Asp Val Asp Pro
            245                 250                 255

Ser Leu Asn Tyr Cys Gly Pro Gly Asn Ile Val Arg Arg Ala Ala Val
            260                 265                 270

Ser Ala Ile Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
            325                 330                 335

Ser Val Lys Lys Glu Glu Val Leu Thr Gly Asn Leu Gln Thr Leu
            340                 345                 350

Lys Ile Arg Val His Glu Gly Tyr Glu Glu Phe Thr Met Val Gly Lys
        355                 360                 365

Arg Ala Thr Ala Ile Leu Arg Lys Ala Thr Arg Leu Val Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
            405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Ser Val Met Gly Met Val Gly Val Leu
450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
            485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Ser Leu Thr
        515                 520                 525

Ile Thr Tyr Ser Ser Met Met Trp Glu Ile Asn Gly Pro Glu Ser
530                 535                 540

Asp Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
            565                 570                 575

Phe Glu Pro Phe Gln Ser Leu Val Pro Lys Ala Ile Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
        610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
```

```
                        645                 650                 655
Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Ile Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn Tyr Cys
            755                 760

<210> SEQ ID NO 138
<211> LENGTH: 757
<212> TYPE: PRT
<213> ORGANISM: Influenza A virus
<220> FEATURE:
<223> OTHER INFORMATION: influenza A virus serotype H3N2 strain
      A/California/7/2004 basic polymerase B1 (PB1)

<400> SEQUENCE: 138

Met Asp Val Asn Pro Thr Leu Leu Phe Leu Lys Val Pro Ala Gln Asn
 1               5                  10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240
```

-continued

Ile Ala Thr Pro Gly Met Gln Ile Arg Gly Phe Val Tyr Phe Val Glu
            245                 250                 255

Thr Leu Ala Arg Ser Ile Cys Glu Lys Leu Glu Gln Ser Gly Leu Pro
        260                 265                 270

Val Gly Gly Asn Glu Lys Lys Ala Lys Leu Ala Asn Val Val Arg Lys
    275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Arg Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asn Tyr Arg Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg

```
                    660                 665                 670
Ser Ile Leu Asn Thr Ser Gln Arg Gly Ile Leu Glu Asp Glu Gln Met
                675                 680                 685

Tyr Gln Lys Cys Cys Asn Leu Phe Glu Lys Phe Phe Pro Ser Ser Ser
            690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755

<210> SEQ ID NO 139
<211> LENGTH: 90
<212> TYPE: PRT
<213> ORGANISM: Influenza A virus
<220> FEATURE:
<223> OTHER INFORMATION: influenza A virus serotype H3N2 strain
      A/California/7/2004 basic polymerase frame 2 (PB1-F2)

<400> SEQUENCE: 139

Met Glu Gln Glu Gln Gly Thr Pro Trp Thr Gln Ser Thr Glu His Thr
1               5                   10                  15

Asn Ile Gln Arg Arg Gly Ser Gly Arg Gln Ile Gln Lys Leu Gly His
            20                  25                  30

Pro Asn Ser Thr Gln Leu Met Asp His Tyr Leu Arg Ile Met Ser Arg
        35                  40                  45

Val Asp Met His Lys Gln Thr Val Ser Trp Arg Leu Trp Pro Ser Leu
    50                  55                  60

Lys Asn Pro Thr Gln Val Ser Leu Arg Thr His Ala Leu Lys Gln Trp
65                  70                  75                  80

Lys Ser Phe Asn Lys Gln Gly Trp Thr Asn
                85                  90

<210> SEQ ID NO 140
<211> LENGTH: 716
<212> TYPE: PRT
<213> ORGANISM: Influenza A virus
<220> FEATURE:
<223> OTHER INFORMATION: influenza A virus serotype H3N2 strain
      A/California/7/2004 acidic polymerase (PA)

<400> SEQUENCE: 140

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Met Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
```

```
                 100                 105                 110
Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Asn Thr His
            130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
            180                 185                 190

Gln Ser Glu Arg Gly Glu Glu Thr Ile Glu Glu Lys Phe Glu Asn Leu
            195                 200                 205

Arg Thr Met Arg Ser Phe Ala Asp Gln Ser Leu Pro Pro Asn Phe Ser
            210                 215                 220

Cys Leu Glu Ile Leu Glu Pro Met Trp Met Asp Ser Asn Arg Thr Gly
225                 230                 235                 240

Cys Ile Glu Gly Lys Leu Ser Gln Met Ser Lys Glu Val Asn Ala Lys
                245                 250                 255

Ile Glu Pro Phe Leu Lys Lys Thr Pro Arg Pro Ile Lys Leu Pro Asn
                260                 265                 270

Gly Pro Pro Cys Tyr Gln Arg Ser Lys Phe Leu Leu Met Asp Ala Leu
            275                 280                 285

Lys Leu Ser Ile Glu Asp Pro Ser His Glu Gly Glu Gly Ile Pro Leu
            290                 295                 300

Tyr Asp Ala Ile Lys Cys Met Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
            340                 345                 350

Lys Ile Pro Arg Thr Lys Asn Met Lys Lys Thr Ser Gln Leu Lys Trp
            355                 360                 365

Ala Leu Gly Glu Asn Met Ala Pro Glu Lys Val Asp Phe Asp Asn Cys
            370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Ile Trp Ile Glu Leu Asp Glu Ile Gly Glu Asp Val
                420                 425                 430

Ala Pro Ile Glu Tyr Ile Ala Ser Met Arg Arg Asn Tyr Phe Thr Ala
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Thr Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525
```

```
Asp Pro Arg Leu Glu Pro His Lys Trp Glu Lys Tyr Cys Val Leu Glu
            530                 535                 540

Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ile Lys Glu Lys Asp Met Thr
        595                 600                 605

Lys Glu Phe Phe Glu Asn Lys Ser Glu Ala Trp Pro Ile Gly Glu Ser
            610                 615                 620

Pro Lys Gly Val Glu Glu Gly Ser Ile Gly Lys Val Cys Arg Thr Ile
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
            690                 695                 700

Ser Trp Phe Asn Ser Phe Leu Thr His Ala Leu Lys
705                 710                 715

<210> SEQ ID NO 141
<211> LENGTH: 583
<212> TYPE: PRT
<213> ORGANISM: Influenza A virus
<220> FEATURE:
<223> OTHER INFORMATION: influenza A virus serotype H3N2 strain
      A/California/7/2004 haemagglutinin (HA)

<400> SEQUENCE: 141

Met Val Gln Leu Val Arg Pro Gln Arg Lys Gln Gly Ile Ile Leu Leu
1               5                   10                  15

Thr Met Lys Thr Ile Ile Ala Leu Ser Tyr Ile Leu Cys Leu Val Phe
            20                  25                  30

Ala Gln Lys Leu Pro Gly Asn Asp Asn Ser Thr Ala Thr Leu Cys Leu
        35                  40                  45

Gly His His Ala Val Pro Asn Gly Thr Ile Val Lys Thr Ile Thr Asn
    50                  55                  60

Asp Gln Ile Glu Val Thr Asn Ala Thr Glu Leu Val Gln Ser Ser Ser
65                  70                  75                  80

Thr Gly Gly Ile Cys Asp Ser Pro His Gln Ile Leu Asp Gly Glu Asn
                85                  90                  95

Cys Thr Leu Ile Asp Ala Leu Leu Gly Asp Pro Gln Cys Asp Gly Phe
            100                 105                 110

Gln Asn Lys Lys Trp Asp Leu Phe Val Glu Arg Ser Lys Ala Tyr Ser
        115                 120                 125

Asn Cys Tyr Pro Tyr Asp Val Pro Asp Tyr Ala Ser Leu Arg Ser Leu
    130                 135                 140

Val Ala Ser Ser Gly Thr Leu Glu Phe Asn Asn Glu Ser Phe Asn Trp
145                 150                 155                 160

Thr Gly Val Thr Gln Asn Gly Thr Ser Ser Ser Cys Lys Arg Arg Ser
```

```
                165                 170                 175
Asn Asn Ser Phe Phe Ser Arg Leu Asn Trp Leu Thr His Leu Lys Phe
            180                 185                 190
Lys Tyr Pro Ala Leu Asn Val Thr Met Pro Asn Asn Glu Lys Phe Asp
        195                 200                 205
Lys Leu Tyr Ile Trp Gly Val His His Pro Gly Thr Asn His Asp Gln
    210                 215                 220
Ile Ser Leu Tyr Thr Gln Ala Ser Gly Arg Ile Thr Val Ser Thr Lys
225                 230                 235                 240
Arg Ser Gln Gln Thr Val Ile Pro Asn Ile Gly Ser Arg Pro Arg Val
            245                 250                 255
Arg Asp Ile Pro Ser Arg Ile Ser Ile Tyr Trp Thr Ile Val Lys Pro
        260                 265                 270
Gly Asp Ile Leu Leu Ile Asn Ser Thr Gly Asn Leu Ile Ala Pro Arg
    275                 280                 285
Gly Tyr Phe Lys Ile Arg Ser Gly Lys Ser Ser Ile Met Arg Ser Asp
    290                 295                 300
Ala Pro Ile Gly Lys Cys Asn Ser Glu Cys Ile Thr Pro Asn Gly Ser
305                 310                 315                 320
Ile Pro Asn Asp Lys Pro Phe Gln Asn Val Asn Arg Ile Thr Tyr Gly
            325                 330                 335
Ala Cys Pro Arg Tyr Val Lys Gln Asn Thr Leu Lys Leu Ala Thr Gly
        340                 345                 350
Met Arg Asn Val Pro Glu Lys Gln Thr Arg Gly Ile Phe Gly Ala Ile
    355                 360                 365
Ala Gly Phe Ile Glu Asn Gly Trp Glu Gly Met Val Asp Gly Trp Tyr
    370                 375                 380
Gly Phe Arg His Gln Asn Ser Glu Gly Ile Gly Gln Ala Ala Asp Leu
385                 390                 395                 400
Lys Ser Thr Gln Ala Ala Ile Asn Gln Ile Asn Gly Lys Leu Asn Arg
            405                 410                 415
Leu Ile Gly Lys Thr Asn Glu Lys Phe His Gln Ile Glu Lys Glu Phe
        420                 425                 430
Ser Glu Val Glu Gly Arg Ile Gln Asp Leu Glu Lys Tyr Val Glu Asp
    435                 440                 445
Thr Lys Ile Asp Leu Trp Ser Tyr Asn Ala Glu Leu Leu Val Ala Leu
    450                 455                 460
Glu Asn Gln His Thr Ile Asp Leu Thr Asp Ser Glu Met Asn Lys Leu
465                 470                 475                 480
Phe Glu Arg Thr Lys Lys Gln Leu Arg Glu Asn Ala Glu Asp Met Gly
            485                 490                 495
Asn Gly Cys Phe Lys Ile Tyr His Lys Cys Asp Asn Ala Cys Ile Gly
        500                 505                 510
Ser Ile Arg Asn Gly Thr Tyr Asp His Asp Val Tyr Arg Asp Glu Ala
    515                 520                 525
Leu Asn Asn Arg Phe Gln Ile Lys Gly Val Glu Leu Lys Ser Gly Tyr
    530                 535                 540
Lys Asp Trp Ile Leu Trp Ile Ser Phe Ala Ile Ser Cys Phe Leu Leu
545                 550                 555                 560
Cys Val Ala Leu Leu Gly Phe Ile Met Trp Ala Cys Gln Lys Gly Asn
            565                 570                 575
Ile Arg Cys Asn Ile Cys Ile
        580
```

```
<210> SEQ ID NO 142
<211> LENGTH: 482
<212> TYPE: PRT
<213> ORGANISM: Influenza A virus
<220> FEATURE:
<223> OTHER INFORMATION: influenza A virus serotype H3N2 strain
      A/California/7/2004 nucleoprotein (NP)

<400> SEQUENCE: 142
```

Met Ala Ser Gln Gly Thr Lys Arg Ser Tyr Glu Gln Met Glu Thr Asp
 1               5                  10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp His Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Lys Lys Val
            340                 345                 350

Ser Pro Arg Gly Lys Leu Ser Thr Arg Gly Val Gln Ile Ala Ser Asn

```
                355                 360                 365
Glu Asn Met Asp Asn Met Gly Ser Ser Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
                420                 425                 430

Thr Glu Gly Arg Thr Ser Asp Met Arg Ala Glu Ile Ile Arg Met Met
                435                 440                 445

Glu Gly Ala Lys Pro Glu Glu Val Ser Phe Arg Gly Arg Gly Val Phe
            450                 455                 460

Glu Leu Ser Asp Glu Lys Ala Ala Asn Pro Ile Val Pro Ser Phe Asp
465                 470                 475                 480

Met Ser

<210> SEQ ID NO 143
<211> LENGTH: 484
<212> TYPE: PRT
<213> ORGANISM: Influenza A virus
<220> FEATURE:
<223> OTHER INFORMATION: influenza A virus serotype H3N2 strain
      A/California/7/2004 neuraminidase (NA)

<400> SEQUENCE: 143

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asp Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
        130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
                180                 185                 190

Cys Val Thr Gly Asp Asp Lys Asn Ala Thr Ala Ser Phe Ile Tyr Asn
            195                 200                 205

Gly Arg Leu Val Asp Ser Ile Val Ser Trp Ser Lys Glu Ile Leu Arg
        210                 215                 220

Thr Gln Glu Ser Glu Cys Val Cys Ile Asn Gly Thr Cys Thr Val Val
```

-continued

```
                225                 230                 235                 240
Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
                260                 265                 270

Gln His Val Glu Glu Cys Ser Cys Tyr Pro Arg Tyr Pro Gly Val Arg
                275                 280                 285

Cys Val Cys Arg Asp Asn Trp Lys Gly Ser Asn Met Pro Ile Val Asp
                290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Ser Glu
                355                 360                 365

Lys Leu Arg Ser Gly Tyr Glu Thr Phe Lys Val Ile Glu Gly Trp Ser
                370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
                450                 455                 460

Asn Leu Met Pro Ile Phe Phe Phe Thr Ile Leu Glu Lys Thr Pro Ser
465                 470                 475                 480

Phe Tyr Phe Asn

<210> SEQ ID NO 144
<211> LENGTH: 252
<212> TYPE: PRT
<213> ORGANISM: Influenza A virus
<220> FEATURE:
<223> OTHER INFORMATION: influenza A virus serotype H3N2 strain
      A/California/7/2004 matrix protein 1 (M1)

<400> SEQUENCE: 144

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
                35                  40                  45

Arg Pro Ile Leu Ser Pro Leu Thr Lys Gly Ile Leu Gly Phe Val Phe
                50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
```

```
                    100                 105                 110

Lys Glu Ile Ala Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
        130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Lys His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val His Ala Met Arg Ala Val Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 145
<211> LENGTH: 110
<212> TYPE: PRT
<213> ORGANISM: Influenza A virus
<220> FEATURE:
<223> OTHER INFORMATION: influenza A virus serotype H3N2 strain
      A/California/7/2004 matrix protein 2 (M2)

<400> SEQUENCE: 145

Met Ile Phe Leu Lys Ile Cys Arg Pro Ile Arg Asn Glu Trp Gly Cys
1               5                   10                  15

Arg Cys Asn Asp Ser Ser Asp Pro Leu Val Val Ala Ala Ser Ile Ile
            20                  25                  30

Gly Ile Leu His Leu Ile Leu Trp Ile Leu Asp Arg Leu Phe Phe Lys
        35                  40                  45

Cys Val Tyr Arg Leu Phe Lys His Gly Leu Lys Arg Gly Pro Ser Thr
    50                  55                  60

Glu Gly Val Pro Glu Ser Met Arg Glu Glu Tyr Arg Lys Glu Gln Gln
65                  70                  75                  80

Asn Ala Val Asp Ala Asp Asp Ser His Phe Val Ser Phe Ile Gly Val
                85                  90                  95

Lys Asn Tyr Leu Ile Ser Thr Leu Ile Asn Thr Ala Glu Gln
            100                 105                 110

<210> SEQ ID NO 146
<211> LENGTH: 230
<212> TYPE: PRT
<213> ORGANISM: Influenza A virus
<220> FEATURE:
<223> OTHER INFORMATION: influenza A virus serotype H3N2 strain
      A/California/7/2004 non-structural protein 1 (NS1)

<400> SEQUENCE: 146

Met Asp Ser Asn Thr Val Ser Ser Phe Gln Val Asp Cys Phe Leu Trp
1               5                   10                  15

His Ile Arg Lys Gln Val Val Asp Gln Glu Leu Ser Asp Ala Pro Phe
            20                  25                  30

Leu Asp Arg Leu Arg Arg Asp Gln Arg Ser Leu Arg Gly Arg Gly Asn
```

```
            35                  40                  45
Thr Leu Gly Leu Asp Ile Lys Ala Ala Thr His Val Gly Lys Gln Ile
 50                  55                  60

Val Glu Lys Ile Leu Lys Glu Glu Ser Asp Glu Ala Leu Lys Met Thr
 65                  70                  75                  80

Met Val Ser Thr Pro Ala Ser Arg Tyr Ile Thr Asp Met Thr Ile Glu
                 85                  90                  95

Glu Leu Ser Arg Asn Trp Phe Met Leu Met Pro Lys Gln Lys Val Glu
                100                 105                 110

Gly Pro Leu Cys Ile Arg Met Asp Gln Ala Ile Met Glu Lys Asn Ile
            115                 120                 125

Met Leu Lys Ala Asn Phe Ser Val Ile Phe Asp Arg Leu Glu Thr Ile
130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Asn Leu Gln Arg Phe Ala Trp Arg Ser Ser Asn Glu
        195                 200                 205

Asn Gly Gly Pro Pro Leu Thr Pro Lys Gln Lys Arg Lys Val Ala Arg
210                 215                 220

Thr Ala Arg Ser Lys Val
225                 230

<210> SEQ ID NO 147
<211> LENGTH: 121
<212> TYPE: PRT
<213> ORGANISM: Influenza A virus
<220> FEATURE:
<223> OTHER INFORMATION: influenza A virus serotype H3N2 strain
      A/California/7/2004 non-structural protein 2 (NS2)

<400> SEQUENCE: 147

Met Asp Ser Asn Thr Val Ser Ser Phe Gln Asp Ile Leu Leu Arg Met
 1               5                  10                  15

Ser Lys Met Gln Leu Gly Ser Ser Glu Asp Leu Asn Gly Met Ile
            20                  25                  30

Thr Gln Phe Glu Ser Leu Lys Ile Tyr Arg Asp Ser Leu Gly Glu Ala
            35                  40                  45

Val Met Arg Met Gly Asp Leu His Leu Leu Gln Asn Arg Asn Gly Lys
 50                  55                  60

Trp Arg Glu Gln Leu Gly Gln Lys Phe Glu Glu Ile Arg Trp Leu Ile
 65                  70                  75                  80

Glu Glu Val Arg His Arg Leu Lys Thr Thr Glu Asn Ser Phe Glu Gln
                 85                  90                  95

Ile Thr Phe Met Gln Ala Leu Gln Leu Gln Phe Glu Val Glu Gln Glu
                100                 105                 110

Ile Arg Thr Phe Ser Phe His Leu Ile
            115                 120

<210> SEQ ID NO 148
<211> LENGTH: 24
<212> TYPE: PRT
<213> ORGANISM: Influenza A virus
```

-continued

<400> SEQUENCE: 148

Lys Leu Ser Ile Glu Asp Pro Ser His Glu Gly Glu Gly Ile Pro Leu
1               5                   10                  15

Tyr Asp Ala Ile Lys Cys Met Lys
            20

<210> SEQ ID NO 149
<211> LENGTH: 29
<212> TYPE: PRT
<213> ORGANISM: Influenza A virus

<400> SEQUENCE: 149

Ile Asn Pro Asn Tyr Leu Leu Ala Trp Lys Gln Val Leu Ala Glu Leu
1               5                   10                  15

Gln Asp Ile Glu Asn Glu Glu Lys Ile Pro Lys Thr Lys
            20                  25

<210> SEQ ID NO 150
<211> LENGTH: 41
<212> TYPE: PRT
<213> ORGANISM: Influenza A virus

<400> SEQUENCE: 150

Lys Ser Asp Gln Ile Cys Ile Gly Tyr His Ala Asn Asn Ser Thr Glu
1               5                   10                  15

Gln Val Asp Thr Ile Met Glu Lys Asn Val Thr Val Thr His Ala Gln
            20                  25                  30

Asp Ile Leu Glu Lys Lys His Asn Gly
        35                  40

<210> SEQ ID NO 151

<400> SEQUENCE: 151

000

<210> SEQ ID NO 152
<211> LENGTH: 31
<212> TYPE: PRT
<213> ORGANISM: Influenza A virus

<400> SEQUENCE: 152

Ala Cys Pro Tyr Gln Gly Lys Ser Ser Phe Phe Arg Asn Val Val Trp
1               5                   10                  15

Leu Ile Lys Lys Asn Ser Thr Tyr Pro Thr Ile Lys Arg Ser Tyr
            20                  25                  30

<210> SEQ ID NO 153
<211> LENGTH: 35
<212> TYPE: PRT
<213> ORGANISM: Influenza A virus

<400> SEQUENCE: 153

Ala Tyr Lys Ile Val Lys Lys Gly Asp Ser Thr Ile Met Lys Ser Glu
1               5                   10                  15

Leu Glu Tyr Gly Asn Cys Asn Thr Lys Cys Gln Thr Pro Met Gly Ala
            20                  25                  30

Ile Asn Ser
        35

<210> SEQ ID NO 154

<211> LENGTH: 26
<212> TYPE: PRT
<213> ORGANISM: Influenza A virus

<400> SEQUENCE: 154

Ile Met Lys Ser Glu Leu Glu Tyr Gly Asn Cys Asn Thr Lys Cys Gln
1               5                   10                  15

Thr Pro Met Gly Ala Ile Asn Ser Ser Met
            20                  25

<210> SEQ ID NO 155
<211> LENGTH: 43
<212> TYPE: PRT
<213> ORGANISM: Influenza A virus

<400> SEQUENCE: 155

Lys Cys Gln Thr Pro Met Gly Ala Ile Asn Ser Ser Met Pro Phe His
1               5                   10                  15

Asn Ile His Pro Leu Thr Ile Gly Glu Cys Pro Lys Tyr Val Lys Ser
            20                  25                  30

Asn Arg Leu Val Leu Ala Thr Gly Leu Arg Asn
        35                  40

<210> SEQ ID NO 156
<211> LENGTH: 20
<212> TYPE: PRT
<213> ORGANISM: Influenza A virus

<400> SEQUENCE: 156

Met Gly Ala Ile Asn Ser Ser Met Pro Phe His Asn Ile His Pro Leu
1               5                   10                  15

Thr Ile Gly Glu
            20

<210> SEQ ID NO 157
<211> LENGTH: 44
<212> TYPE: PRT
<213> ORGANISM: Influenza A virus

<400> SEQUENCE: 157

His Asn Ile His Pro Leu Thr Ile Gly Glu Cys Pro Lys Tyr Val Lys
1               5                   10                  15

Ser Asn Arg Leu Val Leu Ala Thr Gly Leu Arg Asn Ser Pro Gln Arg
            20                  25                  30

Glu Arg Arg Arg Lys Lys Arg Gly Leu Phe Gly Ala
        35                  40

<210> SEQ ID NO 158
<211> LENGTH: 23
<212> TYPE: PRT
<213> ORGANISM: Influenza A virus

<400> SEQUENCE: 158

Thr Ile Gly Glu Cys Pro Lys Tyr Val Lys Ser Asn Arg Leu Val Leu
1               5                   10                  15

Ala Thr Gly Leu Arg Asn Ser
            20

<210> SEQ ID NO 159
<211> LENGTH: 80
<212> TYPE: PRT
<213> ORGANISM: Influenza A virus

<400> SEQUENCE: 159

Ser Asn Glu Gln Gly Ser Gly Tyr Ala Ala Asp Lys Glu Ser Thr Gln
1               5                   10                  15

Lys Ala Ile Asp Gly Val Thr Asn Lys Val Asn Ser Ile Ile Asp Lys
            20                  25                  30

Met Asn Thr Gln Phe Glu Ala Val Gly Arg Glu Phe Asn Asn Leu Glu
        35                  40                  45

Arg Arg Ile Glu Asn Leu Asn Lys Lys Met Glu Asp Gly Phe Leu Asp
    50                  55                  60

Val Trp Thr Tyr Asn Ala Glu Leu Leu Val Leu Met Glu Asn Glu Arg
65                  70                  75                  80

<210> SEQ ID NO 160
<211> LENGTH: 19
<212> TYPE: PRT
<213> ORGANISM: Influenza A virus

<400> SEQUENCE: 160

Glu Gln Gly Ser Gly Tyr Ala Ala Asp Lys Glu Ser Thr Gln Lys Ala
1               5                   10                  15

Ile Asp Gly

<210> SEQ ID NO 161
<211> LENGTH: 20
<212> TYPE: PRT
<213> ORGANISM: Influenza A virus

<400> SEQUENCE: 161

Gly Ser Gly Tyr Ala Ala Asp Lys Glu Ser Thr Gln Lys Ala Ile Asp
1               5                   10                  15

Gly Val Thr Asn
            20

<210> SEQ ID NO 162
<211> LENGTH: 76
<212> TYPE: PRT
<213> ORGANISM: Influenza A virus

<400> SEQUENCE: 162

Ala Asp Lys Glu Ser Thr Gln Lys Ala Ile Asp Gly Val Thr Asn Lys
1               5                   10                  15

Val Asn Ser Ile Ile Asp Lys Met Asn Thr Gln Phe Glu Ala Val Gly
            20                  25                  30

Arg Glu Phe Asn Asn Leu Glu Arg Arg Ile Glu Asn Leu Asn Lys Lys
        35                  40                  45

Met Glu Asp Gly Phe Leu Asp Val Trp Thr Tyr Asn Ala Glu Leu Leu
    50                  55                  60

Val Leu Met Glu Asn Glu Arg Thr Leu Asp Phe His
65                  70                  75

<210> SEQ ID NO 163
<211> LENGTH: 28
<212> TYPE: PRT
<213> ORGANISM: Influenza A virus

<400> SEQUENCE: 163

Gln Lys Ala Ile Asp Gly Val Thr Asn Lys Val Asn Ser Ile Ile Asp
1               5                   10                  15

```
Lys Met Asn Thr Gln Phe Glu Ala Val Gly Arg Glu
            20                  25
```

<210> SEQ ID NO 164
<211> LENGTH: 33
<212> TYPE: PRT
<213> ORGANISM: Influenza A virus

<400> SEQUENCE: 164

```
Ala Ile Asp Gly Val Thr Asn Lys Val Asn Ser Ile Ile Asp Lys Met
1               5                   10                  15

Asn Thr Gln Phe Glu Ala Val Gly Arg Glu Phe Asn Asn Leu Glu Arg
            20                  25                  30

Arg
```

<210> SEQ ID NO 165
<211> LENGTH: 22
<212> TYPE: PRT
<213> ORGANISM: Influenza A virus

<400> SEQUENCE: 165

```
Thr Asn Lys Val Asn Ser Ile Ile Asp Lys Met Asn Thr Gln Phe Glu
1               5                   10                  15

Ala Val Gly Arg Glu Phe
            20
```

<210> SEQ ID NO 166
<211> LENGTH: 56
<212> TYPE: PRT
<213> ORGANISM: Influenza A virus

<400> SEQUENCE: 166

```
Gln Leu Arg Asp Asn Ala Lys Glu Leu Gly Asn Gly Cys Phe Glu Phe
1               5                   10                  15

Tyr His Lys Cys Asp Asn Glu Cys Met Glu Ser Val Arg Asn Gly Thr
            20                  25                  30

Tyr Asp Tyr Pro Gln Tyr Ser Glu Glu Ala Arg Leu Lys Arg Glu Glu
        35                  40                  45

Ile Ser Gly Val Lys Leu Glu Ser
    50                  55
```

<210> SEQ ID NO 167
<211> LENGTH: 24
<212> TYPE: PRT
<213> ORGANISM: Influenza A virus

<400> SEQUENCE: 167

```
Gln Leu Arg Asp Asn Ala Lys Glu Leu Gly Asn Gly Cys Phe Glu Phe
1               5                   10                  15

Tyr His Lys Cys Asp Asn Glu Cys
            20
```

<210> SEQ ID NO 168
<211> LENGTH: 59
<212> TYPE: PRT
<213> ORGANISM: Influenza A virus

<400> SEQUENCE: 168

```
Asn Ser Ile Thr Ile Glu Arg Met Val Leu Ser Ala Phe Asp Glu Arg
1               5                   10                  15

Arg Asn Arg Tyr Leu Glu Glu His Pro Ser Ala Gly Lys Asp Pro Lys
```

```
            20                  25                  30

Lys Thr Gly Gly Pro Ile Tyr Arg Arg Arg Asp Gly Lys Trp Val Arg
        35                  40                  45

Glu Leu Ile Leu Tyr Asp Lys Glu Glu Ile Arg
    50                  55

<210> SEQ ID NO 169
<211> LENGTH: 39
<212> TYPE: PRT
<213> ORGANISM: Influenza A virus

<400> SEQUENCE: 169

Thr Glu Ile Ile Arg Met Met Glu Ser Ala Arg Pro Glu Asp Val Ser
 1               5                  10                  15

Phe Gln Gly Arg Gly Val Phe Glu Leu Ser Asp Glu Lys Ala Thr Asn
            20                  25                  30

Pro Ile Val Pro Ser Phe Asp
        35

<210> SEQ ID NO 170
<211> LENGTH: 28
<212> TYPE: PRT
<213> ORGANISM: Influenza A virus

<400> SEQUENCE: 170

Glu Pro Ile Ser Asn Thr Asn Phe Leu Thr Glu Lys Ala Val Ala Ser
 1               5                  10                  15

Val Lys Leu Ala Gly Asn Ser Ser Leu Cys Pro Ile
            20                  25

<210> SEQ ID NO 171
<211> LENGTH: 29
<212> TYPE: PRT
<213> ORGANISM: Influenza A virus

<400> SEQUENCE: 171

Thr Ile Gly Ile Ser Gly Pro Asp Asn Gly Ala Val Ala Val Leu Lys
 1               5                  10                  15

Tyr Asn Gly Ile Ile Thr Asp Thr Ile Lys Ser Trp Arg
            20                  25

<210> SEQ ID NO 172
<211> LENGTH: 33
<212> TYPE: PRT
<213> ORGANISM: Influenza A virus

<400> SEQUENCE: 172

Ala Cys Val Asn Gly Ser Cys Phe Thr Val Met Thr Asp Gly Pro Ser
 1               5                  10                  15

Asn Gly Gln Ala Ser His Lys Ile Phe Lys Met Glu Lys Gly Lys Val
            20                  25                  30

Val

<210> SEQ ID NO 173
<211> LENGTH: 24
<212> TYPE: PRT
<213> ORGANISM: Influenza A virus

<400> SEQUENCE: 173

His Lys Ile Phe Lys Met Glu Lys Gly Lys Val Val Lys Ser Val Glu
 1               5                  10                  15
```

```
<210> SEQ ID NO 174
<211> LENGTH: 21
<212> TYPE: PRT
<213> ORGANISM: Influenza A virus

<400> SEQUENCE: 174

Ile Cys Ser Gly Val Phe Gly Asp Asn Pro Arg Pro Asn Asp Gly Thr
1               5                   10                  15

Gly Ser Cys Gly Pro
            20

<210> SEQ ID NO 175
<211> LENGTH: 44
<212> TYPE: PRT
<213> ORGANISM: Influenza A virus

<400> SEQUENCE: 175

Ile Ala Asp Ser Gln His Arg Ser His Arg Gln Met Ala Thr Ile Thr
1               5                   10                  15

Asn Pro Leu Ile Arg His Glu Asn Arg Met Val Leu Ala Ser Thr Thr
            20                  25                  30

Ala Lys Ala Met Glu Gln Met Ala Gly Ser Ser Glu
        35                  40

<210> SEQ ID NO 176
<211> LENGTH: 29
<212> TYPE: PRT
<213> ORGANISM: Influenza A virus

<400> SEQUENCE: 176

Met Ala Gly Ser Ser Glu Gln Ala Ala Glu Ala Met Glu Ile Ala Asn
1               5                   10                  15

Gln Ala Arg Gln Met Val Gln Ala Met Arg Thr Ile Gly
            20                  25

<210> SEQ ID NO 177
<211> LENGTH: 45
<212> TYPE: DNA
<213> ORGANISM: Artificial Sequence
<220> FEATURE:
<223> OTHER INFORMATION: synthetic specifically-bound phage sequence

<400> SEQUENCE: 177
gcctaatgag tgagctaact cacattaatt gcgttgcgct cactg              45

<210> SEQ ID NO 178
<211> LENGTH: 570
<212> TYPE: PRT
<213> ORGANISM: Influenza A virus

<400> SEQUENCE: 178

Val Lys Met Glu Lys Ile Val Leu Leu Phe Ala Ile Val Ser Leu Val
1               5                   10                  15

Lys Ser Asp Gln Ile Cys Ile Gly Tyr His Ala Asn Asn Ser Thr Glu
            20                  25                  30

Gln Val Asp Thr Ile Met Glu Lys Asn Val Thr Val Thr His Ala Gln
        35                  40                  45

Asp Ile Leu Glu Lys Lys His Asn Gly Lys Leu Cys Asp Leu Asp Gly
```

(preceding fragment)

Leu Asp Ala Pro Asn Tyr His Tyr
            20

```
            50                  55                  60
Val Lys Pro Leu Ile Leu Arg Asp Cys Ser Val Ala Gly Trp Leu Leu
 65                  70                  75                  80

Gly Asn Pro Met Cys Asp Glu Phe Ile Asn Val Pro Glu Trp Ser Tyr
                 85                  90                  95

Ile Val Glu Lys Ala Asn Pro Val Asn Asp Leu Cys Tyr Pro Gly Asp
                100                 105                 110

Phe Asn Asp Tyr Glu Glu Leu Lys His Leu Leu Ser Arg Ile Asn His
                115                 120                 125

Phe Glu Lys Ile Gln Ile Ile Pro Lys Ser Ser Trp Ser Ser His Glu
130                 135                 140

Ala Ser Leu Gly Val Ser Ser Ala Cys Pro Tyr Gln Gly Lys Ser Ser
145                 150                 155                 160

Phe Phe Arg Asn Val Val Trp Leu Ile Lys Lys Asn Ser Thr Tyr Pro
                165                 170                 175

Thr Ile Lys Arg Ser Tyr Asn Asn Thr Asn Gln Glu Asp Leu Leu Val
                180                 185                 190

Leu Trp Gly Ile His His Pro Asn Asp Ala Ala Glu Gln Thr Lys Leu
                195                 200                 205

Tyr Gln Asn Pro Thr Thr Tyr Ile Ser Val Gly Thr Ser Thr Leu Asn
210                 215                 220

Gln Arg Leu Val Pro Arg Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
                260                 265                 270

Lys Ile Val Lys Lys Gly Asp Ser Thr Ile Met Lys Ser Glu Leu Glu
                275                 280                 285

Tyr Gly Asn Cys Asn Thr Lys Cys Gln Thr Pro Met Gly Ala Ile Asn
                290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Lys Lys Arg Gly Leu Phe Gly
                340                 345                 350

Ala Ile Ala Gly Phe Ile Glu Gly Gly Trp Gln Gly Met Val Asp Gly
                355                 360                 365

Trp Tyr Gly Tyr His His Ser Asn Glu Gln Gly Ser Gly Tyr Ala Ala
                370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
                420                 425                 430

Glu Asp Gly Phe Leu Asp Val Trp Thr Tyr Asn Ala Glu Leu Leu Val
                435                 440                 445

Leu Met Glu Asn Glu Arg Thr Leu Asp Phe His Asp Ser Asn Val Lys
                450                 455                 460

Asn Leu Tyr Asp Lys Val Arg Leu Gln Leu Arg Asp Asn Ala Lys Glu
465                 470                 475                 480
```

```
Leu Gly Asn Gly Cys Phe Glu Phe Tyr His Lys Cys Asp Asn Glu Cys
            485                 490                 495

Met Glu Ser Val Arg Asn Gly Thr Tyr Asp Tyr Pro Gln Tyr Ser Glu
        500                 505                 510

Glu Ala Arg Leu Lys Arg Glu Glu Ile Ser Gly Val Lys Leu Glu Ser
        515                 520                 525

Ile Gly Ile Tyr Gln Ile Leu Ser Ile Tyr Ser Thr Val Ala Ser Ser
        530                 535                 540

Leu Ala Leu Ala Ile Met Val Ala Gly Leu Ser Leu Trp Met Cys Ser
545                 550                 555                 560

Asn Gly Ser Leu Gln Cys Arg Ile Cys Ile
                565                 570

<210> SEQ ID NO 179
<211> LENGTH: 566
<212> TYPE: PRT
<213> ORGANISM: Influenza A virus

<400> SEQUENCE: 179

Lys Met Glu Lys Ile Val Leu Leu Leu Ala Ile Val Ser Leu Val Lys
1               5                   10                  15

Ser Asp Gln Ile Cys Ile Gly Tyr His Ala Asn Asn Ser Thr Glu Gln
            20                  25                  30

Val Asp Thr Ile Met Glu Lys Asn Val Thr Val Thr His Ala Gln Asp
        35                  40                  45

Ile Leu Glu Lys Thr His Asn Gly Lys Leu Cys Asp Leu Asp Gly Val
    50                  55                  60

Lys Pro Leu Ile Leu Arg Asp Cys Ser Val Ala Gly Trp Leu Leu Gly
65                  70                  75                  80

Asn Pro Met Cys Asp Glu Phe Ile Asn Val Pro Glu Trp Ser Tyr Ile
                85                  90                  95

Val Glu Lys Ala Asn Pro Thr Asn Asp Leu Cys Tyr Pro Gly Ser Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Asp His Glu Ala
    130                 135                 140

Ser Ser Gly Val Ser Ser Ala Cys Pro Tyr Leu Gly Ser Pro Ser Phe
145                 150                 155                 160

Phe Arg Asn Val Val Trp Leu Ile Lys Lys Asn Ser Thr Tyr Pro Thr
                165                 170                 175

Ile Lys Lys Ser Tyr Asn Asn Thr Asn Gln Glu Asp Leu Leu Val Leu
            180                 185                 190

Trp Gly Ile His His Pro Asn Asp Ala Ala Glu Gln Thr Arg Leu Tyr
        195                 200                 205

Gln Asn Pro Thr Thr Tyr Ile Ser Ile Gly Thr Ser Thr Leu Asn Gln
    210                 215                 220

Arg Leu Val Pro Lys Ile Ala Thr Arg Ser Lys Val Asn Gly Gln Ser
225                 230                 235                 240

Gly Arg Met Glu Phe Phe Trp Thr Ile Leu Lys Pro Asn Asp Ala Ile
                245                 250                 255

Asn Phe Glu Ser Asn Gly Asn Phe Ile Ala Pro Glu Tyr Ala Tyr Lys
            260                 265                 270

Ile Val Lys Lys Gly Asp Ser Ala Ile Met Lys Ser Glu Leu Glu Tyr
```

```
                275                 280                 285
Gly Asn Cys Asn Thr Lys Cys Gln Thr Pro Met Gly Ala Ile Asn Ser
    290                 295                 300
Ser Met Pro Phe His Asn Ile His Pro Leu Thr Ile Gly Glu Cys Pro
305                 310                 315                 320
Lys Tyr Val Lys Ser Asn Arg Leu Val Leu Ala Thr Gly Leu Arg Asn
                325                 330                 335
Ser Pro Gln Arg Glu Ser Arg Arg Lys Lys Arg Gly Leu Phe Gly Ala
            340                 345                 350
Ile Ala Gly Phe Ile Glu Gly Gly Trp Gln Gly Met Val Asp Gly Trp
                355                 360                 365
Tyr Gly Tyr His His Ser Asn Glu Gln Gly Ser Gly Tyr Ala Ala Asp
            370                 375                 380
Lys Glu Ser Thr Gln Lys Ala Ile Asp Gly Val Thr Asn Lys Val Asn
385                 390                 395                 400
Ser Ile Ile Asp Lys Met Asn Thr Gln Phe Glu Ala Val Gly Arg Glu
                405                 410                 415
Phe Asn Asn Leu Glu Arg Arg Ile Glu Asn Leu Asn Lys Lys Met Glu
            420                 425                 430
Asp Gly Phe Leu Asp Val Trp Thr Tyr Asn Ala Glu Leu Leu Val Leu
                435                 440                 445
Met Glu Asn Glu Arg Thr Leu Asp Phe His Asp Ser Asn Val Lys Asn
450                 455                 460
Leu Tyr Asp Lys Val Arg Leu Gln Leu Arg Asp Asn Ala Lys Glu Leu
465                 470                 475                 480
Gly Asn Gly Cys Phe Glu Phe Tyr His Lys Cys Asp Asn Glu Cys Met
                485                 490                 495
Glu Ser Ile Arg Asn Gly Thr Tyr Asn Tyr Pro Gln Tyr Ser Glu Glu
            500                 505                 510
Ala Arg Leu Lys Arg Glu Glu Ile Ser Gly Val Lys Leu Glu Ser Ile
            515                 520                 525
Gly Thr Tyr Gln Ile Leu Ser Ile Tyr Ser Thr Val Ala Ser Ser Leu
    530                 535                 540
Ala Leu Ala Ile Met Ala Gly Leu Ser Leu Trp Met Cys Ser Asn Gly
545                 550                 555                 560
Ser Leu Gln Cys Arg Ile
                565

<210> SEQ ID NO 180
<211> LENGTH: 4
<212> TYPE: PRT
<213> ORGANISM: Influenza A virus

<400> SEQUENCE: 180

Glu Ala Ser Leu
 1

<210> SEQ ID NO 181
<211> LENGTH: 4
<212> TYPE: PRT
<213> ORGANISM: Influenza A virus

<400> SEQUENCE: 181

Gln Ile Ile Pro
 1
```

-continued

```
<210> SEQ ID NO 182
<211> LENGTH: 4
<212> TYPE: PRT
<213> ORGANISM: Influenza A virus

<400> SEQUENCE: 182

Gly Val Lys Pro
1

<210> SEQ ID NO 183
<211> LENGTH: 11
<212> TYPE: PRT
<213> ORGANISM: Influenza A virus
<220> FEATURE:
<221> NAME/KEY: VARIANT
<222> LOCATION: (10)...(10)
<223> OTHER INFORMATION: Xaa = Arg or Gly

<400> SEQUENCE: 183

Pro Gln Gly Glu Arg Arg Arg Lys Lys Xaa Leu
1               5                   10

<210> SEQ ID NO 184
<211> LENGTH: 4
<212> TYPE: PRT
<213> ORGANISM: Influenza A virus

<400> SEQUENCE: 184

Glu Ala Ser Ser
1

<210> SEQ ID NO 185
<211> LENGTH: 4
<212> TYPE: PRT
<213> ORGANISM: Influenza A virus

<400> SEQUENCE: 185

Tyr Asn Asn Thr
1

<210> SEQ ID NO 186
<211> LENGTH: 51
<212> TYPE: PRT
<213> ORGANISM: Influenza A virus

<400> SEQUENCE: 186

Gly Tyr His His Ser Asn Glu Gln Gly Ser Gly Tyr Ala Ala Asp Lys
1               5                   10                  15

Glu Ser Thr Gln Lys Ala Ile Asp Gly Val Thr Asn Lys Val Asn Ser
            20                  25                  30

Ile Ile Asp Lys Met Asn Thr Gln Phe Glu Ala Val Gly Arg Glu Phe
        35                  40                  45

Asn Asn Leu
    50

<210> SEQ ID NO 187
<211> LENGTH: 9
<212> TYPE: PRT
<213> ORGANISM: Influenza A virus

<400> SEQUENCE: 187

Ser Leu Leu Thr Glu Val Glu Thr Pro
1               5
```

```
<210> SEQ ID NO 188
<211> LENGTH: 15
<212> TYPE: PRT
<213> ORGANISM: Influenza A virus

<400> SEQUENCE: 188

Thr Arg Asn Glu Trp Glu Cys Arg Cys Ser Asp Ser Ser Asp Pro
1               5                   10                  15

<210> SEQ ID NO 189
<211> LENGTH: 583
<212> TYPE: PRT
<213> ORGANISM: Artificial Sequence
<220> FEATURE:
<223> OTHER INFORMATION: synthetic influenza A virus strain H5N1
      haemagglutinin (HA) consensus sequence

<400> SEQUENCE: 189

Ile Cys Lys Met Glu Lys Ile Val Leu Leu Ala Ile Val Ser Leu
1               5                   10                  15

Val Lys Ser Asp Gln Ile Cys Ile Gly Tyr His Ala Asn Asn Ser Thr
            20                  25                  30

Glu Gln Val Asp Thr Ile Met Glu Lys Asn Val Thr Val Thr His Ala
        35                  40                  45

Gln Asp Ile Leu Glu Lys Thr His Asn Gly Lys Leu Cys Asp Leu Asp
    50                  55                  60

Gly Val Lys Pro Leu Ile Leu Arg Asp Cys Ser Val Ala Gly Trp Leu
65                  70                  75                  80

Leu Gly Asn Pro Met Cys Asp Glu Phe Ile Asn Val Pro Glu Trp Ser
                85                  90                  95

Tyr Ile Val Glu Lys Ala Asn Pro Ala Asn Asp Leu Cys Tyr Pro Gly
            100                 105                 110

Asn Phe Asn Asp Tyr Glu Glu Leu Lys His Leu Leu Ser Arg Ile Asn
        115                 120                 125

His Phe Glu Lys Ile Ala Gln Ile Ile Pro Lys Ser Ser Trp Ser Asp
    130                 135                 140

His Glu Ala Ser Ser Gly Val Ser Ser Ala Cys Pro Tyr Gln Gly Arg
145                 150                 155                 160

Ser Ser Phe Phe Arg Asn Val Val Trp Leu Ile Lys Lys Asn Ser Thr
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Arg Leu Tyr Gln Asn Pro Thr Thr Tyr Ile Ser Val Gly Thr Ser Thr
    210                 215                 220

Leu Asn Gln Arg Leu Val Pro Lys Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Thr Ile Met Lys Ser Glu
        275                 280                 285

Leu Glu Tyr Gly Asn Cys Asn Thr Pro Lys Cys Gln Thr Pro Met Gly
    290                 295                 300

Ala Ile Gly Ala Ile Asn Ser Ser Met Pro Phe His Asn Ile His Pro
```

```
            305                 310                 315                 320
Leu Thr Ile Gly Glu Cys Pro Lys Tyr Val Lys Ser Asn Arg Leu Val
                325                 330                 335
Leu Ala Thr Gly Leu Arg Asn Ser Pro Gln Arg Glu Arg Arg Arg Lys
                340                 345                 350
Lys Arg Gly Leu Phe Gly Ala Ile Ala Gly Phe Ile Glu Gly Gly Trp
                355                 360                 365
Gln Gly Met Val Asp Gly Trp Tyr Gly Tyr His His Ser Asn Glu Gln
                370                 375                 380
Gly Ser Gly Tyr Ala Ala Asp Lys Glu Ser Thr Gln Lys Ala Ile Asp
385                 390                 395                 400
Gly Val Thr Asn Lys Val Asn Ser Ile Ile Asp Lys Met Asn Thr Gln
                405                 410                 415
Phe Glu Ala Val Gly Arg Glu Phe Asn Asn Leu Glu Arg Arg Ile Glu
                420                 425                 430
Asn Leu Asn Lys Lys Met Glu Asp Gly Phe Leu Asp Val Trp Thr Tyr
                435                 440                 445
Asn Ala Glu Leu Leu Val Leu Met Glu Asn Glu Arg Thr Leu Asp Phe
                450                 455                 460
His Asp Ser Asn Val Lys Asn Leu Tyr Asp Lys Val Arg Leu Gln Leu
465                 470                 475                 480
Arg Asp Asn Ala Lys Glu Leu Gly Asn Gly Cys Phe Glu Phe Tyr His
                485                 490                 495
Lys Cys Asp Asn Glu Cys Met Glu Ser Val Arg Asn Gly Thr Tyr Asp
                500                 505                 510
Tyr Pro Gln Tyr Ser Glu Glu Ala Arg Leu Lys Arg Glu Glu Ile Ser
                515                 520                 525
Gly Val Lys Leu Glu Ser Ile Gly Thr Tyr Gln Ile Leu Ser Ile Tyr
                530                 535                 540
Ser Thr Val Ala Ser Ser Leu Ala Leu Ala Ile Met Val Ala Gly Leu
545                 550                 555                 560
Ser Leu Trp Met Cys Ser Asn Gly Ser Leu Gln Cys Arg Ile Cys Ile
                565                 570                 575
Lys Phe Cys Glu Asp Arg Leu
                580

<210> SEQ ID NO 190
<211> LENGTH: 571
<212> TYPE: PRT
<213> ORGANISM: Influenza A virus

<400> SEQUENCE: 190

Arg Ile Val Leu Leu Phe Ala Ile Val Ser Leu Val Lys Ser Asp Gln
1               5                   10                  15
Ile Cys Ile Gly Tyr His Ala Asn Asn Ser Thr Glu Gln Val Asp Thr
                20                  25                  30
Ile Met Glu Lys Asn Val Thr Val Thr His Ala Gln Asp Ile Leu Glu
                35                  40                  45
Lys Thr His Asn Gly Lys Leu Cys Asp Leu Asp Gly Val Lys Pro Leu
        50                  55                  60
Ile Leu Arg Asp Cys Ser Val Ala Gly Trp Leu Leu Gly Asn Pro Met
65                  70                  75                  80
Cys Asp Glu Phe Ile Asn Val Pro Glu Trp Ser Tyr Ile Val Glu Lys
                85                  90                  95
```

```
Pro Asn Pro Ala Asn Asp Leu Cys Tyr Pro Gly Asp Phe Asn Asp Tyr
            100                 105                 110

Glu Glu Leu Lys His Leu Leu Ser Arg Ile Asn His Phe Glu Lys Ile
        115                 120                 125

Gln Ile Ile Pro Lys Ser Ser Trp Ser His Glu Ala Ser Val Gly
    130                 135                 140

Val Ser Ser Ala Cys Pro Tyr Gln Gly Lys Ser Ser Phe Phe Arg Asn
145                 150                 155                 160

Val Val Trp Leu Ile Lys Lys Asn Ser Thr Tyr Pro Thr Ile Lys Arg
                165                 170                 175

Ser Tyr Asn Asn Thr Asn Gln Glu Asp Leu Leu Val Leu Trp Gly Ile
            180                 185                 190

His His Pro Asn Asp Ala Ala Glu Gln Thr Lys Leu Tyr Gln Asn Pro
        195                 200                 205

Thr Thr Tyr Ile Ser Val Gly Thr Ser Thr Leu Asn Gln Arg Leu Val
    210                 215                 220

Pro Arg Ile Ala Thr Arg Ser Lys Val Asn Gly Gln Ser Gly Arg Met
225                 230                 235                 240

Glu Phe Phe Trp Thr Ile Leu Lys Pro Asn Asp Ala Ile Asn Phe Glu
                245                 250                 255

Ser Asn Gly Asn Phe Ile Ala Pro Glu Tyr Ala Tyr Lys Ile Val Lys
            260                 265                 270

Lys Gly Asp Ser Thr Ile Met Lys Ser Glu Leu Glu Tyr Gly Asn Cys
        275                 280                 285

Asn Thr Lys Cys Gln Thr Pro Met Gly Ala Ile Asn Ser Ser Met Pro
    290                 295                 300

Phe His Asn Ile His Pro Leu Thr Ile Gly Glu Cys Pro Lys Tyr Val
305                 310                 315                 320

Lys Ser Asn Arg Leu Val Leu Ala Thr Gly Leu Arg Asn Ser Pro Gln
                325                 330                 335

Arg Glu Lys Arg Arg Lys Lys Arg Gly Leu Phe Gly Ala Ile Ala Gly
            340                 345                 350

Phe Ile Glu Gly Gly Trp Gln Gly Met Val Asp Gly Trp Tyr Gly Tyr
        355                 360                 365

His His Ser Asn Glu Gln Gly Ser Gly Tyr Ala Ala Asp Lys Glu Ser
    370                 375                 380

Thr Gln Lys Ala Ile Asp Gly Val Thr Asn Lys Val Asn Ser Ile Ile
385                 390                 395                 400

Asp Lys Met Asn Thr Gln Phe Glu Ala Val Gly Arg Glu Phe Asn Asn
                405                 410                 415

Leu Glu Arg Arg Ile Glu Asn Leu Asn Lys Lys Met Glu Asp Gly Phe
            420                 425                 430

Leu Asp Val Trp Thr Tyr Asn Ala Glu Leu Leu Val Leu Met Glu Asn
        435                 440                 445

Glu Arg Thr Leu Asp Phe His Asp Ser Asn Val Lys Asn Leu Tyr Asp
    450                 455                 460

Lys Val Arg Leu Gln Leu Arg Asp Asn Ala Lys Glu Leu Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Gln Tyr Ser Glu Glu Ala Arg Leu
            500                 505                 510

Lys Arg Glu Glu Ile Ser Gly Val Lys Leu Glu Ser Ile Gly Ile Tyr
```

```
                515                 520                 525
Gln Ile Leu Ser Ile Tyr Ser Thr Val Ala Ser Ser Leu Ala Leu Ala
    530                 535                 540

Ile Met Val Ala Gly Leu Ser Leu Trp Met Cys Ser Asn Gly Ser Leu
545                 550                 555                 560

Gln Cys Arg Ile Cys Ile Lys Leu Glu Ser Asp
                565                 570

<210> SEQ ID NO 191
<211> LENGTH: 546
<212> TYPE: PRT
<213> ORGANISM: Influenza A virus

<400> SEQUENCE: 191

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
    50                  55                  60

Cys Asp Glu Phe Leu Asn Val Pro Glu Trp Ser Tyr Ile Val Glu Lys
65                  70                  75                  80

Ile Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Arg Ser Ser Phe Phe Arg Asn
    130                 135                 140

Val Val Trp Leu Ile Lys Lys Asp Asn Ala Tyr Pro Thr Ile Lys Arg
145                 150                 155                 160

Ser Tyr Asn Asn Thr Asn Gln Glu Asp Leu Leu Val Leu Trp Gly Ile
                165                 170                 175

His His Pro Asn Asp Ala Ala Glu Gln Thr Arg Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Ser Gly Arg Met
    210                 215                 220

Glu Phe Phe Trp Thr Ile Leu Lys Ser Asn Asp Ala Ile Asn Phe Glu
225                 230                 235                 240

Ser Asn Gly Asn Phe Ile Ala Pro Glu Asn Ala Tyr Lys Ile Val Lys
                245                 250                 255

Lys Gly Asp Ser Thr Ile Met Lys Ser Glu Leu Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
    290                 295                 300

Lys Ser Asn Arg Leu Ile Leu Ala Thr Gly Leu Arg Asn Ser Pro Gln
305                 310                 315                 320
```

Gly Glu Arg Arg Arg Lys Lys Arg Gly Leu Phe Gly Ala Ile Ala Gly
                325                 330                 335

Phe Ile Glu Gly Gly Trp Gln Gly Met Val Asp Gly Trp Tyr Gly Tyr
            340                 345                 350

His His Ser Asn Glu Gln Gly Ser Gly Tyr Ala Ala Asp Lys Glu Ser
            355                 360                 365

Thr Gln Lys Ala Ile Asp Gly Val Thr Asn Lys Val Asn Ser Ile Ile
        370                 375                 380

Asp Lys Met Asn Thr Gln Phe Glu Ala Val Gly Arg Glu Phe Asn Asn
385                 390                 395                 400

Leu Glu Arg Arg Ile Glu Asn Leu Asn Lys Lys Met Glu Asp Gly Phe
                405                 410                 415

Leu Asp Val Trp Thr Tyr Asn Ala Glu Leu Leu Val Leu Met Glu Asn
            420                 425                 430

Glu Arg Thr Leu Asp Phe His Asp Ser Asn Val Lys Asn Leu Tyr Asp
            435                 440                 445

Lys Val Arg Leu Gln Leu Arg Asp Asn Ala Lys Glu Leu Gly Asn Gly
        450                 455                 460

Cys Phe Glu Phe Tyr His Arg Cys Asp Asn Glu Cys Met Glu Ser Val
465                 470                 475                 480

Arg Asn Gly Thr Tyr Asp Tyr Pro Gln Tyr Ser Glu Glu Ala Arg Leu
                485                 490                 495

Lys Arg Glu Glu Ile Ser Gly Val Lys Leu Glu Ser Ile Gly Thr Tyr
            500                 505                 510

Gln Ile Leu Ser Ile Tyr Ser Thr Val Ala Ser Ser Leu Ala Leu Ala
        515                 520                 525

Ile Met Val Ala Gly Leu Phe Leu Trp Met Cys Ser Asn Gly Ser Leu
530                 535                 540

Gln Cys
545

<210> SEQ ID NO 192
<211> LENGTH: 552
<212> TYPE: PRT
<213> ORGANISM: Influenza A virus

<400> SEQUENCE: 192

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

```
Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
            165                 170                 175

Gly Ile His His Pro Asn Asp Gly Ala Glu Gln Thr Arg Leu Tyr Gln
        180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
        210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
            245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
            325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
            355                 360                 365

Glu Ser Thr Gln Arg Ala Ile Asp Gly Val Thr Asn Lys Val Asn Ser
        370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
        450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
            485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
            515                 520                 525

Leu Ala Ile Met Met Ala Gly Leu Ser Leu Trp Met Cys Ser Asn Gly
        530                 535                 540

Ser Leu Gln Cys Arg Ile Cys Ile
545                 550
```

-continued

```
<210> SEQ ID NO 193
<211> LENGTH: 552
<212> TYPE: PRT
<213> ORGANISM: Influenza A virus

<400> SEQUENCE: 193
```

| | | | | | | | | | | | | | |
|---|---|---|---|---|---|---|---|---|---|---|---|---|---|
| Asp | Gln | Ile | Cys | Ile | Gly | Tyr | His | Ala | Asn | Asn | Ser | Thr | Glu | Gln | Val |
| 1 | | | | 5 | | | | | 10 | | | | | 15 | |

| Asp | Thr | Ile | Met | Glu | Lys | Asn | Val | Thr | Val | Thr | His | Ala | Gln | Asp | Ile |
| | | | 20 | | | | | 25 | | | | | 30 | | |

| Leu | Glu | Lys | Thr | His | Asn | Gly | Lys | Leu | Cys | Asp | Leu | Asp | Gly | Val | Lys |
| | | | 35 | | | | | 40 | | | | | 45 | | |

| Pro | Leu | Ile | Leu | Arg | Asp | Cys | Ser | Val | Ala | Gly | Trp | Leu | Leu | Gly | Asn |
| 50 | | | | | 55 | | | | | 60 | | | | | |

| Pro | Met | Cys | Asp | Glu | Phe | Ile | Asn | Val | Pro | Glu | Trp | Ser | Tyr | Ile | Val |
| 65 | | | | | 70 | | | | | 75 | | | | | 80 |

| Glu | Lys | Ala | Asn | Pro | Thr | Asn | Gly | Leu | Cys | Tyr | Pro | Gly | Ser | Phe | Asn |
| | | | | 85 | | | | | 90 | | | | | 95 | |

| Asp | Tyr | Glu | Glu | Leu | Lys | His | Leu | Leu | Ser | Arg | Ile | Asn | His | Phe | Glu |
| | | | 100 | | | | | 105 | | | | | 110 | | |

| Lys | Ile | Gln | Ile | Ile | Pro | Lys | Ser | Ser | Trp | Ser | Asp | His | Glu | Ala | Ser |
| | | | 115 | | | | | 120 | | | | | 125 | | |

| Ser | Gly | Val | Ser | Ser | Ala | Cys | Pro | Tyr | Leu | Gly | Ser | Pro | Ser | Phe | Phe |
| 130 | | | | | 135 | | | | | 140 | | | | | |

| Arg | Asn | Val | Val | Trp | Leu | Ile | Lys | Lys | Asn | Ser | Thr | Tyr | Pro | Thr | Ile |
| 145 | | | | | 150 | | | | | 155 | | | | | 160 |

| Lys | Lys | Ser | Tyr | Asn | Asn | Thr | Asn | Gln | Glu | Asp | Leu | Leu | Val | Leu | Trp |
| | | | | 165 | | | | | 170 | | | | | 175 | |

| Gly | Ile | His | His | Pro | Asn | Asp | Ala | Ala | Glu | Gln | Thr | Arg | Leu | Tyr | Gln |
| | | | 180 | | | | | 185 | | | | | 190 | | |

| Asn | Pro | Thr | Thr | Tyr | Ile | Ser | Ile | Gly | Thr | Ser | Thr | Leu | Asn | Gln | Arg |
| | | | 195 | | | | | 200 | | | | | 205 | | |

| Leu | Val | Pro | Lys | Ile | Ala | Thr | Arg | Ser | Lys | Val | Asn | Gly | Gln | Ser | Gly |
| 210 | | | | | 215 | | | | | 220 | | | | | |

| Arg | Met | Glu | Phe | Phe | Trp | Thr | Ile | Leu | Lys | Pro | Asn | Asp | Ala | Ile | Asn |
| 225 | | | | | 230 | | | | | 235 | | | | | 240 |

| Phe | Glu | Ser | Asn | Gly | Asn | Phe | Ile | Ala | Pro | Glu | Tyr | Ala | Tyr | Lys | Ile |
| | | | | 245 | | | | | 250 | | | | | 255 | |

| Val | Lys | Lys | Gly | Asp | Ser | Ala | Ile | Met | Lys | Ser | Glu | Leu | Glu | Tyr | Gly |
| | | | 260 | | | | | 265 | | | | | 270 | | |

| Asn | Cys | Asn | Thr | Lys | Cys | Gln | Thr | Pro | Met | Gly | Ala | Ile | Asn | Ser | Ser |
| | | | 275 | | | | | 280 | | | | | 285 | | |

| Met | Pro | Phe | His | Asn | Ile | His | Pro | Leu | Thr | Ile | Gly | Glu | Cys | Pro | Lys |
| 290 | | | | | 295 | | | | | 300 | | | | | |

| Tyr | Val | Lys | Ser | Asn | Arg | Leu | Val | Leu | Ala | Thr | Gly | Leu | Arg | Asn | Ser |
| 305 | | | | | 310 | | | | | 315 | | | | | 320 |

| Pro | Gln | Arg | Glu | Ser | Arg | Arg | Lys | Lys | Arg | Gly | Leu | Phe | Gly | Ala | Ile |
| | | | | 325 | | | | | 330 | | | | | 335 | |

| Ala | Gly | Phe | Ile | Glu | Gly | Gly | Trp | Gln | Gly | Met | Val | Asp | Gly | Trp | Tyr |
| | | | 340 | | | | | 345 | | | | | 350 | | |

| Gly | Tyr | His | His | Ser | Asn | Glu | Gln | Gly | Ser | Gly | Tyr | Ala | Ala | Asp | Lys |
| | | | 355 | | | | | 360 | | | | | 365 | | |

| Glu | Ser | Thr | Gln | Lys | Ala | Ile | Asp | Gly | Val | Thr | Asn | Lys | Val | Asn | Ser |
| 370 | | | | | 375 | | | | | 380 | | | | | |

```
Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Met Ala Gly Leu Ser Leu Trp Met Cys Ser Asn Gly
    530                 535                 540

Ser Leu Gln Cys Arg Ile Cys Ile
545                 550

<210> SEQ ID NO 194
<211> LENGTH: 553
<212> TYPE: PRT
<213> ORGANISM: Influenza A virus

<400> SEQUENCE: 194

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
```

```
                195                 200                 205
Leu Val Pro Lys Ile Ala Thr Arg Ser Lys Val Asn Gly Gln Ser Gly
210                 215                 220

Arg Met Glu Phe Phe Trp Thr Ile Leu Asn Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Pro Lys Cys Gln Thr Pro Met Gly Ala Ile Asn Ser
        275                 280                 285

Ser Met Pro Phe His Asn Ile His Pro Leu Thr Ile Gly Glu Cys Pro
290                 295                 300

Lys Tyr Val Lys Ser Asn Arg Leu Val Leu Ala Thr Gly Leu Arg Asn
305                 310                 315                 320

Ser Pro Gln Arg Glu Ser Arg Arg Lys Lys Arg Gly Leu Phe Gly Ala
                325                 330                 335

Ile Ala Gly Phe Ile Glu Gly Gly Trp Gln Gly Met Val Asp Gly Trp
            340                 345                 350

Tyr Gly Tyr His His Ser Asn Glu Gln Gly Ser Gly Tyr Ala Ala Asp
        355                 360                 365

Lys Glu Ser Thr Gln Lys Ala Ile Asp Gly Val Thr Asn Lys Val Asn
370                 375                 380

Ser Ile Ile Asp Lys Met Asn Thr Gln Phe Glu Ala Val Gly Arg Glu
385                 390                 395                 400

Phe Asn Asn Leu Glu Arg Arg Ile Glu Asn Leu Asn Lys Lys Met Glu
                405                 410                 415

Asp Gly Phe Leu Asp Val Trp Thr Tyr Asn Ala Glu Leu Leu Val Leu
            420                 425                 430

Met Glu Asn Glu Arg Thr Leu Asp Phe His Asp Ser Asn Val Lys Asn
        435                 440                 445

Leu Tyr Asp Lys Val Arg Leu Gln Leu Arg Asp Asn Ala Lys Glu Leu
450                 455                 460

Gly Asn Gly Cys Phe Glu Phe Tyr His Lys Cys Asp Asn Glu Cys Met
465                 470                 475                 480

Glu Ser Ile Arg Asn Gly Thr Tyr Asn Tyr Pro Gln Tyr Ser Glu Glu
                485                 490                 495

Ala Arg Leu Lys Arg Glu Glu Ile Ser Gly Val Lys Leu Glu Ser Ile
            500                 505                 510

Gly Thr Tyr Gln Ile Leu Ser Ile Tyr Ser Thr Val Ala Ser Ser Leu
        515                 520                 525

Ala Leu Ala Ile Met Met Ala Gly Leu Ser Leu Trp Met Cys Ser Asn
530                 535                 540

Gly Ser Leu Gln Cys Arg Ile Cys Ile
545                 550

<210> SEQ ID NO 195
<211> LENGTH: 552
<212> TYPE: PRT
<213> ORGANISM: Influenza A virus

<400> SEQUENCE: 195

Asp Gln Ile Cys Ile Gly Tyr His Ala Asn Asn Ser Thr Glu Gln Val
1               5                   10                  15
```

-continued

```
Asp Thr Ile Met Glu Lys Asn Val Thr Val Thr His Ala Gln Asp Ile
             20                  25                  30

Leu Glu Lys Thr His Asn Gly Lys Leu Cys Asp Leu Asp Gly Val Lys
         35                  40                  45

Pro Leu Ile Leu Lys Asp Cys Ser Val Ala Gly Trp Leu Leu Gly Asn
     50                  55                  60

Pro Met Cys Asp Glu Phe Ile Asn Val Pro Glu Trp Ser Tyr Ile Val
 65                  70                  75                  80

Glu Lys Ala Asn Pro Thr Asn Asp Leu Cys Tyr Pro Gly Ser Phe Asn
                 85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Ser Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
```

```
            435                 440                 445
Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
                500                 505                 510

Thr Tyr Gln Ile Leu Ser Ile Tyr Ser Thr Val Ala Ser Ser Leu Ala
                515                 520                 525

Leu Ala Ile Met Ile Ala Gly Leu Ser Leu Trp Met Cys Ser Asn Gly
                530                 535                 540

Ser Leu Gln Cys Arg Ile Cys Ile
545                 550

<210> SEQ ID NO 196
<211> LENGTH: 552
<212> TYPE: PRT
<213> ORGANISM: Influenza A virus

<400> SEQUENCE: 196

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Thr His Asn Gly Lys Leu Cys Asp Leu Asp Gly Val Lys
                35                  40                  45

Pro Leu Ile Leu Lys Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
                100                 105                 110

Lys Ile Gln Ile Ile Pro Lys Ser Ser Trp Ser Asp His Glu Ala Ser
                115                 120                 125

Ser Gly Val Ser Ser Ala Cys Pro Tyr Leu Gly Ser Pro Ser Phe Phe
130                 135                 140

Arg Asn Val Val Trp Leu Ile Lys Lys Asn Ser Thr Tyr Pro Thr Ile
145                 150                 155                 160

Lys Glu Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
                180                 185                 190

Asn Pro Thr Thr Tyr Ile Ser Ile Gly Thr Ser Thr Leu Asn Gln Arg
                195                 200                 205

Leu Val Pro Lys Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255
```

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
        290                 295                 300

Tyr Val Lys Ser Asn Lys Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
        370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
        450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
            515                 520                 525

Leu Ala Ile Met Ile Ala Gly Leu Ser Leu Trp Met Cys Ser Asn Gly
        530                 535                 540

Ser Leu Gln Cys Arg Ile Cys Ile
545                 550

<210> SEQ ID NO 197
<211> LENGTH: 568
<212> TYPE: PRT
<213> ORGANISM: Influenza A virus

<400> SEQUENCE: 197

Met Glu Lys Ile Val Leu Leu Leu Ser Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
      50                  55                  60

Pro Leu Ile Leu Lys Asp Cys Ser Val Ala Gly Trp Leu Leu Gly Asn
65                  70                  75                  80

```
Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asn Glu Glu Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Ser
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Ser Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495
```

-continued

```
Ser Ile Arg Asn Gly Thr Tyr Asn Tyr Pro Gln Tyr Ser Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Ile Ala Gly Leu Ser Leu Trp Met Cys Ser Asn Gly
545                 550                 555                 560

Ser Leu Gln Cys Arg Ile Cys Ile
                565

<210> SEQ ID NO 198
<211> LENGTH: 548
<212> TYPE: PRT
<213> ORGANISM: Influenza A virus

<400> SEQUENCE: 198

Asp Gln Ile Cys Ile Gly Tyr His Ala Asn Asn Ser Thr Glu Gln Val
1               5                  10                  15

Asp Thr Ile Met Glu Lys Asn Val Thr Val Thr His Ala Gln Asp Ile
            20                  25                  30

Leu Glu Lys Thr His Asn Gly Lys Leu Cys Asn Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Ile Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asn Ser Trp Ser Asp His Glu Ala Ser
        115                 120                 125

Gly Val Ser Ser Ala Cys Pro Tyr Gln Gly Arg Ser Ser Phe Phe Arg
    130                 135                 140

Asn Val Val Trp Leu Thr Lys Lys Asp Asn Ala Tyr Pro Thr Ile Lys
145                 150                 155                 160

Arg Ser Tyr Asn Asn Thr Asn Gln Glu Asp Leu Leu Val Leu Trp Gly
                165                 170                 175

Ile His His Pro Asn Asp Ala Ala Glu Gln Thr Arg Leu Tyr Gln Asn
            180                 185                 190

Pro Thr Thr Tyr Ile Ser Val Gly Thr Ser Thr Leu Asn Gln Arg Leu
        195                 200                 205

Val Pro Lys Ile Ala Thr Arg Ser Lys Val Asn Gly Gln Ser Gly Arg
    210                 215                 220

Met Glu Phe Phe Trp Thr Ile Leu Lys Ser Asn Asp Ala Ile Asn Phe
225                 230                 235                 240

Glu Ser Asn Gly Asn Phe Ile Ala Pro Glu Asn Ala Tyr Lys Ile Val
                245                 250                 255

Lys Lys Gly Asp Ser Thr Ile Met Lys Ser Glu Leu Gly Tyr Gly Asn
            260                 265                 270

Cys Asn Thr Lys Cys Gln Thr Pro Ile Gly Ala Ile Asn Ser Ser Met
        275                 280                 285

Pro Phe His Asn Ile His Pro Leu Thr Ile Gly Glu Cys Pro Lys Tyr
    290                 295                 300
```

```
Val Lys Ser Asn Arg Leu Val Leu Ala Thr Gly Leu Arg Asn Ser Pro
305                 310                 315                 320

Gln Gly Glu Arg Arg Lys Lys Arg Gly Leu Phe Gly Ala Ile Ala
            325                 330                 335

Gly Phe Ile Glu Gly Gly Trp Gln Gly Met Val Asp Gly Trp Tyr Gly
                340                 345                 350

Tyr His His Ser Asn Glu Gln Gly Ser Gly Tyr Ala Ala Asp Lys Glu
            355                 360                 365

Ser Thr Gln Lys Ala Ile Asp Gly Val Thr Asn Lys Val Asn Ser Ile
370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
            405                 410                 415

Phe Leu Asp Val Trp Thr Tyr Asn Ala Glu Leu Leu Val Leu Met Glu
                420                 425                 430

Asn Glu Arg Thr Leu Asp Phe His Asp Ser Asn Val Lys Asn Leu Tyr
            435                 440                 445

Asp Lys Val Arg Leu Gln Leu Arg Asp Asn Ala Lys Glu Leu Gly Asn
450                 455                 460

Gly Cys Phe Glu Phe Tyr His Arg Cys Asp Asn Glu Cys Met Glu Ser
465                 470                 475                 480

Val Arg Asn Gly Thr Tyr Asp Tyr Pro Gln Tyr Ser Glu Glu Ala Arg
            485                 490                 495

Leu Lys Arg Glu Glu Ile Ser Gly Val Lys Leu Glu Ser Ile Gly Thr
                500                 505                 510

Tyr Gln Ile Leu Ser Ile Tyr Ser Thr Val Ala Ser Ser Leu Ala Leu
            515                 520                 525

Ala Ile Met Val Ala Gly Leu Phe Leu Trp Met Cys Ser Asn Gly Ser
530                 535                 540

Leu Gln Cys Arg
545

<210> SEQ ID NO 199
<211> LENGTH: 549
<212> TYPE: PRT
<213> ORGANISM: Influenza A virus

<400> SEQUENCE: 199

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Leu Asn Val Pro Glu Trp Ser Tyr Ile Val
65                  70                  75                  80

Glu Lys Ile Asn Pro Ala Asn Asp Leu Cys Tyr Pro Gly Asn Phe Asn
            85                  90                  95

Asp Tyr Glu Glu Leu Lys His Leu Leu Ser Arg Ile Asn His Phe Glu
        100                 105                 110

Lys Ile Gln Ile Ile Pro Lys Ser Ser Trp Ser Asp His Glu Ala Ser
```

```
            115                 120                 125
Ser Gly Val Ser Ser Ala Cys Pro Tyr Gln Gly Arg Ser Phe Phe
130                 135                 140
Arg Asn Val Val Trp Leu Ile Lys Lys Asp Asn Ala Tyr Pro Thr Ile
145                 150                 155                 160
Lys Arg Ser Tyr Asn Asn Thr Asn Gln Glu Asp Leu Leu Val Leu Trp
                165                 170                 175
Gly Ile His His Pro Asn Asp Ala Ala Glu Gln Thr Arg Leu Tyr Gln
            180                 185                 190
Asn Pro Thr Thr Tyr Ile Ser Val Gly Thr Ser Thr Leu Asn Gln Arg
        195                 200                 205
Leu Val Pro Lys Ile Ala Thr Arg Ser Lys Val Asn Gly Gln Ser Gly
    210                 215                 220
Arg Met Glu Phe Phe Trp Thr Ile Leu Lys Ser Asn Asp Ala Ile Asn
225                 230                 235                 240
Phe Glu Ser Asn Gly Asn Phe Ile Ala Pro Glu Asn Ala Tyr Lys Ile
                245                 250                 255
Val Lys Lys Gly Asp Ser Thr Ile Met Lys Ser Glu Leu Glu Tyr Gly
            260                 265                 270
Asn Cys Asn Thr Lys Cys Gln Thr Pro Ile Gly Ala Ile Asn Ser Ser
        275                 280                 285
Met Pro Phe His Asn Ile His Pro Leu Thr Ile Gly Glu Cys Pro Lys
    290                 295                 300
Tyr Val Lys Ser Asn Arg Leu Val Leu Ala Thr Gly Leu Arg Asn Ser
305                 310                 315                 320
Pro Gln Gly Glu Arg Arg Lys Lys Arg Gly Leu Phe Gly Ala Ile
                325                 330                 335
Ala Gly Phe Ile Glu Gly Gly Trp Gln Gly Met Val Asp Gly Trp Tyr
            340                 345                 350
Gly Tyr His His Ser Asn Glu Gln Gly Ser Gly Tyr Ala Ala Asp Lys
        355                 360                 365
Glu Ser Thr Gln Lys Ala Ile Asp Gly Val Thr Asn Lys Val Asn Ser
    370                 375                 380
Ile Ile Asp Lys Met Asn Thr Gln Phe Glu Ala Val Gly Arg Glu Phe
385                 390                 395                 400
Asn Asn Leu Glu Arg Arg Ile Glu Asn Leu Asn Lys Lys Met Glu Asp
                405                 410                 415
Gly Phe Leu Asp Val Trp Thr Tyr Asn Ala Glu Leu Leu Val Leu Met
            420                 425                 430
Glu Asn Glu Arg Thr Leu Asp Phe His Asp Ser Asn Val Lys Asn Leu
        435                 440                 445
Tyr Asp Lys Val Arg Leu Gln Leu Arg Asp Asn Ala Lys Glu Leu Gly
    450                 455                 460
Asn Gly Cys Phe Glu Phe Tyr His Arg Cys Asp Asn Glu Cys Met Glu
465                 470                 475                 480
Ser Val Arg Asn Gly Thr Tyr Asp Tyr Pro Gln Tyr Ser Glu Glu Ala
                485                 490                 495
Arg Leu Lys Arg Glu Glu Ile Ser Gly Val Lys Leu Glu Ser Ile Gly
            500                 505                 510
Thr Tyr Gln Ile Leu Ser Ile Tyr Ser Thr Val Ala Ser Ser Leu Ala
        515                 520                 525
Leu Ala Ile Met Val Ala Gly Leu Phe Leu Trp Met Cys Ser Asn Gly
    530                 535                 540
```

Ser Leu Gln Cys Arg
545

<210> SEQ ID NO 200
<211> LENGTH: 549
<212> TYPE: PRT
<213> ORGANISM: Influenza A virus

<400> SEQUENCE: 200

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Ile Asn Pro Ala Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Arg Ser Ser Phe Phe
    130                 135                 140

Arg Asn Val Val Trp Leu Ile Lys Lys Asn Asn Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Ser Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Ile Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Gly Glu Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys

```
                355                 360                 365
Glu Ser Thr Gln Lys Ala Ile Asp Gly Val Thr Asn Lys Val Asn Ser
    370                 375                 380

Ile Ile Asn Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Arg Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Ile Tyr Gln Ile Leu Ser Ile Tyr Ser Thr Val Ala Ser Ser Leu Ala
        515                 520                 525

Leu Ala Ile Met Val Ala Gly Leu Phe Leu Trp Met Cys Ser Asn Gly
    530                 535                 540

Ser Leu Gln Cys Arg
545

<210> SEQ ID NO 201
<211> LENGTH: 568
<212> TYPE: PRT
<213> ORGANISM: Influenza A virus

<400> SEQUENCE: 201

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Ser Ser Phe Phe
145                 150                 155                 160

Arg Asn Val Val Trp Leu Ile Lys Lys Asn Ser Thr Tyr Pro Thr Ile
                165                 170                 175
```

-continued

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Thr Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Ile Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 202
<211> LENGTH: 569
<212> TYPE: PRT

<213> ORGANISM: Influenza A virus

<400> SEQUENCE: 202

```
Met Glu Lys Ile Val Leu Leu Leu Ala

Ser Ile Ile Asp Lys Met Asn Thr Gln Phe Glu Ala Val Gly Arg Glu
            405                 410                 415

Phe Asn Asn Leu Glu Arg Arg Ile Glu Asn Leu Asn Lys Lys Met Glu
        420                 425                 430

Asp Gly Phe Leu Asp Val Trp Thr Tyr Asn Ala Glu Leu Leu Val Leu
        435                 440                 445

Met Glu Asn Glu Arg Thr Leu Asp Phe His Asp Ser Asn Val Lys Asn
450                 455                 460

Leu Tyr Asp Lys Val Arg Leu Gln Leu Arg Asp Asn Ala Lys Glu Leu
465                 470                 475                 480

Gly Asn Gly Cys Phe Glu Phe Tyr His Lys Cys Asp Asn Glu Cys Met
                485                 490                 495

Glu Ser Ile Arg Asn Gly Thr Tyr Asn Tyr Pro Gln Tyr Ser Glu Glu
            500                 505                 510

Ala Arg Leu Lys Arg Glu Glu Ile Ser Gly Val Lys Leu Glu Ser Ile
        515                 520                 525

Gly Thr Tyr Gln Ile Leu Ser Ile Tyr Ser Thr Val Ala Ser Ser Leu
        530                 535                 540

Ala Leu Ala Ile Met Ile Ala Gly Leu Ser Leu Trp Met Cys Ser Asn
545                 550                 555                 560

Gly Ser Leu Gln Cys Arg Ile Cys Ile
                565

<210> SEQ ID NO 203
<211> LENGTH: 568
<212> TYPE: PRT
<213> ORGANISM: Influenza A virus

<400> SEQUENCE: 203

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
            210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 204
<211> LENGTH: 568
<212> TYPE: PRT
<213> ORGANISM: Influenza A virus

<400> SEQUENCE: 204

Met Glu Lys Ile Val Leu Leu Leu Ala Ile Val Ser Leu Val Lys Ser

```
              1               5                  10                 15
            Asp Gln Ile Cys Ile Gly Tyr His Ala Asn Asn Ser Thr Glu Gln Val
                            20                 25                 30

Asp Thr Ile Met Glu Lys Asn Val Thr Val Thr His Ala Gln Asp Ile
                            35                 40                 45

Leu Glu Lys Thr His Asn Gly Lys Leu Cys Asp Leu Asp Gly Val Lys
                50                  55                 60

Pro Leu Ile Leu Arg Asp Cys Ser Val Ala Gly Trp Leu Leu Gly Asn
            65                  70                 75                 80

Pro Met Cys Asp Glu Phe Ile Asn Val Pro Glu Trp Ser Tyr Ile Val
                            85                 90                 95

Glu Lys Ala Asn Pro Thr Asn Asp Leu Cys Tyr Pro Gly Ser Phe Asn
                            100                105                110

Asp Tyr Glu Glu Leu Lys His Leu Leu Ser Arg Ile Asn His Phe Glu
                            115                120                125

Lys Ile Gln Ile Ile Pro Lys Ser Ser Trp Ser Asp His Glu Ala Ser
                            130                135                140

Ser Gly Val Ser Ser Ala Cys Pro Tyr Leu Gly Ser Pro Ser Phe Phe
            145                 150                155                160

Arg Asn Val Val Trp Leu Ile Lys Lys Asn Ser Thr Tyr Pro Thr Ile
                            165                170                175

Lys Lys Ser Tyr Asn Asn Thr Asn Gln Glu Asp Leu Leu Val Leu Trp
                            180                185                190

Gly Ile His His Pro Asn Asp Ala Ala Glu Gln Thr Arg Leu Tyr Gln
                            195                200                205

Asn Pro Thr Thr Tyr Ile Ser Ile Gly Thr Ser Thr Leu Asn Gln Arg
                            210                215                220

Leu Val Pro Lys Ile Ala Thr Arg Ser Lys Val Asn Gly Gln Ser Gly
            225                 230                235                240

Arg Met Glu Phe Phe Trp Thr Ile Leu Lys Pro Asn Asp Ala Ile Asn
                            245                250                255

Phe Glu Ser Asn Gly Asn Phe Ile Ala Pro Glu Tyr Ala Tyr Lys Ile
                            260                265                270

Val Lys Lys Gly Asp Ser Ala Ile Met Lys Ser Glu Leu Glu Tyr Gly
                            275                280                285

Asn Cys Asn Thr Lys Cys Gln Thr Pro Met Gly Ala Ile Asn Ser Ser
                            290                295                300

Met Pro Phe His Asn Ile His Pro Leu Thr Ile Gly Glu Cys Pro Lys
            305                 310                315                320

Tyr Val Lys Ser Asn Arg Leu Val Leu Ala Thr Gly Leu Arg Asn Ser
                            325                330                335

Pro Gln Arg Glu Ser Arg Arg Lys Lys Arg Gly Leu Phe Gly Ala Ile
                            340                345                350

Ala Gly Phe Ile Glu Gly Gly Trp Gln Gly Met Val Asp Gly Trp Tyr
                            355                360                365

Gly Tyr His His Ser Asn Glu Gln Gly Ser Gly Tyr Ala Ala Asp Lys
                            370                375                380

Glu Ser Thr Gln Lys Ala Ile Asp Gly Val Thr Asn Lys Val Asn Ser
            385                 390                395                400

Ile Ile Asp Lys Met Asn Thr Gln Phe Glu Ala Val Gly Arg Glu Phe
                            405                410                415

Asn Asn Leu Glu Arg Arg Ile Glu Asn Leu Asn Lys Lys Met Glu Asp
                            420                425                430
```

-continued

```
Gly Phe Leu Asp Val Trp Thr Tyr Asn Ala Glu Leu Val Leu Met
            435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Ile Ala Gly Leu Ser Leu Trp Met Cys Ser Asn Gly
545                 550                 555                 560

Ser Leu Gln Cys Arg Ile Cys Ile
                565

<210> SEQ ID NO 205
<211> LENGTH: 555
<212> TYPE: PRT
<213> ORGANISM: Influenza A virus

<400> SEQUENCE: 205

Met Glu Lys Ile Val Leu Leu Leu Ala Thr Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Arg Thr His Asn Gly Lys Leu Cys Asp Leu Asn Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Glu Ile Ala Thr Arg Pro Lys Val Asn Gly Gln Ser Gly
```

```
                225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
                260                 265                 270
Val Lys Lys Gly Asp Ser Thr Ile Met Lys Ser Glu Leu Glu Tyr Gly
                275                 280                 285
Asn Cys Asn Thr Lys Cys Gln Thr Pro Met Gly Ala Ile Asn Ser Ser
                290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Thr
                325                 330                 335
Pro Gln Arg Glu Arg Arg Arg Lys Lys Arg Gly Leu Phe Gly Ala Ile
                340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Gln
                370                 375                 380
Glu Ser Thr Gln Lys Ala Ile Asp Gly Val Thr Asn Lys Val Asn Ser
385                 390                 395                 400
Ile Ile Asn Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
                420                 425                 430
Gly Phe Leu Asp Val Trp Thr Tyr Asn Ala Glu Leu Leu Val Leu Met
                435                 440                 445
Glu Asn Glu Arg Thr Leu Asp Phe His Asp Ser Asn Val Lys Asn Leu
                450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Lys Asn Gly Thr Tyr Asp Tyr Pro Gln Tyr Ser Glu Glu Ala
                500                 505                 510
Arg Leu Asn Arg Glu Glu Ile Ser Gly Val Lys Leu Glu Ser Met Gly
                515                 520                 525
Thr Tyr Gln Ile Leu Ser Ile Tyr Ser Thr Val Ala Ser Ser Leu Ala
                530                 535                 540
Leu Ala Ile Met Val Ala Gly Leu Ser Leu Trp
545                 550                 555

<210> SEQ ID NO 206
<211> LENGTH: 568
<212> TYPE: PRT
<213> ORGANISM: Influenza A virus

<400> SEQUENCE: 206

Met Glu Lys Ile Val Leu Leu Leu Ala Ile Val Ser Leu Val Lys Ser
1               5                   10                  15
Asp Gln Ile Cys Ile Gly Tyr His Ala Asn Asn Ser Thr Glu Gln Val
                20                  25                  30
Asp Thr Ile Met Glu Lys Asn Val Thr Val Thr His Ala Gln Asp Ile
                35                  40                  45
```

```
Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asn Ala Ala Glu Gln Thr Arg Leu Tyr Gln
        195                 200                 205

Asn Pro Thr Thr Tyr Ile Ser Ile Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
```

```
                465                 470                 475                 480
Asn Gly Cys Phe Glu Phe Tyr His Lys Cys Asp Asn Glu Cys Met Glu
                    485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Ile Ala Gly Leu Ser Leu Trp Met Cys Ser Asn Gly
545                 550                 555                 560

Ser Leu Gln Cys Arg Ile Cys Ile
                565

<210> SEQ ID NO 207
<211> LENGTH: 57
<212> TYPE: PRT
<213> ORGANISM: Influenza A virus

<400> SEQUENCE: 207

Met Glu Lys Ile Val Leu Leu Leu Ala Thr Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu
    50                  55

<210> SEQ ID NO 208
<211> LENGTH: 57
<212> TYPE: PRT
<213> ORGANISM: Influenza A virus

<400> SEQUENCE: 208

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu
    50                  55

<210> SEQ ID NO 209
<211> LENGTH: 25
<212> TYPE: PRT
<213> ORGANISM: Influenza A virus

<400> SEQUENCE: 209

Asp Thr Ile Met Glu Lys Asn Val Thr Val Thr His Ala Gln Asp Ile
1               5                   10                  15

Leu Glu Lys Thr His Asn Gly Lys Leu
            20                  25

<210> SEQ ID NO 210
<211> LENGTH: 238
<212> TYPE: PRT
<213> ORGANISM: Influenza A virus
```

<400> SEQUENCE: 210

Cys Asp Leu Asn Gly Val Lys Pro Leu Ile Leu Arg Asp Cys Ser Val
1               5                   10                  15

Ala Gly Trp Leu Leu Gly Asn Pro Met Cys Asp Glu Phe Ile Asn Val
            20                  25                  30

Pro Glu Trp Ser Tyr Ile Val Glu Lys Ala Ser Pro Ala Asn Asp Leu
        35                  40                  45

Cys Tyr Pro Gly Asn Phe Asn Asp Tyr Glu Glu Leu Lys His Leu Leu
    50                  55                  60

Ser Arg Ile Ser His Phe Glu Lys Ile Gln Ile Ile Pro Lys Ser Ser
65                  70                  75                  80

Trp Ser Asn His Asp Ala Ser Ser Gly Val Ser Ser Ala Cys Pro Tyr
                85                  90                  95

Leu Gly Lys Ser Ser Phe Phe Arg Asn Val Val Trp Leu Ile Lys Lys
            100                 105                 110

Asn Ser Thr Tyr Pro Thr Ile Lys Arg Ser Tyr Asn Asn Thr Asn Gln
        115                 120                 125

Glu Asp Leu Leu Val Leu Trp Gly Ile His His Pro Asn Asp Ala Ala
130                 135                 140

Glu Gln Thr Lys Leu Tyr Gln Asn Pro Thr Thr Tyr Ile Ser Val Gly
145                 150                 155                 160

Thr Ser Thr Leu Asn Gln Arg Leu Val Pro Glu Ile Ala Thr Arg Pro
                165                 170                 175

Lys Val Asn Gly Gln Ser Gly Arg Ile Glu Phe Phe Trp Thr Ile Leu
            180                 185                 190

Lys Pro Asn Asp Ala Ile Asn Phe Glu Ser Asn Gly Asn Phe Ile Ala
        195                 200                 205

Pro Glu Tyr Ala Tyr Lys Ile Val Lys Lys Gly Asp Ser Thr Ile Met
    210                 215                 220

Lys Ser Glu Leu Glu Tyr Gly Asn Cys Asn Thr Lys Cys Gln
225                 230                 235

<210> SEQ ID NO 211
<211> LENGTH: 238
<212> TYPE: PRT
<213> ORGANISM: Influenza A virus

<400> SEQUENCE: 211

Cys Asp Leu Asn Gly Val Lys Pro Leu Ile Leu Arg Asp Cys Ser Val
1               5                   10                  15

Ala Gly Trp Leu Leu Gly Asn Pro Met Cys Asp Glu Phe Ile Asn Val
            20                  25                  30

Pro Glu Trp Ser Tyr Ile Val Glu Lys Ala Ser Pro Ala Asn Asp Leu
        35                  40                  45

Cys Tyr Pro Gly Asn Phe Asn Asp Tyr Glu Glu Leu Lys His Leu Leu
    50                  55                  60

Ser Arg Ile Asn His Phe Glu Lys Ile Gln Ile Ile Pro Lys Ser Ser
65                  70                  75                  80

Trp Ser Asn His Asp Ala Ser Ser Gly Val Ser Ser Ala Cys Pro Tyr
                85                  90                  95

Leu Gly Arg Ser Ser Phe Phe Arg Asn Val Val Trp Leu Ile Lys Lys
            100                 105                 110

Asn Ser Ala Tyr Pro Thr Ile Lys Arg Ser Tyr Asn Asn Thr Asn Gln
        115                 120                 125

Glu Asp Leu Leu Val Leu Trp Gly Val His His Pro Asn Asp Ala Ala
    130                 135                 140

Glu Gln Thr Lys Leu Tyr Gln Asn Pro Thr Thr Tyr Ile Ser Val Gly
145                 150                 155                 160

Thr Ser Thr Leu Asn Gln Arg Leu Val Pro Glu Ile Ala Thr Arg Pro
                165                 170                 175

Lys Val Asn Gly Gln Ser Gly Arg Met Glu Phe Phe Trp Thr Ile Leu
                180                 185                 190

Lys Pro Asn Asp Ala Ile Asn Phe Glu Ser Asn Gly Asn Phe Ile Ala
                195                 200                 205

Pro Glu Tyr Ala Tyr Lys Ile Val Lys Lys Gly Asp Ser Thr Ile Met
                210                 215                 220

Lys Ser Glu Leu Glu Tyr Gly Asn Cys Asn Thr Lys Cys Gln
225                 230                 235

<210> SEQ ID NO 212
<211> LENGTH: 238
<212> TYPE: PRT
<213> ORGANISM: Influenza A virus

<400> SEQUENCE: 212

Cys Asp Leu Asn Gly Val Lys Pro Leu Ile Leu Arg Asp Cys Ser Val
1               5                   10                  15

Ala Gly Trp Leu Leu Gly Asn Pro Met Cys Asp Glu Phe Ile Asn Val
                20                  25                  30

Pro Glu Trp Ser Tyr Ile Val Glu Lys Ala Ser Pro Ala Asn Asp Leu
            35                  40                  45

Cys Tyr Pro Gly Asn Phe Asn Asp Tyr Glu Glu Leu Lys His Leu Leu
    50                  55                  60

Ser Arg Ile Asn His Phe Glu Lys Ile Gln Ile Ile Pro Lys Ser Ser
65                  70                  75                  80

Trp Ser Asn His Asp Ala Ser Ser Gly Val Ser Ser Ala Cys Pro Tyr
                85                  90                  95

Leu Gly Arg Ser Ser Phe Phe Arg Asn Val Val Trp Leu Ile Lys Lys
                100                 105                 110

Asn Ser Ala Tyr Pro Thr Ile Lys Arg Ser Tyr Asn Asn Thr Asn Gln
            115                 120                 125

Glu Asp Leu Leu Val Leu Trp Gly Ile His His Pro Asn Asp Ala Ala
    130                 135                 140

Glu Gln Thr Lys Leu Tyr Gln Asn Pro Thr Thr Tyr Ile Ser Val Gly
145                 150                 155                 160

Thr Ser Thr Leu Asn Gln Arg Leu Val Pro Glu Ile Ala Thr Arg Pro
                165                 170                 175

Lys Val Asn Gly Gln Ser Gly Arg Met Glu Phe Phe Trp Thr Ile Leu
                180                 185                 190

Lys Pro Asn Asp Ala Ile Asn Phe Glu Ser Asn Gly Asn Phe Ile Ala
                195                 200                 205

Pro Glu Tyr Ala Tyr Lys Ile Val Lys Lys Gly Asp Ser Thr Ile Met
                210                 215                 220

Lys Ser Glu Leu Glu Tyr Gly Asn Cys Asn Thr Lys Cys Gln
225                 230                 235

<210> SEQ ID NO 213
<211> LENGTH: 60
<212> TYPE: PRT

-continued

<213> ORGANISM: Influenza A virus

<400> SEQUENCE: 213

Cys Asp Leu Asp Gly Val L

```
<212> TYPE: PRT
<213> ORGANISM: Influenza A virus

<400> SEQUENCE: 217

Lys His Leu Leu Ser Arg Ile Asn His Phe Glu Lys Ile Gln Ile Ile
1               5                   10                  15

Pro Lys Ser Ser Trp Ser Ser His Glu Ala Ser Leu Gly Val Ser Ser
            20                  25                  30

Ala Cys Pro Tyr Gln Gly Lys Ser Ser Phe Phe Arg Asn Val Val Trp
        35                  40                  45

Leu Ile Lys Lys Asn Ser Thr Tyr Pro Thr Ile Lys Arg Ser Tyr Asn
    50                  55                  60

Asn Thr Asn Gln Glu Asp Leu Leu Val Met Trp Gly Ile His His Pro
65                  70                  75                  80

Asn Asp Ala Ala Glu Gln Thr Lys Leu Tyr Gln Asn Pro Thr Thr Tyr
                85                  90                  95

Ile Ser Val Gly Thr Ser Thr Leu Asn Gln Arg Leu Val Pro Arg Ile
            100                 105                 110

Ala Thr Arg Ser Lys Val Asn Gly Gln Ser Gly Arg Met Glu Phe Phe
        115                 120                 125

Trp Thr Ile Leu Lys Pro Asn Asp Ala Ile Asn Phe Glu Ser Asn Gly
    130                 135                 140

Asn Phe Ile Ala Pro Glu Tyr Ala Tyr Lys Ile Val Lys Lys Gly Asp
145                 150                 155                 160

Ser Thr Ile Met Lys Ser Glu Leu Glu Tyr Gly Asn Cys Asn Thr Lys
                165                 170                 175

Cys Gln

<210> SEQ ID NO 218
<211> LENGTH: 178
<212> TYPE: PRT
<213> ORGANISM: Influenza A virus

<400> SEQUENCE: 218

Lys His Leu Leu Ser Arg Ile Asn His Phe Glu Lys Ile Gln Ile Ile
1               5                   10                  15

Pro Lys Ser Ser Trp Ser Ser His Glu Ala Ser Leu Gly Val Ser Ala
            20                  25                  30

Ala Cys Pro Tyr Gln Gly Lys Ser Ser Phe Phe Arg Asn Val Val Trp
        35                  40                  45

Leu Ile Lys Lys Asn Ser Thr Tyr Pro Thr Ile Lys Arg Ser Tyr Asn
    50                  55                  60

Asn Thr Asn Gln Glu Asp Leu Leu Val Met Trp Gly Ile His His Pro
65                  70                  75                  80

Asn Asp Ala Ala Glu Gln Ala Lys Leu Tyr Gln Asn Pro Thr Thr Tyr
                85                  90                  95

Ile Ser Val Gly Thr Ser Thr Leu Asn Gln Arg Leu Val Pro Arg Ile
            100                 105                 110

Ala Thr Arg Ser Lys Val Asn Gly Gln Ser Gly Arg Met Glu Phe Phe
        115                 120                 125

Trp Thr Ile Leu Lys Pro Asn Asp Ala Ile Asn Phe Glu Ser Asn Gly
    130                 135                 140

Asn Phe Ile Ala Pro Glu Tyr Ala Tyr Lys Ile Val Lys Lys Gly Asp
145                 150                 155                 160

Ser Thr Ile Met Lys Ser Glu Leu Glu Tyr Gly Asn Cys Asn Thr Lys
```

<210> SEQ ID NO 219
<211> LENGTH: 366
<212> TYPE: PRT
<213> ORGANISM: Influenza A virus

<400> SEQUENCE: 219

Lys Arg Ser Tyr Asn Asn Thr Asn Gln Glu Asp Leu Leu Val Met Trp
1               5                   10                  15

Gly Ile His His Pro Asn Asp Ala Ala Glu Gln Thr Lys Leu Tyr Gln
            20                  25                  30

Asn Pro Thr Thr Tyr Ile Ser Val Gly Thr Ser Thr Leu Asn Gln Arg
        35                  40                  45

Leu Val Pro Arg Ile Ala Thr Arg Ser Lys Val Asn Gly Gln Ser Gly
    50                  55                  60

Arg Met Glu Phe Phe Trp Thr Ile Leu Lys Pro Asn Asp Ala Ile Asn
65                  70                  75                  80

Phe Glu Ser Asn Gly Asn Phe Ile Ala Pro Glu Tyr Ala Tyr Lys Ile
                85                  90                  95

Val Lys Lys Gly Asp Ser Thr Ile Met Lys Ser Glu Leu Glu Tyr Gly
            100                 105                 110

Asn Cys Asn Thr Lys Cys Gln Thr Pro Met Gly Ala Ile Asn Ser Ser
        115                 120                 125

Met Pro Phe His Asn Ile His Pro Leu Thr Ile Gly Glu Cys Pro Lys
130                 135                 140

Tyr Val Lys Ser Asn Arg Leu Val Leu Ala Thr Gly Leu Arg Asn Ser
145                 150                 155                 160

Pro Gln Arg Glu Arg Arg Arg Lys Lys Arg Gly Leu Phe Gly Ala Ile
                165                 170                 175

Ala Gly Phe Ile Glu Gly Gly Trp Gln Gly Met Val Asp Gly Trp Tyr
            180                 185                 190

Gly Tyr His His Ser Asn Glu Gln Gly Ser Gly Tyr Ala Ala Asp Lys
        195                 200                 205

Glu Ser Thr Gln Lys Ala Ile Asp Gly Val Thr Asn Lys Val Asn Ser
    210                 215                 220

Ile Ile Asp Lys Met Asn Thr Gln Phe Glu Ala Val Gly Arg Glu Phe
225                 230                 235                 240

Asn Asn Leu Glu Arg Arg Ile Glu Asn Leu Asn Lys Lys Met Glu Asp
                245                 250                 255

Gly Phe Leu Asp Val Trp Thr Tyr Asn Ala Glu Leu Leu Val Leu Met
            260                 265                 270

Glu Asn Glu Arg Thr Leu Asp Phe His Asp Ser Asn Val Lys Asn Leu
        275                 280                 285

Tyr Asp Lys Val Arg Leu Gln Leu Arg Asp Asn Ala Lys Glu Leu Gly
    290                 295                 300

Asn Gly Cys Phe Glu Phe Tyr His Lys Cys Asp Asn Glu Cys Met Glu
305                 310                 315                 320

Ser Val Arg Asn Gly Thr Tyr Asp Tyr Pro Gln Tyr Ser Glu Glu Ala
                325                 330                 335

Arg Leu Lys Arg Glu Glu Ile Ser Gly Val Lys Leu Glu Ser Ile Gly
            340                 345                 350

Ile Tyr Gln Ile Leu Ser Ile Tyr Ser Thr Val Ala Ser Ser

<210> SEQ ID NO 220
<211> LENGTH: 388
<212> TYPE: PRT
<213> ORGANISM: Influenza A virus

<400> SEQUENCE: 220

| Lys | Arg | Ser | Tyr | Asn | Asn | Thr | Asn | Gln | Glu | Asp | Leu | Leu | Val | Met | Trp |
|---|---|---|---|---|---|---|---|---|---|---|---|---|---|---|---|
| 1 | | | | 5 | | | | | 10 | | | | | 15 | |

Gly Ile His His Pro Asn Asp Ala Ala Glu Gln Thr Arg Leu Tyr Gln
            20                  25                  30

Asn Pro Thr Thr Tyr Ile Ser Val Gly Thr Ser Thr Leu Asn Gln Arg
        35                  40                  45

Leu Val Pro Arg Ile Ala Thr Arg Ser Lys Val Asn Gly Gln Ser Gly
    50                  55                  60

Arg Met Glu Phe Phe Trp Thr Ile Leu Lys Pro Asn Asp Ala Ile Asn
65                  70                  75                  80

Phe Glu Ser Asn Gly Asn Phe Ile Ala Pro Glu Tyr Ala Tyr Lys Ile
                85                  90                  95

Val Lys Lys Gly Asp Ser Thr Ile Met Lys Ser Glu Leu Glu Tyr Gly
            100                 105                 110

Asn Cys Asn Thr Lys Cys Gln Thr Pro Met Gly Ala Ile Asn Ser Ser
        115                 120                 125

Met Pro Phe His Asn Ile His Pro Leu Thr Ile Gly Glu Cys Pro Lys
    130                 135                 140

Tyr Val Lys Ser Asn Arg Leu Val Leu Ala Thr Gly Leu Arg Asn Ser
145                 150                 155                 160

Pro Gln Arg Glu Arg Arg Arg Lys Lys Arg Gly Leu Phe Gly Ala Ile
                165                 170                 175

Ala Gly Phe Ile Glu Gly Gly Trp Gln Gly Met Val Asp Gly Trp Tyr
            180                 185                 190

Gly Tyr His His Ser Asn Glu Gln Gly Ser Gly Tyr Ala Ala Asp Lys
        195                 200                 205

Glu Ser Thr Gln Lys Ala Ile Asp Gly Val Thr Asn Lys Val Asn Ser
    210                 215                 220

Ile Ile Asp Lys Met Asn Thr Gln Phe Glu Ala Val Gly Arg Glu Phe
225                 230                 235                 240

Asn Asn Leu Glu Arg Arg Ile Glu Asn Leu Asn Lys Lys Met Glu Asp
                245                 250                 255

Gly Phe Leu Asp Val Trp Thr Tyr Asn Ala Glu Leu Leu Val Leu Met
            260                 265                 270

Glu Asn Glu Arg Thr Leu Asp Phe His Asp Ser Asn Val Lys Asn Leu
        275                 280                 285

Tyr Asp Lys Val Arg Leu Gln Leu Arg Asp Asn Ala Lys Glu Leu Gly
    290                 295                 300

Asn Gly Cys Phe Glu Phe Tyr His Lys Cys Asp Asn Glu Cys Met Glu
305                 310                 315                 320

Ser Val Arg Asn Gly Thr Tyr Asp Tyr Pro Gln Tyr Ser Glu Glu Ala
                325                 330                 335

Arg Leu Lys Arg Glu Glu Ile Ser Gly Val Lys Leu Glu Ser Ile Gly
            340                 345                 350

Ile Tyr Gln Ile Leu Ser Ile Tyr Ser Thr Val Ala Ser Ser Leu Ala
        355                 360                 365

```
Leu Ala Ile Met Val Ala Gly Leu Ser Leu Trp Met Cys Ser Asn Gly
370                 375                 380

Ser Leu Gln Cys
385

<210> SEQ ID NO 221
<211> LENGTH: 60
<212> TYPE: PRT
<213> ORGANISM: Influenza A virus

<400> SEQUENCE: 221

Lys Arg Ser Tyr Asn Asn Thr Asn Gln Glu Asp Leu Leu Val Met Trp
1               5                   10                  15

Gly Ile His His Pro Asn Asp Ala Ala Glu Gln Ala Lys Leu Tyr Gln
            20                  25                  30

Asn Pro Thr Thr Tyr Ile Ser Val Gly Thr Ser Thr Leu Asn Gln Arg
        35                  40                  45

Leu Val Pro Arg Ile Ala Thr Arg Ser Lys Val Asn
    50                  55                  60

<210> SEQ ID NO 222
<211> LENGTH: 59
<212> TYPE: PRT
<213> ORGANISM: Influenza A virus

<400> SEQUENCE: 222

Gly Gln Ser G

```
            130                 135                 140
Tyr Asn Ala Glu Leu Leu Val Leu Met Glu Asn Glu Arg Thr Leu Asp
145                 150                 155                 160

Phe His Asp Ser Asn Val Lys Asn Leu Tyr Asp Lys Val Arg Leu Gln
                165                 170                 175

Leu Arg Asp Asn Ala Lys Glu Leu Gly Asn Gly Cys Phe Glu Phe Tyr
                180                 185                 190

His Lys Cys Asp Asn Glu Cys Met Glu Ser Val Lys Asn Gly Thr Tyr
                195                 200                 205

Asp Tyr Pro Gln Tyr Ser Glu Glu Ala Arg Leu Asn Arg Glu Glu Ile
                210                 215                 220

Ser Gly Val Lys Leu Glu Ser Met Gly Thr Tyr Gln Ile Leu Ser Leu
225                 230                 235                 240

Tyr Ser Thr Val Ala Ser Ser Leu Ala Leu Ala Ile Met Val Ala Gly
                245                 250                 255

Leu Ser Leu Trp
                260

<210> SEQ ID NO 224
<211> LENGTH: 260
<212> TYPE: PRT
<213> ORGANISM: Influenza A virus

<400> SEQUENCE: 224

Thr Pro Met Gly Ala Ile Asn Ser Ser Met Pro Phe His Asn Ile His
1               5                   10                  15

Pro Leu Thr Ile Gly Glu Cys Pro Lys Tyr Val Lys Ser Asn Arg Leu
                20                  25                  30

Val Leu Ala Thr Gly Leu Arg Asn Thr Pro Gln Arg Glu Arg Arg Arg
                35                  40                  45

Lys Lys Arg Gly Leu Phe Gly Ala Ile Ala Gly Phe Ile Glu Gly Gly
                50                  55                  60

Trp Gln Gly Met Val Asp Gly Trp Tyr Gly Tyr His His Ser Asn Glu
65              70                  75                  80

Gln Gly Ser Gly Tyr Ala Ala Asp Lys Glu Ser Thr Gln Lys Ala Ile
                85                  90                  95

Asp Gly Val Thr Asn Lys Val Asn Ser Ile Ile Asn Lys Met Asn Thr
                100                 105                 110

Gln Phe Glu Ala Val Gly Arg Glu Phe Asn Asn Leu Glu Arg Arg Ile
                115                 120                 125

Glu Asn Leu Asn Lys Lys Met Glu Asp Gly Phe Leu Asp Val Trp Thr
130                 135                 140

Tyr Asn Ala Glu Leu Leu Val Leu Met Glu Asn Glu Arg Thr Leu Asp
145                 150                 155                 160

Phe His Asp Ser Asn Val Lys Asn Leu Tyr Asp Lys Val Arg Leu Gln
                165                 170                 175

Leu Arg Asp Asn Ala Lys Glu Leu Gly Asn Gly Cys Phe Glu Phe Tyr
                180                 185                 190

His Lys Cys Asp Asn Glu Cys Met Glu Ser Val Lys Asn Gly Thr Tyr
                195                 200                 205

Asp Tyr Pro Gln Tyr Ser Glu Glu Ala Arg Leu Asn Arg Glu Glu Ile
                210                 215                 220

Ser Gly Val Lys Leu Glu Ser Met Gly Thr Tyr Gln Ile Leu Ser Ile
225                 230                 235                 240
```

```
            Tyr Ser Thr Val Ala Ser Ser Leu Ala Leu Ala Ile Met Val Ala Gly
                            245                 250                 255

Leu Ser Leu Trp
                    260

<210> SEQ ID NO 225
<211> LENGTH: 273
<212> TYPE: PRT
<213> ORGANISM: Influenza A virus

<400> SEQUENCE: 225

Thr Pro Met Gly Ala Ile Asn Ser Ser Met Pro Phe His Asn Ile His
            1               5                   10                  15

Pro Leu Thr Ile Gly Glu Cys Pro Lys Tyr Val Lys Ser Asn Arg Leu
                            20                  25                  30

Val Leu Ala Thr Gly Leu Arg Asn Ser Pro Gln Arg Glu Lys Arg Arg
                        35                  40                  45

Lys Lys Arg Gly Leu Phe Gly Ala Ile Ala Gly Phe Ile Glu Gly Gly
                    50                  55                  60

Trp Gln Gly Met Val Asp Gly Trp Tyr Gly Tyr His His Ser Asn Glu
            65                  70                  75                  80

Gln Gly Ser Gly Tyr Ala Ala Asp Lys Glu Ser Thr Gln Lys Ala Ile
                            85                  90                  95

Asp Gly Val Thr Asn Lys Val Asn Ser Ile Ile Asp Lys Met Asn Thr
                        100                 105                 110

Gln Phe Glu Ala Val Gly Arg Glu Phe Asn Asn Leu Glu Arg Arg Ile
                    115                 120                 125

Glu Asn Leu Asn Lys Lys Met Glu Asp Gly Phe Leu Asp Val Trp Thr
            130                 135                 140

Tyr Asn Ala Glu Leu Leu Val Leu Met Glu Asn Glu Arg Thr Leu Asp
            145                 150                 155                 160

Phe His Asp Ser Asn Val Lys Asn Leu Tyr Asp Lys Val Arg Leu Gln
                            165                 170                 175

Leu Arg Asp Asn Ala Lys Glu Leu Gly Asn Gly Cys Phe Glu Phe Tyr
                        180                 185                 190

His Lys Cys Asp Asn Glu Cys Met Glu Ser Val Arg Asn Gly Thr Tyr
                    195                 200                 205

Asp Tyr Pro Gln Tyr Ser Glu Glu Ala Arg Leu Lys Arg Glu Glu Ile
            210                 215                 220

Ser Gly Val Lys Leu Glu Ser Ile Gly Ile Tyr Gln Ile Leu Ser Ile
            225                 230                 235                 240

Tyr Ser Thr Val Ala Ser Ser Leu Ala Leu Ala Ile Met Val Ala Gly
                            245                 250                 255

Leu Ser Leu Trp Met Cys Ser Asn Gly Ser Leu Gln Cys Arg Ile Cys
                    260                 265                 270

Ile

<210> SEQ ID NO 226
<211> LENGTH: 484
<212> TYPE: PRT
<213> ORGANISM: Artificial Sequence
<220> FEATURE:
<223> OTHER INFORMATION: synthetic influenza A virus strain H5N1
      neuraminidase (NA) consensus sequence

<400> SEQUENCE: 226

Ile Phe Leu Arg Glu Gln Lys Gln Glu Phe Lys Met Asn Pro Asn Gln
```

-continued

```
             1               5                  10                 15
Lys Ile Ile Thr Ile Gly Ser Ile Cys Met Val Ile Gly Ile Val Ser
                 20                 25                 30
Leu Met Leu Gln Ile Gly Asn Met Asp Ile Ser Ile Trp Gly Val Ser
                 35                 40                 45
His Ser Ile Gln Thr Gly Asn Gln His Gln Ala Glu Pro Cys Asn Gln
 50                 55                 60
Ser Ile Ile Thr Tyr Glu Asn Asn Thr Trp Val Asn Gln Thr Tyr Val
 65                 70                 75                 80
Asn Ile Ser Asn Thr Asn Phe Leu Thr Glu Lys Ala Val Ala Ser Val
                 85                 90                 95
Thr Leu Ala Gly Asn Ser Ser Leu Cys Pro Ile Arg Gly Trp Ala Val
                100                105                110
Tyr Ser Lys Asp Asn Ser Ile Arg Ile Gly Ser Lys Gly Asp Val Phe
                115                120                125
Val Ile Arg Glu Pro Phe Ile Ser Cys Ser His Leu Glu Cys Arg Thr
                130                135                140
Phe Phe Leu Thr Gln Gly Ala Leu Leu Asn Asp Lys His Ser Asn Gly
145                150                155                160
Thr Val Lys Asp Arg Ser Pro His Arg Thr Leu Met Ser Cys Pro Val
                165                170                175
Gly Glu Ala Pro Ser Pro Tyr Asn Ser Arg Phe Glu Ser Val Ala Trp
                180                185                190
Ser Ala Ser Ala Cys His Asp Gly Thr Ser Trp Leu Thr Ile Gly Ile
                195                200                205
Ser Gly Pro Asp Asn Gly Ala Val Ala Val Leu Lys Tyr Asn Gly Ile
                210                215                220
Ile Thr Asp Thr Ile Lys Ser Trp Arg Asn Asn Ile Leu Arg Thr Gln
225                230                235                240
Glu Ser Glu Cys Ala Cys Val Asn Gly Ser Cys Phe Thr Val Met Thr
                245                250                255
Asp Gly Pro Ser Asn Gly Gln Ala Ser Tyr Lys Ile Phe Lys Met Gly
                260                265                270
Glu Lys Gly Lys Val Val Lys Ser Val Glu Leu Asp Ala Pro Asn Tyr
                275                280                285
His Tyr Glu Glu Cys Ser Cys Tyr Pro Asp Ala Gly Glu Ile Thr Cys
                290                295                300
Val Cys Arg Asp Asn Trp His Gly Ser Asn Arg Pro Trp Val Ser Phe
305                310                315                320
Asn Gln Asn Leu Glu Tyr Gln Ile Gly Tyr Ile Cys Ser Gly Val Phe
                325                330                335
Gly Asp Asn Pro Arg Pro Asn Asp Gly Thr Gly Ser Cys Gly Pro Val
                340                345                350
Ser Pro Asn Gly Ala Tyr Gly Val Lys Gly Phe Ser Phe Lys Tyr Gly
                355                360                365
Asn Gly Val Trp Ile Gly Arg Thr Lys Ser Thr Asn Ser Arg Ser Gly
                370                375                380
Phe Glu Met Ile Trp Asp Pro Asn Gly Trp Thr Glu Thr Asp Ser Ser
385                390                395                400
Phe Ser Val Lys Gln Asp Ile Val Ala Ile Thr Asp Trp Ser Gly Tyr
                405                410                415
Ser Gly Ser Phe Val Gln His Pro Glu Leu Thr Gly Leu Asp Cys Ile
                420                425                430
```

```
Arg Pro Cys Phe Trp Val Glu Leu Ile Arg Gly Arg Pro Lys Glu Ser
        435                 440                 445

Thr Ile Trp Thr Ser Gly Ser Ser Ile Ser Phe Cys Gly Val Asn Ser
        450                 455                 460

Asp Thr Val Gly Trp Ser Trp Pro Asp Gly Ala Glu Leu Pro Phe Thr
465                 470                 475                 480

Ile Asp Lys Tyr

<210> SEQ ID NO 227
<211> LENGTH: 449
<212> TYPE: PRT
<213> ORGANISM: Influenza A virus

<400> SEQUENCE: 227

Met Asn Pro Asn Lys Lys Ile Ile Thr Ile Gly Ser Ile Cys Met Val
1               5                   10                  15

Thr Gly Met Val Ser Leu Met Leu Gln Ile Gly Asn Leu Ile Ser Ile
                20                  25                  30

Trp Val Ser His Ser Ile His Thr Gly Asn Gln Gln Lys Ala Glu Pro
            35                  40                  45

Ile Ser Asn Thr Asn Phe Leu Thr Glu Lys Ala Val Ala Ser Val Lys
50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ser Leu Leu Asn Asp Lys His Ser Asn Gly Thr
        115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Ser Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
210                 215                 220

Gly Pro Ser Asn Gly Gln Ala Ser His Lys Ile Phe Lys Met Asp Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
        290                 295                 300

Thr Pro Arg Pro Asn Asp Gly Thr Gly Ser Cys Gly Pro Val Ser Ser
305                 310                 315                 320
```

```
Asn Gly Thr Tyr Gly Val Lys Gly Phe Ser Phe Lys Tyr Gly Asn Gly
            325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
            355                 360                 365

Val Lys Gln Asp Ile Val Ala Ile Thr Asp Trp Ser Gly Tyr Ser Gly
            370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
            435                 440                 445

Lys

<210> SEQ ID NO 228
<211> LENGTH: 449
<212> TYPE: PRT
<213> ORGANISM: Influenza A virus

<400> SEQUENCE: 228

Met Asn Pro Asn Gln Lys Ile Ile Thr Ile Gly Ser Ile Cys Met Val
  1                 5                  10                  15

Ile Gly Ile Val Ser Leu Met Leu Gln Ile Gly Asn Met Ile Ser Ile
             20                  25                  30

Trp Val Ser His Ser Ile Gln Lys Gly Asn Gln His Gln Ala Glu Ser
             35                  40                  45

Ile Ser Asn Thr Asn Pro Leu Thr Glu Lys Ala Val Ala Ser Val Thr
 50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
             85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
            115                 120                 125

Val Lys Asp Arg Ser Pro His Arg Thr Leu Met Ser Cys Pro Val Gly
            130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
            165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
            195                 200                 205

Ser Glu Cys Ala Cys Val Asn Gly Ser Cys Phe Thr Val Met Thr Asp
            210                 215                 220

Gly Pro Ser Asn Gly Gln Ala Ser Tyr Lys Ile Phe Lys Met Glu Lys
225                 230                 235                 240
```

```
Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
        435                 440                 445

Lys

<210> SEQ ID NO 229
<211> LENGTH: 449
<212> TYPE: PRT
<213> ORGANISM: Influenza A virus

<400> SEQUENCE: 229

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Val Gln Thr Gly Asn Gln His Gln Ala Glu Ser
        35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160
```

```
Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
        435                 440                 445

Lys

<210> SEQ ID NO 230
<211> LENGTH: 449
<212> TYPE: PRT
<213> ORGANISM: Influenza A virus

<400> SEQUENCE: 230

Met Asn Pro Asn Gln Lys Ile Ile Thr Ile Gly Ser Ile Cys Met Val
  1               5                  10                  15

Ile Gly Ile Val Ser Leu Met Leu Gln Ile Gly Asn Met Ile Ser Ile
                 20                  25                  30

Trp Val Ser His Ser Thr Gln Lys Gly Asn Gln His Gln Ala Glu Ser
             35                  40                  45

Ile Ser Asn Thr Asn Pro Leu Thr Glu Lys Ala Val Ala Ser Val Thr
         50                  55                  60

Leu Ala Gly Asn Ser Ser Leu Cys Pro Ile Arg Gly Trp Ala Val His
 65                  70                  75                  80
```

Ser Lys Asp Asn Asn Ile Arg Ile Gly Ser Lys Gly Asp Val Phe Val
            85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
            115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
            165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
            195                 200                 205

Ser Glu Cys Ala Cys Val Asn Gly Ser Cys Phe Thr Val Met Thr Asp
            210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
            245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
            275                 280                 285

Asn Leu Glu Tyr Gln Ile Gly Tyr Ile Cys Ser Gly Ile Phe Gly Asp
            290                 295                 300

Asn Pro Arg Pro Asn Asp Gly Thr Gly Ser Cys Gly Pro Met Phe Pro
305                 310                 315                 320

Asn Gly Ala Tyr Gly Val Lys Gly Phe Ser Phe Lys Tyr Gly Asn Gly
            325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
            355                 360                 365

Val Lys Gln Asp Ile Val Ala Ile Thr Asp Trp Ser Gly Tyr Ser Gly
            370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
            435                 440                 445

Lys

<210> SEQ ID NO 231
<211> LENGTH: 449
<212> TYPE: PRT
<213> ORGANISM: Influenza A virus

<400> SEQUENCE: 231

```
Met Asn Pro Asn Arg Lys Ile Ile Thr Ile Gly Ser Ile Cys Met Val
 1               5                  10                  15

Ile Gly Met Val Ser Leu Met Leu Gln Ile Gly Asn Met Ile Ser Ile
            20                  25                  30

Trp Val Ser His Ser Ile Gln Thr Gly Asn Gln His Gln Ala Glu Ser
            35                  40                  45

Ile Ser Asn Thr Asn Pro Leu Thr Glu Lys Ala Val Ala Ser Val Thr
 50                  55                  60

Leu Ala Gly Asn Ser Ser Leu Cys Pro Ile Arg Gly Trp Ala Val His
 65                  70                  75                  80

Ser Lys Asp Asn Asn Ile Arg Ile Gly Ser Lys Gly Asp Val Phe Val
                 85                  90                  95

Ile Arg Glu Pro Phe Ile Ser Cys Ser His Leu Glu Cys Arg Thr Phe
                100                 105                 110

Phe Leu Thr Gln Gly Ala Leu Leu Asn Asp Lys His Ser Asn Gly Thr
            115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
                180                 185                 190

Thr Asp Thr Ile Lys Ser Trp Arg Asn Asn Ile Leu Arg Thr Gln Glu
            195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Val Ala Pro Asn Tyr His Tyr
                245                 250                 255

Glu Glu Cys Ser Cys Tyr Pro Asp Ala Gly Glu Ile Thr Cys Val Cys
                260                 265                 270

Arg Asp Asn Trp His Gly Ser Asn Arg Pro Trp Val Ser Phe Asn Gln
            275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
    355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415
```

```
Trp Thr Ser Gly Ser Ser Ile Ser Phe Cys Gly Val Asn Ser Asp Thr
            420                 425                 430

Ala Ser Trp Ser Trp Pro Asp Gly Ala Glu Leu Pro Phe Thr Ile Asp
            435                 440                 445

Lys

<210> SEQ ID NO 232
<211> LENGTH: 443
<212> TYPE: PRT
<213> ORGANISM: Influenza A virus

<400> SEQUENCE: 232

Lys Gln Glu Phe Lys Met Asn Pro Asn Lys Lys Ile Ile Thr Ile Gly
  1               5                  10                  15

Ser Ile Cys Met Val Thr Gly Met Val Ser Leu Met Leu Gln Ile Gly
             20                  25                  30

Asn Leu Ile Ser Ile Trp Leu Ser Arg Ser Ile His Thr Gly Asn Gln
         35                  40                  45

Gln Lys Ala Glu Pro Ile Ser Asn Thr Asn Phe Leu Thr Glu Lys Ala
     50                  55                  60

Val Ala Ser Val Lys Leu Ala Gly Asn Ser Ser Leu Cys Pro Ile Asn
 65                  70                  75                  80

Gly Trp Ala Val Tyr Ser Lys Asp Asn Ser Ile Arg Ile Gly Ser Lys
                 85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ser Leu Leu Asn Asp Lys
        115                 120                 125

His Ser Asn Gly Thr Val Lys Asp Arg Ser Pro His Arg Thr Leu Met
130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Thr Ser Trp Leu
                165                 170                 175

Thr Ile Gly Ile Ser Gly Pro Asp Ser Gly Ala Val Ala Val Leu Lys
            180                 185                 190

Tyr Asn Gly Ile Ile Thr Asp Thr Ile Lys Ser Trp Arg Asn Asn Thr
        195                 200                 205

Leu Arg Thr Gln Glu Ser Glu Cys Ala Cys Val Asn Gly Ser Cys Phe
    210                 215                 220

Thr Val Met Thr Asp Gly Pro Ser Asn Gly Gln Ala Ser His Lys Ile
225                 230                 235                 240

Phe Lys Trp Lys Lys Gly Lys Trp Leu Asn Gln Ser Gln Leu Asp Ala
                245                 250                 255

Pro Asn Tyr His Tyr Glu Glu Cys Ser Cys Tyr Pro Asp Ala Gly Glu
            260                 265                 270

Ile Thr Cys Val Cys Arg Asp Asn Trp His Gly Ser Asn Arg Pro Trp
        275                 280                 285

Val Ser Phe Asn Gln Asn Leu Gly Tyr Gln Ile Gly Tyr Ile Cys Ser
    290                 295                 300

Gly Val Phe Gly Asp Thr Pro Arg Pro Asn Asp Gly Thr Gly Ser Cys
305                 310                 315                 320

Gly Pro Val Ser Ser Asn Gly Thr Tyr Gly Val Lys Gly Phe Ser Phe
                325                 330                 335
```

```
Lys Tyr Gly Asn Gly Val Trp Ile Gly Arg Thr Lys Ser Thr Asn Ser
                340                 345                 350

Arg Ser Gly Phe Glu Met Ile Trp Asp Pro Asn Gly Trp Thr Glu Thr
            355                 360                 365

Asp Ser Ser Phe Ser Val Lys Gln Asp Ile Val Ala Ile Thr Asp Trp
370                 375                 380

Ser Gly Tyr Ser Gly Ser Phe Val Gln His Pro Glu Leu Thr Gly Leu
385                 390                 395                 400

Asn Cys Ile Arg Pro Cys Phe Trp Val Glu Leu Ile Arg Gly Arg Pro
                405                 410                 415

Lys Glu Ser Thr Ile Trp Thr Ser Gly Ser Ser Ile Ser Phe Cys Gly
                420                 425                 430

Val Asn Ser Asp Thr Val Gly Gly Ser Trp Pro
                435                 440

<210> SEQ ID NO 233
<211> LENGTH: 449
<212> TYPE: PRT
<213> ORGANISM: Influenza A virus

<400> SEQUENCE: 233

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
                20                  25                  30

Trp Val Ser His Ser Ile Gln Thr Gly Asn Gln His Gln Ala Glu Ser
            35                  40                  45

Ile Ser Asn Thr Asn Pro Leu Thr Glu Lys Ala Val Val Ser Val Thr
50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
                100                 105                 110

Phe Leu Thr Gln Gly Ala Leu Leu Asn Asp Lys His Ser Asn Gly Thr
            115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
                180                 185                 190

Thr Asp Thr Ile Lys Ser Trp Arg Asn Asn Ile Leu Arg Thr Gln Glu
            195                 200                 205

Ser Glu Cys Ala Cys Val Asn Gly Ser Cys Phe Thr Val Met Thr Asp
210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
                260                 265                 270
```

```
Arg Asp Asn Trp His Gly Ser Asn Arg Pro Trp Val Ser Phe Asn Gln
        275                 280                 285

```
Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Asp Gly Glu Ile Thr Cys Val Cys
                260                 265                 270

Arg Asp Asn Trp His Gly Ser Asn Arg Pro Trp Val Ser Phe Asn Gln
                275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
                340                 345                 350

Met Ile Trp Asp Pro Asn Gly Trp Thr Gly Thr Asp Ser Ser Phe Ser
                355                 360                 365

Val Lys Gln Asp Ile Val Ala Ile Thr Asp Trp Ser Gly Tyr Ser Gly
                370                 375                 380

Ser Phe Val Gln His Pro Glu Leu Thr Gly Leu Asp Cys Ile Arg Pro
385                 390                 395                 400

<210> SEQ ID NO 235
<211> LENGTH: 451
<212> TYPE: PRT
<213> ORGANISM: Influenza A virus

<400> SEQUENCE: 235

Met Asn Pro Asn Gln Lys Ile Ile Thr Ile Gly Ser Ile Cys Met Val
1               5                   10                  15

Val Gly Ile Ile Ser Leu Met Leu Gln Ile Gly Asn Ile Ile Ser Val
                20                  25                  30

Trp Val Ser His Ile Ile Gln Thr Trp His Pro Asn Gln Pro Glu Pro
            35                  40                  45

Cys Asn Asn Gln Ser Ile Asn Phe Tyr Thr Glu Gln Ala Ala Ala Ser
    50                  55                  60

Val Thr Leu Ala Gly Asn Ser Ser Leu Cys Pro Ile Ser Gly Trp Ala
65                  70                  75                  80

Ile Tyr Ser Lys Asp Asn Ser Ile Arg Ile Gly Ser Lys Gly Asp Val
                85                  90                  95

Phe Val Ile Arg Glu Pro Phe Ile Ser Cys Ser His Leu Glu Cys Arg
            100                 105                 110

Thr Phe Phe Leu Thr Gln Gly Ala Leu Leu Asn Asp Lys His Ser Asn
        115                 120                 125

Gly Thr Val Lys Asp Arg Ser Pro Tyr Arg Thr Leu Met Ser Cys Pro
    130                 135                 140

Val Gly Glu Ala Pro Ser Pro Tyr Asn Ser Arg Phe Glu Ser Val Ala
145                 150                 155                 160

Trp Ser Ala Ser Ala Cys His Asp Gly Ile Ser Trp Leu Thr Ile Gly
```

```
            165                 170                 175
Ile Ser Gly Pro Asp Asn Gly Ala Val Ala Val Leu Lys Tyr Asn Gly
            180                 185                 190

Ile Ile Thr Asp Thr Ile Lys Ser Trp Arg Asn Asn Ile Leu Arg Thr
            195                 200                 205

Gln Glu Ser Glu Cys Ala Cys Val Asn Gly Ser Cys Phe Thr Val Met
            210                 215                 220

Thr Asp Gly Pro Ser Asn Glu Gln Ala Ser Tyr Lys Ile Phe Lys Ile
225                 230                 235                 240

Glu Lys Gly Arg Val Val Lys Ser Val Glu Leu Asn Ala Pro Asn Tyr
            245                 250                 255

His Tyr Glu Glu Cys Ser Cys Tyr Pro Asp Ala Gly Glu Ile Thr Cys
            260                 265                 270

Val Cys Arg Asp Asn Trp His Gly Ser Asn Arg Pro Trp Val Ser Phe
            275                 280                 285

Asn Gln Asn Leu Glu Tyr Gln Ile Gly Tyr Ile Cys Ser Gly Val Phe
            290                 295                 300

Gly Asp Ser Pro Arg Pro Asn Asp Gly Thr Gly Ser Cys Gly Pro Val
305                 310                 315                 320

Ser Leu Asn Gly Ala Tyr Gly Val Lys Gly Phe Ser Phe Lys Tyr Gly
            325                 330                 335

Asn Gly Val Trp Ile Gly Arg Thr Lys Ser Thr Ser Ser Arg Ser Gly
            340                 345                 350

Phe Glu Met Ile Trp Asp Pro Asn Gly Trp Thr Glu Thr Asp Ser Ser
            355                 360                 365

Phe Ser Leu Lys Gln Asp Ile Ile Ala Ile Thr Asp Trp Ser Gly Tyr
            370                 375                 380

Ser Gly Ser Phe Ile Gln His Pro Glu Leu Thr Gly Leu Asn Cys Met
385                 390                 395                 400

Arg Pro Cys Phe Trp Val Glu Leu Ile Arg Gly Arg Pro Lys Glu Lys
            405                 410                 415

Thr Ile Trp Thr Ser Gly Ser Ser Ile Ser Phe Cys Gly Val Asn Ser
            420                 425                 430

Asp Thr Val Gly Trp Ser Trp Pro Asp Gly Ala Glu Leu Pro Phe Thr
            435                 440                 445

Ile Asp Lys
    450

<210> SEQ ID NO 236
<211> LENGTH: 451
<212> TYPE: PRT
<213> ORGANISM: Influenza A virus

<400> SEQUENCE: 236

Met Asn Pro Asn Gln Lys Ile Ile Thr Ile Gly Ser Ile Cys Met Val
1               5                   10                  15

Val Gly Ile Ile Asn Leu Met Leu Gln Ile Gly Asn Thr Ile Ser Val
            20                  25                  30

Trp Val Ser His Ile Ile Lys Thr Trp His Pro Asn Gln Pro Glu Pro
            35                  40                  45

Cys Asn Gln Ser Ile Asn Phe Tyr Thr Glu Gln Ala Ala Ala Ser Val
            50                  55                  60

Thr Leu Ala Gly Asn Ser Ser Leu Cys Pro Ile Ser Gly Trp Ala Ile
65              70                  75                  80
```

```
Tyr Ser Lys Asp Lys Ser Ile Arg Ile Gly Ser Lys Gly Asp Val Phe
                85                  90                  95

Val Ile Lys Glu Pro Phe Ile Ser Cys Ser His Leu Glu Cys Arg Thr
            100                 105                 110

Phe Phe Leu Thr Gln Gly Ala Leu Leu Asn Asp Lys His Ser Asn Gly
            115                 120                 125

Thr Val Lys Asp Arg Ser Pro Tyr Arg Thr Leu Met Ser Cys Pro Val
            130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Ile Leu Arg Thr Gln
            195                 200                 205

Glu Ser Glu Cys Ala Cys Val Asn Gly Ser Cys Phe Thr Val Met Thr
    210                 215                 220

Asp Gly Pro Ser Asn Gly Gln Ala Ser Tyr Lys Ile Phe Lys Met Gly
225                 230                 235                 240

Glu Lys Gly Lys Val Val Lys Ser Val Glu Leu Asp Ala Pro Asn Tyr
                245                 250                 255

His Tyr Glu Glu Cys Ser Cys Tyr Pro Asp Ala Gly Glu Ile Thr Cys
                260                 265                 270

Val Cys Arg Asp Asn Trp His Gly Ser Asn Arg Pro Trp Val Ser Phe
            275                 280                 285

Asn Gln Asn Leu Glu Tyr Gln Ile Gly Tyr Ile Cys Ser Gly Val Phe
            290                 295                 300

Gly Asp Asn Pro Arg Pro Asn Asp Gly Thr Gly Ser Cys Gly Pro Val
305                 310                 315                 320

Ser Pro Asn Gly Ala Tyr Gly Val Lys Gly Phe Ser Phe Lys Tyr Gly
                325                 330                 335

Asn Gly Val Trp Ile Gly Arg Thr Lys Ser Thr Asn Ser Arg Ser Gly
            340                 345                 350

Phe Glu Met Ile Trp Asp Pro Asn Gly Trp Thr Glu Thr Asp Ser Ser
            355                 360                 365

Phe Ser Val Lys Gln Asp Ile Val Ala Ile Thr Asp Trp Ser Gly Tyr
            370                 375                 380

Ser Gly Ser Phe Val Gln His Pro Glu Leu Thr Gly Leu Asp Cys Ile
385                 390                 395                 400

Arg Pro Cys Phe Trp Val Glu Leu Ile Arg Gly Arg Pro Lys Glu Ser
                405                 410                 415

Thr Ile Trp Thr Ser Gly Ser Ser Ile Ser Phe Cys Gly Val Asn Ser
            420                 425                 430

Asp Thr Val Gly Trp Ser Trp Pro Asp Gly Ala Glu Leu Pro Phe Thr
            435                 440                 445

Ile Asp Lys
    450

<210> SEQ ID NO 237
<211> LENGTH: 450
<212> TYPE: PRT
<213> ORGANISM: Influenza A virus

<400> SEQUENCE: 237
```

```
Met Asn Pro Asn Gln Lys Ile Thr Ile Gly Ser Ile Cys Met Val
  1               5                  10                  15

Val Gly Ile Ile Ser Leu Met Leu Gln Ile Gly Asn Ile Ile Ser Val
             20                  25                  30

Trp Val Ser His Ile Ile Gln Thr Trp His Pro Asn Gln Pro Glu Pro
             35                  40                  45

Cys Asn Gln Ser Ile Asn Phe Tyr Thr Glu Gln Ala Ala Ala Ser Val
 50                  55                  60

Thr Leu Ala Gly Asn Ser Ser Leu Cys Pro Ile Ser Gly Trp Ala Ile
 65                  70                  75                  80

Tyr Ser Lys Asp Lys Ser Ile Arg Ile Gly Ser Lys Gly Asp Val Phe
                 85                  90                  95

Val Ile Arg Glu Pro Phe Ile Ser Cys Ser His Leu Glu Cys Arg Thr
            100                 105                 110

Phe Phe Leu Thr Gln Gly Ala Leu Leu Asn Asp Lys His Ser Asn Gly
            115                 120                 125

Thr Val Lys Asp Arg Ser Pro Tyr Gly Thr Leu Met Ser Cys Pro Val
            130                 135                 140

Gly Glu Thr Pro Ser Pro Tyr Asn Ser Arg Phe Glu Ser Val Ala Trp
145                 150                 155                 160

Ser Ala Ser Ala Cys His Asp Ser Ile Ser Trp Leu Thr Ile Gly Ile
                165                 170                 175

Ser Gly Pro Asp Asn Gly Ala Val Ala Val Leu Lys Tyr Asn Gly Met
                180                 185                 190

Ile Thr Asp Thr Ile Lys Ser Trp Arg Lys Asn Ile Leu Arg Thr Gln
                195                 200                 205

Glu Ser Glu Cys Ala Cys Val Asn Gly Ser Cys Phe Thr Val Met Thr
            210                 215                 220

Asp Gly Pro Ser Asn Glu Gln Ala Ser Tyr Lys Ile Phe Lys Ile Glu
225                 230                 235                 240

Lys Gly Arg Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
            260                 265                 270

Cys Arg Asp Asn Trp His Gly Ser Asn Arg Pro Trp Val Ser Phe Asn
            275                 280                 285

Gln Asn Leu Glu Tyr Gln Ile Gly Tyr Ile Cys Ser Gly Val Phe Gly
            290                 295                 300

Asp Ser Pro Arg Pro Asn Asp Gly Thr Gly Ser Cys Gly Pro Val Ser
305                 310                 315                 320

Leu Asn Gly Ala Tyr Gly Val Lys Gly Phe Ser Phe Lys Tyr Gly Asn
                325                 330                 335

Gly Val Trp Ile Gly Arg Thr Lys Ser Thr Ser Ser Arg Ser Gly Phe
            340                 345                 350

Glu Met Ile Trp Asp Pro Asn Gly Trp Thr Glu Thr Asp Ser Ser Phe
            355                 360                 365

Ser Leu Lys Gln Asp Ile Ile Ala Ile Thr Asp Trp Ser Gly Tyr Ser
            370                 375                 380

Gly Ser Phe Ile Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415
```

```
Ile Trp Thr Ser Gly Ser Ser Ile Ser Phe Cys Gly Val Asp Ser Asp
            420                 425                 430

Thr Val Gly Trp Ser Trp Pro Asp Asp Ala Glu Leu Pro Phe Thr Ile
        435                 440                 445

Asp Lys
    450

<210> SEQ ID NO 238
<211> LENGTH: 449
<212> TYPE: PRT
<213> ORGANISM: Influenza A virus

<400> SEQUENCE: 238

Met Asn Pro Asn Lys Lys Ile Ile Thr Ile Gly Ser Ile Cys Met Val
  1               5                  10                  15

Thr Gly Met Val Ser Leu Met Leu Gln Ile Gly Asn Leu Ile Ser Ile
             20                  25                  30

Trp Val Ser His Ser Ile His Thr Gly Asn Gln His Lys Ala Glu Pro
         35                  40                  45

Ile Ser Asn Thr Asn Phe Leu Thr Glu Lys Ala Val Ala Ser Val Lys
     50                  55                  60

Leu Ala Gly Asn Ser Ser Leu Cys Pro Ile Asn Gly Trp Ala Val Tyr
 65                  70                  75                  80

Ser Lys Asp Asn Ser Ile Arg Ile Gly Ser Lys Gly Asp Val Phe Val
                 85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335
```

```
Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
            355                 360                 365

Val Lys Gln Asp Ile Val Ala Ile Thr Asp Trp Ser Gly Tyr Ser Gly
370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
            435                 440                 445

Lys
```

```
<210> SEQ ID NO 239
<211> LENGTH: 191
<212> TYPE: PRT
<213> ORGANISM: Influenza A virus

<400> SEQUENCE: 239

Leu Ala Ser Ala Cys His Asp Gly Thr Ser Trp Leu Thr Ile Gly Ile
1               5                   10                  15

Ser Gly Pro Asp Asn Gly Ala Val Ala Val Leu Lys Tyr Asn Gly Ile
            20                  25                  30

Ile Thr Asp Thr Ile Lys Ser Trp Arg Asn Asn Ile Leu Arg Thr Gln
        35                  40                  45

Glu Ser Glu Cys Ala Cys Val Asn Gly Ser Cys Phe Thr Val Met Thr
    50                  55                  60

Asp Gly Pro Ser Asn Gly Gln Ala Ser His Lys Ile Phe Lys Met Glu
65                  70                  75                  80

Lys Gly Lys Val Val Lys Ser Val Glu Leu Asp Ala Pro Asn Tyr His
                85                  90                  95

Tyr Glu Glu Cys Ser Cys Tyr Pro Asp Ala Gly Glu Ile Thr Cys Val
            100                 105                 110

Cys Arg Asp Asn Trp His Gly Ser Asn Arg Pro Trp Val Ser Phe Asn
        115                 120                 125

Gln Asn Leu Glu Tyr Gln Ile Gly Tyr Ile Cys Ser Gly Val Phe Gly
    130                 135                 140

Asp Asn Pro Arg Pro Asn Asp Gly Thr Gly Ser Cys Gly Pro Val Ser
145                 150                 155                 160

Ser Asn Gly Ala Tyr Gly Val Lys Gly Phe Ser Phe Lys Tyr Gly Asn
                165                 170                 175

Gly Val Trp Ile Gly Arg Thr Lys Ser Thr Asn Ser Arg Ser Gly
            180                 185                 190
```

```
<210> SEQ ID NO 240
<211> LENGTH: 449
<212> TYPE: PRT
<213> ORGANISM: Influenza A virus

<400> SEQUENCE: 240

Met Asn Pro Asn Gln Lys Ile Ile Thr Ile Gly Ser Ile Cys Met Val
1               5                   10                  15
```

```
Thr Gly Ile Val Ser Leu Met Leu Gln Val Gly Asn Met Ile Ser Ile
            20                  25                  30

Trp Val Ser His Ser Ile His Thr Gly Asn Gln His Gln Ala Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Thr Asp Thr
            420                 425                 430

Val Gly Trp Ser Trp Pro Asp Gly Ala Glu Leu Pro Phe Thr Ile Asp
```

-continued

```
            435                 440                 445
Lys

<210> SEQ ID NO 241
<211> LENGTH: 449
<212> TYPE: PRT
<213> ORGANISM: Influenza A virus

<400> SEQUENCE: 241

Met Asn Pro Asn Gln Lys Ile Ile Thr Ile Gly Ser Ile Cys Met Val
1               5                   10                  15

Thr Gly Ile Val Ser Leu Met Leu Gln Val Gly Asn Met Ile Ser Ile
            20                  25                  30

Trp Val Ser His Ser Ile Asn Thr Gly Asn Gln His Gln Ala Glu Pro
        35                  40                  45

Ile Ser Asn Ala Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Thr Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
```

|         |         |         |         | 355     |         |         |         |         | 360     |         |         |         |         | 365     |
|---------|---------|---------|---------|---------|---------|---------|---------|---------|---------|---------|---------|---------|---------|---------|

Val Lys Gln Asp Ile Val Ala Ile Thr Asp Trp Ser Gly Tyr Ser Gly
       370                375               380

Ser Phe Val Gln His Pro Glu Leu Thr Gly Leu Asp Cys Ile Arg Pro
385               390               395            400

Cys Phe Trp Val Glu Leu Ile Arg Gly Arg Pro Lys Glu Ser Thr Ile
             405               410            415

Trp Thr Ser Gly Ser Ser Ile Ser Phe Cys Gly Val Asn Ser Asp Thr
        420                425            430

Val Gly Trp Ser Trp Pro Asp Gly Ala Glu Leu Pro Phe Thr Ile Asp
       435                440            445

Lys

<210> SEQ ID NO 242
<211> LENGTH: 432
<212> TYPE: PRT
<213> ORGANISM: Influenza A virus

<400> SEQUENCE: 242

Ile Gly Ser Ile Cys Met Val Ile Gly Ile Val Ser Leu Met Leu Gln
1               5                 10              15

Ile Gly Asn Met Ile Ser Ile Trp Val Ser His Ser Ile Gln Thr Gly
        20               25              30

Asn Gln His Gln Val Gly Pro Ile Ser Asn Thr Asn Phe Leu Thr Glu
           35              40            45

Lys Ala Val Ala Ser Val Thr Leu Ala Gly Asn Ser Ser Leu Cys Pro
50                55               60

Ile Arg Gly Trp Ala Val His Ser Lys Asp Asn Ser Ile Arg Ile Gly
65               70              75            80

Ser Lys Gly Asp Val Phe Val Ile Arg Glu Pro Phe Ile Ser Cys Ser
           85              90            95

His Leu Glu Cys Arg Thr Phe Phe Leu Thr Gln Gly Ala Leu Leu Asn
          100            105            110

Asp Lys His Ser Asn Gly Thr Val Lys Asp Arg Ser Pro His Arg Thr
        115              120            125

Leu Met Ser Cys Pro Val Gly Glu Ala Pro Ser Pro Tyr Asn Ser Arg
130               135               140

Phe Glu Ser Val Ala Trp Ser Ala Ser Ala Cys His Asp Gly Thr Ser
145               150               155           160

Trp Leu Thr Ile Gly Ile Ser Gly Pro Asp Asn Gly Ala Val Ala Val
          165            170            175

Leu Lys Tyr Asn Gly Met Ile Thr Asp Thr Ile Lys Ser Trp Arg Asn
        180              185            190

Asn Ile Leu Arg Thr Gln Glu Ser Glu Cys Val Cys Val Asn Gly Ser
          195            200            205

Cys Phe Thr Val Met Thr Asp Gly Pro Ser Asn Gly Gln Ala Ser Tyr
210               215               220

Lys Ile Phe Lys Met Glu Lys Gly Lys Val Val Lys Ser Val Glu Leu
225               230               235           240

Asp Ala Pro Asn Tyr His Tyr Glu Glu Cys Ser Cys Tyr Pro Asp Ala
        245              250            255

Gly Glu Ile Thr Cys Val Cys Arg Asp Asn Trp His Gly Ser Asn Arg
          260            265            270

Pro Trp Val Ser Phe Asn Gln Asn Leu Glu Tyr Gln Ile Gly Tyr Ile

```
                275                 280                 285
Cys Ser Gly Val Phe Gly Asp Asn Pro Arg Pro Asn Asp Gly Thr Gly
    290

```
Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Asp Ala Glu Leu Pro
        435                 440

<210> SEQ ID NO 244
<211> LENGTH: 444
<212> TYPE: PRT
<213> ORGANISM: Influenza A virus

<400> SEQUENCE: 244

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
                20                  25                  30

Trp Val Ser His Ser Ile Gln Thr Gly Asn Gln His Gln Ala Glu Ser
            35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160
```

-continued

```
Ala Ser Ala Cys His Asp Gly Thr Ser Trp Leu Thr Ile Gly Ile Ser
                165                 170                 175
Gly Pro Asp Asn Glu Ala Val Ala Val Leu Lys Tyr Asn Gly Ile Ile
                180                 185                 190
Thr Asp Thr Ile Lys Ser Trp Arg Asn Asn Ile Leu Arg Thr Gln Glu
                195                 200                 205
Ser Glu Cys Ala Cys Val Asn Gly Ser Cys Phe Thr Val Met Thr Asp
            210                 215                 220
Gly Pro Ser Asn Gly Gln Ala Ser Tyr Lys Ile Phe Lys Met Glu Lys
225                 230                 235                 240
Gly Lys Val Val Lys Ser Val Glu Leu Asp Ala Pro Asn Tyr His Tyr
                245                 250                 255
Glu Glu Cys Ser Cys Tyr Pro Asp Ala Gly Glu Ile Thr Cys Val Cys
                260                 265                 270
Arg Asp Asn Trp His Gly Ser Asn Arg Pro Trp Val Ser Phe Asn Gln
            275                 280                 285
Asn Leu Glu Tyr Gln Ile Gly Tyr Ile Cys Ser Gly Val Phe Gly Asp
            290                 295                 300
Asn Pro Arg Pro Asn Asp Gly Thr Gly Ser Cys Gly Pro Met Ser Pro
305                 310                 315                 320
Asn Gly Ala Tyr Gly Val Lys Gly Phe Ser Phe Lys Tyr Gly Asn Gly
                325                 330                 335
Val Trp Ile Gly Arg Thr Lys Ser Thr Asn Ser Arg Ser Gly Phe Glu
                340                 345                 350
Met Ile Trp Asp Pro Asn Gly Trp Thr Gly Thr Asp Ser Ser Phe Ser
            355                 360                 365
Val Lys Gln Asp Ile Val Ala Ile Thr Asn Trp Ser Gly Tyr Ser Gly
            370                 375                 380
Ser Phe Val Gln His Pro Glu Leu Thr Gly Leu Asp Cys Ile Arg Pro
385                 390                 395                 400
Cys Phe Trp Val Glu Leu Ile Arg Gly Arg Pro Lys Glu Ser Thr Ile
                405                 410                 415
Trp Thr Ser Gly Ser Ser Ile Ser Phe Cys Gly Val Asn Ser Asp Thr
            420                 425                 430
Val Ser Trp Ser Trp Pro Asp Asp Ala Glu Leu Pro
            435                 440
```

What is claimed is:

1. An isolated polypeptide that corresponds to an H5N1 HA polypeptide fragment, wherein the H5N1 HA polypeptide fragment consists of the isolated polypeptide with the amino acid sequence that is at least 80% identical to the amino acid sequence of the polypeptide starting at amino acid 5 and ending at amino acid 247 of SEQ ID NO: 129.

2. An isolated H5N1 HA polypeptide fragment fused to a heterologous polypeptide, wherein the H5N1 HA polypeptide fragment consists of the amino acid sequence that is at least 80% identical to the amino acid sequence of the polypeptide starting at amino acid 5 and ending at amino acid 247 of SEQ ID NO: 129, wherein the heterologous polypeptide comprises all or a portion of a filamentous bacteriophage coat protein.

3. An isolated H5N1 HA polypeptide fragment fused to a heterologous polypeptide, wherein the H5N1 HA polypeptide fragment consists of the amino acid sequence that is at least 80% identical to the amino acid sequence of the polypeptide starting at amino acid 5 and ending at amino acid 247 of SEQ ID NO: 129, wherein the heterologous polypeptide is selected from the group consisting of bovine serum albumin, keyhole limpet hemacyanin, ovalbumin, mouse serum albumin and rabbit serum albumin.

4. The polypeptide of claim 1, wherein the H5N1 HA polypeptide fragment is bound to a solid substrate.

5. A composition comprising a carrier and an effective amount of the H5N1 HA polypeptide fragment of claim 1.

6. The composition of the claim 5, wherein the carrier is an adjuvant selected form the group consisting of aluminum hydroxide, lipid A, killed bacteria, polysaccharide, mineral oil, Freund's incomplete adjuvant, Freund's complete adjuvant, aluminum phosphate, iron, zinc, a calcium salt, acylated tyrosine, an acylated sugar, a CpG oligonucleotide, a cationically derivatized polysaccharide, an anionically derivatized polysaccharide, a polyphosphazine, a biodegradable microsphere, a monophosphoryl lipid A, MF59, oil in water emulsions AS03 and AS04, ISCOM, and quil A.

* * * * *